United States Patent
Amans et al.

(10) Patent No.: US 10,407,407 B2
(45) Date of Patent: Sep. 10, 2019

(54) BENZOIMIDAZOLE DERIVATIVES AS PAD4 INHIBITORS

(71) Applicant: GLAXOSMITHKLINE INTELLECTUAL PROPERTY DEVELOPMENT LIMITED, Brentford (GB)

(72) Inventors: Dominique Amans, Singapore (SG); Stephen John Atkinson, Stevenage (GB); Michael David Barker, Stevenage (GB); Matthew Campbell, Stevenage (GB); Hawa Diallo, Stevenage (GB); Clement Douault, Stevenage (GB); Neil Stuart Garton, Stevenage (GB); John Liddle, Stevenage (GB); Jessica Fanny Renaux, Middlesex (GB); Robert John Sheppard, Stevenage (GB); Ann Louise Walker, Stevenage (GB); Christopher Roland Wellaway, Stevenage (GB); David Matthew Wilson, Madrid (ES)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 15/575,583

(22) PCT Filed: May 19, 2016

(86) PCT No.: PCT/IB2016/000761
§ 371 (c)(1),
(2) Date: Nov. 20, 2017

(87) PCT Pub. No.: WO2016/185279
PCT Pub. Date: Nov. 24, 2016

(65) Prior Publication Data
US 2018/0297983 A1    Oct. 18, 2018

Related U.S. Application Data

(60) Provisional application No. 62/164,906, filed on May 21, 2015.

(51) Int. Cl.
| | |
|---|---|
| *C07D 401/14* | (2006.01) |
| *C07D 405/14* | (2006.01) |
| *C07D 413/14* | (2006.01) |
| *C07D 403/14* | (2006.01) |
| *C07D 498/06* | (2006.01) |
| *C07D 498/04* | (2006.01) |

(52) U.S. Cl.
CPC ......... *C07D 401/14* (2013.01); *C07D 403/14* (2013.01); *C07D 405/14* (2013.01); *C07D 413/14* (2013.01); *C07D 498/04* (2013.01); *C07D 498/06* (2013.01)

(58) Field of Classification Search
CPC .. C07D 401/14; C07D 403/14; C07D 405/14; C07D 413/14; C07D 498/04; C07D 498/06
See application file for complete search history.

(56) References Cited

U.S. PATENT DOCUMENTS

| | | | |
|---|---|---|---|
| 6,119,853 | A  | 9/2000  | Garrill et al. |
| 6,179,118 | B1 | 1/2001  | Garrill et al. |
| 6,315,112 | B1 | 11/2001 | Garrill et al. |
| 6,352,152 | B1 | 3/2002  | Anderson et al. |
| 6,360,739 | B1 | 3/2002  | Rand et al. |
| 6,390,291 | B1 | 5/2002  | Herman et al. |
| 6,431,168 | B1 | 8/2002  | Rand et al. |

(Continued)

FOREIGN PATENT DOCUMENTS

| | | |
|---|---|---|
| WO | 1996032099 | 10/1996 |
| WO | 2005044354 | 5/2005 |
| WO | 2014015905 | 1/2014 |

OTHER PUBLICATIONS

Lewis, et al., Inhibition of PAD4 activity is sufficient to disrupt mouse and human NET formation, Nature Chemical Biology, 11(3), 189-191, ISSN: 1552-4450 (2015). (Year: 2015).*

(Continued)

*Primary Examiner* — Erich A Leeser
(74) *Attorney, Agent, or Firm* — Andrea L. C. Reid; Dechert LLP

(57) ABSTRACT

Compounds of formula (I): wherein X, Y, $R_1$ and $R_3$-$R_{11}$ are as herein defined, and salts thereof are PAD4 inhibitors and may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis.

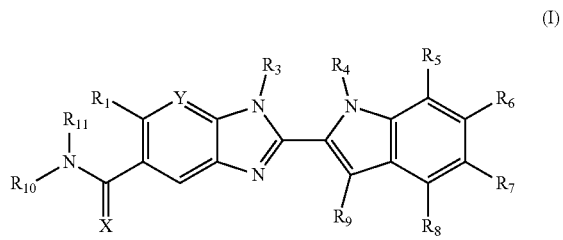

(I)

16 Claims, No Drawings

(56) References Cited

U.S. PATENT DOCUMENTS 6,679,374 B2    1/2004  Garrill et al.

OTHER PUBLICATIONS

Brinkmann et al., "Neutrophil extracellular traps kill bacteria," Science, vol. 303, No. 5663, Mar. 2004 (pp. 1532-1535).
Chang et al., "Increased PADI4 expression in blood and tissues of patients with malignant tumors," BMC Cancer, vol. 9, No. 40, Jan. 2009 (11 pages).
Christophorou et al., "Citrullination regulates pluripotency and histone H1 binding to chromatin," Nature, vol. 507, No. 7490, Mar. 2014 (pp. 104-108).
Chumanevich et al., "Suppression of colitis in mice by Cl-amidine: a novel peptidylarginine deiminase inhibitor," American Journal of Physiology-Gastrointestinal and Liver Physiology, vol. 300, No. 6, Jun. 2011 (pp. G929-G938).
Clark et al., "Platelet TLR4 activates neutrophil extracellular traps to ensnare bacteria in septic blood," Nature Medicine, vol. 13, No. 4, Apr. 2007 (pp. 463-469).
Darrah et al., "Erosive rheumatoid arthritis is associated with antibodies that activate PAD4 by increasing calcium sensitivity," Science Translational Medicine, vol. 5, No. 186, May 2013 (19 pages).
Dworski et al., Eosinophil and neutrophil extracellular DNA traps in human allergic asthmatic airways, The Journal of Allergy and Clinical Immunology, vol. 127, No. 5, May 2011 (pp. 1260-1266).
Dwyer et al., "Cystic Fibrosis Sputum DNA Has NETosis Characteristics and NET Release Is Regulated by MIF," Journal of Innate Immunity, vol. 6, No. 6, May 2014 (pp. 765-779).
Fuchs et al., "Extracellular DNA traps promote thrombosis," Proceedings of the National Academy of Science, U.S.A., vol. 107, No. 36, Sep. 2010 (pp. 15880-15885).
Hakkim et al., "Impairment of neutrophil extracellular trap degradation is associated with lupus nephritis," Proceedings of the National Academy of Science, U.S.A., vol. 107, No. 21, May 2010 (pp. 9813-9818).
International Search Report and Written Opinion issued by the European Patent Office as International Searching Authority for International Patent Application No. PCT/IB2016/000761, dated Oct. 6, 2016 (17 pages).
Jones et al., "Protein arginine deiminase 4 (PAD4): Current understanding and future therapeutic potential," Current Opinion in Drug Discovery and Development, vol. 12, No. 5, Sep. 2009 (pp. 616-627).
Kessenbrock et al., "Netting neutrophils in autoimmune small-vessel vasculitis," Nature Medicine, vol. 15, No. 6, Jun. 2009 (pp. 623-625).
Knight et al., "Peptidylarginine Deiminase Inhibition Reduces Vascular Damage and Modulates Innate Immune Responses in Murine Models of Atherosclerosis Novelty and Significance," Circulation Research, vol. 114, No. 6, Mar. 2014 (pp. 947-956).
Kochi et al., "PADI4 polymorphism predisposes male smokers to rheumatoid arthritis," Annals of the Rheumatic Disease, vol. 70, No. 3, Mar. 2011 (pp. 512-515).
Lange et al., "Protein deiminases: new players in the developmentally regulated loss of neural regenerative ability," Developmental Biology, vol. 355, No. 2, Jul. 2011 (pp. 205-214).
Lewis et al., "Inhibition of PAD4 activity is sufficient to disrupt mouse and human NET formation," Nature Chemical Biology, vol. 11, No. 3, Jan. 2015 (pp. 189-191).
Lewis et al., "Supplemental Information For: Inhibition of PAD4 activity is sufficient to disrupt mouse and human NET formation," Nature Chemical Biology, vol. 11, No. 3, Jan. 2015 (34 pages).
Li et al., "PAD4 is essential for antibacterial innate immunity mediated by neutrophil extracellular traps," Journal of Experimental Medicine, vol. 207, No. 9, Aug. 2010 (pp. 1853-1862).
Li et al., "Regulation of p53 target gene expression by peptidylarginine deiminase 4," Molecular and Cellular Biology, vol. 28, No. 15, Aug. 2008 (pp. 4745-4758).
Lin et al., "Mast cells and neutrophils release IL-17 through extracellular trap formation in psoriasis," Journal of Immunology, vol. 187, No. 1, Jul. 2011 (pp. 490-500).
Neeli et al., "Histone Deimination as a Response to Inflammatory Stimuli in Neutrophils," The Journal of Immunology, vol. 180, No. 3, Feb. 2008 (pp. 1895-1902).
Ohlsson et al., "Neutrophils from vasculitis patients exhibit an increased propensity for activation by anti-neutrophil cytoplasmic antibodies," Clinical & Experimental Immunology, vol. 176, No. 3, Jun. 2014 (pp. 363-372).
Savchenko et al., "Long pentraxin 3 (PTX3) expression and release by neutrophils in vitro and in ulcerative colitis," Pathology International, vol. 61, No. 5, May 2011 (pp. 290-297).
Slack et al., "Protein arginine deiminase 4: a target for an epigenetic cancer therapy," Cellular and Molecular Life Sciences, vol. 68, No. 4, Feb. 2011 (pp. 709-720).
Villanueva et al., "Netting Neutrophils Induce Endothelial Damage, Infiltrate Tissues, and Expose Immunostimulatory Molecules in Systemic Lupus Erythematosus," The Journal of Immunology, vol. 187, No. 1, Jul. 2011 (538-552).
Vitkov et al., "Neutrophil Fate in Gingival Crevicular Fluid," Ultrastructural Pathology, vol. 34, No. 1, Jan. 2010 (pp. 25-30).
Wegner et al., "Autoimmunity to specific citrullinated proteins gives the first clues to the etiology of rheumatoid arthritis," Immunological Reviews, vol. 233, No. 1, Jan. 2010 (pp. 34-54).
Willis et al., "N-α-Benzoyl-N5-(2-Chloro-1-Iminoethyl)-L-Ornithine Amide, a Protein Arginine Deiminase Inhibitor, Reduces the Severity of Murine Collagen-Induced Arthritis," The Journal of Immunology, vol. 186, No. 7, Apr. 2011 (pp. 4396-4404).

* cited by examiner

BENZOIMIDAZOLE DERIVATIVES AS PAD4 INHIBITORS

FIELD OF THE INVENTION

The present invention is directed to certain compounds which are inhibitors of PAD4, processes for their preparation, pharmaceutical compositions comprising the compounds, and the use of the compounds or the compositions in the treatment of various disorders. Compounds which inhibit PAD4 may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors may also have wider applicability as tools and therapeutics for human disease through epigenetic mechanisms.

Inhibitors of PAD4 may have utility against Rheumatoid Arthritis (RA). RA is an auto-immune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (for example Kochi Y. et al, Ann. Rheum. Dis., 70, (2011), 512-515). PAD4 (along with family member PAD2) has been detected in synovial tissue where it is responsible for the deamination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease (Darrah E et al, Sci Transl Med. 2013 May 22:5(186)).

PAD4 inhibitors may also be useful for the reduction of pathological neutrophil activity in a variety of diseases. Studies suggest that the process of Neutrophil Extracellular Trap (NET) formation, an innate defense mechanism by which neutrophils are able to immobilise and kill pathogens, is associated with histone citrullination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med., 15(6), (2009), 623-625; Ohlsson S M et al, Clin Exp Immunol. 2014 June; 176(3): 363-72), systemic lupus erythematosus (Hakkim A. et al, Proc. Natl. Acad. Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis (Dwyer M et. al., J Innate Immun. 2014; 6(6): 765-79), asthma (Dworski R. et al, J. Allergy Clin. Immunol., 127(5), (2011), 1260-6), deep vein thrombosis (Fuchs T. et al, Proc. Natl. Acad. Sci. USA, 107(36), (2010), 15880-5), periodontitis (Vitkov L. et al, Ultrastructural Pathol., 34(1), (2010), 25-30), sepsis (Clark S. R. et al, Nat. Med., 13(4), (2007), 463-9), appendicitis (Brinkmann V. et al, Science, 303, (2004), 1532-5), type 2 diabetes and stroke. In addition, there is evidence that NETs may contribute to pathology in diseases affecting the skin, eg in cutaneous lupus erythematosis (Villanueva E. et al, J. Immunol., 187(1), (2011), 538-52) and psoriasis (Lin A. M. et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), lupus-prone MRL/lpr mice, atherosclerosis and arterial thrombosis (Knight J S et al, Circ Res. 2014 Mar. 14; 114(6):947-56), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors may also be useful in the treatment of cancers (Slack. J. L. et al, Cell. Mol. Life Sci., 68(4), (2011), 709-720). Over-expression of PAD4 has been demonstrated in numerous cancers (Chang X. et al, BMC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a general role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors may therefore be useful as epigenetic tools or therapeutics for affecting expression of varied target genes in additional disease settings. PAD4 inhibitors may also be effective in controlling citrullination levels and the switch between pluripotency and differentiation in stem cells (Christophorou M A et al, *Nature.* 2014 Mar. 6; 507(7490): 104-8) and may therefore therapeutically affect the pluripotency status and differentiation potential of diverse stem cells including, but not limited to, embryonic stem cells, neural stem cells, haematopoietic stem cells and cancer stem cells.

SUMMARY OF THE INVENTION

The invention is directed to compounds of formula (I):

(I)

wherein X, Y, $R_1$, $R_2$, $R_3$, $R_4$, $R_5$, $R_6$, $R_7$, $R_8$, $R_9$, $R_{10}$ and $R_{11}$ are as defined below;
and salts thereof.

Certain compounds of the invention have been shown to be PAD4 inhibitors and may also show enhanced selectivity for PAD4 with respect to PAD2. For example, certain compounds of the invention indicate 100-fold selectivity for PAD4 inhibition over PAD2 inhibition. Compounds which inhibit PAD4 may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis. Accordingly, the invention is further directed to pharmaceutical compositions comprising a compound of formula (I), or a pharmaceutically acceptable salt thereof. The invention is still further directed to methods of treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

In a first aspect, there are provided compounds of formula (I):

(I)

and salts thereof;
wherein:
X is O or S;
Y is N or $CR_2$
$R_1$ is —H or —$C_{1-6}$alkyl;
$R_2$ is —H, —OH, —$C_{1-6}$alkyl, —O—$C_{1-6}$alkyl, —CN, -halo, —C(=O)NH$_2$, —$C_{1-6}$haloalkyl, —O—$C_{1-6}$alkyl-O—$C_{1-6}$alkyl, —O—$C_{1-6}$alkyl-OH, —O—$C_{1-6}$alkyl-C(=O)NH$_2$, —O—$C_{1-6}$alkyl-CN, —O—$C_{1-6}$haloalkyl, —NH—$C_{1-6}$alkyl, —N($C_{1-6}$alkyl)$_2$ or heteroaryl;
$R_3$ is —$C_{1-6}$alkyl, —$C_{1-6}$alkyl-NH$_2$, or —$C_{1-6}$alkyl-O—$C_{1-6}$alkyl;
$R_4$ is H, —$C_{1-6}$alkyl, —$C_{1-6}$haloalkyl, —$C_{1-6}$alkyl-heteroaryl (wherein the heteroaryl group is optionally substituted by one, two or three $C_{1-6}$alkyl groups), —$C_{1-6}$alkyl-phenyl (wherein the phenyl group is optionally substituted by one, two or three substituents selected from the list consisting of halo, $C_{1-6}$alkyl and —O—$C_{1-6}$alkyl), —$C_{1-6}$alkyl-heterocyclyl, —$C_{1-6}$alkyl-$C_{3-6}$cycloalkyl, —$C_{1-6}$alkyl-OH, —$C_{1-6}$alkyl-CN or —$C_{1-6}$alkyl-O—$C_{1-6}$alkyl;
$R_5$ is —H, —$C_{1-6}$alkyl, —O—$C_{1-6}$alkyl, —OH, -halo, or —CN;
or $R_4$ together with $R_5$ are —($R_4$)—CH$_2$CH$_2$O—($R_5$)—, —($R_4$)—CH$_2$CH$_2$CH$_2$O—($R_5$)— or —($R_4$)—CH(Me)CH$_2$O—($R_5$)—, wherein —($R_4$)— and —($R_5$)— denote the positions of attachment of the alkenyloxy chain to the respective ring atoms;
$R_6$ is —H, -halo, —CN, —$C_{1-6}$alkyl, —O—$C_{1-6}$alkyl, or —OH;
$R_7$ is —H, -halo, —CN, —$C_{1-6}$alkyl, —O—$C_{1-6}$alkyl, or —OH;
$R_8$ is —H, —F or —$C_{1-6}$alkyl;
$R_9$ is —H or —$C_{1-6}$alkyl; and
$R_{10}$ is —H and $R_{11}$ is a 5-7 membered monocyclic saturated heterocycle (containing one nitrogen atom and optionally one oxygen atom) or a 7 membered bicyclic heterocycle (containing one nitrogen atom) or —CH$_2$CH$_2$NH$_2$; or
$NR_{10}R_{11}$ taken together form a 5-7 membered mono- or bi-cyclic saturated or unsaturated heterocycle containing one nitrogen atom, wherein the heterocycle is substituted by one, two or three substituents independently selected from the list consisting of —NH$_2$, —$C_{1-6}$alkyl-NH$_2$, —NH—$C_{1-6}$alkyl, —NHC(=NH)CH$_2$Cl, —$C_{1-6}$alkyl, -halo, —O—$C_{1-6}$alkyl, —OH and —C(O)NH$_2$.

In one embodiment, there are provided compounds of formula (I):

(I)

and salts thereof;
wherein:
X is O or S;
Y is N or $CR_2$
$R_1$ is —H or —$C_{1-6}$alkyl;
$R_2$ is —H, —OH, —$C_{1-6}$alkyl, —O—$C_{1-6}$alkyl, —CN, -halo, —C(=O)NH$_2$, —$C_{1-6}$haloalkyl, —O—$C_{1-6}$alkyl-O—$C_{1-6}$alkyl, —O—$C_{1-6}$alkyl-OH, —O—$C_{1-6}$alkyl-C(=O)NH$_2$, —O—$C_{1-6}$alkyl-CN, —O—$C_{1-6}$haloalkyl, —NH—$C_{1-6}$alkyl, —N($C_{1-6}$alkyl)$_2$ or heteroaryl;
$R_3$ is —$C_{1-6}$alkyl, —$C_{1-6}$alkyl-NH$_2$, or —$C_{1-6}$alkyl-O—$C_{1-6}$alkyl;
$R_4$ is H, —$C_{1-6}$alkyl, —$C_{1-6}$haloalkyl, —$C_{1-6}$alkyl-heteroaryl (wherein the heteroaryl group is optionally substituted by one, two or three $C_{1-6}$alkyl groups), —$C_{1-6}$alkyl-phenyl (wherein the phenyl group is optionally substituted by one, two or three substituents selected from the list consisting of halo, $C_{1-6}$alkyl and —O—$C_{1-6}$alkyl), —$C_{1-6}$alkyl-heterocyclyl, —$C_{1-6}$alkyl-$C_{3-6}$cycloalkyl, —$C_{1-6}$alkyl-OH, —$C_{1-6}$alkyl-CN or —$C_{1-6}$alkyl-O—$C_{1-6}$alkyl; $R_5$ is —H, —$C_{1-6}$alkyl, —O—$C_{1-6}$alkyl, —OH, -halo, or —CN;

or $R_4$ together with $R_5$ are —($R_4$)—$CH_2CH_2O$—($R_5$)—, —($R_4$)—$CH_2CH_2CH_2O$—($R_5$)— or —($R_4$)—CH(Me)$CH_2O$—($R_5$)—, wherein —($R_4$)— and —($R_5$)— denote the positions of attachment of the alkenyloxy chain to the respective ring atoms;

$R_6$ is —H, -halo, —CN, —$C_{1-6}$alkyl, —O—$C_{1-6}$alkyl, or —OH;

$R_7$ is —H, -halo, —CN, —$C_{1-6}$alkyl, —O—$C_{1-6}$alkyl, or —OH;

$R_8$ is —H, —F or —$C_{1-6}$alkyl;

$R_9$ is —H or —$C_{1-6}$alkyl; and $R_{10}$ is —H and $R_{11}$ is a 5-7 membered monocyclic saturated heterocycle (containing one nitrogen atom and optionally one oxygen atom) or a 7 membered bicyclic heterocycle (containing one nitrogen atom) or —$CH_2CH_2NH_2$; or $NR_{10}R_{11}$ taken together form a 5-7 membered mono- or bi-cyclic saturated or unsaturated heterocycle containing one nitrogen atom, wherein the heterocycle is substituted by one, two or three substituents independently selected from the list consisting of —$NH_2$, —$C_{1-6}$alkyl-$NH_2$, —NH—$C_{1-6}$alkyl, —NHC(=NH)$CH_2$Cl, —$C_{1-6}$alkyl, -halo, —O—$C_{1-6}$alkyl, —OH and —C(O)$NH_2$; provided that the compound of formula (I) is not (3-aminopiperidin-1-yl)(1-methyl-2-(1-methyl-1H-indol-2-yl)-1H-benzo[d]imidazol-5-yl)methanone, ((3S,4R)-3-amino-4-hydroxypiperidin-1-yl)(2-(1-(cyclopropylmethyl)-1H-indol-2-yl)-7-methoxy-1-methyl-1H-benzo[d]imidazol-5-yl)methanone or (R)-(3-aminopiperidin-1-yl)(2-(1-ethyl-1H-indol-2-yl)-1-methyl-1H-benzo[d]imidazol-5-yl)methanone.

In one embodiment, there are provided compounds of formula (I):

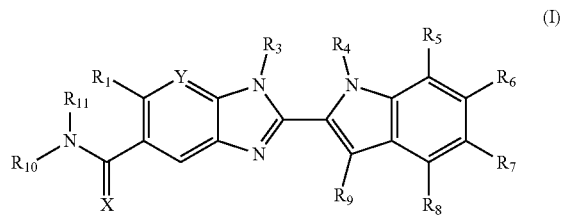

and salts thereof;
wherein:
X is O or S;
Y is N or $CR_2$
$R_1$ is —H or —$C_{1-6}$alkyl;
$R_2$ is —H, —OH, —$C_{1-6}$alkyl, —O—$C_{1-6}$alkyl, —CN, -halo, —C(=O)$NH_2$, —$C_{1-6}$haloalkyl, —O—$C_{1-6}$alkyl-O—$C_{1-6}$alkyl, —O—$C_{1-6}$alkyl-OH, —O—$C_{1-6}$alkyl-C(=O)$NH_2$, —O—$C_{1-6}$alkyl-CN, —O—$C_{1-6}$haloalkyl, —NH—$C_{1-6}$alkyl, —N($C_{1-6}$alkyl)$_2$ or heteroaryl;
$R_3$ is —$C_{2-6}$alkyl, —$C_{1-6}$alkyl-$NH_2$, or —$C_{1-6}$alkyl-O—$C_{1-6}$alkyl;
$R_4$ is H, —$C_{1-6}$alkyl, —$C_{1-6}$haloalkyl, —$C_{1-6}$alkyl-heteroaryl (wherein the heteroaryl group is optionally substituted by one, two or three $C_{1-6}$alkyl groups), —$C_{1-6}$alkyl-phenyl (wherein the phenyl group is optionally substituted by one, two or three substituents selected from the list consisting of halo, $C_{1-6}$alkyl and —O—$C_{1-6}$alkyl), —$C_{1-6}$alkyl-heterocyclyl, —$C_{1-6}$alkyl-$C_{3-6}$cycloalkyl, —$C_{1-6}$alkyl-OH, —$C_{1-6}$alkyl-CN or —$C_{1-6}$alkyl-O—$C_{1-6}$alkyl;

$R_5$ is —H, —$C_{1-6}$alkyl, —O—$C_{1-6}$alkyl, —OH, -halo, or —CN;

or $R_4$ together with $R_5$ are —($R_4$)—$CH_2CH_2O$—($R_5$)—, —($R_4$)—$CH_2CH_2CH_2O$—($R_5$)— or —($R_4$)—CH(Me)$CH_2O$—($R_5$)—, wherein —($R_4$)— and —($R_5$)— denote the positions of attachment of the alkenyloxy chain to the respective ring atoms;

$R_6$ is —H, -halo, —CN, —$C_{1-6}$alkyl, —O—$C_{1-6}$alkyl, or —OH;

$R_7$ is —H, -halo, —CN, —$C_{1-6}$alkyl, —O—$C_{1-6}$alkyl, or —OH;

$R_8$ is —H, —F or —$C_{1-6}$alkyl;

$R_9$ is —H or —$C_{1-6}$alkyl; and $R_{10}$ is —H and $R_1$ is a 5-7 membered monocyclic saturated heterocycle (containing one nitrogen atom and optionally one oxygen atom) or a 7 membered bicyclic heterocycle (containing one nitrogen atom) or —$CH_2CH_2NH_2$; or $NR_{10}R_{11}$ taken together form a 5-7 membered mono- or bi-cyclic saturated or unsaturated heterocycle containing one nitrogen atom, wherein the heterocycle is substituted by one, two or three substituents independently selected from the list consisting of —$NH_2$, —$C_{1-6}$alkyl-$NH_2$, —NH—$C_{1-6}$alkyl, —NHC(=NH)$CH_2$Cl, —$C_{1-6}$alkyl, -halo, —O—$C_{1-6}$alkyl, —OH and —C(O)$NH_2$.

In one embodiment X is O.
In one embodiment X is S.
In one embodiment Y is N.
In one embodiment Y is $CR_2$.
In one embodiment, $R_1$ is —H or -methyl.
In one embodiment $R_1$ is —H.
In one embodiment $R_2$ is —H, —O-Me, —O—$CF_3$, —CN, —Br, —$CF_3$, -3-pyridinyl, —C(=O)$NH_2$, —$NMe_2$, —NHMe, ethyl, methyl, —O—$CH_2CH_2CH_2$—OH, —O-Et, —O—$CH_2CH_2$—O—$CH_3$, —O—$CH_2CH_2$—OH, —OCH$_2$CN, —O—$CH_2$C(O)$NH_2$, or —OH.
In one embodiment $R_2$ is —H or —O—$C_{1-6}$alkyl.
In one embodiment $R_2$ is —H or —O-Me.
In one embodiment $R_3$ is -methyl, —$CH_2CH_2NH_2$, —$CH_2CH_2CH_2NH_2$, -ethyl, —$CH_2CH_2OCH_3$, or -isopropyl.
In one embodiment $R_3$ is —$C_{1-6}$alkyl.
In one embodiment $R_3$ is -methyl.
In one embodiment $R_4$ is H, —$C_{1-6}$alkyl, —$C_{1-6}$haloalkyl, —$C_{1-6}$alkyl-heteroaryl (optionally substituted by one methyl), —$C_{1-6}$alkyl-phenyl (optionally substituted by one or two substituents independently selected from the list consisting of Cl, I, -Me and —OMe), —$C_{1-6}$alkyl-heterocyclyl, —$C_{1-6}$alkyl-$C_{3-6}$cycloalkyl, —$C_{1-6}$alkyl-OH, —$C_{1-6}$alkyl-CN or —$C_{1-6}$alkyl-O—$C_{1-6}$alkyl;

In one embodiment $R_4$ is —H, methyl, ethyl, cyclopropylmethyl, —$CH_2CN$, 2,2,2-trifluoroethyl, iso-propyl, 3-chlorobenzyl, 3-pyridinylmethyl, 4-methylbenzyl, -isobutyl, (1-methy-1H-pyrazol-4-yl)methyl, —$CH_2CH_2OCH_3$, benzyl, 4-iodobenzyl, 2-pyridinylmethyl, hydroxyethyl, 4-chlorobenzyl, (R)-3-hydroxy-2-methylprop-1-yl, 3,4-dichlorobenzyl, 4-methoxybenzyl, tetrahydro-2H-pyran-4-ylmethyl, —$CH_2CH_2CH_2OCH_3$, or (S)-3-hydroxy-2-methylprop-1-yl.

In one embodiment $R_4$ is —$C_{1-6}$alkyl-$C_{3-6}$cycloalkyl, —$C_{1-6}$haloalkyl, —$C_{1-6}$alkyl, —$C_{1-6}$alkyl-heteroaryl (optionally substituted by one methyl), or —$C_{1-6}$alkyl-phenyl.

In one embodiment R₄ is cyclopropylmethyl, 2,2,2-trifluoroethyl, benzyl, 3-pyridinylmethyl, or (1-methy-1H-pyrazol-4-yl)methyl or ethyl.

In one embodiment R₅ is —H, —O-Me, -methyl, -ethyl, —Br, —OH, —F, or —CN.

In one embodiment R₅ is —H.

In one embodiment R₄ together with R₅ are —(R₄)—CH₂CH₂O—(R₅)—, —(R₄)—CH₂CH₂CH₂O—(R₅)— or —(R₄)—CH(Me)CH₂O—(R₅)—.

In one embodiment R₆ is —H, —O-Me, —F, —CN, —Br, -methyl, or —O-Et.

In one embodiment R₆ is —H.

In one embodiment R₇ is —H, —O-Me, —Cl, —F, -methyl, —CN, or —OH.

In one embodiment R₇ is —H.

In one embodiment R₈ is —H, -methyl, or —F.

In one embodiment R₈ is —H.

In one embodiment R₉ is —H, or -ethyl.

In one embodiment R₉ is H.

In one embodiment, R₁₀ is —H and R₁₁ is azepan-3-yl, 1,4-oxazepan-3-yl, —CH₂CH₂NH₂, or 3-azabicyclo[4.1.0]heptan-1-yl.

In one embodiment, —NR₁₀R₁₁ is selected from the list consisting of piperidinyl (optionally substituted by one or two substituents selected from the list consisting of —NH₂, —NH—C₁₋₆alkyl, —C₁₋₆alkyl-NH₂, —O—C₁₋₆alkyl, —OH, —C₁₋₆alkyl, -halo, —C(=O)NH₂, and —NHC(=NH)CH₂Cl), dihydropiperidinyl (optionally substituted by —NH₂), azabicyclo[3.1.0]hexanyl (optionally substituted by —NH₂) and pyrrolidinyl (optionally substituted by one or two substituents selected from the list consisting of —NH₂, —C₁₋₆alkyl and —C₁₋₆alkyl-NH₂).

In one embodiment —NR₁₀R₁₁ is selected from the list consisting of:

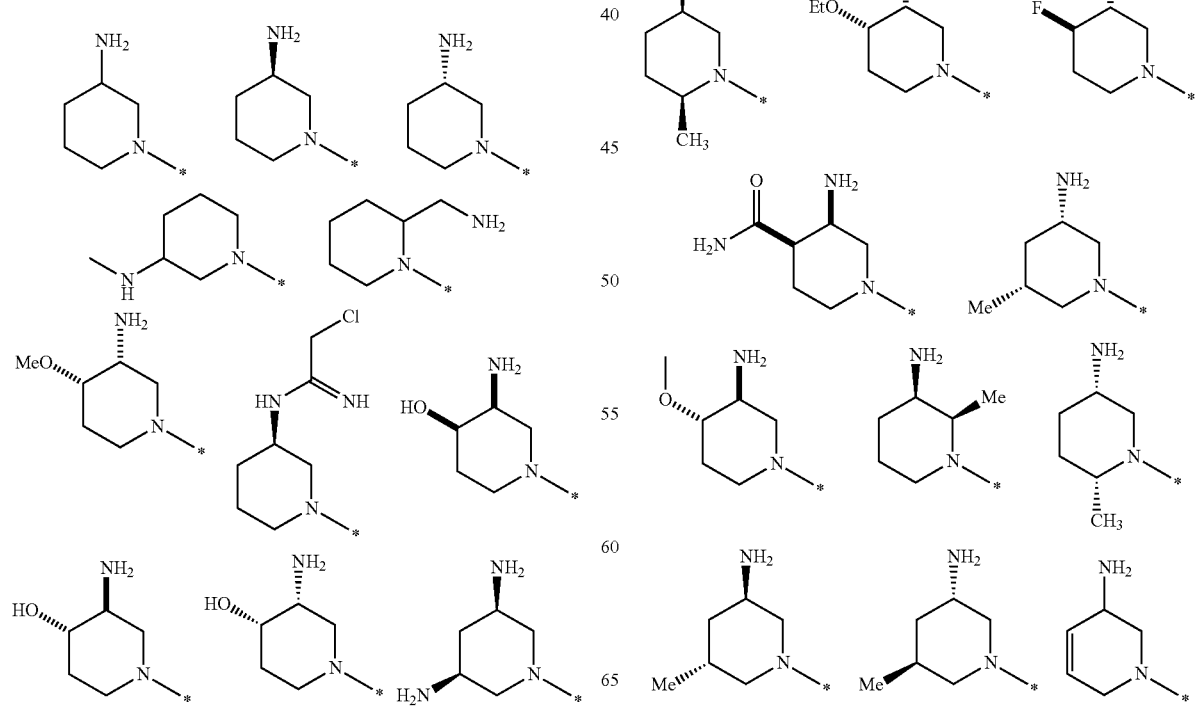

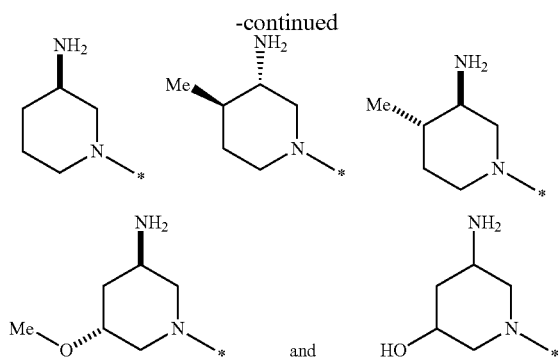

wherein * denotes the point of attachment to the carbonyl or thiocarbonyl residue In one embodiment —NR₁₀R₁₁ is

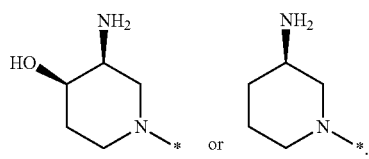

In one embodiment, —NR₁₀R₁₁ is

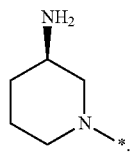

In one embodiment, the compound of the invention is selected from the list consisting of:

(3R)-1-{[2-(1-ethyl-1H-indol-2-yl)-1-methyl-1H-benzimidazol-5-yl]carbonyl}-3-piperidinamine;
(3R)-1-({2-[1-ethyl-7-(methyloxy)-1H-indol-2-yl]-1-methyl-1H-benzimidazol-5-yl}carbonyl)-3-piperidinamine;
(3R)-1-{[2-(3,4-dihydro-2H-[1,4]oxazepino[2,3,4-hi]indol-6-yl)-1-methyl-1H-benzimidazol-5-yl]carbonyl}-3-piperidinamine;
(3R)-1-{[2-(2,3-dihydro[1,4]oxazino[2,3,4-hi]indol-5-yl)-1-methyl-1H-benzimidazol-5-yl]carbonyl}-3-piperidinamine;
(3R)-1-{[1-methyl-2-(3-methyl-2,3-dihydro[1,4]oxazino[2,3,4-hi]indol-5-yl)-1H-benzimidazol-5-yl]carbonyl}-3-piperidinamine;
(3R)-1-{[2-(1-ethyl-1H-indol-2-yl)-1-methyl-7-(methyloxy)-1H-benzimidazol-5-yl]carbonyl}-3-piperidinamine;
(3R)-1-({2-[1-(cyclopropylmethyl)-5-(methyloxy)-1H-indol-2-yl]-1-methyl-1H-benzimidazol-5-yl}carbonyl)-3-piperidinamine;
(3R)-1-({2-[1-ethyl-6-(methyloxy)-1H-indol-2-yl]-1-methyl-1H-benzimidazol-5-yl}carbonyl)-3-piperidinamine;
[2-(5-{[(3R)-3-amino-1-piperidinyl]carbonyl}-1-methyl-1H-benzimidazol-2-yl)-1H-indol-1-yl]acetonitrile;
(3R)-1-{[2-(1-ethyl-6-fluoro-1H-indol-2-yl)-1-methyl-1H-benzimidazol-5-yl]carbonyl}-3-piperidinamine;
(3R)-1-({1-methyl-2-[1-(2,2,2-trifluoroethyl)-1H-indol-2-yl]-1H-benzimidazol-5-yl}carbonyl)-3-piperidinamine;
(3R)-1-({1-methyl-2-[1-(1-methylethyl)-1H-indol-2-yl]-1H-benzimidazol-5-yl}carbonyl)-3-piperidinamine;
2-(5-{[(3R)-3-amino-1-piperidinyl]carbonyl}-1-methyl-1H-benzimidazol-2-yl)-1-ethyl-1H-indole-6-carbonitrile;
(3R)-1-[(2-{1-[(3-chlorophenyl)methyl]-1H-indol-2-yl}-1-methyl-1H-benzimidazol-5-yl)carbonyl]-3-piperidinamine;
(3R)-1-({1-methyl-2-[1-(3-pyridinylmethyl)-1H-indol-2-yl]-1H-benzimidazol-5-yl}) carbonyl)-3-piperidinamine;
(3R)-1-({2-[1-(cyclopropylmethyl)-1H-indol-2-yl]-1-methyl-1H-benzimidazol-5-yl}) carbonyl)-3-piperidinamine;
(3R)-1-[(1-methyl-2-{1-[(4-methylphenyl)methyl]-1H-indol-2-yl}-1H-benzimidazol-5-yl)carbonyl]-3-piperidinamine;
(3R)-1-{[2-(1H-indol-2-yl)-1-methyl-1H-benzimidazol-5-yl]carbonyl}-3-piperidinamine;
(3R)-1-({1-methyl-2-[1-(2-methylpropyl)-1H-indol-2-yl]-1H-benzimidazol-5-yl}carbonyl)-3-piperidinamine;
(3R)-1-[(1-methyl-2-{1-[(1-methyl-1H-pyrazol-4-yl)methyl]-1H-indol-2-yl}-1H-benzimidazol-5-yl)carbonyl]-3-piperidinamine;
(3R)-1-{[2-(5-chloro-1-ethyl-1H-indol-2-yl)-1-methyl-1H-benzimidazol-5-yl]carbonyl}-3-piperidinamine;
(3R)-1-[(1-methyl-2-{1-[2-(methyloxy)ethyl]-1H-indol-2-yl}-1H-benzimidazol-5-yl)carbonyl]-3-piperidinamine;
(3R)-1-{[2-(6-bromo-1-ethyl-1H-indol-2-yl)-1-methyl-1H-benzimidazol-5-yl]carbonyl}-3-piperidinamine;
(3R)-1-({1-methyl-2-[1-(phenylmethyl)-1H-indol-2-yl]-1H-benzimidazol-5-yl}carbonyl)-3-piperidinamine;
(3R)-1-[(2-{1-[(4-iodophenyl)methyl]-1H-indol-2-yl}-1-methyl-1H-benzimidazol-5-yl)carbonyl]-3-piperidinamine;
(3R)-1-{[2-(1-ethyl-6-methyl-1H-indol-2-yl)-1-methyl-1H-benzimidazol-5-yl]carbonyl}-3-piperidinamine;
(3R)-1-({1-methyl-2-[1-(2-pyridinylmethyl)-1H-indol-2-yl]-1H-benzimidazol-5-yl}) carbonyl)-3-piperidinamine;
(3R)-1-({1-methyl-2-[1-(4-pyridinylmethyl)-1H-indol-2-yl]-1H-benzimidazol-5-yl}) carbonyl)-3-piperidinamine;
2-[2-(5-{[(3R)-3-amino-1-piperidinyl]carbonyl}-1-methyl-1H-benzimidazol-2-yl)-1H-indol-1-yl]ethanol;
(3R)-1-[(2-{1-[(4-chlorophenyl)methyl]-1H-indol-2-yl}-1-methyl-1H-benzimidazol-5-yl)carbonyl]-3-piperidinamine;
(R)-(3-aminopiperidin-1-yl)(2-(1-ethyl-6,7-dimethoxy-1H-indol-2-yl)-1-methyl-1H-benzo[d]imidazol-5-yl)methanone;
(R)-(3-aminopiperidin-1-yl)(2-(6-ethoxy-1-ethyl-1H-indol-2-yl)-1-methyl-1H-benzo[d]imidazol-5-yl)methanone;
((R)-3-aminopiperidin-1-yl)(2-(1-((R)-3-hydroxy-2-methylpropyl)-1H-indol-2-yl)-7-methoxy-1-methyl-1H-benzo[d]imidazol-5-yl)methanone;
(R)-(3-aminopiperidin-1-yl)(2-(1-ethyl-1H-indol-2-yl)-1-methyl-7-(trifluoromethoxy)-1H-benzo[d]imidazol-5-yl)methanone;
(R)-5-(3-aminopiperidine-1-carbonyl)-2-(1-ethyl-1H-indol-2-yl)-1-methyl-1H-benzo[d]imidazole-7-carbonitrile;
(R)-(3-aminopiperidin-1-yl)(7-bromo-2-(1-ethyl-1H-indol-2-yl)-1-methyl-1H-benzo[d]imidazol-5-yl)methanone;
(R)-(3-aminopiperidin-1-yl)(1-methyl-2-(1-methyl-1H-indol-2-yl)-1H-benzo[d]imidazol-5-yl)methanone;
(R)-(3-aminopiperidin-1-yl)(2-(1-(3,4-dichlorobenzyl)-1H-indol-2-yl)-1-methyl-1H-benzo[d]imidazol-5-yl)methanone;
(R)-(3-aminopiperidin-1-yl)(2-(1-(4-methoxybenzyl)-1H-indol-2-yl)-1-methyl-1H-benzo[d]imidazol-5-yl)methanone;

1-({1-methyl-2-[1-(tetrahydro-2H-pyran-4-ylmethyl)-1H-indol-2-yl]-1H-benzimidazol-5-yl}carbonyl)-3-piperidinamine;

1-{[2-(6-bromo-1-ethyl-1H-indol-2-yl)-1-methyl-1H-benzimidazol-5-yl]carbonyl}-3-piperidinamine;

(R)-(3-aminopiperidin-1-yl)(2-(1-ethyl-1H-indol-2-yl)-1,6-dimethyl-1H-benzo[d]imidazol-5-yl)methanone;

(3R)-1-({1-methyl-2-[1-(2,2,2-trifluoroethyl)-1H-indol-2-yl]-1H-benzimidazol-5-yl}carbonyl)-3-piperidinamine;

((R)-3-aminopiperidin-1-yl)(2-(1-((R)-3-hydroxy-2-methylpropyl)-1H-indol-2-yl)-7-methoxy-1-methyl-1H-benzo[d]imidazol-5-yl)methanone;

(R)-(3-aminopiperidin-1-yl)(2-(1-(cyclopropylmethyl)-1H-indol-2-yl)-7-methoxy-1-methyl-1H-benzo[d]imidazol-5-yl)methanone;

(R)-(3-aminopiperidin-1-yl)(7-methoxy-1-methyl-2-(1-(2,2,2-trifluoroethyl)-1H-indol-2-yl)-1H-benzo[d]imidazol-5-yl)methanone;

(3S)-1-({1-methyl-2-[1-(phenylmethyl)-1H-indol-2-yl]-1H-benzimidazol-5-yl}carbonyl)-3-piperidinamine;

(S)-(3-aminopiperidin-1-yl)(1-methyl-2-(1-methyl-1H-indol-2-yl)-1H-benzo[d]imidazol-5-yl)methanone;

(1R,5S)-3-{[2-(1-ethyl-1H-indol-2-yl)-1-methyl-1H-benzimidazol-5-yl]carbonyl}-3-azabicyclo[3.1.0]hexan-1-amine;

(R)-(1-(2-aminoethyl)-2-(1-ethyl-1H-indol-2-yl)-1H-benzo[d]imidazol-5-yl)(3-aminopiperidin-1-yl)methanone;

(R)-(3-aminopiperidin-1-yl)(2-(1-ethyl-1H-indol-2-yl)-1-methyl-7-(trifluoromethyl)-1H-benzo[d]imidazol-5-yl)methanone;

(+/−)-cis-(3-amino-4-ethoxypiperidin-1-yl)(2-(1-ethyl-1H-indol-2-yl)-1-methyl-1H-benzo[d]imidazol-5-yl)methanone;

(+/−)-((cis)-3-amino-4-methoxypiperidin-1-yl)(2-(1-ethyl-1H-indol-2-yl)-1-methyl-1H-benzo[d]imidazol-5-yl)methanone;

cis-(3-amino-2-methylpiperidin-1-yl)(2-(1-ethyl-1H-indol-2-yl)-1-methyl-1H-benzo[d]imidazol-5-yl)methanone;

cis-(5-amino-2-methylpiperidin-1-yl)(2-(1-ethyl-1H-indol-2-yl)-1-methyl-1H-benzo[d]imidazol-5-yl)methanone;

N-(azepan-3-yl)-2-(1-(cyclopropylmethyl)-1H-indol-2-yl)-1-methyl-1H-benzo[d]imidazole-5-carboxamide;

(3-aminopyrrolidin-1-yl)(2-(1-ethyl-1H-indol-2-yl)-7-methoxy-1-methyl-1H-benzo[d]imidazol-5-yl)methanone;

(3-aminocyclopentyl)(2-(1-benzyl-1H-indol-2-yl)-1-methyl-1H-benzo[d]imidazol-5-yl)methanone;

((3S,4R)-3-amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone;

((3R,4S)-3-amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone;

(3R)-1-[(1-methyl-2-{1-[(1-methyl-1H-pyrazol-4-yl)methyl]-1H-indol-2-yl}-1H-benzimidazol-5-yl)carbonyl]-3-piperidinamine;

(R)-(3-aminopiperidin-1-yl)(2-(1-ethyl-5-fluoro-1H-indol-2-yl)-1-methyl-1H-benzo[d]imidazol-5-yl)methanone;

(R)-(3-aminopiperidin-1-yl)(2-(1-ethyl-1H-indol-2-yl)-1-methyl-7-(pyridin-3-yl)-1H-benzo[d]imidazol-5-yl)methanone;

(R)-5-(3-aminopiperidine-1-carbonyl)-2-(1-ethyl-1H-indol-2-yl)-1-methyl-1H-benzo[d]imidazole-7-carboxamide;

(R)-(3-aminopiperidin-1-yl)(7-(dimethylamino)-2-(1-ethyl-1H-indol-2-yl)-1-methyl-1H-benzo[d]imidazol-5-yl)methanone;

2-(1-ethyl-1H-indol-2-yl)-1-methyl-N-(1,4-oxazepan-6-yl)-1H-benzo[d]imidazole-5-carboxamide;

((3S,4R)-3-amino-4-hydroxypiperidin-1-yl)(2-(1-(cyclopropylmethyl)-1H-indol-2-yl)-1-methyl-1H-benzo[d]imidazol-5-yl)methanone;

((3S,4R)-3-amino-4-hydroxypiperidin-1-yl)(2-(1-(cyclopropylmethyl)-1H-indol-2-yl)-7-methoxy-1-methyl-1H-benzo[d]imidazol-5-yl)methanone;

((3S,4R)-3-amino-4-hydroxypiperidin-1-yl)(2-(1-ethyl-1H-indol-2-yl)-7-methoxy-1-methyl-1H-benzo[d]imidazol-5-yl)methanone;

(R)-(3-aminopiperidin-1-yl)(2-(1-ethyl-1H-indol-2-yl)-1-methyl-7-(methylamino)-1H-benzo[d]imidazol-5-yl)methanone;

(R)-(3-aminopiperidin-1-yl)(7-methoxy-2-(1-(3-methoxypropyl)-1H-indol-2-yl)-1-methyl-1H-benzo[d]imidazol-5-yl)methanone;

(R)-(3-aminopiperidin-1-yl)(7-methoxy-1-methyl-2-(1-((tetrahydro-2H-pyran-4-yl)methyl)-1H-indol-2-yl)-1H-benzo[d]imidazol-5-yl)methanone;

(R)-(3-aminopiperidin-1-yl)(7-methoxy-2-(1-(2-methoxyethyl)-1H-indol-2-yl)-1-methyl-1H-benzo[d]imidazol-5-yl)methanone;

(R)-(3-aminopiperidin-1-yl)(2-(1-(2-hydroxyethyl)-1H-indol-2-yl)-7-methoxy-1-methyl-1H-benzo[d]imidazol-5-yl)methanone;

((R)-3-aminopiperidin-1-yl)(2-(1-((S)-3-hydroxy-2-methylpropyl)-1H-indol-2-yl)-7-methoxy-1-methyl-1H-benzo[d]imidazol-5-yl)methanone;

(R)-2-(2-(5-(3-aminopiperidine-1-carbonyl)-7-methoxy-1-methyl-1H-benzo[d]imidazol-2-yl)-1H-indol-1-yl)acetonitrile;

(R)-(3-aminopiperidin-1-yl)(7-ethyl-2-(1-ethyl-1H-indol-2-yl)-1-methyl-1H-benzo[d]imidazol-5-yl)methanone;

N-(azepan-3-yl)-2-(1-ethyl-1H-indol-2-yl)-1-methyl-1H-benzo[d]imidazole-5-carboxamide;

(S)—N-(azepan-3-yl)-2-(1-ethyl-1H-indol-2-yl)-1-methyl-1H-benzo[d]imidazole-5-carboxamide;

(R)—N-(1-(2-(1-benzyl-1H-indol-2-yl)-1-methyl-1H-benzo[d]imidazole-5-carbonyl)piperidin-3-yl)-2-chloroacetimidamide;

(R)-(3-aminopiperidin-1-yl)(2-(7-ethyl-1H-indol-2-yl)-1-methyl-1H-benzo[d]imidazol-5-yl)methanone;

(R)-(3-aminopiperidin-1-yl)(2-(1-ethyl-5,6-dimethoxy-1H-indol-2-yl)-1-methyl-1H-benzo[d]imidazol-5-yl)methanone;

(R)-(3-aminopiperidin-1-yl)(2-(3-ethyl-1H-indol-2-yl)-1-methyl-1H-benzo[d]imidazol-5-yl)methanone;

1-{[2-(1-ethyl-7-methyl-1H-indol-2-yl)-1-methyl-1H-benzimidazol-5-yl]carbonyl}-3-piperidinamine;

N-(2-aminoethyl)-1-methyl-2-[1-(phenylmethyl)-1H-indol-2-yl]-1H-benzimidazole-5-carboxamide;

1-{[2-(1-ethyl-5-methyl-1H-indol-2-yl)-1-methyl-1H-benzimidazol-5-yl]carbonyl}-3-piperidinamine;

1-{[2-(1-ethyl-4-methyl-1H-indol-2-yl)-1-methyl-1H-benzimidazol-5-yl]carbonyl}-3-piperidinamine;

(R)-2-(5-(3-aminopiperidine-1-carbonyl)-1-methyl-1H-benzo[d]imidazol-2-yl)-1-ethyl-1H-indole-5-carbonitrile;

2-(1-ethyl-1H-indol-2-yl)-1-methyl-N-(piperidin-3-yl)-1H-benzo[d]imidazole-5-carboxamide;

(S)-(3-(aminomethyl)pyrrolidin-1-yl)(2-(1-ethyl-1H-indol-2-yl)-1-methyl-1H-benzo[d]imidazol-5-yl)methanone;

(2-(1-ethyl-1H-indol-2-yl)-1-methyl-1H-benzo[d]imidazol-5-yl)(3-(methylamino)piperidin-1-yl)methanone;

N-(2-aminoethyl)-2-(1-ethyl-1H-indol-2-yl)-1-methyl-1H-benzo[d]imidazole-5-carboxamide   (3,4-cis)-1-{[2-(1- ethyl-1H-indol-2-yl)-1-methyl-1H-benzimidazol-5-yl] carbonyl}-3,4-piperidinediamine;
(+/−)-((cis)-4-amino-2-methylpyrrolidin-1-yl)(2-(1-ethyl-1H-indol-2-yl)-1-methyl-1H-benzo[d]imidazol-5-yl) methanone;
(R)-(3-aminopiperidin-1-yl)(2-(1-ethyl-1H-indol-2-yl)-1,7-dimethyl-1H-benzo[d]imidazol-5-yl)methanone;
(R)-(3-aminopiperidin-1-yl)(1-(3-aminopropyl)-2-(1-ethyl-1H-indol-2-yl)-1H-benzo[d]imidazol-5-yl)methanone;
(R)-(3-aminopiperidin-1-yl)(1-ethyl-2-(1-ethyl-1H-indol-2-yl)-1H-benzo[d]imidazol-5-yl)methanone;
(R)-(3-aminopiperidin-1-yl)(2-(1-ethyl-1H-indol-2-yl)-3-methyl-3H-imidazo[4,5-b]pyridin-6-yl)methanone;
trans (+/−)-3-amino-4-fluoropiperidin-1-yl)(2-(1-ethyl-1H-indol-2-yl)-1-methyl-1H-benzo[d]imidazol-5-yl)methanone;
cis-((+/−)-3-amino-4-hydroxypiperidin-1-yl)(2-(1-ethyl-1H-indol-2-yl)-1-methyl-1H-benzo[d]imidazol-5-yl) methanone;
trans-((+/−)-3-amino-4-hydroxypiperidin-1-yl)(2-(1-ethyl-1H-indol-2-yl)-1-methyl-1H-benzo[d]imidazol-5-yl) methanone;
cis (+/−)-3-amino-4-methoxypiperidin-1-yl)(2-(1-ethyl-1H-indol-2-yl)-1-methyl-1H-benzo[d]imidazol-5-yl)methanone;
(3R)-1-{[2-(7-bromo-1-ethyl-1H-indol-2-yl)-1-methyl-1H-benzimidazol-5-yl]carbonyl}-3-piperidinamine;
2-(5-{[(3R)-3-amino-1-piperidinyl]carbonyl}-1-methyl-1H-benzimidazol-2-yl)-1-ethyl-1H-indol-7-ol;
2-(5-{[(3R)-3-amino-1-piperidinyl]carbonyl}-1-methyl-1H-benzimidazol-2-yl)-1-(cyclopropylmethyl)-1H-indol-5-ol;
2-(5-{[(3R)-3-amino-1-piperidinyl]carbonyl}-1-methyl-1H-benzimidazol-2-yl)-1-ethyl-1H-indol-6-ol;
(3R)-1-{[2-(1-ethyl-7-fluoro-1H-indol-2-yl)-1-methyl-1H-benzimidazol-5-yl]carbonyl}-3-piperidinamine;
(R)-(3-aminopiperidin-1-yl)(2-(1-ethyl-4-fluoro-1H-indol-2-yl)-1-methyl-1H-benzo[d]imidazol-5-yl)methanone;
2-(5-{[(3R)-3-amino-1-piperidinyl]carbonyl}-1-methyl-1H-benzimidazol-2-yl)-1-ethyl-1H-indole-7-carbonitrile;
5-Amino-5,6-dihydropyridin-1(2H)-yl)(2-(1-ethyl-1H-indol-2-yl)-1-methyl-1H-benzo[d]imidazol-5-yl)methanone;
(R)-(3-aminopiperidin-1-yl)(2-(1-ethyl-1H-indol-2-yl)-7-(3-hydroxypropoxy)-1-methyl-1H-benzo[d]imidazol-5-yl)methanone;
(R)-(3-aminopiperidin-1-yl)(7-ethoxy-2-(1-ethyl-1H-indol-2-yl)-1-methyl-1H-benzo[d]imidazol-5-yl)methanone;
(R)-(3-aminopiperidin-1-yl)(2-(1-ethyl-1H-indol-2-yl)-7-(2-methoxyethoxy)-1-methyl-1H-benzo[d]imidazol-5-yl) methanone;
(R)-(3-aminopiperidin-1-yl)(2-(1-ethyl-1H-indol-2-yl)-7-(2-hydroxyethoxy)-1-methyl-1H-benzo[d]imidazol-5-yl) methanone;
(R)-2-((5-(3-aminopiperidine-1-carbonyl)-2-(1-ethyl-1H-indol-2-yl)-1-methyl-1H-benzo[d]imidazol-7-yl)oxy)acetonitrile;
(R)-2-((5-(3-aminopiperidine-1-carbonyl)-2-(1-ethyl-1H-indol-2-yl)-1-methyl-1H-benzo[d]imidazol-7-yl)oxy)acetamide;
(R)-(3-aminopiperidin-1-yl)(2-(1-ethyl-1H-indol-2-yl)-7-hydroxy-1-methyl-1H-benzo[d]imidazol-5-yl)methanone;
(+/−)-(3-amino-4-methylpiperidin-1-yl)(2-(1-ethyl-1H-indol-2-yl)-1-methyl-1H-benzo[d]imidazol-5-yl)methanone, trans-isomer;
trans-3-amino-4-methylpiperidin-1-yl)(2-(1-ethyl-1H-indol-2-yl)-1-methyl-1H-benzo[d]imidazol-5-yl)methanone;
(+/−)-(3-amino-4-methylpiperidin-1-yl)(2-(1-ethyl-1H-indol-2-yl)-1-methyl-1H-benzo[d]imidazol-5-yl)methanone, cis-isomer;
cis-3-amino-4-methylpiperidin-1-yl)(2-(1-ethyl-1H-indol-2-yl)-1-methyl-1H-benzo[d]imidazol-5-yl)methanone;
(+/−)-cis-5-amino-1-(2-(1-ethyl-1H-indol-2-yl)-1-methyl-1H-benzo[d]imidazole-5-carbonyl)piperidine-3-carboxamide;
(3-amino-5-methylpiperidin-1-yl)(2-(1-ethyl-1H-indol-2-yl)-1-methyl-1H-benzo[d]imidazol-5-yl)methanone;
cis-(3-amino-5-methylpiperidin-1-yl)(2-(1-ethyl-1H-indol-2-yl)-1-methyl-1H-benzo[d]imidazol-5-yl)methanone;
trans-(3-amino-5-methylpiperidin-1-yl)(2-(1-ethyl-1H-indol-2-yl)-1-methyl-1H-benzo[d]imidazol-5-yl)methanone;
(3-amino-5-fluoropiperidin-1-yl)(2-(1-ethyl-1H-indol-2-yl)-1-methyl-1H-benzo[d]imidazol-5-yl)methanone;
(+/−)-((cis)-3,5-diaminopiperidin-1-yl)(2-(1-ethyl-1H-indol-2-yl)-1-methyl-1H-benzo[d]imidazol-5-yl)methanone;
(+/−)-((trans)-3-amino-5-methoxypiperidin-1-yl)(2-(1-ethyl-1H-indol-2-yl)-1-methyl-1H-benzo[d]imidazol-5-yl)methanone;
(3-amino-5-hydroxypiperidin-1-yl)(2-(1-ethyl-1H-indol-2-yl)-1-methyl-1H-benzo[d]imidazol-5-yl)methanone;
(+/−)-cis-3-amino-1-(2-(1-ethyl-1H-indol-2-yl)-1-methyl-1H-benzo[d]imidazole-5-carbonyl)piperidine-4-carboxamide;
(3-aminopiperidin-1-yl)(1-methyl-2-(1-methyl-1H-indol-2-yl)-1H-benzo[d]imidazol-5-yl)methanone;
(R)-(3-aminopiperidin-1-yl)(2-(1-benzyl-1H-indol-2-yl)-1-(2-methoxyethyl)-1H-benzo[d]imidazol-5-yl)methanone;
(R)-(3-aminopiperidin-1-yl)(2-(1-benzyl-1H-indol-2-yl)-1-isopropyl-1H-benzo[d]imidazol-5-yl)methanone;
(R)-(3-aminopiperidin-1-yl)(2-(1-ethyl-1H-indol-2-yl)-1-methyl-1H-benzo[d]imidazol-5-yl)methanethione;
(cis-(+/−)-3-amino-4-fluoropiperidin-1-yl)(2-(1-ethyl-1H-indol-2-yl)-1-methyl-1H-benzo[d]imidazol-5-yl)methanone;
(+/−)-(2-(aminomethyl)piperidin-1-yl)(2-(1-ethyl-1H-indol-2-yl)-1-methyl-1H-benzo[d]imidazol-5-yl)methanone;
((3S,4R)-3-amino-4-fluoropiperidin-1-yl)(2-(1-ethyl-1H-indol-2-yl)-1-methyl-1H-benzo[d]imidazol-5-yl)methanone;
((3R,4S)-3-amino-4-fluoropiperidin-1-yl)(2-(1-ethyl-1H-indol-2-yl)-1-methyl-1H-benzo[d]imidazol-5-yl)methanone;
(R)-(3-aminopiperidin-1-yl)(2-(1-(cyclopropylmethyl)-6-methoxy-1H-indol-2-yl)-1-methyl-1H-benzo[d]imidazol-5-yl)methanone;
N-(3-azabicyclo[4.1.0]heptan-1-yl)-2-(1-ethyl-1H-indol-2-yl)-1-methyl-1H-benzo[d]imidazole-5-carboxamide; and
(3-aminopiperidin-1-yl)(2-(1-benzyl-1H-indol-2-yl)-1-methyl-1H-benzo[d]imidazol-5-yl)methanone;
and salts thereof.
In one embodiment, the compound of the invention is selected from the list consisting of:
(3R)-1-{[2-(1-ethyl-1H-indol-2-yl)-1-methyl-1H-benzimidazol-5-yl]carbonyl}-3-piperidinamine;
(3R)-1-{[2-(1-ethyl-1H-indol-2-yl)-1-methyl-1H-benzimidazol-5-yl]carbonyl}-3-piperidinamine hydrochloride salt (3R)-1-({2-[1-ethyl-7-(methyloxy)-1H-indol-2-yl]-1-methyl-1H-benzimidazol-5-yl}carbonyl)-3-piperidinamine;

(3R)-1-{[2-(3,4-dihydro-2H-[1,4]oxazepino[2,3,4-hi]indol-6-yl)-1-methyl-1H-benzimidazol-5-yl]carbonyl}-3-piperidinamine;

(3R)-1-{[2-(2,3-dihydro[1,4]oxazino[2,3,4-hi]indol-5-yl)-1-methyl-1H-benzimidazol-5-yl]carbonyl}-3-piperidinamine;

(3R)-1-{[1-methyl-2-(3-methyl-2,3-dihydro[1,4]oxazino[2,3,4-hi]indol-5-yl)-1H-benzimidazol-5-yl]carbonyl}-3-piperidinamine;

(3R)-1-{[2-(1-ethyl-1H-indol-2-yl)-1-methyl-7-(methyloxy)-1H-benzimidazol-5-yl]carbonyl}-3-piperidinamine;

(3R)-1-{[2-(1-ethyl-1H-indol-2-yl)-1-methyl-7-(methyloxy)-1H-benzimidazol-5-yl]carbonyl}-3-piperidinamine hydrochloride salt;

(3R)-1-({2-[1-(cyclopropylmethyl)-5-(methyloxy)-1H-indol-2-yl]-1-methyl-1H-benzimidazol-5-yl}carbonyl)-3-piperidinamine;

(3R)-1-({2-[1-ethyl-6-(methyloxy)-1H-indol-2-yl]-1-methyl-1H-benzimidazol-5-yl}carbonyl)-3-piperidinamine;

[2-(5-{[(3R)-3-amino-1-piperidinyl]carbonyl}-1-methyl-1H-benzimidazol-2-yl)-1H-indol-1-yl]acetonitrile;

(3R)-1-{[2-(1-ethyl-6-fluoro-1H-indol-2-yl)-1-methyl-1H-benzimidazol-5-yl]carbonyl}-3-piperidinamine;

(3R)-1-({1-methyl-2-[1-(2,2,2-trifluoroethyl)-1H-indol-2-yl]-1H-benzimidazol-5-yl}carbonyl)-3-piperidinamine;

(3R)-1-({1-methyl-2-[1-(1-methylethyl)-1H-indol-2-yl]-1H-benzimidazol-5-yl}carbonyl)-3-piperidinamine;

2-(5-{[(3R)-3-amino-1-piperidinyl]carbonyl}-1-methyl-1H-benzimidazol-2-yl)-1-ethyl-1H-indole-6-carbonitrile;

(3R)-1-[(2-{1-[(3-chlorophenyl)methyl]-1H-indol-2-yl}-1-methyl-1H-benzimidazol-5-yl)carbonyl]-3-piperidinamine;

(3R)-1-({1-methyl-2-[1-(3-pyridinylmethyl)-1H-indol-2-yl]-1H-benzimidazol-5-yl}carbonyl)-3-piperidinamine;

(3R)-1-({2-[1-(cyclopropylmethyl)-1H-indol-2-yl]-1-methyl-1H-benzimidazol-5-yl}carbonyl)-3-piperidinamine;

(3R)-1-[(1-methyl-2-{1-[(4-methylphenyl)methyl]-1H-indol-2-yl}-1H-benzimidazol-5-yl)carbonyl]-3-piperidinamine;

(3R)-1-{[2-(1H-indol-2-yl)-1-methyl-1H-benzimidazol-5-yl]carbonyl}-3-piperidinamine;

(3R)-1-({1-methyl-2-[1-(2-methylpropyl)-1H-indol-2-yl]-1H-benzimidazol-5-yl}carbonyl)-3-piperidinamine;

(3R)-1-[(1-methyl-2-{1-[(1-methyl-1H-pyrazol-4-yl)methyl]-1H-indol-2-yl}-1H-benzimidazol-5-yl)carbonyl]-3-piperidinamine;

(3R)-1-{[2-(5-chloro-1-ethyl-1H-indol-2-yl)-1-methyl-1H-benzimidazol-5-yl]carbonyl}-3-piperidinamine;

(3R)-1-[(1-methyl-2-{1-[2-(methyloxy)ethyl]-1H-indol-2-yl}-1H-benzimidazol-5-yl)carbonyl]-3-piperidinamine;

(3R)-1-{[2-(6-bromo-1-ethyl-1H-indol-2-yl)-1-methyl-1H-benzimidazol-5-yl]carbonyl}-3-piperidinamine;

(3R)-1-({1-methyl-2-[1-(phenylmethyl)-1H-indol-2-yl]-1H-benzimidazol-5-yl}carbonyl)-3-piperidinamine;

(3R)-1-[(2-{1-[(4-iodophenyl)methyl]-1H-indol-2-yl}-1-methyl-1H-benzimidazol-5-yl)carbonyl]-3-piperidinamine;

(3R)-1-{[2-(1-ethyl-6-methyl-1H-indol-2-yl)-1-methyl-1H-benzimidazol-5-yl]carbonyl}-3-piperidinamine;

(3R)-1-({1-methyl-2-[1-(2-pyridinylmethyl)-1H-indol-2-yl]-1H-benzimidazol-5-yl}carbonyl)-3-piperidinamine;

(3R)-1-({1-methyl-2-[1-(4-pyridinylmethyl)-1H-indol-2-yl]-1H-benzimidazol-5-yl}carbonyl)-3-piperidinamine;

2-[2-(5-{[(3R)-3-amino-1-piperidinyl]carbonyl}-1-methyl-1H-benzimidazol-2-yl)-1H-indol-1-yl]ethanol;

(3R)-1-[(2-{1-[(4-chlorophenyl)methyl]-1H-indol-2-yl}-1-methyl-1H-benzimidazol-5-yl)carbonyl]-3-piperidinamine;

(R)-(3-aminopiperidin-1-yl)(2-(1-ethyl-6,7-dimethoxy-1H-indol-2-yl)-1-methyl-1H-benzo[d]imidazol-5-yl)methanone;

(R)-(3-aminopiperidin-1-yl)(2-(6-ethoxy-1-ethyl-1H-indol-2-yl)-1-methyl-1H-benzo[d]imidazol-5-yl)methanone;

((R)-3-aminopiperidin-1-yl)(2-(1-((R)-3-hydroxy-2-methylpropyl)-1H-indol-2-yl)-7-methoxy-1-methyl-1H-benzo[d]imidazol-5-yl)methanone;

(R)-(3-aminopiperidin-1-yl)(2-(1-ethyl-1H-indol-2-yl)-1-methyl-7-(trifluoromethoxy)-1H-benzo[d]imidazol-5-yl)methanone;

(R)-5-(3-aminopiperidine-1-carbonyl)-2-(1-ethyl-1H-indol-2-yl)-1-methyl-1H-benzo[d]imidazole-7-carbonitrile, hydrochloride salt;

(R)-(3-aminopiperidin-1-yl)(7-bromo-2-(1-ethyl-1H-indol-2-yl)-1-methyl-1H-benzo[d]imidazol-5-yl)methanone;

(R)-(3-aminopiperidin-1-yl)(1-methyl-2-(1-methyl-1H-indol-2-yl)-1H-benzo[d]imidazol-5-yl)methanone;

(R)-(3-aminopiperidin-1-yl)(2-(1-(3,4-dichlorobenzyl)-1H-indol-2-yl)-1-methyl-1H-benzo[d]imidazol-5-yl)methanone;

(R)-(3-aminopiperidin-1-yl)(2-(1-(4-methoxybenzyl)-1H-indol-2-yl)-1-methyl-1H-benzo[d]imidazol-5-yl)methanone;

1-({1-methyl-2-[1-(tetrahydro-2H-pyran-4-ylmethyl)-1H-indol-2-yl]-1H-benzimidazol-5-yl}carbonyl)-3-piperidinamine;

1-{[2-(6-bromo-1-ethyl-1H-indol-2-yl)-1-methyl-1H-benzimidazol-5-yl]carbonyl}-3-piperidinamine;

(R)-(3-aminopiperidin-1-yl)(2-(1-ethyl-1H-indol-2-yl)-1,6-dimethyl-1H-benzo[d]imidazol-5-yl)methanone;

(3R)-1-({1-methyl-2-[1-(2,2,2-trifluoroethyl)-1H-indol-2-yl]-1H-benzimidazol-5-yl}carbonyl)-3-piperidinamine hydrochloride salt;

((R)-3-aminopiperidin-1-yl)(2-(1-((R)-3-hydroxy-2-methylpropyl)-1H-indol-2-yl)-7-methoxy-1-methyl-1H-benzo[d]imidazol-5-yl)methanone, hydrochloride salt;

(R)-(3-aminopiperidin-1-yl)(2-(1-(cyclopropylmethyl)-1H-indol-2-yl)-7-methoxy-1-methyl-1H-benzo[d]imidazol-5-yl)methanone, hydrochloride salt;

(R)-(3-aminopiperidin-1-yl)(7-methoxy-1-methyl-2-(1-(2,2,2-trifluoroethyl)-1H-indol-2-yl)-1H-benzo[d]imidazol-5-yl)methanone, hydrochloride salt;

(3S)-1-({1-methyl-2-[1-(phenylmethyl)-1H-indol-2-yl]-1H-benzimidazol-5-yl}carbonyl)-3-piperidinamine;

(S)-(3-aminopiperidin-1-yl)(1-methyl-2-(1-methyl-1H-indol-2-yl)-1H-benzo[d]imidazol-5-yl)methanone;

(1R,5S)-3-{[2-(1-ethyl-1H-indol-2-yl)-1-methyl-1H-benzimidazol-5-yl]carbonyl}-3-azabicyclo[3.1.0]hexan-1-amine;

(R)-(1-(2-aminoethyl)-2-(1-ethyl-1H-indol-2-yl)-1H-benzo[d]imidazol-5-yl)(3-aminopiperidin-1-yl)methanone;

(R)-(3-aminopiperidin-1-yl)(2-(1-ethyl-1H-indol-2-yl)-1-methyl-7-(trifluoromethyl)-1H-benzo[d]imidazol-5-yl)methanone;

(+/−)-cis-(3-amino-4-ethoxypiperidin-1-yl)(2-(1-ethyl-1H-indol-2-yl)-1-methyl-1H-benzo[d]imidazol-5-yl)methanone;

(+/−)-((cis)-3-amino-4-methoxypiperidin-1-yl)(2-(1-ethyl-1H-indol-2-yl)-1-methyl-1H-benzo[d]imidazol-5-yl)methanone;

cis-(3-amino-2-methylpiperidin-1-yl)(2-(1-ethyl-1H-indol-2-yl)-1-methyl-1H-benzo[d]imidazol-5-yl)methanone hydrochloride salt;

cis-(5-amino-2-methylpiperidin-1-yl)(2-(1-ethyl-1H-indol-2-yl)-1-methyl-1H-benzo[d]imidazol-5-yl)methanone hydrochloride salt;

cis-(5-amino-2-methylpiperidin-1-yl)(2-(1-ethyl-1H-indol-2-yl)-1-methyl-1H-benzo[d]imidazol-5-yl)methanone hydrochloride salt;

N-(azepan-3-yl)-2-(1-(cyclopropylmethyl)-1H-indol-2-yl)-1-methyl-1H-benzo[d]imidazole-5-carboxamide hydrochloride salt;

(3-aminopyrrolidin-1-yl)(2-(1-ethyl-1H-indol-2-yl)-7-methoxy-1-methyl-1H-benzo[d]imidazol-5-yl)methanone hydrochloride salt;

(3-aminocyclopentyl)(2-(1-benzyl-1H-indol-2-yl)-1-methyl-1H-benzo[d]imidazol-5-yl)methanone;

((3S,4R)-3-amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone;

((3S,4R)-3-amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone, hydrochloride salt;

((3R,4S)-3-amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone;

(3R)-1-[(1-methyl-2-{1-[(1-methyl-1H-pyrazol-4-yl)methyl]-1H-indol-2-yl}-1H-benzimidazol-5-yl)carbonyl]-3-piperidinamine hydrochloride salt;

(R)-(3-aminopiperidin-1-yl)(2-(1-ethyl-5-fluoro-1H-indol-2-yl)-1-methyl-1H-benzo[d]imidazol-5-yl)methanone, Hydrochloride;

(R)-(3-aminopiperidin-1-yl)(2-(1-ethyl-1H-indol-2-yl)-1-methyl-7-(pyridin-3-yl)-1H-benzo[d]imidazol-5-yl)methanone, hydrochloride salt;

(R)-5-(3-aminopiperidine-1-carbonyl)-2-(1-ethyl-1H-indol-2-yl)-1-methyl-1H-benzo[d]imidazole-7-carboxamide, hydrochloride salt;

(R)-(3-aminopiperidin-1-yl)(7-(dimethylamino)-2-(1-ethyl-1H-indol-2-yl)-1-methyl-1H-benzo[d]imidazol-5-yl)methanone, hydrochloride salt;

2-(1-ethyl-1H-indol-2-yl)-1-methyl-N-(1,4-oxazepan-6-yl)-1H-benzo[d]imidazole-5-carboxamide hydrochloride salt;

((3S,4R)-3-amino-4-hydroxypiperidin-1-yl)(2-(1-(cyclopropylmethyl)-1H-indol-2-yl)-1-methyl-1H-benzo[d]imidazol-5-yl)methanone hydrochloride salt;

((3S,4R)-3-amino-4-hydroxypiperidin-1-yl)(2-(1-(cyclopropylmethyl)-1H-indol-2-yl)-7-methoxy-1-methyl-1H-benzo[d]imidazol-5-yl)methanone, hydrochloride salt;

((3S,4R)-3-amino-4-hydroxypiperidin-1-yl)(2-(1-ethyl-1H-indol-2-yl)-7-methoxy-1-methyl-1H-benzo[d]imidazol-5-yl)methanone, hydrochloride salt;

(R)-(3-aminopiperidin-1-yl)(2-(1-ethyl-1H-indol-2-yl)-1-methyl-7-(methylamino)-1H-benzo[d]imidazol-5-yl)methanone, hydrochloride salt;

(R)-(3-aminopiperidin-1-yl)(7-methoxy-2-(1-(3-methoxypropyl)-1H-indol-2-yl)-1-methyl-1H-benzo[d]imidazol-5-yl)methanone, hydrochloride salt;

(R)-(3-aminopiperidin-1-yl)(7-methoxy-1-methyl-2-(1-((tetrahydro-2H-pyran-4-yl)methyl)-1H-indol-2-yl)-1H-benzo[d]imidazol-5-yl)methanone, hydrochloride salt;

(R)-(3-aminopiperidin-1-yl)(7-methoxy-2-(1-(2-methoxyethyl)-1H-indol-2-yl)-1-methyl-1H-benzo[d]imidazol-5-yl)methanone, hydrochloride salt;

(R)-(3-aminopiperidin-1-yl)(2-(1-(2-hydroxyethyl)-1H-indol-2-yl)-7-methoxy-1-methyl-1H-benzo[d]imidazol-5-yl)methanone, hydrochloride salt;

((R)-3-aminopiperidin-1-yl)(2-(1-((S)-3-hydroxy-2-methylpropyl)-1H-indol-2-yl)-7-methoxy-1-methyl-1H-benzo[d]imidazol-5-yl)methanone, hydrochloride salt;

(R)-2-(2-(5-(3-aminopiperidine-1-carbonyl)-7-methoxy-1-methyl-1H-benzo[d]imidazol-2-yl)-1H-indol-1-yl)acetonitrile, hydrochloride salt;

(R)-(3-aminopiperidin-1-yl)(7-ethyl-2-(1-ethyl-1H-indol-2-yl)-1-methyl-1H-benzo[d]imidazol-5-yl)methanone, hydrochloride salt;

N-(azepan-3-yl)-2-(1-ethyl-1H-indol-2-yl)-1-methyl-1H-benzo[d]imidazole-5-carboxamide;

(S)—N-(azepan-3-yl)-2-(1-ethyl-1H-indol-2-yl)-1-methyl-1H-benzo[d]imidazole-5-carboxamide;

(R)—N-(1-(2-(1-benzyl-1H-indol-2-yl)-1-methyl-1H-benzo[d]imidazole-5-carbonyl)piperidin-3-yl)-2-chloroacetimidamide;

(R)-(3-aminopiperidin-1-yl)(2-(7-ethyl-1H-indol-2-yl)-1-methyl-1H-benzo[d]imidazol-5-yl)methanone;

(R)-(3-aminopiperidin-1-yl)(2-(1-ethyl-5,6-dimethoxy-1H-indol-2-yl)-1-methyl-1H-benzo[d]imidazol-5-yl)methanone;

(R)-(3-aminopiperidin-1-yl)(2-(3-ethyl-1H-indol-2-yl)-1-methyl-1H-benzo[d]imidazol-5-yl)methanone;

1-{[2-(1-ethyl-7-methyl-1H-indol-2-yl)-1-methyl-1H-benzimidazol-5-yl]carbonyl}-3-piperidinamine;

N-(2-aminoethyl)-1-methyl-2-[1-(phenylmethyl)-1H-indol-2-yl]-1H-benzimidazole-5-carboxamide;

1-{[2-(1-ethyl-5-methyl-1H-indol-2-yl)-1-methyl-1H-benzimidazol-5-yl]carbonyl}-3-piperidinamine;

1-{[2-(1-ethyl-4-methyl-1H-indol-2-yl)-1-methyl-1H-benzimidazol-5-yl]carbonyl}-3-piperidinamine;

(R)-2-(5-(3-aminopiperidine-1-carbonyl)-1-methyl-1H-benzo[d]imidazol-2-yl)-1-ethyl-1H-indole-5-carbonitrile;

2-(1-ethyl-1H-indol-2-yl)-1-methyl-N-(piperidin-3-yl)-1H-benzo[d]imidazole-5-carboxamide;

(S)-(3-(aminomethyl)pyrrolidin-1-yl)(2-(1-ethyl-1H-indol-2-yl)-1-methyl-1H-benzo[d]imidazol-5-yl)methanone;

(2-(1-ethyl-1H-indol-2-yl)-1-methyl-1H-benzo[d]imidazol-5-yl)(3-(methylamino)piperidin-1-yl)methanone;

N-(2-aminoethyl)-2-(1-ethyl-1H-indol-2-yl)-1-methyl-1H-benzo[d]imidazole-5-carboxamide;

(3,4-cis)-1-{[2-(1-ethyl-1H-indol-2-yl)-1-methyl-1H-benzimidazol-5-yl]carbonyl}-3,4-piperidinediamine;

(+/−)-((cis)-4-amino-2-methylpyrrolidin-1-yl)(2-(1-ethyl-1H-indol-2-yl)-1-methyl-1H-benzo[d]imidazol-5-yl)methanone, hydrochloride salt;

(R)-(3-aminopiperidin-1-yl)(2-(1-ethyl-1H-indol-2-yl)-1,7-dimethyl-1H-benzo[d]imidazol-5-yl)methanone;

(R)-(3-aminopiperidin-1-yl)(1-(3-aminopropyl)-2-(1-ethyl-1H-indol-2-yl)-1H-benzo[d]imidazol-5-yl)methanone, bis-hydrochloride salt;

(R)-(3-aminopiperidin-1-yl)(1-ethyl-2-(1-ethyl-1H-indol-2-yl)-1H-benzo[d]imidazol-5-yl)methanone, hydrochloride salt;

(R)-(3-aminopiperidin-1-yl)(2-(1-ethyl-1H-indol-2-yl)-3-methyl-3H-imidazo[4,5-b]pyridin-6-yl)methanone, hydrochloride salt;

trans (+/−)-3-amino-4-fluoropiperidin-1-yl)(2-(1-ethyl-1H-indol-2-yl)-1-methyl-1H-benzo[d]imidazol-5-yl)methanone;

cis-((+/−)-3-amino-4-hydroxypiperidin-1-yl)(2-(1-ethyl-1H-indol-2-yl)-1-methyl-1H-benzo[d]imidazol-5-yl)methanone;
trans-((+/−)-3-amino-4-hydroxypiperidin-1-yl)(2-(1-ethyl-1H-indol-2-yl)-1-methyl-1H-benzo[d]imidazol-5-yl)methanone;
cis (+/−)-3-amino-4-methoxypiperidin-1-yl)(2-(1-ethyl-1H-indol-2-yl)-1-methyl-1H-benzo[d]imidazol-5-yl)methanone;
(3R)-1-{[2-(7-bromo-1-ethyl-1H-indol-2-yl)-1-methyl-1H-benzimidazol-5-yl]carbonyl}-3-piperidinamine;
2-(5-{[(3R)-3-amino-1-piperidinyl]carbonyl}-1-methyl-1H-benzimidazol-2-yl)-1-ethyl-1H-indol-7-ol;
2-(5-{[(3R)-3-amino-1-piperidinyl]carbonyl}-1-methyl-1H-benzimidazol-2-yl)-1-(cyclopropylmethyl)-1H-indol-5-ol;
2-(5-{[(3R)-3-amino-1-piperidinyl]carbonyl}-1-methyl-1H-benzimidazol-2-yl)-1-ethyl-1H-indol-6-ol;
(3R)-1-{[2-(1-ethyl-7-fluoro-1H-indol-2-yl)-1-methyl-1H-benzimidazol-5-yl]carbonyl}-3-piperidinamine;
(R)-(3-aminopiperidin-1-yl)(2-(1-ethyl-4-fluoro-1H-indol-2-yl)-1-methyl-1H-benzo[d]imidazol-5-yl)methanone;
2-(5-{[(3R)-3-amino-1-piperidinyl]carbonyl}-1-methyl-1H-benzimidazol-2-yl)-1-ethyl-1H-indole-7-carbonitrile;
5-Amino-5,6-dihydropyridin-1(2H)-yl)(2-(1-ethyl-1H-indol-2-yl)-1-methyl-1H-benzo[d]imidazol-5-yl)methanone;
(R)-(3-aminopiperidin-1-yl)(2-(1-ethyl-1H-indol-2-yl)-7-(3-hydroxypropoxy)-1-methyl-1H-benzo[d]imidazol-5-yl)methanone;
(R)-(3-aminopiperidin-1-yl)(7-ethoxy-2-(1-ethyl-1H-indol-2-yl)-1-methyl-1H-benzo[d]imidazol-5-yl)methanone;
(R)-(3-aminopiperidin-1-yl)(2-(1-ethyl-1H-indol-2-yl)-7-(2-methoxyethoxy)-1-methyl-1H-benzo[d]imidazol-5-yl)methanone;
(R)-(3-aminopiperidin-1-yl)(2-(1-ethyl-1H-indol-2-yl)-7-(2-hydroxyethoxy)-1-methyl-1H-benzo[d]imidazol-5-yl)methanone;
(R)-2-((5-(3-aminopiperidine-1-carbonyl)-2-(1-ethyl-1H-indol-2-yl)-1-methyl-1H-benzo[d]imidazol-7-yl)oxy)acetonitrile;
(R)-2-((5-(3-aminopiperidine-1-carbonyl)-2-(1-ethyl-1H-indol-2-yl)-1-methyl-1H-benzo[d]imidazol-7-yl)oxy)acetamide;
(R)-(3-aminopiperidin-1-yl)(2-(1-ethyl-1H-indol-2-yl)-7-hydroxy-1-methyl-1H-benzo[d]imidazol-5-yl)methanone;
(+/−)-(3-amino-4-methylpiperidin-1-yl)(2-(1-ethyl-1H-indol-2-yl)-1-methyl-1H-benzo[d]imidazol-5-yl)methanone, trans-isomer;
trans-3-amino-4-methylpiperidin-1-yl)(2-(1-ethyl-1H-indol-2-yl)-1-methyl-1H-benzo[d]imidazol-5-yl)methanone, hydrochloride salt;
(+/−)-(3-amino-4-methylpiperidin-1-yl)(2-(1 -ethyl-1H-indol-2-yl)-1-methyl-1H-benzo[d]imidazol-5-yl)methanone, cis-isomer;
cis-3-amino-4-methylpiperidin-1-yl)(2-(1-ethyl-1H-indol-2-yl)-1-methyl-1H-benzo[d]imidazol-5-yl)methanone, hydrochloride salt;
(+/−)-cis-5-amino-1-(2-(1-ethyl-1H-indol-2-yl)-1-methyl-1H-benzo[d]imidazole-5-carbonyl)piperidine-3-carboxamide;
(3-amino-5-methylpiperidin-1-yl)(2-(1-ethyl-1H-indol-2-yl)-1-methyl-1H-benzo[d]imidazol-5-yl)methanone hydrochloride salt;
cis-(3-amino-5-methylpiperidin-1-yl)(2-(1-ethyl-1H-indol-2-yl)-1-methyl-1H-benzo[d]imidazol-5-yl)methanone hydrochloride salt;
trans-(3-amino-5-methylpiperidin-1-yl)(2-(1-ethyl-1H-indol-2-yl)-1-methyl-1H-benzo[d]imidazol-5-yl)methanone hydrochloride salt;
(3-amino-5-fluoropiperidin-1-yl)(2-(1-ethyl-1H-indol-2-yl)-1-methyl-1H-benzo[d]imidazol-5-yl)methanone;
(+/−)-((cis)-3,5-diaminopiperidin-1-yl)(2-(1-ethyl-1H-indol-2-yl)-1-methyl-1H-benzo[d]imidazol-5-yl)methanone hydrochloride salt;
(+/−)-((trans)-3-amino-5-methoxypiperidin-1-yl)(2-(1-ethyl-1H-indol-2-yl)-1-methyl-1H-benzo[d]imidazol-5-yl)methanone hydrochloride salt;
(3-amino-5-hydroxypiperidin-1-yl)(2-(1-ethyl-1H-indol-2-yl)-1-methyl-1H-benzo[d]imidazol-5-yl)methanone, hydrochloride salt, diastereomeric mixture;
(+/−)-cis-3-amino-1-(2-(1-ethyl-1H-indol-2-yl)-1-methyl-1H-benzo[d]imidazole-5-carbonyl)piperidine-4-carboxamide hydrochloride salt;
(3-aminopiperidin-1-yl)(1-methyl-2-(1-methyl-1H-indol-2-yl)-1H-benzo[d]imidazol-5-yl)methanone;
(R)-(3-aminopiperidin-1-yl)(2-(1-benzyl-1H-indol-2-yl)-1-(2-methoxyethyl)-1H-benzo[d]imidazol-5-yl)methanone;
(R)-(3-aminopiperidin-1-yl)(2-(1-benzyl-1H-indol-2-yl)-1-isopropyl-1H-benzo[d]imidazol-5-yl)methanone;
(R)-(3-aminopiperidin-1-yl)(2-(1-ethyl-1H-indol-2-yl)-1-methyl-1H-benzo[d]imidazol-5-yl)methanethione hydrochloride salt;
(cis-(+/−)-3-amino-4-fluoropiperidin-1-yl)(2-(1-ethyl-1H-indol-2-yl)-1-methyl-1H-benzo[d]imidazol-5-yl)methanone;
(+/−)-(2-(aminomethyl)piperidin-1-yl)(2-(1-ethyl-1H-indol-2-yl)-1-methyl-1H-benzo[d]imidazol-5-yl)methanone;
((3S,4R)-3-amino-4-fluoropiperidin-1-yl)(2-(1-ethyl-1H-indol-2-yl)-1-methyl-1H-benzo[d]imidazol-5-yl)methanone;
((3S,4R)-3-Amino-4-fluoropiperidin-1-yl)(2-(1-ethyl-1H-indol-2-yl)-1-methyl-1H-benzo[d]imidazol-5-yl)methanone hydrochloride salt;
((3R,4S)-3-amino-4-fluoropiperidin-1-yl)(2-(1-ethyl-1H-indol-2-yl)-1-methyl-1H-benzo[d]imidazol-5-yl)methanone;
((3R,4S)-3-amino-4-fluoropiperidin-1-yl)(2-(1-ethyl-1H-indol-2-yl)-1-methyl-1H-benzo[d]imidazol-5-yl)methanone hydrochloride salt;
(R)-(3-aminopiperidin-1-yl)(2-(1-(cyclopropylmethyl)-6-methoxy-1H-indol-2-yl)-1-methyl-1H-benzo[d]imidazol-5-yl)methanone;
(R)-(3-aminopiperidin-1-yl)(2-(1-(cyclopropylmethyl)-6-methoxy-1H-indol-2-yl)-1-methyl-1H-benzo[d]imidazol-5-yl)methanone, hydrochloride salt;
N-(3-azabicyclo[4.1.0]heptan-1-yl)-2-(1-ethyl-1H-indol-2-yl)-1-methyl-1H-benzo[d]imidazole-5-carboxamide; and
(3-Aminopiperidin-1-yl)(2-(1-benzyl-1H-indol-2-yl)-1-methyl-1H-benzo[d]imidazol-5-yl)methanone.

In one embodiment, the compound of the invention is selected from the list consisting of:
(3R)-1-[2-(1-benzyl-1H-indol-2-yl)-1-methyl-1H-1,3-benzodiazole-5-carb nyl]piperidin-3-amine;
(3R)-1-{1-methyl-2-[1-(pyridin-3-ylmethyl)-1H-indol-2-yl]-1H-1,3-benzodiazole-5-carbonyl}piperidin-3-amine;
(3R)-1-{1-methyl-2-[1-(2,2,2-trifluoroethyl)-1H-indol-2-yl]-1H-1,3-benzodiazole-5-carbonyl}piperidin-3-amine;
(3R)-1-{2-[1-(cyclopropylmethyl)-1H-indol-2-yl]-1-methyl-1H-1,3-benzodiazole-5-carbonyl}piperidin-3-amine;

(3R)-1-(1-methyl-2-{1-[(1-methyl-1H-pyrazol-4-yl)
   methyl]-1H-indol-2-yl}-1H-1,3-benzodiazole-5-carbo-
   nyl)piperidin-3-amine;
(3R)-1-[2-(1-ethyl-1H-indol-2-yl)-7-methoxy-1-methyl-
   1H-1,3-benzodiazole-5-carbonyl]piperidin-3-amine;
(3R)-1-{2-[1-(cyclopropylmethyl)-1H-indol-2-yl]-7-
   methoxy-1-methyl-1H-1,3-benzodiazole-5-
   carbonyl}piperidin-3-amine;
(3R)-1-{7-methoxy-1-methyl-2-[1-(2,2,2-trifluoroethyl)-
   1H-indol-2-yl]-1H-1,3-benzodiazole-5-
   carbonyl}piperidin-3-amine;
(3S,4R)-3-amino-1-{7-methoxy-1-methyl-2-[1-(2,2,2-trif-
   luoroethyl)-1H-indol-2-yl]-1H-1,3-benzodiazole-5-
   carbonyl}piperidin-4-ol; and
(3S,4R)-3-amino-1-{2-[1-(cyclopropylmethyl)-1H-indol-2-
   yl]-1-methyl-1H-1,3-benzodiazole-5-carbonyl}piperidin-
   4-ol;
and salts thereof.

In one embodiment, the compound of the invention is selected from the list consisting of:
(3R)-1-[2-(1-benzyl-1H-indol-2-yl)-1-methyl-1H-1,3-ben-
   zodiazole-5-carb nyl]piperidin-3-amine;
(3R)-1-{1-methyl-2-[1-(pyridin-3-ylmethyl)-1H-indol-2-
   yl]-1H-1,3-benzodiazole-5-carbonyl}piperidin-3-amine;
(3R)-1-{1-methyl-2-[1-(2,2,2-trifluoroethyl)-1H-indol-2-
   yl]-1H-1,3-benzodiazole-5-carbonyl}piperidin-3-amine;
(3R)-1-{2-[1-(cyclopropylmethyl)-1H-indol-2-yl]-1-
   methyl-1H-1,3-benzodiazole-5-carbonyl}piperidin-3-
   amine;
(3R)-1-(1-methyl-2-{1-[(1-methyl-1H-pyrazol-4-yl)
   methyl]-1H-indol-2-yl}-1H-1,3-benzodiazole-5-carbo-
   nyl)piperidin-3-amine hydrochloride salt;
(3R)-1-[2-(1-ethyl-1H-indol-2-yl)-7-methoxy-1-methyl-
   1H-1,3-benzodiazole-5-carbonyl]piperidin-3-amine
   hydrochloride salt;
(3R)-1-{2-[1-(cyclopropylmethyl)-1H-indol-2-yl]-7-
   methoxy-1-methyl-1H-1,3-benzodiazole-5-
   carbonyl}piperidin-3-amine hydrochloride salt;
(3R)-1-{7-methoxy-1-methyl-2-[1-(2,2,2-trifluoroethyl)-
   1H-indol-2-yl]-1H-1,3-benzodiazole-5-
   carbonyl}piperidin-3-amine hydrochloride salt;
(3S,4R)-3-amino-1-{7-methoxy-1-methyl-2-[1-(2,2,2-trif-
   luoroethyl)-1H-indol-2-yl]-1H-1,3-benzodiazole-5-
   carbonyl}piperidin-4-ol; and
(3S,4R)-3-amino-1-{2-[1-(cyclopropylmethyl)-1H-indol-2-
   yl]-1-methyl-1H-1,3-benzodiazole-5-carbonyl}piperidin-
   4-ol hydrochloride salt.

TERMS AND DEFINITIONS

Compounds of Formula (I) and salts thereof are referred to hereinafter as 'Compounds of the invention'.

'Alkyl' refers to a saturated hydrocarbon chain having the specified number of carbon atoms. For example, $C_{1-6}$alkyl refers to an alkyl group having from 1 to 6 carbon atoms, for example 1 to 3 carbon atoms. For example $C_{2-6}$alkyl refers to an alkyl group having from 2-6 carbon atoms, for instance 2-3 carbon atoms. Alkyl groups may be straight or branched. Representative branched alkyl groups have one, two, or three branches. 'Alkyl' includes methyl, ethyl, iso-propyl and iso-butyl.

'Cycloalkyl' refers to a saturated hydrocarbon ring having the specified number of member atoms. For example, $C_{3-6}$cycloalkyl refers to a cycloalkyl group having from 3 to 6 member atoms, for example 3 member atoms. 'Cycloalkyl' includes cyclopropyl.

'Enantiomeric excess' (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

'Enantiomerically enriched' refers to products whose enantiomeric excess (ee) is greater than zero. For example, 'enantiomerically enriched' refers to products whose enantiomeric excess is greater than 50% ee, greater than 75% ee, and greater than 90% ee.

'Enantiomerically pure' refers to products whose enantiomeric excess is 99% or greater.

'Half-life' (or 'half-lives') refers to the time required for half of a quantity of a substance to be converted to another chemically distinct species in vitro or in vivo.

'Halo' refers to a halogen radical, for example, fluoro, chloro, bromo, or iodo.

'Haloalkyl' refers to an alkyl group, as hereinbefore defined, in which at least one of the hydrogen atoms has been replaced with a halogen radical. '$C_{1-6}$haloalkyl' refers to a $C_{1-6}$ alkyl group in which at least one of the hydrogen atoms has been replaced with a halogen radical. An example of 'haloalkyl' is trifluoromethyl or 2,2,2-trifluoroethyl.

'Heterocyclic' and 'heterocyclyl' refer to saturated or unsaturated monocyclic aliphatic rings containing 5, 6, or 7 ring members including 1 or 2 heteroatoms or to saturated or unsaturated bicyclic aliphatic rings containing 5, 6 or 7 ring members including 1 or 2 heteroatoms. In certain embodiments, 'heterocyclyl' groups are saturated. In other embodiments, 'heterocyclyl' groups are unsaturated. 'Heterocyclyl' groups containing more than one heteroatom may contain different heteroatoms. 'Heterocyclyl' groups may be substituted with one or more substituents as defined herein. 'Heterocyclyl' includes piperidinyl, tetrahydropyranyl, azepinyl, oxazepinyl, azabicyclo[3.1.0]hexanyl or azabicyclo[4.1.0]heptnyl.

'Heteroaryl' refers to aromatic rings containing from 1 to 3 heteroatoms as member atoms in the ring. 'Heteroaryl' groups containing more than one heteroatom may contain different heteroatoms. 'Heteroaryl' groups may be substituted with one or more substituents if so defined herein. The 'heteroaryl' rings have 5 or 6 member atoms. 'Heteroaryl' includes pyridinyl, and pyrazolyl.

'Heteroatom' refers to a nitrogen, sulfur, or oxygen atom, for example a nitrogen atom or an oxygen atom.

'Member atoms' refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

'Substituted' in reference to a group indicates that a hydrogen atom attached to a member atom within a group is replaced. It should be understood that the term 'substituted' includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

'Pharmaceutically acceptable' refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

ABBREVIATIONS

AcOH Acetic acid
$BH_3$-THF Borane tetrahydrofuran complex
BOC/Boc tert-Butoxycarbonyl
$BOC_2O$ Di-tert-butyl dicarbonate
nBuLi n-Butyllithium
BuOH Butanol
Bz benzyl
Cbz carboxybenzyl
cHex Cyclohexane
$Cs_2CO_3$ Caesium carbonate
CV Column volumes
DCM/$CH_2Cl_2$ Dichloromethane
DIAD diisopropyl azodicarboxylate
Dioxane 1,4-dioxane
DIPEA N, N-diisopropylethylamine
DMSO Dimethylsulfoxide
DMF N,N-dimethylformamide
$Et_3N$ Triethylamine
Ether Diethyl ether
EtOAc Ethyl acetate
GC Gas chromatography
h. Hours
HATU o-(7-Azabenzotriazol-1-yl)-N,N,N',N'-tetramethyl-uronium hexafluorophosphate
HPLC High performance liquid chromatography
IPA isopropyl alcohol
$K_2CO_3$ Potassium carbonate
KOH Potassium hydroxide
LiCl Lithium chloride
LiOH Lithium hydroxide
LCMS or LC/MS Liquid chromatography-mass spectroscopy
MDAP Mass directed automated preparative chromatography
MeOH Methanol
$MeNH_2$ Methylamine
min. Minutes
$Na_2SO_4$ Sodium sulfate
$NaHCO_3$ Sodium bicarbonate
$NH_4Cl$ Ammonium chloride
NMP 1-Methyl-2-pyrrolidinone
Palladium tetrakis palladium tetrakistriphenylphosphine
Pd/C Palladium on carbon
PE Petroleum ether
PTSA p-Toluenesulfonic acid
rb round-bottomed (flask)
r.t/rt. Room temperature
Rt Retention time
SNAP Biotage™ flash chromatography cartridge
SPE Solid phase extraction
SP4 Biotage™ flash purification system
TFA Trifluoroacetic acid
TFAA Trifluoroacetic anhydride
THF/thf Tetrahydrofuran
TLC/tlc Thin layer chromatography
TMEDA Tetramethylethylenediamine Included within the scope of the 'compounds of the invention' are all solvates (including hydrates), complexes, polymorphs, prodrugs, radiolabelled derivatives, and stereoisomers of the compounds of formula (I) and salts thereof.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as 'hydrates'. Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as 'polymorphs'. The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^3H$, $^{11}C$, $^{14}C$ and $^{18}F$.

The compounds according to formula (I) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

It will be appreciated that pharmaceutically acceptable salts of the compounds according to formula (I) may be prepared. Indeed, in certain embodiments of the invention, pharmaceutically acceptable salts of the compounds according to formula (I) may be preferred over the respective free base because such salts impart greater stability or solubility to the molecule thereby facilitating formulation into a dosage form. Accordingly, the invention is further directed to compounds of formula (I) and pharmaceutically acceptable salts thereof.

As used herein, the term 'pharmaceutically acceptable salts' refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

Compounds according to formula (I) contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, iso-butyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and naphthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

A compound of formula (I) may be prepared by coupling of a diamino-(hetero)aryl compound of formula (II) with a carboxylic acid of formula (III) according to Scheme 1.

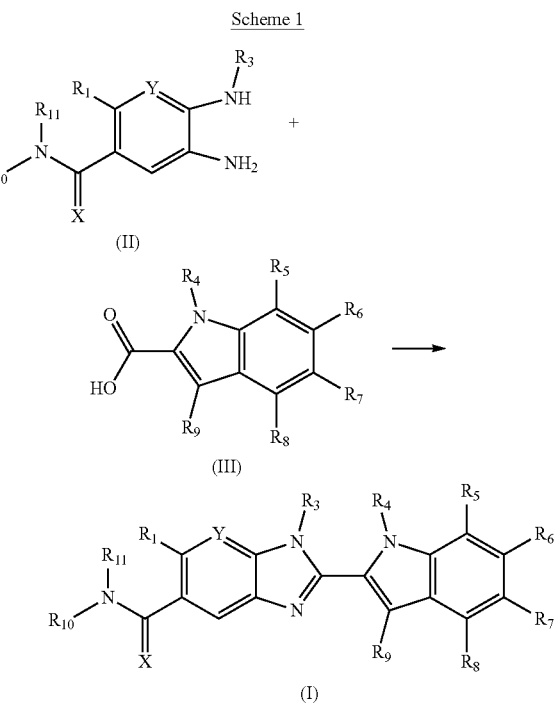

Accordingly in a first aspect there is provided a process for the preparation of a compound of formula (I) by coupling of a compound of formula (II) with a compound of formula (III), wherein Y, X, $R_1$ and $R_3$-$R_{11}$ are as hereinbefore defined, and thereafter, if required, preparing a salt of the compound so formed.

For example, to a solution of a compound of formula (III) in a suitable solvent, for example N,N-dimethylformamide, is added a coupling agent, for example HATU, and a suitable base, for example DIPEA, followed by a compound for formula (II), and the reaction stirred at a suitable temperature, for example ambient temperature, for a suitable length of time, for example 1-3 hours. The amide intermediate is obtained using routine purification methods. The amide intermediate is dissolved in a suitable solvent (for instance toluene) and treated with a suitable acid, for instance acetic acid, at a suitable temperature, for instance reflux, for a suitable length of time, for instance 1.5 h. Standard purification procedures afford the compound of formula (I).

Alternatively, a compound of formula (I) may be prepared by coupling of a nitro-substituted amino-(hetero)aryl of formula (IV) with an aldehyde of formula (V) according to Scheme 2.

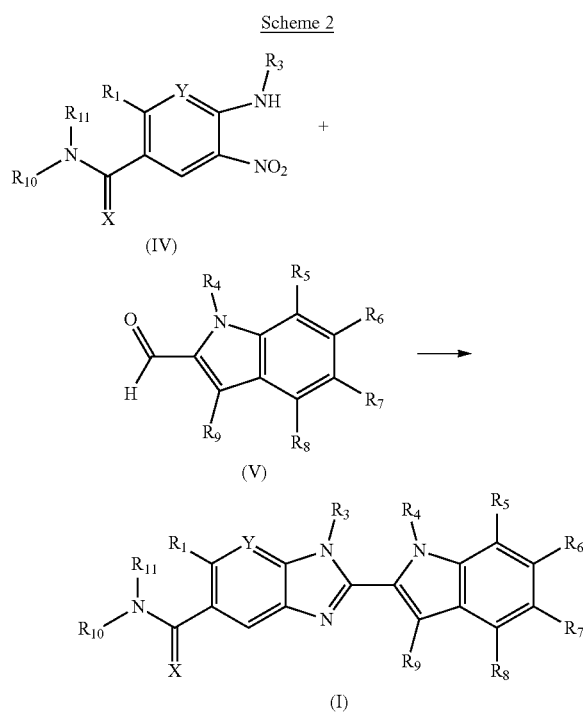

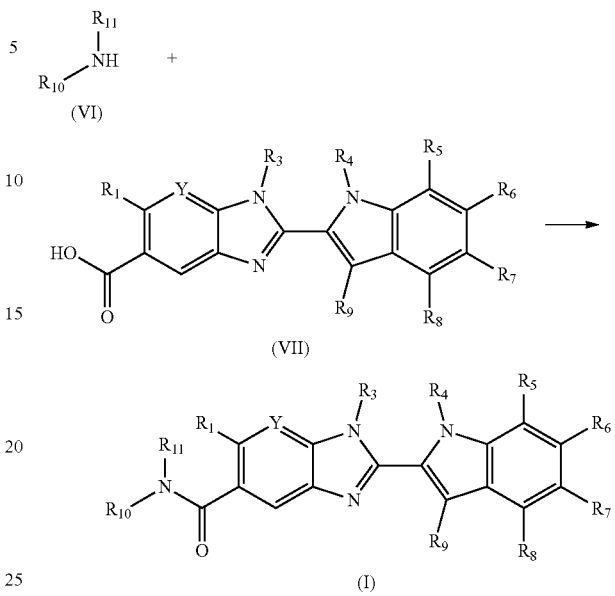

Accordingly, in a further aspect there is provided a process for the preparation of a compound of formula (I) by coupling of a compound of formula (IV) with a compound of formula (V) wherein Y, X, $R_1$ and $R_3$-$R_{11}$ are as hereinbefore defined, and thereafter, if required, preparing a salt of the compound so formed.

For example, to a solution of a compound of formula (IV) in a suitable solvent, for example ethanol, is added sodium hydrosulphite in a suitable solvent, for example ethanol/water mixture, and a compound for formula (V), and the reaction stirred at a suitable temperature, for example elevated temperature, for example 85° C., for a suitable length of time, for example overnight. The reaction mixture the undergoes standard work up and purification to afford the compound of formula (I)

Alternatively, compounds of formula (I), wherein X is O, may be prepared by coupling of an amine of formula (VI) with a carboxylic acid of formula (VII) according to Scheme 3.

Compounds of formula (I), wherein X is S, may be prepared from the corresponding amide (compound of formula (I) wherein X is O) according to Scheme 10.

Accordingly, in a further aspect there is provided a process for the preparation of a compound of formula (I) by coupling of an amine of formula (VI) with a carboxylic acid or of formula (VII) wherein Y, X, $R_1$ and $R_3$-$R_{11}$ are as hereinbefore defined, and thereafter, if required, preparing a salt of the compound so formed.

For example, to a solution of a compound of formula (VII) in a suitable solvent, for example N,N-dimethylformamide, is added a peptide coupling agent, for example o-(7-azabenzotriazol-1-yl)-N,N,N',N'-tetramethyluronium hexafluorophosphate (HATU), and a suitable base, for example diisopropylethylamine (DIPEA), followed by a compound for formula (VI), and the reaction stirred at a suitable temperature, for example ambient temperature, for a suitable length of time, for example 1-3 hours.

A compound of formula (II) may be prepared from the ester (XIII) by treatment of the ester with amine (IX) to afford the ester (X) followed by treatment of the ester (X) with amine (VI) to afford the nitro-compound (IV), and reduction of the nitro-compound (IV) to afford the amine (II), according to Scheme 4.

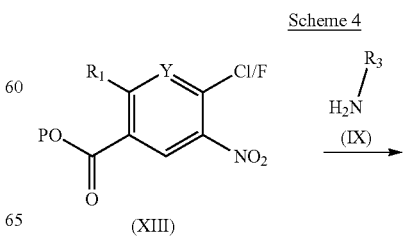

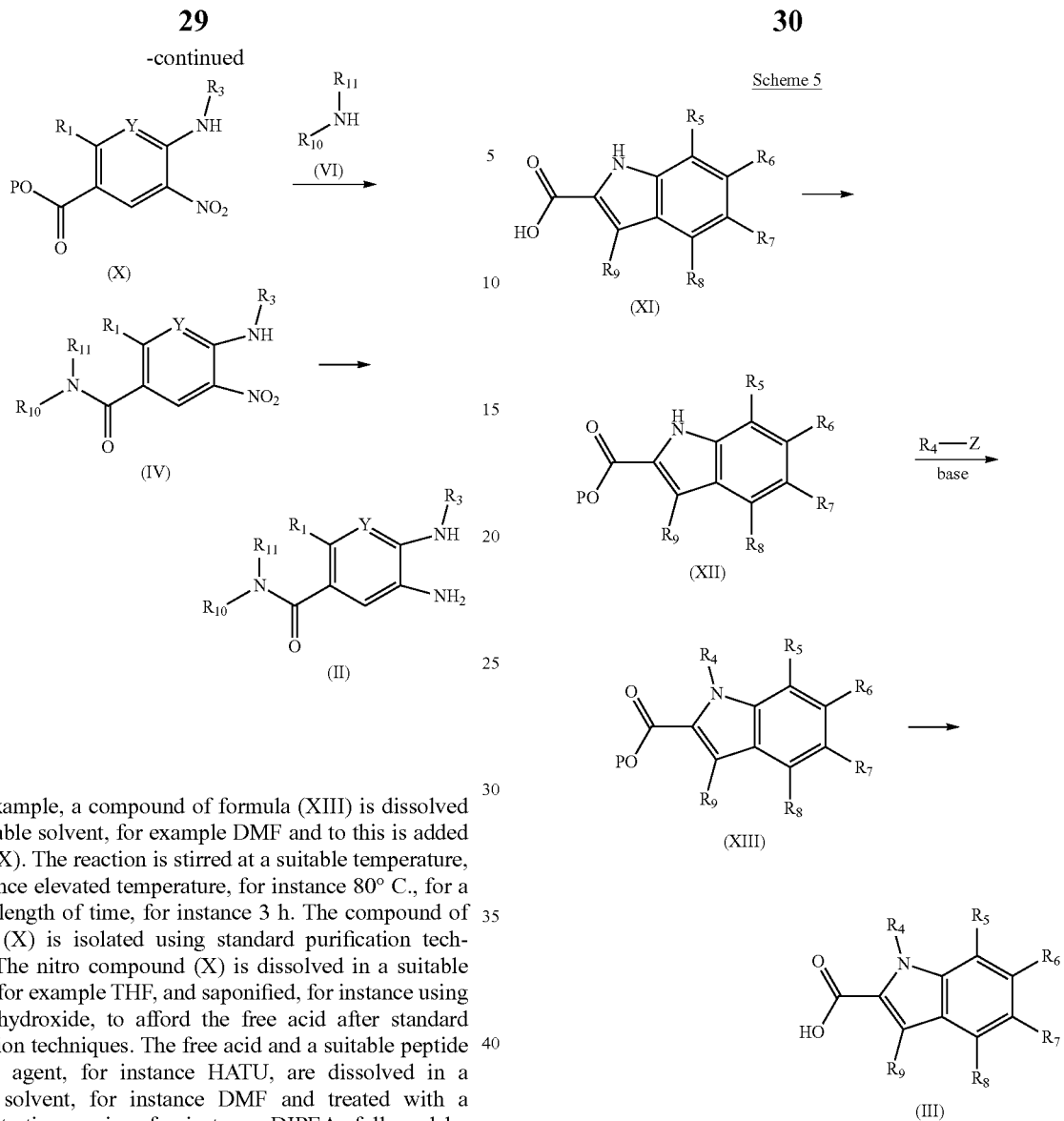

For example, a compound of formula (XIII) is dissolved in a suitable solvent, for example DMF and to this is added amine (IX). The reaction is stirred at a suitable temperature, for instance elevated temperature, for instance 80° C., for a suitable length of time, for instance 3 h. The compound of formula (X) is isolated using standard purification techniques. The nitro compound (X) is dissolved in a suitable solvent, for example THF, and saponified, for instance using lithium hydroxide, to afford the free acid after standard purification techniques. The free acid and a suitable peptide coupling agent, for instance HATU, are dissolved in a suitable solvent, for instance DMF and treated with a suitable tertiary amine, for instance DIPEA, followed by addition of amine (VI). The mixture is stirred at a suitable temperature, for instance ambient temperature, for a suitable length of time, for instance 1.5 h. The carbamate compound (VI) is isolated by standard purification techniques. The carbamate compound (VI) in a suitable solvent, for example ethanol, is added to a flushed hydrogenation flask containing a suitable hydrogenation catalyst, for example palladium on charcoal, and stirred under a hydrogen atmosphere for a suitable length of time, for instance 44 h. The catalyst is removed by filtration and the diamine (II) is obtained through standard purification conditions.

Amines of formula (IX) are commercially available (for instance from Sigma Aldrich). Compounds of formula (III) wherein $R_4$ is other than H can be obtained from the carboxylic acid (XI) (a compound of formula (III) wherein $R_4$ is H) by protection of the carboxylic acid to form the ester (XII) followed by alkylation to afford the protected ester (XIII) followed by saponification to afford the carboxylic acid (III), according to Scheme 5.

Carboxylic acids of formula (XI) are commercially available. Some esters of formula (XII) are commercially available.

For example a compound of formula (XII) in a suitable solvent, for example DMF, is treated with a base, for example sodium hydride, at a suitable temperature, for instance 0° C., for a suitable length of time, for instance 1 h. A suitable alkylating agent $R_4$—Z, for instance iodoethane, is added and the mixture stirred at a suitable temperature, for instance 0° C., for a suitable length of time, for instance over 2 days. The N-alkylated ester (XIII) is isolated using standard purification techniques. The ester (XIII) is dissolved in a suitable solvent, for instance a water/methanol/THF mixture, and a base, for instance lithium hydroxide monohydrate, is added and the mixture stirred at a suitable temperature, for instance ambient temperature, for a suitable length of time, for instance overnight. The carboxylic acid (III) is obtained using standard purification techniques.

Compounds of formula (VIII) may be prepared from the corresponding carboxylic acid (XIV) by nitration of the carboxylic acid to afford the nitro-compound (XV) followed by esterification to afford (VIII) according to Scheme 6.

Carboxylic acids of formula (XIV), and many acids of formula (XV) and esters of formula (VIII), are commercially available.

Scheme 6

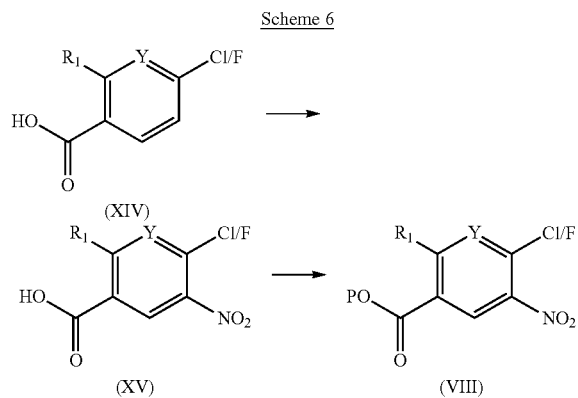

For example a compound of formula (XIV) is treated with concentrated sulphuric acid at a suitable temperature, for instance −20° C. and fuming nitric acid is added and the mixture allowed to warm to a suitable temperature, for instance ambient temperature, for a suitable length of time, for instance 2 hours. Standard workup affords the nitrated carboxylic acid (XV). The compound (XV) is dissolved in a suitable protic solvent, for instance methanol, and treated with an acid, for instance hydrochloric acid, at a suitable temperature, for instance elevated temperature, for instance 80° C., for a suitable length of time, for instance overnight. After acidification and standard workup, the ester (VIII) is obtained.

Aldehydes of formula (V) may be obtained from the indole of formula (XVI) according to Scheme 7. Aldehydes of formula (V) may also be prepared by alkylation of commercially available aldehydes of formula (XVIII).

Scheme 7

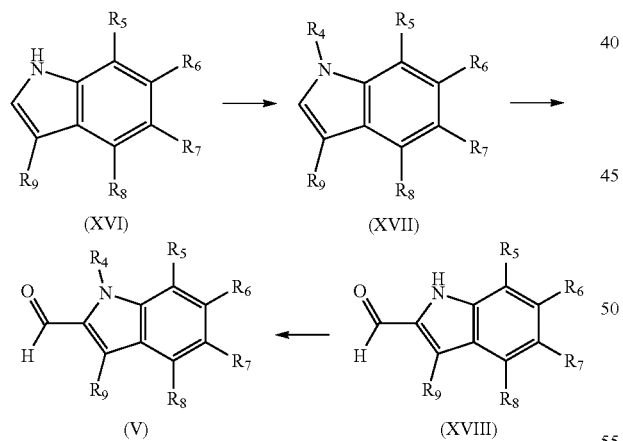

For instance a compound of formula (XVI) is dissolved in a suitable solvent, for instance DMF, and treated with a suitable base, for instance sodium hydride, at a suitable temperature, for instance ambient temperature, for a suitable length of time, for instance 2 minutes. The mixture is then treated with a suitable alkylating agent, for instance ethyl iodide, at a suitable temperature, for instance ambient temperature, for a suitable length of time, for instance 4.5 h. Standard workup affords the indole of formula (XVII). The indole (XVII) is dissolved in a suitable solvent, for instance anhydrous THF, at a suitable temperature, for instance 0° C.

A suitable base, for instance n-butyl lithium in hexanes, is then added over a suitable length of time, for instance 10 minutes, at a suitable temperature, for instance 0° C. The reaction is stirred for a suitable length of time, for instance 1.5 h, at a suitable temperature, for instance ambient temperature. The reaction is the cooled to a suitable temperature, for instance −78° C. and DMF is added and the reaction stirred for a further suitable length of time, for instance 2.5 hours. The reaction is quenched by addition of a suitable reagent, for instance sodium hydrogen carbonate solution. The aldehyde of formula (V) can be obtained using standard purification techniques.

The carboxylic acid of formula (VII) may be obtained from the corresponding halo-substituted indole of formula (XX) which may be obtained by reacting the aldehyde of formula (V) with the brominated compound of formula (XIX), according to Scheme 8.

Scheme 8

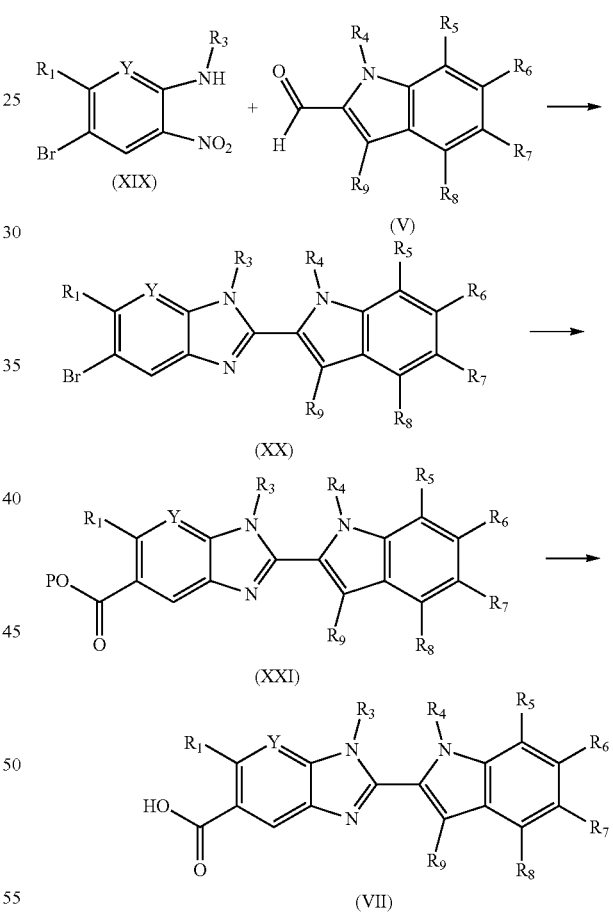

For example, a solution of sodium dithionate in a suitable solvent, for instance water, is is added to a microwave vial and a solution of nitro compound of formula (XIX) and aldehyde of formula (V) in a suitable solvent, for instance ethanol, is added. The reaction vessel is sealed and heated using a microwave at a suitable temperature, for instance 100° C., for a suitable length of time, for instance 5 hours. The reaction mixture is diluted with a suitable solvent, for instance DCM, followed by standard purification techniques to obtain the indole compound of formula (XX).

The indole compound of formula (XX), a suitable acid protecting group provider, for instance methanol, a suitable base, for instance DIPEA and a suitable nucleophilic catalyst, for instance DMAP, and a suitable catalyst, for instance molybdenum hexacarbonyl and acetoxy(2-(di-o-tolylphosphino)benzyl palladium, are dissolved in a suitable solvent, for instance 1,4-dioxane, in a microwave vessel. The vessel is sealed and heated using microwaves at a suitable temperature, for instance 180° C., for a suitable length of time, for instance 3 hours, then allowed to cool. Standard purification techniques afford the ester of formula (XXI).

To a solution of the ester of formula (XXI) in a suitable solvent, for instance THF/water mixture, is added a suitable base, for instance lithium hydroxide, and the mixture is stirred for a suitable length of time, for instance 68 h, at a suitable temperature, for instance room temperature. The reaction mixture is filtered and then acidified using a suitable acid, for instance hydrochloric acid. Standard workup affords the carboxylic acid of formula (VII).

Alternatively, carboxylic acid derivatives of formula (VII) may be prepared by coupling of the nitro compound (X) with the aldehyde (V) to afford the ester (XXI), followed by saponification of the ester (XXI) to afford the carboxylic acid derivative (VII), according to Scheme 9.

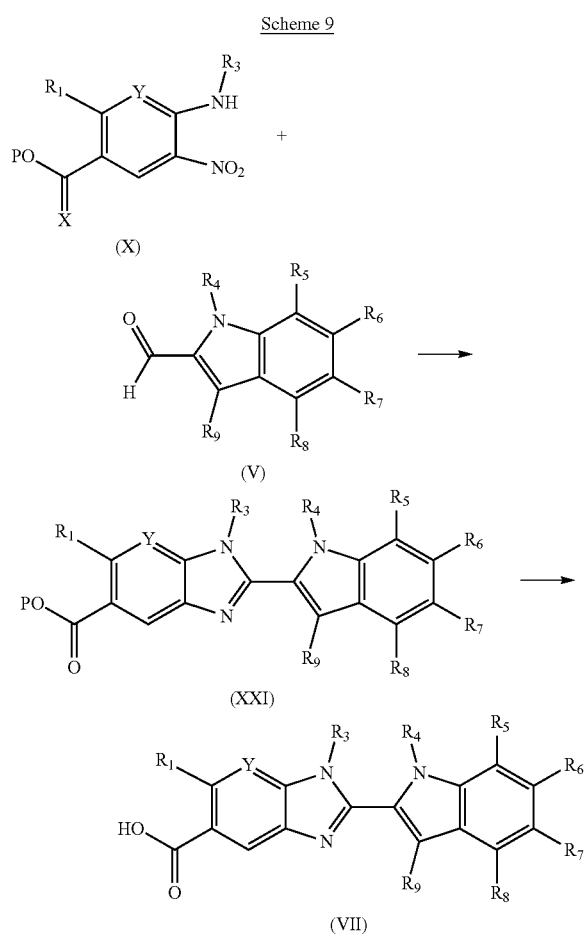

instance dimethoxyethane, at a suitable temperature, for instance reflux, for a suitable length of time, for instance 1 h. Standard purification affords the thioamide (compound of formula (I) wherein X is S).

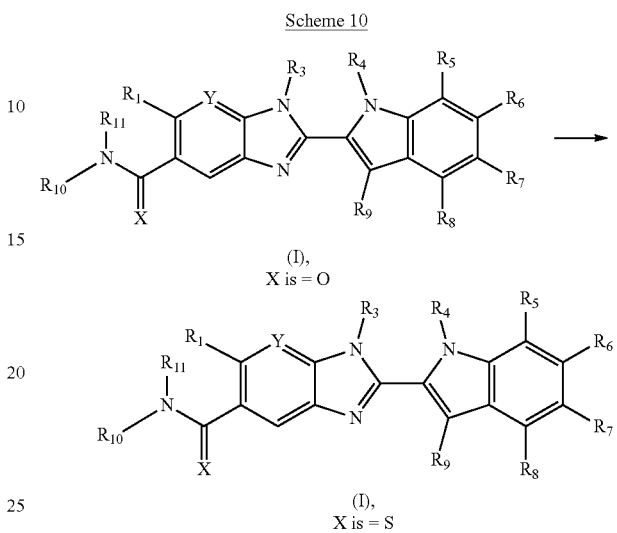

Accordingly, in a further aspect there is provided a process for the preparation of a compound of formula (I) wherein X is S by treatment of a compound of formula (I) wherein X is O and wherein Y, $R_1$ and $R_3$-$R_{11}$ are as hereinbefore defined, with Lawessons reagent, and thereafter, if required, preparing a salt of the compound so formed.

Examples of other protecting groups that may be employed in the synthetic routes described herein and the means for their removal can be found in T. W. Greene 'Protective Groups in Organic Synthesis', 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography or VCD (vibrational circular dichroism) analysis.

Compounds of formula (I) wherein X is S may be obtain from the corresponding amide (compound of formula (I) wherein X is O) according to Scheme 10, by treatment with Lawesons reagent and acetonitrile in a suitable solvent, for Methods of Use The compounds of the invention are inhibitors of PAD4. Compounds which inhibit PAD4 may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis.

The methods of treatment of the invention comprise administering a safe and effective amount of a compound of formula (I), or a pharmaceutically acceptable salt thereof, to a patient in need thereof. Individual embodiments of the invention include methods of treating any one of the above-mentioned disorders by administering a safe and effective amount of a compound of formula (I), or a pharmaceutically acceptable salt thereof, to a patient in need thereof.

As used herein, 'treat' in reference to a disorder means: (1) to ameliorate or prevent the disorder or one or more of the biological manifestations of the disorder, (2) to interfere with (a). one or more points in the biological cascade that leads to or is responsible for the disorder, or (b). one or more of the biological manifestations of the disorder, (3) to alleviate one or more of the symptoms or effects associated with the disorder, or (4) to slow the progression of the disorder or one or more of the biological manifestations of the disorder.

As indicated above, 'treatment' of a disorder includes prevention of the disorder. It will be appreciated that 'prevention' is not an absolute term. In medicine, 'prevention' is understood to refer to the prophylactic administration of a drug to substantially diminish the likelihood or severity of a disorder or biological manifestation thereof, or to delay the onset of such disorder or biological manifestation thereof.

As used herein, 'safe and effective amount' in reference to a compound of formula (I), or a pharmaceutically acceptable salt thereof, or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (for example, the potency, efficacy, and half-life of the compound will be considered); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, 'patient' refers to a human (including adults and children) or other animal. In one embodiment, 'patient' refers to a human.

The compounds of formula (I), or pharmaceutically acceptable salts thereof, may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered topically. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.1 mg to 10 mg per kg of total body weight, for example from 1 mg to 5 mg per kg of total body weight. For example, daily dosages for oral administration may be from 5 mg to 1 g per patient, such as 5 mg to 500 mg per patient, or 5 mg to 250 mg.

Additionally, the compounds of formula (I) may be administered as prodrugs. As used herein, a 'prodrug' of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by PAD4 activity comprising administering a safe and effective amount of a compound of formula (I), or a pharmaceutically acceptable salt thereof, to a patient in need thereof.

In one embodiment, the disorder mediated by PAD4 activity is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by PAD4 activity is rheumatoid arthritis. In a further embodiment, the disorder mediated by PAD4 activity is systemic lupus. In a further embodiment, the disorder mediated by PAD4 activity is vasculitis. In a further embodiment, the disorder mediated by PAD4 activity is cutaneous lupus erythematosis. In a further embodiment, the disorder mediated by PAD4 activity is psoriasis.

In one embodiment there is provided a method of treating rheumatoid arthritis, vasculitis, systemic lupus erythematosus, ulcerative colitis, cancer, cystic fibrosis, asthma, cutaneous lupus erythematosis, or psoriasis, which method comprises administering to a patient in need thereof, a therapeutically effective amount of a compound of formula (I), or a pharmaceutically acceptable salt thereof.

In one embodiment there is provided a method of treating rheumatoid arthritis, which method comprises administering to a patient in need thereof, a therapeutically effective amount of a compound of formula (I), or a pharmaceutically acceptable salt thereof. In one embodiment there is provided a method of treating systemic lupus, which method comprises administering to a patient in need thereof, a therapeutically effective amount of a compound of formula (I), or a pharmaceutically acceptable salt thereof. In one embodiment there is provided a method of treating vasculitis, which method comprises administering to a patient in need thereof, a therapeutically effective amount of a compound of formula (I), or a pharmaceutically acceptable salt thereof. In one embodiment there is provided a method of treating cutaneous lupus erythematosis, which method comprises administering to a patient in need thereof, a therapeutically effective amount of a compound of formula (I), or a pharmaceutically acceptable salt thereof. In one embodiment there is provided a method of treating psoriasis, which method comprises administering to a patient in need thereof, a therapeutically effective amount of a compound of formula (I), or a pharmaceutically acceptable salt thereof.

In one embodiment, the invention provides a compound of formula (I), or a pharmaceutically acceptable salt thereof, for use in therapy. In another embodiment, the invention provides a compound of formula (I), or a pharmaceutically acceptable salt thereof, for use in the treatment of a disorder mediated by PAD4 activity. In another embodiment, the invention provides a compound of formula (I), or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a compound of formula (I), or a pharmaceutically acceptable salt thereof, for use in the treatment of rheumatoid arthritis. In another embodiment, the invention provides a compound of formula (I), or a pharmaceutically acceptable salt thereof, for use in the treatment of systemic lupus. In another embodiment, the invention provides a compound of formula (I), or a pharmaceutically acceptable salt thereof, for use in the treatment of vasculitis. In another embodiment, the invention provides a compound of formula (I), or a pharmaceutically acceptable salt thereof, for use in the treatment of cutaneous lupus erythematosis. In another embodiment, the invention provides a compound of formula (I), or a pharmaceutically acceptable salt thereof, for use in the treatment of psoriasis. In another embodiment, the invention provides the use of a compound of formula (I), or a pharmaceutically acceptable salt thereof, in the manufacture of a medicament for use in the treatment of a disorder mediated by PAD4 activity. In another embodiment, the invention provides the use of a compound of formula (I), or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a compound of formula (I), or a pharmaceutically acceptable salt thereof, in the manufacture of a medicament for use in the treatment of rheumatoid arthritis. In another embodiment, the invention provides the use of a compound of formula (I), or a pharmaceutically acceptable salt thereof, in the manufacture of a medicament for use in the treatment of systemic lupus. In another embodiment, the invention provides the use of a compound of formula (I), or a pharmaceutically acceptable salt thereof, in the manufacture of a medicament for use in the treatment of vasculitis. In another embodiment, the invention provides the use of a compound of formula (I), or a pharmaceutically acceptable salt thereof, in the manufacture of a medicament for use in the treatment of cutaneous lupus erythematosis. In another embodiment, the invention provides the use of a compound of formula (I), or a pharmaceutically acceptable salt thereof, in the manufacture of a medicament for use in the treatment of psoriasis.

In a further embodiment, the invention provides a pharmaceutical composition for the treatment or prophylaxis of a disorder mediated by PAD4 activity comprising a compound of formula (I) or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a compound of formula (I) or a pharmaceutically acceptable salt thereof. In a further embodiment, the invention provides a pharmaceutical composition for the treatment or prophylaxis of rheumatoid arthritis comprising a compound of formula (I) or a pharmaceutically acceptable salt thereof. In a further embodiment, the invention provides a pharmaceutical composition for the treatment or prophylaxis of systemic lupus comprising a compound of formula (I) or a pharmaceutically acceptable salt thereof. In a further embodiment, the invention provides a pharmaceutical composition for the treatment or prophylaxis of vasculitis comprising a compound of formula (I) or a pharmaceutically acceptable salt thereof. In a further embodiment, the invention provides a pharmaceutical composition for the treatment or prophylaxis of cutaneous lupus erythematosis comprising a compound of formula (I) or a pharmaceutically acceptable salt thereof. In a further embodiment, the invention provides a pharmaceutical composition for the treatment or prophylaxis of psoriasis comprising a compound of formula (I) or a pharmaceutically acceptable salt thereof Compositions The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. In a further aspect the invention is directed to pharmaceutical compositions for the treatment or prophylaxis of a disorder mediated by PAD4 activity comprising a compound of formula (I) or a pharmaceutically acceptable salt thereof.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

As used herein, 'pharmaceutically acceptable excipient' means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrroli done, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavoured aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilisers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

In another aspect, the invention is directed to a dosage form adapted for administration to a patient by inhalation, for example, as a dry powder, an aerosol, a suspension, or a solution composition.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 200 µg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 200 µg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.01 to 10% by weight. Generally, for most types of preparations, the proportion used will be within the range of from 0.05 to 1%, for example from 0.1 to 0.5%.

Aerosol formulations are preferably arranged so that each metered dose or 'puff' of aerosol contains from 20 g to 10 mg, preferably from 20 µg to 5 mg, more preferably from about 20 µg to 0.5 mg of a compound of formula (I). Administration may be once daily or several times daily, for example 2, 3, 4 or 8 times, giving for example 1, 2 or 3 doses each time. The overall daily dose with an aerosol will be within the range from 100 µg to 10 mg, for example from 200 µg to 5 mg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the 'twin impinger' analytical process. As used herein reference to the 'twin impinger' assay means 'Determination of the deposition of the emitted dose in pressurised inhalations using apparatus A' as defined in British Pharmacopaeia 1988, pages A204-207, Appendix XVII C. Such techniques enable the 'respirable fraction' of the aerosol formulations to be calculated. One method used to calculate the 'respirable fraction' is by reference to 'fine particle fraction' which is the amount of active ingredient collected in the lower impingement chamber per actuation expressed as a percentage of the total amount of active ingredient delivered per actuation using the twin impinger method described above.

The term 'metered dose inhaler' or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO 96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO 96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebuliser. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulfosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO 05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO 05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research,* 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area. Over skin areas, occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The invention will now be illustrated by way of the following non-limiting examples.

General Methods

Unless stated otherwise, starting materials were commercially available. All solvents and commercial reagents were of laboratory grade and were used as received.

Where diastereoisomers are represented and only the relative stereochemistry is referred to, the bold or hashed solid bond symbols (━ / ⁞⁞⁞⁞) are used. where the absolute stereochemistry is known and the compound is a single enantiomer, the bold or hashed wedges symbols (━ / ⁞⁞⁞⁞) are used as appropriate.

Analytical Methods

Method A

LCMS was conducted on an Acquity UPLC BEH $C_{18}$ column (50 mm×2.1 mm i.d. 1.7 µm packing diameter) at 40 degrees centigrade, eluting with 10 mM ammonium bicarbonate in water adjusted to pH 10 with ammonia solution (Solvent A) and acetonitrile (Solvent B) using the following elution gradient: 0-1.5 min: 1-97% B, 1.5-1.9 min: 97% B, 1.9-2.0 min: 100% B at a flow rate of 1 mL/min. The UV detection was a summed signal from wavelength of 210 nm to 350 nm. The mass spectra were recorded on a Waters ZQ Mass Spectrometer using Alternate-scan Positive and Negative Electrospray. Ionisation data were rounded to the nearest integer.

Method B

LCMS was conducted on an Acquity UPLC BEH $C_{18}$ column (50 mm×2.1 mm i.d. 1.7 µm packing diameter) at 40 degrees centigrade, eluting with 0.1% v/v solution of formic acid in water (Solvent A) and 0.1% v/v solution of formic acid in acetonitrile (Solvent B) using the following elution gradient: 0-1.5 min: 3-100% B, 1.5-1.9 min: 100% B, 1.9-2.0 min: 3% B at a flow rate of 1 mL/min. The UV detection was a summed signal from wavelength of 210 nm to 350 nm. The mass spectra were recorded on a Waters ZQ Mass Spectrometer using Alternate-scan Positive and Negative Electrospray. Ionisation data were rounded to the nearest integer.

Method C

LCMS was conducted on an Acquity UPLC BEH $C_{18}$ column (50 mm×2.1 mm i.d. 1.7 µm packing diameter) at 40 degrees centigrade, eluting with 0.1% v/v solution of trifluoroacetic acid in water (Solvent A) and 0.1% v/v solution of trifluoroacetic acid in acetonitrile (Solvent B) using the following elution gradient: 0-1.5 min: 3-100% B, 1.5-1.9 min: 100% B, 1.9-2.0 min: 3% B at a flow rate of 1 mL/min. The UV detection was a summed signal from wavelength of 210 nm to 350 nm. The mass spectra were recorded on a Waters ZQ Mass Spectrometer using Alternate-scan Positive and Negative Electrospray. Ionisation data were rounded to the nearest integer.

Method D

LCMS was conducted on a HALO $C_{18}$ column (50 mm×4.6 mm i.d. 2.7 µm packing diameter) at 40 degrees centigrade, eluting with 0.1% v/v solution of formic acid in water (Solvent A) and 0.1% v/v solution of formic acid in acetonitrile (Solvent B) using the following elution gradient: 0-1 min: 5% B, 1-2.01 min: 95% B, 2.01-2.5 min: 5% B at a flow rate of 1.8 mL/min. The UV detection was a summed signal at wavelength: 214 nm and 254 nm. MS: Ion Source: ESI; Drying Gas Flow: 10 L/min; Nebuliser Pressure: 45 psi; Drying Gas Temperature: 330° C.; Capillary Voltage: 4000V.

Method E

LCMS was conducted on a HALO $C_{18}$ column (50 mm×4.6 mm i.d. 2.7 m packing diameter) at 40 degrees centigrade, eluting with 0.1% v/v solution of formic acid in water (Solvent A) and 0.1% v/v solution of formic acid in acetonitrile (Solvent B) using the following elution gradient: 0-1.8 min: 5% B, 1.8-2.01 min: 100% B, 2.01-2.8 min: 5% B at a flow rate of 1.5 mL/min. The UV detection was a summed signal at wavelength: 214 nm and 254 nm. MS: Ion Source: ESI; Detector Voltage: 1.4 KV; Heat Block temp.: 250'C; CDL temp.: 250° C.; Nebuliser Gas Flow: 1.5 mL/min.

General GCMS Method

GCMS was conducted on an Agilent 6890/5973 GCMS equipment with an Agilent capillary column HP-5 (0.25 ☐m×30 m, i.d. 0.25 mm). The initial temperature was 50° C. The equilibration time was 0.50 min. The initial time was 1.00 min. The temperature then increased to 180° C. with a rate of 10°/min, then rose to 240° C. with a rate of 20° C./min, then was held at 240° C. for 5.00 min. The injection mode was splitless. The gas flow was 1.00 mL/min and the total flow was 23.2 mL/min. The average velocity was 36 cm/sec. The acquisition mode was scan. The ionization method was 70 eV EI (Electronic Ionization).

$^1$H NMR spectra were recorded using a Bruker DPX 400 MHz, referenced to tetramethylsilane.

Silica chromatography techniques include either automated (Flashmaster, Biotage SP4) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Similarly, when a literature or a patent reference is given after the name of a compound, for instance 'compound Y (EP 0 123 456)', this means that the preparation of the compound is described in the named reference.

The names of the intermediates and examples have been obtained using the compound naming programme within ChemBioDraw Ultra v12, or alternatively using "ACD Name Pro 6.02".

General MDAP Purification Methods

Listed below are examples of mass-directed autopreparative chromatography (MDAP) methods that have been used or may be used in compound purification.

MDAP (Method A).

The HPLC analysis was conducted on an XBridge C18 column (100 mm×30 mm i.d. 5 µm packing diameter) at ambient temperature, eluting with 10 mM Ammonium Bicarbonate in water adjusted to pH 10 with Ammonia solution (Solvent A) and Acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method B).

The HPLC analysis was conducted on a Sunfire C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method C).

The HPLC analysis was conducted on a Sunfire C18 column (150 mm×30 mm i.d. 5 μm packing diameter) at ambient temperature, eluting with 0.1% v/v solution of Trifluoroacetic Acid in Water (Solvent A) and 0.1% v/v solution of Trifluoroacetic Acid in Acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

General Chiral HPLC Methods

Method A: Chiral Analytical Chromatography

| | |
|---|---|
| Column | Chiralpak AD-H, 250 × 4.6 mm |
| Mobile Phase | A: n-Hexane    B: Ethanol |
| Gradient Profile | 90:10 mobile phase A:B |
| Flow Rate | 1 mL/min |
| Column Temperature | 20° C. |
| Detection wavelength | 215 nm or UV DAD (300 nm (bandwidth 180 nm, reference 550 nm (bandwidth 100 nm)) |

Method B: Chiral Preparative Chromatography

| | |
|---|---|
| Column | Chiralpak AD-H, 250 × 30 mm, 5 μm [ADH10029-01] |
| Mobile Phase | A: n-Hexane    B: Ethanol |
| Gradient Profile | Stepped Isocratic system - 90:10 mobile phase A:B |
| Run Time | 20 min |
| Flow Rate | 45 mL/min |
| Column Temperature | 20° C. |
| Detection | UV DAD (300 nm (bandwidth 180 nm, reference 550 nm (bandwidth 100 nm)) |

Method C: Chiral Preparative Chromatography

Initial Conditions:

| | |
|---|---|
| Column | Chiralpak AD, 250 × 20 mm, 20 μm [self packed] |
| Mobile Phase | A: n-Hexane    B: Ethanol |
| Gradient Profile | 90:10 mobile phase A:B |
| Flow Rate | 75 mL/min |
| Column Temperature | 20° C. |
| Detection wavelength | 215 nm |

An initial cut of the leading edge of the peak was taken using the initial conditions. This gave an enriched cut of the desired first eluting isomer which was then further purified using the secondary conditions.

Secondary Conditions:

| | |
|---|---|
| Column | Chiralpak AD-H, 250 × 30 mm, 5 μm [ADH10029-01] |
| Mobile Phase | A: n-Hexane    B: Ethanol |
| Gradient Profile | 90:10 mobile phase A:B |
| Flow Rate | 40 mL/min |
| Column Temperature | 20° C. |
| Detection wavelength | 215 nm |

Chiral (Analytical) HPLC Method D:

The analytical chiral HPLC spectra were recorded on a standard Agilent 1100 series HPLC system using a DAD UV detector, fitted with a 25 cm×0.46 cm Chiralpak IC column [ICOOCE-OG022], eluting with 60% isopropanol/heptanes at a rate of 1 mL/min at rt and analysing at a wavelength of 215 nm.

Chiral (Preparative) HPLC Method E:

Approx 110 mg racemate dissolved in IPA (2 mL) and heptane (1 mL). Injection; 1.5 mL of the above sample solution was injected onto the column (2 cm×25 cm Chiralpak IC Lot No.IC00CJ-LG008) eluting with 50% IPA/heptane, at a rate of 20 mL/min and analysing at a wavelength of 215 nm.

Chiral (Preparative) HPLC Method F:

Approx 95 mg racemate dissolved in EtOH (3 mL) and heptane (2 mL). Injection; 1 mL of the above sample solution was injected onto the column (2 cm×25 cm Chiralpak IC Lot No.IC00CJ-LG008) eluting with 30% EtOH/heptane, at a rate of 20 mL/min and analysing at a wavelength of 215 nm.

Chiral (Preparative) HPLC Method G:

Approx 100 mg racemate dissolved in EtOH (1 mL) and heptane (1 mL). Injection; 2 mL of the above sample solution was injected onto the column (30 mm×25 cm Chiralpak IC Lot No.IC10028-01) eluting with 20% EtOH/heptane, at a rate of 30 mL/min and analysing at a wavelength of 215 nm.

Chiral (Preparative) HPLC Method H1:

Approx 100 mg racemate dissolved in EtOH (1 mL) and heptane (1 mL). Injection; 2 mL of the above sample solution was injected onto the column (2 cm×25 cm Chiralpak IC Lot No.IC00CJ-LG008) eluting with 30% EtOH/heptane, at a rate of 20 mL/min and analysing at a wavelength of 215 nm. In total, 8 injections were made. Fraction Collection: Fractions from 21.5-23 mins were bulked and labelled peak 1. Fractions from 23.5-26.5 mins were bulked and labelled peak 2. Fractions from 27-31 mins were bulked and labelled peak 3. The bulked fractions were then concentrated in vacuo using a rotary evaporator and transferred to a weighed flask for final analysis as described by the analytical method (H1) below Peak 1 (36 mg)

Peak 2 (272 mg)

Peak 3 (209 mg)

Analytical HPLC Method H1:

Approx 0.5 mg sample dissolved in 50% EtOH/Heptane (1 mL). Injection; 20 μL of the above sample solution was injected onto the column (4.6 mm×25 cm Chiralpak IC Lot No. IC00CE-LI045) eluting with 50% EtOH/heptane, at a rate of 1 mL/min and analysing at a wavelength of 215 nm.

It was known that peak 2 (272 mg) probably contained two compounds. A second analytical and preperative method were developed to isolate the two compounds (see below).

Analytical HPLC Method H2:

Approx 0.5 mg sample dissolved in 50% IPA/Heptane (1 mL). Injection; 20 μL of the above sample solution was injected onto the column (4.6 mm×25 cm Chiralpak AD Lot No. AD00CE-KF099) eluting with 25% IPA/heptane, at a rate of 1 mL/min and analysing at a wavelength of 215 nm.

Preparative HPLC Method H2:

Approx 100 mg racemate dissolved in IPA (1 mL) and heptane (1 mL). Injection; 2 mL of the above sample solution was injected onto the column (2 cm×25 cm Chiralpak AD Lot No. AD00CJ-JA001) eluting with 20% IPA/heptane, at a rate of 20 mL/min and analysing at a wavelength of 215 nm. In total, 3 injections were made. Fraction Collection: Fractions from 12-16 mins were bulked and labelled peak 1. Fractions from 18-30 mins were bulked and labelled peak 2. The bulked fractions were then concentrated in vacuo using a rotary evaporator and transferred to a weighed flask for final analysis as described by the analytical HPLC method (H2) above.

Peak 1 (28 mg)

Peak 2 (239 mg)—peak 2 was the desired enantiomer and was carried forward

Chiral (Preparative) HPLC Method I:

Approx 24 mg racemate dissolved in EtOH (2 mL) and heptane (2 mL). Injection; 4 mL of the above sample solution was injected onto the column (30 mm×25 cm Chiralpak ADH (5 um) Lot No. ADH10029-01) eluting with 80% EtOH/heptane, at a rate of 30 mL/min and analysing at a wavelength of 215 nm.

Chiral (Preparative) HPLC Method J:

Approx 80 mg racemate dissolved in EtOH (4 mL)+ isopropylamine (1 mL) and heptane (3 mL). Injection; 0.25 mL of the above sample solution was injected onto the column (2 cm×25 cm Chiralpak IB Lot No. IB00CJ-KD002) eluting with 10% EtOH (+0.2% isopropylamine)/heptane, at a rate of 20 mL/min and analysing at a wavelength of 215 nm. Total number of injections=25.

Chiral (Preparative) HPLC Method K:

Sample (275 mg) was dissolved in IPA. Repeat injections of 0.4-0.5 mL were then made manually with plastic 1 mL syringe onto the column (2 cm×25 cm Chiralpak IA (5 um)) eluting with 25% IPA (+0.2% isopropylamine)/hexane, at a rate of 20 mL/min and analysing on a UV DAD at a wavelength of 300 nm (bandwidth 180 nm, reference 550 nm (bandwidth 100 nm)).

Chiral (Preparative) HPLC Method L:

Sample (183 mg) was dissolved in EtOH. Repeat injections of 0.75 mL were then made manually with plastic 1 mL syringe onto the column (2 cm×25 cm Chiralpak IC (5 um)) eluting with 100% EtOH (+0.2% isopropylamine), at a rate of 15 mL/min and analysing on a UV DAD at a wavelength of 300 nm (bandwith 180 nm, reference 550 nm (bandwidth 100 nm), also 218 nm and 280 nm (no reference)). Combined fraction solutions were evaporated to dryness using a rotary evaporator. Chiral analysis of fraction 2 indicated the presence of 5% of isomer 1. This sample was therefore re-chromatographed using the same system (ca 40 mg in 4 mL, 0.5 mL injections) and fractions corresponding to the second eluting isomer in the analysis pooled and concentrated as above.

Chiral (Preparative) HPLC Method M:

Sample (40 mg) was dissolved in EtOH (~4 mL). Repeat injections of 0.5 mL (+0.1 mL isopropylamine) were then made manually with plastic 1 mL syringe onto the column (2 cm×25 cm Chiralpak IA (5 □m)) eluting with 30% EtOH (+0.2% isopropylamine)/heptane, at a rate of 45 mL/min and analysing on a UV DAD at a wavelength of 300 nm (bandwith 180 nm, reference 550 nm (bandwidth 100 nm)). Combined fraction solutions were evaporated to dryness using a rotary evaporator. Chiral analysis of fraction 2 indicated the presence of 5% of isomer 1. This sample was therefore re-chromatographed using the following conditions: 0.45 mL of sample was diluted with 0.45 mL hexane and 100 uL of isopropylamine added. This was injected using a 1 ml glass syringe onto the column (2 cm×25 cm Chiralpak IA (5 um)) eluting with 30%→50% EtOH (+0.2% isopropylamine)/heptane, at a rate of 45 mL/min and analysing on a UV DAD at a wavelength of 300 nm (bandwidth 180 nm, reference 550 nm (bandwidth 100 nm)).

Chiral (Preparative) HPLC Method N:

Approx 110 mg racemate dissolved in EtOH (1 mL) and heptane (1 mL). Injection; 1 mL of the above sample solution was injected onto the column (30 mm×25 cm Chiralpak ADH (5 um) Lot No. ADH10029-01) eluting with 25% EtOH/heptane, at a rate of 40 mL/min and analysing at a wavelength of 215 nm. Total number of injections=2.

Intermediate 1: 1-Ethyl-7-methyl-1H-indole

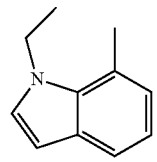

7-Methylindole (2.0 g, 15.25 mmol, commercially available from, for example, Apollo Scientific) in anhydrous DMF (20 mL) was treated with sodium hydride (60% in mineral oil, 0.67 g, 16.75 mmol). The mixture was stirred at ambient temperature under nitrogen for ~2 min, then treated with ethyl iodide (1.34 mL, 16.75 mmol). The reaction was stirred at ambient temperature under nitrogen for ~4.5 h, diluted with water and extracted with DCM (×3). The combined DCM extracts were dried (hydrophobic frit), reduced to dryness in vacuo and further dried at 55° C. under vacuum to give 1-ethyl-7-methyl-1H-indole as a pale brown oil (2.47 g).

$^1$H NMR (400 MHz): (DMSO-d6): δH 7.35 (1H, d), 7.29 (1H, d), 6.89-6.83 (2H, m), 6.40 (1H, d), 4.38 (2H, q), 2.68 (3H, s), 1.33 (3H, t).

Intermediate 2: 1-Ethyl-5-methyl-1H-indole

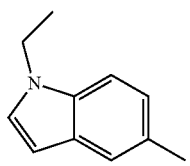

Prepared in a similar manner to Intermediate 1 from 5-methylindole (commercially available, from, for example Lancaster Synthesis Ltd.)

$^1$H NMR (DMSO-d6): δH 7.35-7.30 (3H, m), 6.95 (1H, d), 6.31 (1H, d0, 4.16 (2H, q), 2.37 (3H, s), 1.33 (3H, t)

Intermediate 3: 1-Ethyl-4-methyl-1H-indole

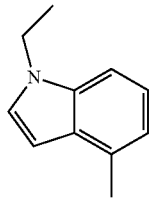

Prepared in a similar manner to Intermediate 1 from 4-methylindole (commercially available, from, for example Chondtech Inc.)

$^1$H NMR (DMSO-d6): δH 7.35 (1H, d), 7.27 (1H, d), 7.02 (1H, t), 6.81 (1H, d), 6.44 (1H, d), 4.18 (2H, q), 2.45 (3H, s), 1.34 (3H, t).

Intermediate 4: 3,4-Dihydro-2H-[1,4]oxazepino[2,3,4-hi]indole

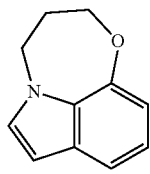 [SMILES: c1cc2c3c(c1)ccn3CCCO2]

To a solution of 7-(3-chloropropoxy)-1H-indole (2.71 g, 12.9 mmol, the preparation of this intermediate has been reported in Patent: US: 1998/5776963 A) in DMF (25 mL) that had been cooled using an ice-water bath, was added portionwise over 10 min sodium hydride (60% suspension in mineral oil, 1.03 g, 25.8 mmol). The reaction mixture was allowed to warm to rt over 1 h then cooled once more using an ice-water bath before HCl (1N, 25 mL) was added dropwise over 10 min with continuous stirring.

The mixture was partitioned using EtOAc (50 mL), the organic layer isolated then the aqueous layer re-extracted with EtOAc (2×50 mL). The combined organic layers were dried over MgSO$_4$ then concentrated under reduced pressure to give a pale brown liquid. The crude material was purified using column chromatography (eluted with cyclohexane and EtOAc from 0 to 20%) to give the title compound as a white solid, 1.78 g (79%).

LCMS (Method A): Rt=1.05 min, MH+=174.0.

Intermediate 5: 1-Ethyl-1H-indole-2-carbaldehyde

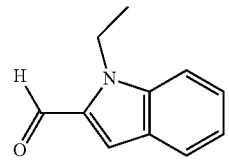

Dimethyl sulfoxide (DMSO) (91 mL) was added to a flask of potassium hydroxide (2.84 g, 50.6 mmol) under nitrogen and the reaction mixture stirred for 10 min at rt. 1H-Indole-2-carbaldehyde (2.04 g, 14.05 mmol, commercially available, for example, from Sigma-Aldrich) was added to the reaction mixture and stirred under nitrogen for 1 h at rt. Ethyl bromide (1.795 mL, 23.89 mmol) was added dropwise and the reaction stirred under nitrogen at rt for 1 h. The reaction was quenched by the cautious addition of water (100 mL). Et$_2$O (100 mL) was added and the layers separated. The aqueous layer was further extracted with Et$_2$O (2×100 mL) and the combined organics back extracted with water (2×50 mL). The organic layer was then dried (Na$_2$SO$_4$) and concentrated in vacuo to afford the crude product as a brown oil. The crude product was purified on silica (100 g) using a gradient of 0% EtOAc/cyclohexane→25% EtOAc/cyclohexane. The appropriate fractions were combined and evaporated under vacuum to afford the product as a yellow solid—1-ethyl-1H-indole-2-carbaldehyde (1.41 g, 8.14 mmol, 57.9% yield)

LCMS (Method B): Rt=1.08 mins, MH$^+$=174.0

Other intermediates indicated in the following table were prepared in a manner similar to Intermediate 5:

| Intermediate | Indole | Yield/% | LCMS |
|---|---|---|---|
| 6: 5-Chloro-1-ethyl-1H-indole-2-carbaldehyde (prepared from 5-chloro-1H-indole-2-carbaldehyde (commercially available from, for example, Sigma-Aldrich)). | | 21 | LCMS (Method B): Rt = 1.19 min, MH+ = 207.9 |
| 7: 1-Ethyl-6-methyl-1H-indole (prepared from 6-methyl-1H-indole (commercially available from, for example, Apollo Scientific)). | | 47 | LCMS (Method B): Rt = 1.21 min, MH+ = 160.0 |
| 8: 1-Ethyl-7-(methyloxy)-1H-indole (prepared from 7-methoxy-1H-indole (available from, for example, Sigma-Aldrich)). | | 90 | LCMS: (Method B) Rt = 1.19 min, MH$^+$ = 176.1 |

| Intermediate | Indole | Yield/% | LCMS |
|---|---|---|---|
| 9: 1-Ethyl-6,7-dimethoxy-1H-indole (prepared from 6,7-dimethoxy-1H-indole (commercially available from, for example, J&W Pharmlab)). | | 91 | LCMS (Method B): Rt = 1.13 min, MH+ = 206.02 |
| 10: 1-Ethyl-5-fluoro-1H-indole-2-carbaldehyde (prepared from 5-fluoro-1H-indole-2-carbaldehyde (available from, for example, Matrix Scientific)). | | 64 | LCMS: (Method B) Rt = 1.08 min, MH+ = 192.1 |

Intermediate 11:
1-Ethyl-7-methyl-1H-indole-2-carbaldehyde

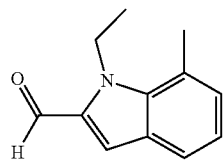

A solution of 1-ethyl-7-methyl-1H-indole (1.5 g, 9.42 mmol) in anhydrous THF (15 mL) under nitrogen was cooled in an ice-salt bath. A solution of n-butyl lithium (1.6 M in hexanes, 7.4 mL, 11.84 mmol) was added dropwise over -10 min. The reaction was stirred for ~2 min post addition of the n-butyl lithium then removed for the ice/salt-bath, allowed to warm to ambient temperature and stirred at ambient temperature under nitrogen for 1.5 h. The reaction was cooled in a $CO_2$/acetone bath and DMF (5 mL) added over ~2 min to the cold solution. The reaction was stirred for a further 2.5 h at −78° C. under nitrogen, then quenched by the addition of saturated aqueous sodium hydrogen carbonate solution and allowed to warm to ambient temperature over the weekend. The reaction was diluted with water and extracted with DCM (×2). The combined DCM extracts were dried (hydrophobic frit) and reduced to dryness in vacuo to give a yellow oil. The residue was dissolved in cyclohexane and applied to a silica cartridge (10 g). The cartridge was eluted with an ethyl acetate/cyclohexane gradient (0-10%). The appropriate fractions were combined and reduced to dryness in vacuo to give 1-ethyl-7-methyl-1H-indole-2-carbaldehyde as a pale yellow oil (0.97 g)

LCMS (Method B): Rt 1.15 min, MH+ 188.

Intermediate 12:
1-Ethyl-5-methyl-1H-indole-2-carbaldehyde

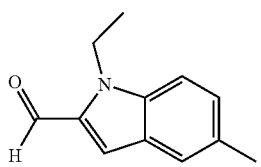

Prepared in a similar manner to Intermediate 11 from 1-ethyl-5-methyl-1H-indole.

$^1$H NMR (DMSO-d6): δH 9.88 (1H, s), 7.55 (2H, m), 7.38 (1H, s), 7.27 (1H, dd), 4.56 (2H, q), 2.41 (3H, s), 1.26 (3H, t)

Intermediate 13:
1-Ethyl-4-methyl-1H-indole-2-carbaldehyde

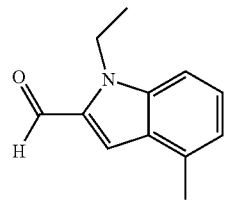

Prepared in a similar manner to Intermediate 12 from 1-ethyl-4-methyl-1H-indole.

$^1$H NMR (DMSO-d6): δH 9.91 (1H, s), 7.54 (1H, s), 7.47 (1H, d), 7.33 (1H, t), 6.98 (1H, d), 4.58 (2H, q), 2.55 (3H, s), 1.27 (3H, t).

Intermediate 14:
1-Ethyl-6-methyl-1H-indole-2-carbaldehyde

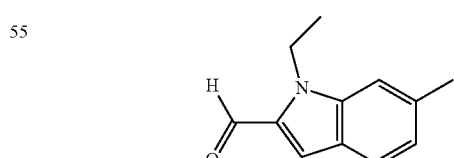

Prepared in a similar manner to Intermediate 12 from 1-ethyl-6-methyl-1H-indole.

LCMS (Method B): Rt=1.17 min, MH+=188.0 Other intermediates in the following table were prepared in a manner similar to Intermediate 11:

| Intermediate | Aldehyde | LCMS |
|---|---|---|
| 15: 1-Ethyl-7-(methyloxy)-1H-indole-2-carbaldehyde (prepared from 1-ethyl-7-(methyloxy)-1H-indole) | | LCMS (Method B) Rt = 1.15 min, MH+ = 204.0 |
| 16: 3,4-Dihydro-2H-[1,4]oxazepino[2,3,4-hi]indole-6-carbaldehyde (prepared from 3,4-dihydro-2H-[1,4]oxazepino[2,3,4-hi]indole). | | LCMS (Method B): Rt = 1.01 min, MH+ = 202.0 |
| 17: 2,3-Dihydro[1,4]oxazino[2,3,4-hi]indole-5-carbaldehyde (prepared from 2,3-dihydro[1,4]oxazino[2,3,4-hi]indole (the preparation of this intermediate is known in the patent: WO 2000006564 A1)). | | LCMS (Method B): Rt = 0.94 min, MH+ = 188.0. |
| 18: 3-Methyl-2,3-dihydro[1,4]oxazino[2,3,4-hi]indole-5-carbaldehyde (prepared from 3-methyl-2,3-dihydro-[1,4]oxazino[2,3,4-hi]indole (preparation of this intermediate reported in *J. Chem. Soc. Perkin Trans.* 1 1987, 9, 2079)). | | LCMS (Method B): Rt = 1.03 min, MH+ = 202.0 |
| 19: 1-Ethyl-6,7-dimethoxy-1H-indole-2-carbaldehyde (prepared from 1-ethyl-6,7-dimethoxy-1H-indole.) | | LCMS (Method B): Rt = 1.08 min, MH+ = 234.0 |

General method for the alkylation of Indoles using $K_2CO_3$ and optionally substituted $ArCH_2X$ (wherein X is a halo group) in DMF:

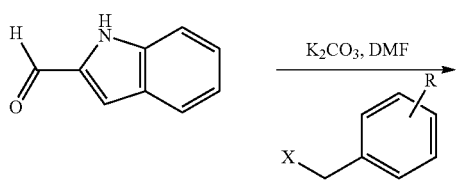

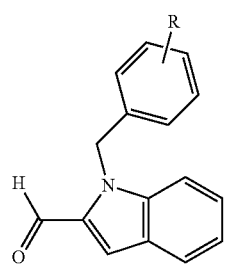

The appropriate benzyl halide (1 eq.) was added to a suspension of 1H-indole-2-carbaldehyde (1 eq.) and potassium carbonate (1 eq.) in N,N-dimethylformamide (DMF) (1.7M) at rt under nitrogen. The reaction mixture was heated to 100° C.-110° C. and stirred for 2-20 h. The reaction was then stopped and quenched by the addition of water. The organics were extracted into EtOAc or $Et_2O$ (3×) and the combined organics washed with water, dried ($Na_2SO_4$) and concentrated in vacuo to afford the crude product. The crude product was purified on silica using the appropriate ratios of EtOAc/cyclohexane. The appropriate fractions were combined and evaporated under vacuum to give the required product.

The following compounds were prepared by this method:

| Intermediate | Aldehyde | Yield/% | LCMS |
|---|---|---|---|
| 20: 1-[(4-Chlorophenyl)methyl]-1H-indole-2-carbaldehyde (prepared from 1H-indole-2-carbaldehyde (commercially available from, for example, Sigma-Aldrich) and 1-(bromomethyl)-4-chlorobenzene). | | 44 | LCMS (Method B): Rt = 1.30 min, MH+ = 270.0 |
| 21: 1-[(4-Iodophenyl)methyl]-1H-indole-2-carbaldehyde (prepared from 1H-indole-2-carbaldehyde (commercially available from, for example, Sigma-Aldrich) and 1-(bromomethyl)-4-iodobenzene). | | 59 | LCMS (Method B): Rt = 1.35 min, MH+ = 361.9 |
| 22: 1-(Phenylmethyl)-1H-indole-2-carbaldehyde (prepared from 1H-indole-2-carbaldehyde (commercially available from, for example, Sigma-Aldrich) and benzyl chloride). | | 81 | LCMS (Method A): Rt = 1.24 min, MH+ = 236.1 |
| 23: 1-[(4-Methylphenyl)methyl]-1H-indole-2-carbaldehyde (prepared from 1H-indole-2-carbaldehyde (commercially available from, for example, Sigma-Aldrich) and 1-(bromomethyl)-4-methylbenzene). | | 35 | LCMS (Method B): Rt = 1.27 min, MH+ = 250.1 |
| 24: 1-[(3-Chlorophenyl)methyl]-1H-indole-2-carbaldehyde (prepared from 1H-indole-2-carbaldehyde (commercially available from, for example, Sigma-Aldrich) and 3-chlorobenzyl bromide). | | 78 | LCMS (Method B): Rt = 1.29 min, MH+ = 270.0 |

| Intermediate | Aldehyde | Yield/% | LCMS |
|---|---|---|---|
| 25: 1-(3,4-Dichlorobenzyl)-1H-indole-2-carbaldehyde (prepared from 1H-indole-2-carbaldehyde (commercially available from, for example, Sigma-Aldrich) and (bromomethyl)-1,2-dichlorobenzene). | | 47 | LCMS: (Method B): Rt = 1.37 min, MH$^+$ = 304.0. |
| 26: 1-(4-Methoxybenzyl)-1H-indole-2-carbaldehyde (prepared from 1H-indole-2-carbaldehyde (commercially available from, for example, Sigma-Aldrich) and -(bromomethyl)-4-methoxybenzene). | | 7 | LCMS: (Method B): Rt = 1.20 min, MH$^+$ = 266.1. |

Intermediate 27: 1-(Cyclopropylmethyl)-5-(methyloxy)-1H-indole-2-carbaldehyde

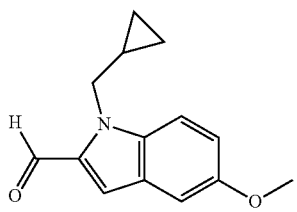 [SMILES: COc1ccc2c(c1)cc(C=O)n2CC1CC1]

A solution of 5-(methyloxy)-1H-indole-2-carbaldehyde (489.1 mg, 2.79 mmol, commercially available from, for example, Fluorochem) in N,N-dimethylformamide (DMF) (12 mL) was added to a flask containing sodium hydride (121.1 mg, 3.03 mmol) and stirred under nitrogen at rt. After 20 min, (bromomethyl)cyclopropane (0.35 mL, 3.61 mmol) was added portionwise. The reaction was allowed to stir at 0° C. for 20 min and then allowed to warm to rt and stirred under nitrogen overnight (16 h). The reaction mixture was quenched by the addition of water (50 mL). Et$_2$O (50 mL) was added and the layers separated. The aqueous layer was further extracted with Et$_2$O (2×50 mL). LCMS of the aqueous mixture showed that there was still some product left. The aqueous layer was further extracted with Et$_2$O (2×60 mL) and the combined organics back extracted with water (3×50 mL). The organic phase was dried with Na$_2$SO$_4$, passed through a hydrophobic frit and concentrated under vacuum to give a brown oil. The crude product was purified on silica (25 g). The column was eluted using a gradient of 0-50% ethyl acetate/cyclohexane. The appropriate fractions were collected and concentrated under vacuum to give a brown oil—1-(cyclopropylmethyl)-5-(methyloxy)-1H-indole-2-carbaldehyde (555 mg, 87%)

LCMS (Method B): Rt=1.14 mins, MH$^+$=230.1

Other examples indicated in the following table were prepared in a manner similar to Intermediate 27.

| Intermediate | Aldehyde | Yield/% | LCMS |
|---|---|---|---|
| 28: 1-(Tetrahydro-2H-pyran-4-ylmethyl)-1H-indole-2-carbaldehyde (prepared from 1H-indole-2-carbaldehyde (commercially available from, for example, Sigma-Aldrich) and 4-(bromomethyl)tetrahydro-2H-pyran (commercially available from, for example, Apollo Scientific)). | | 57 | LCMS (Method A): Rt = 1.08 min, MH+ = 244.1 |
| 29: 6-Bromo-1-ethyl-1H-indole-2-carbaldehyde (prepared from 6-bromo-1H-indole-2-carbaldehyde (commercially available from, for example, Fluorochem)). | | 90 | LCMS (Method A): Rt = 1.26 min, MH+ = 252.0 |

| Intermediate | Aldehyde | Yield/% | LCMS |
|---|---|---|---|
| 30: 1-[2-(Methyloxy)ethyl]-1H-indole-2-carbaldehyde (prepared from 1H-indole-2-carbaldehyde (commercially available from, for example, Sigma-Aldrich) and 2-bromoethyl methyl ether). | | 74 | LCMS (Method B): Rt = 0.99 min, MH+ = 204.2 |
| 31: 1-(2-Methylpropyl)-1H-indole 2-carbaldehyde (prepared from 1H-indole-2-carbaldehyde (commercially available from, for example, Sigma-Aldrich) and 1-bromo-2-methylpropane). | | 74 | LCMS (Method B): Rt = 1.25 min, MH+ = 202.0 |
| 32: 1-(Cyclopropylmethyl)-1H-indole-2-carbaldehyde (prepared from 1H-indole-2-carbaldehyde (commercially available from, for example, Sigma-Aldrich) and (bromoethyl)cyclopropane). | | 47 | LCMS (Method A): Rt = 1.20 min, MH+ = 200.1 |
| 33: 1-(2,2,2-Trifluoroethyl)-1H-indole-2-carbaldehyde (prepared from 1H-indole-2-carbaldehyde (commercially available from, for example, Sigma-Aldrich) and 2,2,2-trifluoroethyl trifluoromethanesulfonate). | | 52 | LCMS (Method A): Rt = 1.12 min, MH+ = 228.1. |
| 34: (R)-1-(3-Hydroxy-2-methylpropyl)-1H-indole-2-carbaldehyde (prepared from 1H-indole-2-carbaldehyde (commercially available from, for example, Sigma-Aldrich) and (S)-3-bromo-2-methylpropan-1-ol (commercially available from, for example, Sigma-Aldrich)). | | 28 | LCMS (Method B): Rt 0.91 min, MH+ = 218.0. |
| 35: (S)-1-(3-Hydroxy-2-methylpropyl)-1H-indole-2-carbaldehyde (prepared from 1H-indole-2-carbaldehyde (commercially available from, for example, Sigma-Aldrich) and (R)-3-bromo-2-methylpropan-1-ol (commercially available from, for example, Sigma-Aldrich)). | | 36 | LCMS (Method B): Rt 0.91 min, MH+ = 218.2. |

| Intermediate | Aldehyde | Yield/% | LCMS |
|---|---|---|---|
| 36: 1-(3-Methoxypropyl)-1H-indole-2-carbaldehyde (prepared from 1H-indole-2-carbaldehyde (commercially available from, for example, Sigma-Aldrich) and 1-bromo-3-methoxypropane. | | 86 | LCMS (Method B): Rt = 1.03 min, MH+ = 218.1. |

Intermediate 37: 1-[(1-Methyl-1H-pyrazol-4-yl)methyl]-1H-indole-2-carbaldehyde

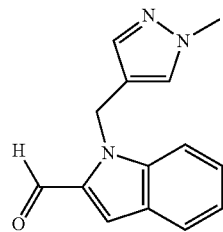 [SMILES: Cn1cc(Cn2c(C=O)cc3ccccc32)cn1]

Intermediate 38: 1-(4-Pyridinylmethyl)-1H-indole-2-carbaldehyde

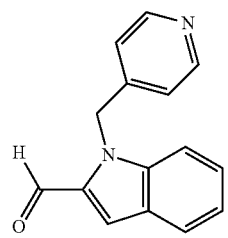 [SMILES: O=Cc1cc2ccccc2n1Cc1ccncc1]

A solution of 1H-indole-2-carbaldehyde (504 mg, 3.47 mmol, commercially available from, for example, Sigma-Aldrich) in N,N-dimethylformamide (DMF) (12 mL) was added to a flask containing sodium hydride (280 mg, 7.00 mmol) and stirred at rt under nitrogen for 1.5 h. 4-(Bromomethyl)-1-methyl-1H-pyrazole (607.8 mg, 3.47 mmol) was dissolved in N,N-dimethylformamide (DMF) (2 mL), then added portionwise to the reaction mixture at 0° C. and left stirring under nitrogen for 1 h. The reaction mixture was brought to rt and left stirring under nitrogen overnight (18 h). Further 4-(bromomethyl)-1-methyl-1H-pyrazole (598.5 mg, 3.42 mmol) in N,N-dimethylformamide (DMF) (2 mL) was added to the reaction mixture and stirred under nitrogen at rt for 4 h. The reaction mixture was quenched by the addition of water (50 mL) and $Et_2O$ (50 mL) was added and the layers separated. The aqueous layer was further extracted with $Et_2O$ (3×50 mL) and the combined organics back extracted with $H_2O$ (2×50 mL). The organic layer was dried with $Na_2SO_4$ and concentrated under vacuum. The crude product was purified on silica (50 g). The column was eluted using a gradient of 15-100% ethyl acetate/cyclohexane. The appropriate fractions were collected and concentrated to afford the desired product as a brown oil—1-[(1-methyl-1H-pyrazol-4-yl)methyl]-1H-indole-2-carbaldehyde (1.27 g, 65%).

LCMS (Method B): Rt=0.90 mins, MH$^+$=240.0

To a suspension of sodium hydride (0.716 g, 17.91 mmol) in tetrahydrofuran (THF) (8.00 mL) was added a solution of 1H-indole-2-carbaldehyde (1 g, 6.89 mmol, commercially available from, for example, Sigma-Aldrich) in N,N-dimethylformamide (DMF) (16 mL) at rt under nitrogen. After 1 h, 4-chloromethylpyridine hydrochloride (1.356 g, 8.27 mmol) was added portionwise. The reaction was allowed to stir at 0° C. for 1 h and then allowed to warm to rt and stirred for 16 h. The reaction was allowed to stand without stirring for 24 h and then quenched by the addition of water (100 mL). $Et_2O$ (100 mL) was added and the layers separated. The aqueous layer was further extracted with $Et_2O$ (2×50 mL) and the combined organics back extracted with $H_2O$ (2×30 mL). The organic phase was dried ($Na_2SO_4$) and concentrated in vacuo to afford the crude product as a brown oil. The crude product was purified on silica (50 g) using a gradient of 40% ethyl acetate/cyclohexane→100% ethyl acetate/cyclohexane. The appropriate fractions were combined and evaporated under vacuum to give the product as a brown solid—1-(4-pyridinylmethyl)-1H-indole-2-carbaldehyde (469 mg, 1.985 mmol, 28.8% yield)

LCMS (Method B): Rt=0.61 mins, MH$^+$=237.1

Other intermediates indicated in the following table were prepared in a manner similar to Intermediate 38:

| Intermediate | Aldehyde | Yield/% | LCMS |
|---|---|---|---|
| 39: 1-(2-Pyridinylmethyl)-1H-indole-2-carbaldehyde (prepared from 1H-indole-2-carbaldehyde and 2-(chloromethyl)pyridine). | | 56 | LCMS (Method B): Rt = 0.86 min, MH+ = 237.1 |
| 40: 1-(3-Pyridinylmethyl)-1H-indole-2-carbaldehyde (prepared from 1H-indole-2-carbaldehyde and 3-(chloromethyl)pyridine). | | 38 | LCMS (Method B): Rt = 0.66 min, MH+ = 237.1 |

Intermediate 41: 1-(2-Hydroxyethyl)-1H-indole-2-

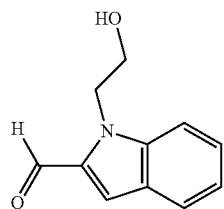 [SMILES: O=Cc1cc2ccccc2n1CCO]

A solution of 1,3-dioxolan-2-one (97 mg, 1.099 mmol), 1H-indole-2-carbaldehyde (145 mg, 0.999 mmol, commercially available from, for example, Sigma-Aldrich) and sodium hydroxide (4.00 mg, 0.100 mmol) (ground from pellets) in N,N-dimethylformamide (DMF) (1 mL) was heated to 140° C. for 16 h. The reaction was allowed to cool and quenched by the addition of water (30 mL) and Et₂O (30 mL). The layers were separated and the aqueous layer extracted with Et₂O (2×30 mL). The combined organics were back extracted with water (2×30 mL) and then dried (Na₂SO₄) and concentrated in vacuo to afford the crude product as a black oil. The crude product was purified on silica (25 g) using a gradient of 100% cyclohexane→100% ethyl acetate/cyclohexane. The appropriate fractions were combined and evaporated under vacuum to give the product as a brown oil—1-(2-hydroxyethyl)-1H-indole-2-carbaldehyde (50 mg, 0.264 mmol, 26.5% yield) which was used without further purification in the next step.

LCMS (Method B): Rt=0.77 mins, MH$^+$=190.1

Intermediate 42: 1-(1-Methylethyl)-1H-indole-2-carbaldehyde

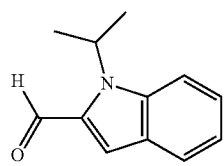

To a flask containing 1H-indole-2-carbaldehyde (500 mg, 3.44 mmol, commercially available from, for example, Sigma-Aldrich) and cesium carbonate (2245 mg, 6.89 mmol) was added acetonitrile (50 mL) at rt. 1-Methylethyl methanesulfonate (1.180 mL, 6.89 mmol) was then added dropwise. The reaction was allowed to stir at rt for 1 h and then heated to 95° C. and stirred for 16 h. The reaction mixture was concentrated in vacuo and the crude product partitioned between water (100 mL) and Et₂O (100 mL). The layers were separated and the aqueous layer was further extracted with Et₂O (2×50 mL). The organic phase was dried (Na₂SO₄) and concentrated in vacuo to afford the crude product as a brown oil. The crude product was purified on silica (25 g) using a gradient of 0% cyclohexane→25% ethyl acetate/cyclohexane. The appropriate fractions were combined and evaporated under vacuum to give the product as a brown solid—1-(1-methylethyl)-1H-indole-2-carbaldehyde (219 mg, 1.170 mmol, 34.0% yield).

LCMS (Method B): Rt=1.16 mins, MH$^+$=188.1

Intermediate 43: (2-Formyl-1H-indol-1-yl)acetonitrile

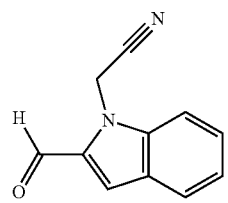 [SMILES: N#CCn1c(C=O)cc2ccccc21]

To N,N-dimethylformamide (DMF) (8 mL) and 1H-indole-2-carbaldehyde (502 mg, 3.46 mmol, commercially available from, for example, Sigma-Aldrich) was added potassium tert-butoxide (578 mg, 5.15 mmol) and the reaction mixture stirred under nitrogen at rt for 1 h. 2-Chloroacetonitrile (0.44 mL, 6.95 mmol) was added dropwise to the reaction mixture and the solution heated to 65° C. for 1 h. The reaction mixture was allowed to cool to rt and stirred under nitrogen for 1 h. The reaction was re-heated to 65° C. and stirred under nitrogen for 1 h. 2-Chloroacetonitrile (1.1 mL) was added to the reaction mixture and stirred under nitrogen at 65° C. for 30 min. The reaction mixture was allowed to cool to rt and left stirring under nitrogen overnight. The reaction was quenched with water (50 mL) and the product separated into diethyl ether (50 mL). The aqueous layer was further extracted with diethyl ether (2×50 mL). The organic layers were combined and back washed with water (2×50 mL). The organic layer was collected, dried using Na$_2$SO$_4$, passed through a hydrophobic frit and concentrated under vacuum to yield a black solid. The crude product was dissolved in a minimum volume of DCM and purified on silica (25 g) eluting with a gradient of 0-65% ethyl acetate/cyclohexane. The appropriate fractions were collected and concentrated under vacuum to give a brown oil—(2-formyl-1H-indol-1-yl)acetonitrile (92 mg, 14%). The product was used in the next reaction without further purification LCMS (Method B): Rt=0.87 min, product does not ionize at correct m/z Intermediate 44: Ethyl 1-ethyl-6-(methyloxy)-1H-indole-2-carboxylate

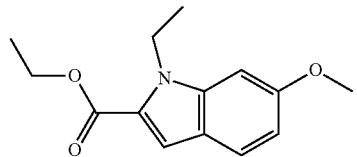 [SMILES: CCOC(=O)c1cc2ccc(OC)cc2n1CC]

6-Methoxy-1H-indole-2-carboxylic acid (502 mg, 2.63 mmol, commercially available from, for example, Amfinecom Inc.) in N,N-dimethylformamide (DMF) (5 mL) was added to a stirred round bottom flask containing potassium carbonate (1.495 g, 10.82 mmol) under nitrogen. Ethyl bromide (1 mL, 13.40 mmol) was added to the reaction mixture and left stirring overnight at 80° C. under Nitrogen (15 h). The mixture was then heated to 100° C. and stirred under nitrogen for 2 h. Further ethyl bromide (0.5 mL), potassium carbonate (828 mg) and N,N-dimethylformamide (DMF) (5 mL) were added to the reaction mixture and left stirring for 3 h at 100° C. The reaction mixture was concentrated under vacuum to give a white solid (~5.2 g). The solid was dried under vacuum. The sample gave >100% yield and was assumed to contain 12.5% of the desired product with inorganic impurities. No purification was carried out and the crude product was used in the next reaction.

LCMS (Method A): Rt=1.30 min, MH$^+$=248.1

Other examples indicated in the following table were prepared in a similar manner to Intermediate 44:

Intermediate 46: Ethyl 6-ethoxy-1-ethyl-1H-indole-2-carboxylate

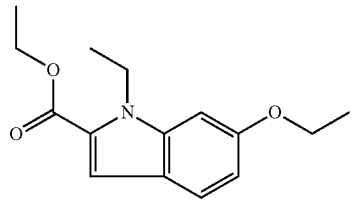 [SMILES: CCOC(=O)c1cc2ccc(OCC)cc2n1CC]

A solution of 6-ethoxy-1H-indole-2-carboxylic acid (434 mg, 2.115 mmol, commercially available from, for example, ACBBlocks) in DMF (5 mL) was added to potassium carbonate (1.461 g, 10.570 mmol) under nitrogen. Ethyl Bromide (0.789 mL, 10.570 mmol) was added and the reaction mixture was stirred at 80° C. under nitrogen over the weekend. The solvent was evaporated under reduced pressure to give the crude product ethyl 6-ethoxy-1-ethyl-1H-indole-2-carboxylate (4.028 g, 15.420 mmol) as an off-white solid. This was used without purification, crude in the subsequent reaction.

LCMS (Method A): Rt=1.38 min, MH$^+$=262.11.

Intermediate 47: Ethyl 1-ethyl-5,6-dimethoxy-1H-indole-2-carboxylate

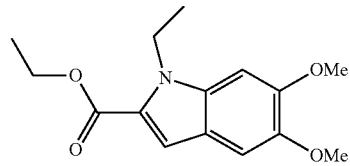 [SMILES: CCOC(=O)c1cc2cc(OC)c(OC)cc2n1CC]

Ethyl 5,6-dimethoxy-1H-indole-2-carboxylate (300 mg, 1.204 mmol, commercially available from, for example, Alfa Aesar) was dissolved in anhydrous N,N-dimethylformamide (DMF) (2 mL) and the resulting solution was cooled in an ice-water bath. Sodium hydride (60% dispersion in mineral oil) (58.6 mg, 1.465 mmol) was added slowly. The resulting solution was allowed to stir in the ice-bath for 1 h, then iodoethane (0.144 mL, 1.805 mmol) was added. The reaction was allowed to warm to rt overnight. The reaction mixture was quenched by the addition of sat. NH$_4$Cl (aq). The reaction mixture was diluted with water and EtOAc. The organic phase was separated and washed sequentially with 2M NaOH(aq) followed by water. The organic phase was passed through a hydrophobic frit and the solvent removed under vacuum to give the crude product as

| Intermediate | Ester | LCMS |
| --- | --- | --- |
| 45: Ethyl 1-ethyl-6-fluoro-1H-indole-2-carboxylate (prepared from 6-fluoro-1H-indole-2-carboxylic acid (commercially available from, for example, Apollo Scientific)). | | LCMS (Method B): Rt = 1.32 min, MH+ = 235.9 | an orange solid. This was purified on a SNAP (20 g) silica cartridge using SP4 column chromotography, the column was eluted with 0-50% EtOAc in cyclohexane (10CV) followed by 50% EtOAc (5CV). The appropriate fractions were combined and the solvent removed under vacuum to give a white solid. This was dried in the vacuum oven overnight to give the title compound (305 mg) as a white solid.

LCMS (Method B): Rt=1.14 min, MH+=278.0.

Intermediate 48:
1-Ethyl-7-fluoro-1H-indole-2-carboxylic acid

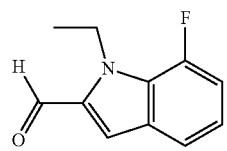

To a solution of 7-fluoroindole carboxylic acid (500 mg, 2.79 mmol, available from, for example, Matrix Scientific) in DMF (5 mL) was added potassium carbonate (771 mg, 11.2 mmol) followed by bromoethane (521 □L, 6.98 mmol). The reaction mixture was heated at 60° C. for 2 h then further bromoethane (521 □L, 6.98 mmol) and potassium carbonate (771 mg, 11.2 mmol) were added. The reaction mixture was heated at 60° C. for a further 2 h then concentrated under reduced pressure to give around 2 g of crude material as a beige solid.

The material was suspended in a solution of THF (20 mL), water (20 mL) and MeOH (5 mL) then LiOH monohydrate (401 mg, 9.56 mmol) was added. The reaction mixture was stirred at rt for 16 h then concentrated under reduced pressure. The resulting crude product was treated with 2N HCl (20 mL, aqueous), and the resulting beige solid filtered under reduced pressure then washed with water then further dried under reduced pressure to give the title compound as a beige solid (436 mg, 75%).

LCMS (formic) MH+=208.0, Rt 1.03 min

Intermediate 49:
7-Bromo-1-ethyl-1H-indole-2-carboxylic acid

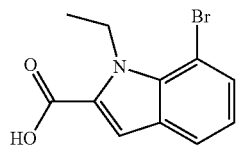

To a solution of ethyl 7-bromo-1H-indole-2-carboxylate (1.11 g, 3.73 mmol, available from, for example, Chem-Impex International Inc.) in DMF (15 mL) was added potassium carbonate (2.06 g, 14.92 mmol) followed by bromoethane (1.4 mL, 18.76 mmol). The reaction mixture was heated at 60° C. for 1.5 h then concentrated under reduced pressure. To the crude product was added LiOH (0.844 g, 35.2 mmol) followed by THF (20 mL), water (20 mL) and MeOH (5 mL). The resulting mixture was stirred under nitrogen at rt for 16 hr then concentrated under reduced pressure. 2N HCl (aq) was added to the reaction mixture and the resulting solid filtered under reduced pressure then washed with 2N HCl then water and dried under reduced pressure to give the title compound as a white solid (905 mg, 90%).

LCMS (formic) MH+=267.3/270.1, Rt=1.13 min

Intermediate 50:
1-Ethyl-6-(methyloxy)-1H-indole-2-carboxylic acid

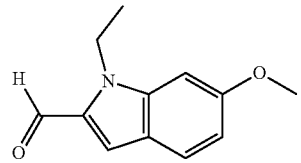

To a heterogenous mixture of ethyl 1-ethyl-6-methoxy-1H-indole-2-carboxylate (estimated 657 mg desired starting material, ~5.2 g crude with inorganics from previous step) in tetrahydrofuran (THF) (20 mL), water (20 mL) and methanol (5 mL) was added lithium hydroxide monohydrate (316 mg, 13.20 mmol) and the mixture stirred at rt overnight (~18 h). Further lithium hydroxide monohydrate (314.2 mg) was added to the reaction mixture and left stirring for 3 h. Distilled water (5 mL) and lithium hydroxide.monohydrate (302.3 mg) were added to the reaction mixture and left stirring overnight at rt. The reaction mixture was concentrated under vacuum and 2M HCl (20 mL) added. The resulting solid was collected via filtration and washed with water. The beige solid was collected and dried under high vacuum for 3 h to afford 1-ethyl-6-(methyloxy)-1H-indole-2-carboxylic acid (429 mg, 97%).

LCMS (Method B): Rt=0.93 min, MH+=220.1 Other examples indicated in the following table were prepared in a manner similar to Intermediate 50:

| Intermediate | Acid | LCMS |
|---|---|---|
| 51: 1-Ethyl-6-fluoro-1H-indole-2-carboxylic acid (prepared from ethyl 1-ethyl-6-fluoro-1H-indole-2-carboxylate). | | LCMS (Method A): Rt = 0.65 min, [M − H]⁻ = 206.1 |

Intermediate 52:
6-Ethoxy-1-ethyl-1H-indole-2-carboxylic acid

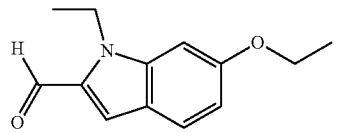 [SMILES: CCOc1ccc2cc(C=O)n(CC)c2c1]

Lithium hydroxide monohydrate (331 mg, 7.89 mmol) was added to a suspension of ethyl 6-ethoxy-1-ethyl-1H-indole-2-carboxylate (4.1 g crude from previous step, estimated 553 mg, 2.115 mmol of desired starting material) in THF (10 mL), water (10 mL) and MeOH (2.5 mL). More lithium hydroxide monohydrate (331 mg, 7.89 mmol) in water (5 mL) was added after 7 h of stirring. The reaction mixture was stirred overnight at rt and more lithium hydroxide monohydrate (533 mg, 12.70 mmol) added. After 5 h of stirring at rt, the reaction mixture was stirred at 40° C. overnight. The reaction mixture was concentrated under reduced pressure to give a beige solid. HCl (14 mL of a 2 M solution) was added to the residue under stirring. The resulting solid was collected by filtration in vacuo, washed with water and subsequently dried under HVAC to give the required product 6-ethoxy-1-ethyl-1H-indole-2-carboxylic acid (431 mg, 1.848 mmol, 87% yield) as an off-white solid.

LCMS (Method A): Rt=0.67 min, MH$^+$=234.15

Intermediate 53:
5-Cyano-1-ethyl-1H-indole-2-carboxylic acid

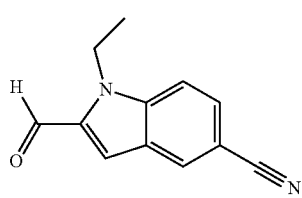

Dimethyl sulfoxide (DMSO) (20 mL) was added to a flask of potassium hydroxide (471 mg, 8.40 mmol) under nitrogen and the reaction mixture stirred for 10 min at rt. Ethyl 5-cyano-1H-indole-2-carboxylate (500 mg, 2.334 mmol, commercially available, for example, from ACB Blocks Ltd.) was added to the reaction mixture and stirred under nitrogen for 2.5 h at rt. Bromoethane (0.296 mL, 3.97 mmol) was added dropwise and the reaction stirred under nitrogen at rt for 1 h. The reaction was quenched by the cautious addition of water (50 mL). Et$_2$O (50 mL) was added and the layers separated. The aqueous layer was further extracted with Et$_2$O (2×50 mL) and the combined organics washed with brine (1×50 mL). The organic layer was then dried (Na$_2$SO$_4$) and concentrated in vacuo to afford ethyl 5-cyano-1-ethyl-1H-indole-2-carboxylate (338 mg, 1.395 mmol, 59.8% yield) as a white wax. The aqueous solution was acidified to pH=4 using 5.0M HCl, a white precipitate was filtered off and left overnight in the vacuum oven to afford a white powder -5-cyano-1-ethyl-1H-indole-2-carboxylic acid (328 mg, 1.531 mmol, 65.6% yield).

LCMS (Method B): Rt 0.86 min, MH+=214.9.

Intermediate 54:
1-Ethyl-5,6-dimethoxy-1H-indole-2-carboxylic acid

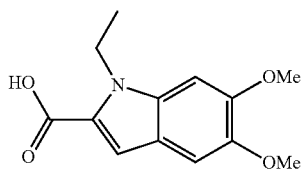 [SMILES: CCn1c(C(=O)O)cc2cc(OC)c(OC)cc21]

Ethyl 1-ethyl-5,6-dimethoxy-1H-indole-2-carboxylate (305 mg, 1.100 mmol) was dissolved in a mixture of water (2 mL), methanol (1 mL) and tetrahydrofuran (THF) (4 mL). To this solution, lithium hydroxide monohydrate (138 mg, 3.30 mmol) was added. The solution was left to stir overnight. The solvent was removed under vacuum and the resulting solid was re-dissolved in a mixture of THF (4 mL) and water (2 mL). The reaction was left overnight. The solution was then heated to 40° C. for 1 h. The solvent was removed under vacuum and the resultant solid was dried in the vacuum oven over the weekend. This gave the title compound as a pale yellow solid (302 mg).

LCMS (Method B): Rt 0.80 min, MH+=249.9.

Intermediate 55: N,N'-3,4-Pyridinediylbis(2,2,2-trifluoroacetamide), Trifluoroacetic Acid Salt

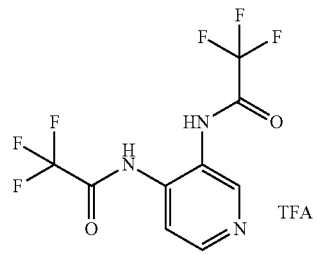 [SMILES: O=C(Nc1ccncc1NC(=O)C(F)(F)F)C(F)(F)F]

To a solution of pyridine-3,4-diamine (1 g, 9.16 mmol, commercially available, for example, from Sigma-Aldrich) in dichloromethane (DCM) (28 mL) at rt was added TFAA (3.24 mL, 22.91 mmol) dropwise. The reaction was stirred at rt for 30 min. A "ball" of solid formed after ~15 min. LCMS analysis of the liquor showed mainly product but analysis of the solid showed mainly starting material. The reaction mixture was sonicated for 1 h. During the course of sonication the reaction mixture was heated slightly (~35° C.) the solid disappeared but a biphasic mixture resulted. Analysis of the higher phase showed mainly product and the lower phase showed product, no starting material, but some mono-protected pyridine. The reaction mixture was concentrated in vacuo and dried in vacuo overnight to afford a colourless viscous oil which still contained ~20% mono-protected pyridine. To push to completion the crude product was taken up in Dichloromethane (DCM) (10 mL) and TFAA (0.647 mL, 4.58 mmol) added. The reaction was sonicated for 30 mins and concentrated in vacuo to afford—N,N'-(pyridine-3,4-diyl)bis(2,2,2-trifluoroacetamide), trifluoroacetic acid salt (4.28 g, 8.76 mmol, 96% yield). This was used in the subsequent reaction without further purification.

LCMS (Method B): Rt=0.82 mins, MH$^+$=301.9

Intermediate 56: 2,2,2-Trifluoro-N-(4-methylpyridin-3-yl)acetamide, Trifluoroacetic Acid Salt

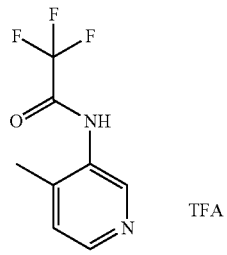

2,2,2-Trifluoroacetic anhydride (1.27 mL, 10.2 mmol) was carefully added to a solution of 4-methylpyridin-3-amine (1 g, 9.25 mmol, commercially available from, for example, Atlantic SciTech Group, Inc.) in anhydrous dichloromethane (10 mL). The resulting solution was stirred at rt for 5 min. The reaction mixture was concentrated under vacuum to give the desired product as a light brown solid (3.02 g, 100%).

LCMS (Method B): Rt 0.44 min, m/z 204.9 (MH$^+$).

Intermediate 57: Methyl 5-(2,2,2-trifluoroacetamido)nicotinate, Trifluoroacetic Acid Salt

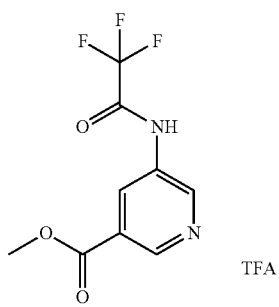 [SMILES: COC(=O)c1cncc(NC(=O)C(F)(F)F)c1]

Prepared in a similar manner to Intermediate 56, from methyl 5-aminonicotinate (commercially available from, for example, Sigma-Aldrich).

LCMS (Method B): Rt=0.75 mins, MH$^+$=248.9

Intermediate 58: 2,2,2-Trifluoro-N-(5-methylpyridin-3-yl)acetamide

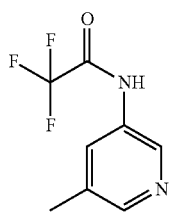

To 5-methylpyridin-3-amine (274 mg, 2.53 mmol, commercially available from, for example, Sigma-Aldrich) in N,N-dimethylformamide (DMF) (4 mL) was added sodium hydride (304 mg, 7.60 mmol) and TFAA (0.716 mL, 5.07 mmol) and the reaction stirred overnight at room temperature under nitrogen. Water was added and the product extracted into DCM (×3). The combined organic layers were evaporated to give a brown oil which was dried under high vacuum to give the title compound as a brown solid (512 mg, 79%).

LCMS (Method B): Rt=0.50 min, MH+=205.0.

Intermediate 59: 2,2,2-Trifluoro-N-(5-fluoropyridin-3-yl)acetamide

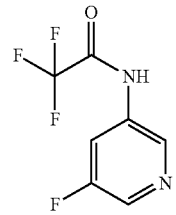

To 5-fluoropyridin-3-amine (548 mg, 4.89 mmol, commercially available from, for example, Fluorochem) in dichloromethane (DCM) (10 mL) was added TFAA (0.898 mL, 6.35 mmol) and the reaction stirred at rt under nitrogen for 30 min. The solvent was removed and the residue dried under high vacuum overnight to give the title compound as a brown oil (1.595 g, yield 96%).

LCMS (Method B): Rt=0.74 min, MH+=209.0.

Intermediate 60: N,N'-(Pyridine-3,5-diyl)bis(2,2,2-trifluoroacetamide)

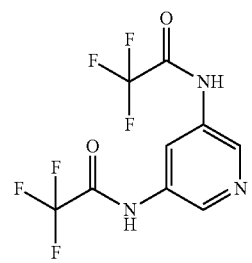 [SMILES: O=C(Nc1cncc(NC(=O)C(F)(F)F)c1)C(F)(F)F]

To pyridine-3,5-diamine (527 mg, 4.83 mmol, commercially available from, for example, 3B Scientific Corporation) in dichloromethane (DCM) (10 mL) was added TFAA (1.773 mL, 12.56 mmol) and the reaction stirred overnight at rt under nitrogen. Solvent was removed and the residue washed with methanol and azeotroped with DCM and dried under high vacuum overnight to give a sticky brown solid (2.2 g, yield 97%).

LCMS (Method B): Rt=0.80 min, MH+=302.0.

Intermediate 61: 2,2,2-Trifluoro-N-(5-methoxypyridin-3-yl)acetamide, Trifluoroacetic Acid Salt

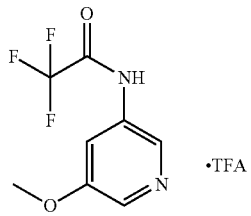

To 5-methoxypyridin-3-amine (975 mg, 7.85 mmol, commercially available from, for example J&W Pharmlab) in dichloromethane (DCM) (5 mL) was added TFAA (1.442 mL, 10.21 mmol) and the reaction left to stir over the weekend. The solvent was removed and the residue was dried under high vacuum overnight to give the title compound as a brown solid (2.0 g, yield 76%).

LCMS (Method B): Rt=0.65 min, MH+=220.9.

Intermediate 62: Methyl 3-(2,2,2-trifluoroacetamido)isonicotinate

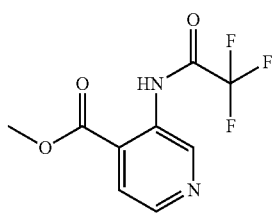 [SMILES: COC(=O)c1ccncc1NC(=O)C(F)(F)F]

To methyl 3-aminoisonicotinate (362 mg, 2.379 mmol, commercially available from, for example, Atlantic Research Chemicals) in dichloromethane (DCM) (8 mL) was added TFAA (0.437 mL, 3.09 mmol) and the reaction stirred at rt under nitrogen for 30 min. The solvent was removed and the residue dried under high vacuum overnight to give a beige solid (850 mg, yield 97%).

LCMS (Method B): Rt=0.84 min, MH+=248.9.

Intermediate 63: N,N'-3,4-Piperidinediylbis(2,2,2-trifluoroacetamide), Acetic Acid Salt

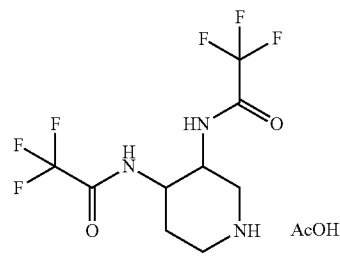 [SMILES: "AcOH" ; O=C(NC1CCNCC1NC(=O)C(F)(F)F)C(F)(F)F]

N,N'-(Pyridine-3,4-diyl)bis(2,2,2-trifluoroacetamide), trifluoroacetic acid salt (780 mg, 1.879 mmol) was dissolved in acetic acid (10 mL) and hydrogenated in a H-cube at 100° C. and 100 bar through a 10% Pd/C cat. cartridge (100 mg, 0.940 mmol) overnight (inlet tube placed into receiver vessel to recycle reaction mixture continuously). LCMS showed no starting pyridine. The reaction mixture was concentrated in vacuo and azeotroped with toluene (2×15 mL) to afford the desired product as a colourless oil—N,N'-(piperidine-3,4-diyl)bis(2,2,2-trifluoroacetamide), acetic acid salt (686 mg, 1.868 mmol, 99% yield). This was used in the subsequent reaction without further purification or characterisation.

LCMS (Method B): Rt=0.46 mins, MH+=308.0

Intermediate 64: 2,2,2-Trifluoro-N-(4-methylpiperidin-3-yl)acetamide

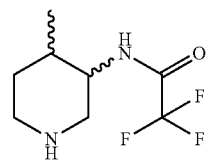

A solution of 2,2,2-trifluoro-N-(4-methylpyridin-3-yl)acetamide, trifluoroacetic acid salt (1.5 g, 4.71 mmol) in acetic acid (15 mL) was run through an H-cube apparatus (flow 1 mL/min) at 80 bars, 100° C., using a 10% Pd/C catalyst cartridge. The solution was recycled through the machine for 6 h and was concentrated under vacuum. The residue was taken up in methanol and eluted through an aminopropyl cartridge (20 g) with methanol. The collected fraction was concentrated under vacuum to give the desired product as a colourless oil (549 mg, 55%). The product is a 2:1 mixture of cis- and trans-isomers.

$^1$H NMR (CDCl$_3$) δ: 7.42 (br. s., 1H), 6.88 (br. s., 1H), 4.07 (br. s., 1H), 3.62-3.49 (m, 1H), 3.16 (dd, J=12.0, 3.9 Hz, 1H), 3.06-2.95 (m, 1H), 2.95-2.89 (m, 1H), 2.79 (dd, J=11.6, 2.0 Hz, 1H), 2.65-2.51 (m, 1H), 2.42 (dd, J=12.1, 9.6 Hz, 1H), 1.82-1.71 (m, 1H), 1.64-1.51 (m, 1H), 1.51-1.42 (m, 1H), 1.36-1.18 (m, 1H), 0.98 (d, J=6.6 Hz, 1H), 0.87 (d, J=6.8 Hz, 2H).

Intermediate 65: Methyl 5-(2,2,2-trifluoroacetamido)piperidine-3-carboxylate

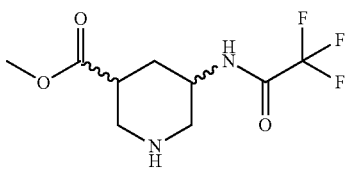 [SMILES: COC(=O)C1CNCC(NC(=O)C(F)(F)F)C1]

Prepared in a similar manner to Intermediate 64, from methyl 5-(2,2,2-trifluoroacetamido)nicotinate, trifluoroacetic acid salt. The product is a 1:1 mixture of cis and trans isomers.

$^1$H NMR (CDCl$_3$) δ: 7.75 (br. s., 1H), 7.08 (br. s., 1H), 4.23-4.15 (m, 1H), 4.04-3.92 (m, 1H), 3.74 (s, 3H), 3.70 (s, 3H), 3.29-2.45 (m, 10H), 2.27-1.74 (m, 4H).

Intermediate 66: 2,2,2-Trifluoro-N-(5-methylpiperidin-3-yl)acetamide, Acetic Acid Salt, Diastereomeric Mixture

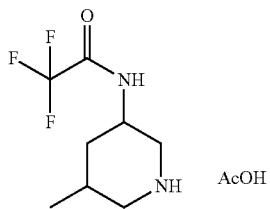

2,2,2-Trifluoro-N-(5-methylpyridin-3-yl)acetamide (512 mg, 2.508 mmol) was dissolved in acetic acid (10 mL) and hydrogenated in a H-cube at 100° C. and 100 bar through a 10% Pd/C cat cart (100 mg, 0.940 mmol) overnight. The solvent was removed and the residue azeotroped with toluene. The residue was dried under high vacuum for 1 h to give a brown oil which was used crude in the next step, (745 mg, 110%).

LCMS (Method B): Rt=0.35 min, MH+=211.0.

Intermediate 67: 5-methylpiperidin-3-ol, Diastereomeric Mixture

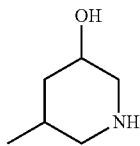

5-Methylpyridin-3-ol (507 mg, 4.65 mmol, commercially available from, for example, Alfa Aesar) in acetic acid (30 mL) (approx 0.15M solution) was hydrogenated through the H-cube using Pd/C cat-cart (49.4 mg, 0.465 mmol) as the catalyst and conditions of 100° C. and 100 bar pressure and recycled constantly at 1 mL minute overnight. Solvent was removed and the residue loaded onto a 10 g SCX-2 cartridge, washing with methanol and then eluting with 2M methanolic ammonia. The solvent was removed and the residue dried under high vacuum overnight to afford the title compound as a yellow oil (458 mg, 86%.)

LCMS (Method B): Rt=0.38 min, MH+=116.0.

Intermediate 68: 2,2,2-Trifluoro-N-(5-fluoropiperidin-3-yl)acetamide, Acetic Acid Salt, Diastereomeric Mixture

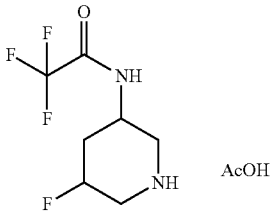 [SMILES: "AcOH" ; O=C(NC1CNCC(F)C1)C(F)(F)F]

2,2,2-Trifluoro-N-(5-fluoropyridin-3-yl)acetamide (800 mg, 3.84 mmol) was dissolved in acetic acid (10 mL) and hydrogenated in a H-cube at 100° C. and 100 bar through a 10% Pd/C cat cart (100 mg, 0.940 mmol) for 3 h. The solvent was removed and the residue dried under high vacuum overnight. The residue was redissolved in acetic acid and hydrogenated in a H-cube at 100° C. and 100 bar through a 10% Pd/C cat cart (100 mg, 0.940 mmol) for 6 h. The solvent was removed and the residue dried under high vacuum overnight to afford a brown oil (331 mg, 31%).

LCMS (Method B): Rt=0.29 min, MH+=215.0.

Intermediate 69: N,N'-(Piperidine-3,5-diyl)bis(2,2,2-trifluoroacetamide), Acetic Acid Salt, Diastereomeric Mixture

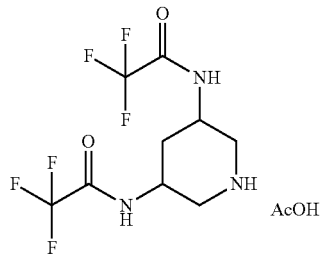 [SMILES: "AcOH" ; O=C(NC1CNCC(NC(=O)C(F)(F)F)C1)C(F)(F)F]

N,N'-(Pyridine-3,5-diyl)bis(2,2,2-trifluoroacetamide) (2.2 g, 7.31 mmol) in acetic acid (15 mL) was hydrogenated in an H-cube through a Pd/C 10% cat cart (30 mg, 0.282 mmol) recycling overnight. The solvent was removed and the residue dried under high vacuum overnight to give an off white solid, which was carried forward crude (2.023 g, 68%).

LCMS (Method B): Rt=0.46 min, MH+=308.0.

Intermediate 70: Methyl 3-(2,2,2-trifluoroacetamido)piperidine-4-carboxylate, Acetic Acid Salt, Diastereomeric Mixture

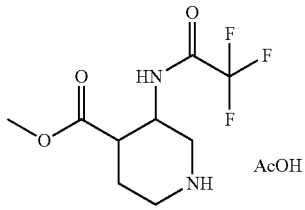 [SMILES: "AcOH" ; COC(=O)C1CCNCC1NC(=O)C(F)(F)F]

Prepared in a similar manner to Intermediate 69, from methyl 3-(2,2,2-trifluoroacetamido)isonicotinate, trifluoroacetic acid salt LCMS (Method B): Rt=0.34 min, MH+=255.0.

Intermediate 71: 2,2,2-Trifluoro-N-(5-methoxypiperidin-3-yl)acetamide, Acetic Acid Salt, Diastereomeric Mixture

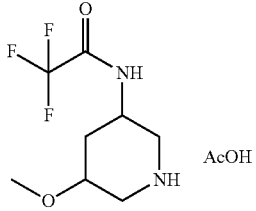

2,2,2-Trifluoro-N-(5-methoxypyridin-3-yl)acetamide, trifluoroacetic acid salt (2000 mg, 5.98 mmol) in acetic acid (10 mL) was hydrogenated in an H-cube at 100° C. at 100 bar for 78 h. The solvent was removed and the residue dried under high vacuum over the weekend to give a brown oil (1.985 g, 116%).

LCMS (Method B): Rt=0.37 min, MH+=227.2.

Intermediate 72: 2,2,2-Trifluoro-N-((cis)-5-methylpyrrolidin-3-yl)acetamide, Trifluoroacetic Acid Salt

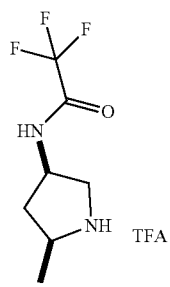

To (cis)-tert-butyl 4-amino-2-methylpyrrolidine-1-carboxylate (120 mg, 0.599 mmol, the preparation of this intermediate has been described in the literature: *ACS Med. Chem. Lett.* 2011, 2, 142) in dichloromethane (DCM) (2 mL) was added Et$_3$N (0.167 mL, 1.198 mmol) and TFAA (0.085 mL, 0.599 mmol) and the reaction left to stir over the weekend. The reaction mixture was partitioned between DCM and water (×3). The combined organic layers were washed with water (×2) and the solvent removed to give a clear oil which was dried under high vacuum overnight to afford (cis)-tert-butyl 2-methyl-4-(2,2,2-trifluoroacetamido)pyrrolidine-1-carboxylate (118 mg).

To (cis)-tert-butyl (1-(2-(1-ethyl-1H-indol-2-yl)-7-methoxy-1-methyl-1H-benzo[d]imidazole-5-carbonyl)pyrrolidin-3-yl)carbamate (9 mg, 0.017 mmol) in dichloromethane (DCM) (1 mL) was added TFA (0.5 mL, 6.49 mmol) and the reaction stirred for 2 h. The solvent was removed and the residue dried under high vacuum overnight to afford a brown oil (120 mg) which was used without purification in the next reaction.

LCMS (Method B): Rt=0.30 min, MH+=197.1.

Intermediate 73: Benzyl 7-oxa-3-azabicyclo[4.1.0]heptane-3-carboxylate

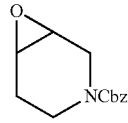

3-Chlorobenzoperoxoic acid (16.79 g, 97 mmol) was added portionwise under an atmosphere of nitrogen to a stirred solution of benzyl 5,6-dihydropyridine-1(2H)-carboxylate (15.1 g, 69.5 mmol) (available, for example, from Fluorochem) in anhydrous dichloromethane (DCM) (100 mL) cooled using an ice bath. The resulting mixture was allowed to reach rt and stirred for 18 h. Water (100 mL) was added to the reaction mixture and the layers were partitioned. The organic layer was added dropwise to a stirred 5% aqueous solution of NaS$_2$O$_5$ (200 mL). At the end of the addition, the mixture was stirred for a further 1 h, then the layers were separated and the aqueous layer was back extracted with DCM (50 mL×2). The organics were combined and washed with 5% aqueous K$_2$CO$_3$ solution (100 mL×3), followed by brine (100 mL). At this stage peroxide test showed there was still 25 mg/mL peroxide in the organic layer. The organics were therefore added to a stirred solution of 5% NaS$_2$O$_5$(aq) (200 mL) and the resultant biphasic mixture stirred for 1 h. Peroxide test now showed <0.5 mg/mL peroxide. The layers were separated and the aqueous layer washed with further DCM (2×50 mL). The combined organics were then dried (Na$_2$SO$_4$). and concentrated in vacuo to afford the crude product as a pale-gold oil. The crude product was purified by silica gel chromatography, (340 g Si), eluting with 30→80% EtOAc/cyclohexane. The appropriate fractions were combined and concentrated in vacuo to afford the title compound as a colourless oil—benzyl 7-oxa-3-azabicyclo[4.1.0]heptane-3-carboxylate (12.75 g, 54.7 mmol, 79% yield).

LCMS (Method B): Rt=0.88 min, MH+=234.2

Intermediate 74: trans-Benzyl 3-((tert-butoxycarbonyl)amino)-4-hydroxypiperidine-1-carboxylate

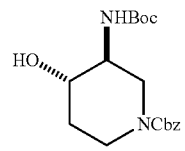 [SMILES: CC(C)(C)OC(=O)N[C@H]1CN(C(=O)OCc2ccccc2)CC[C@@H]1O]

Three separate reactions were performed under the same reaction conditions outlined below. Where reagent/solvent quantities vary, the specific quantities used are outlined in the table. The crude material from the three reactions was combined for purification as indicated:

| Reagent | Solvent: | | |
|---|---|---|---|
| | Reaction 1 | Reaction 2 | Reaction 3 |
| Benzyl 7-oxa-3-aza bicyclo[4.1.0]heptane-3-carboxylate (A) | 4.37 g, 18.73 mmol | 4.45 g, 19.08 mmol | 3.94 g, 16.89 mmol |

|                  | Solvent:    |            |            |
|------------------|-------------|------------|------------|
| Reagent          | Reaction 1  | Reaction 2 | Reaction 3 |
| DCM (B)          | 120 mL      | 100 mL     | 100 mL     |
| Triethylamine (C)| 2.87 mL,    | 2.92 mL,   | 2.59 mL,   |
|                  | 20.61 mmol  | 20.98 mmol | 18.58 mmol |
| Boc$_2$O (D)     | 4.35 mL,    | 4.43 mL,   | 3.92 mL,   |
|                  | 18.73 mmol  | 19.08 mmol | 16.89 mmol |

A solution of benzyl 7-oxa-3-azabicyclo[4.1.0]heptane-3-carboxylate (A) in 25-30% ammonium hydroxide aqueous solution (150 ml, 3766 mmol) and ethanol (100 mL) was stirred in a HASTC alloy bomb at 70° C. for 5 h. The reaction mixture was transferred to a rb flask and concentrated in vacuo by half (caution large amount of NH$_3$ given off). The resultant solution was diluted with brine (50 mL) and the organics extracted into DCM (100 mL). Subsequently the aqueous layer was further extracted with 10% MeOH/DCM (3×50 mL). The combined organic layers were dried (Na$_2$SO$_4$) and concentrated in vacuo to give the intermediate primary amine as a yellow oil. The oily residue was diluted with dichloromethane (DCM) (B) and triethylamine (C) and Boc$_2$O (D) added dropwise. The reaction was allowed to stir for 2 h. LCMS showed complete reaction to two regiomeric products with similar Rt. The reaction mixture was quenched with sat. NH$_4$Cl (aq) (100 mL) and the layers separated. The aqueous was further extracted with DCM (2×75 mL). The combined organics were dried through a hydrophobic frit and the solvent was removed under vacuum to give a white gum.

The crude material from the three reactions was combined for purification: The combined residue was dissolved in DCM and split in two and purified by column chromatography on two 340 g silica cartridges, using a gradient of 0-100% ethyl acetate/cyclohexane. The appropriate fractions were combined and evaporated in vacuo to give two main products:

First Eluting Peak from Column:
trans-benzyl 4-((tert-butoxycarbonyl)amino)-3-hydroxypiperidine-1-carboxylate (10.492 g, 29.9 mmol, 59% yield) as a white solid (undesired regioisomer).

Second Eluting Peak from Column:
trans-benzyl 3-((tert-butoxycarbonyl)amino)-4-hydroxypiperidine-1-carboxylate (6.485 g, 18.51 mmol, 37% yield) as a white solid (desired regioisomer indicated above.)

LCMS (Method B): Rt=0.96 min, MH$^+$=351.2

Intermediate 75: cis-Benzyl 4-(benzoyloxy)-3-((tert-butoxycarbonyl)amino)piperidine-1-carboxylate

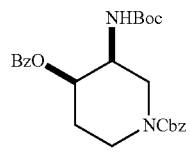

To a solution of triphenylphosphine (5.83 g, 22.24 mmol) in tetrahydrofuran (THF) (60 mL) was added DIAD (4.38 mL, 22.24 mmol) and the mixture was stirred in an ice-water bath for 15 min and then allowed to warm to rt. To the suspension was added a suspension of trans-benzyl 3-((tert-butoxycarbonyl)amino)-4-hydroxypiperidine-1-carboxylate (6.495 g, 18.54 mmol) in tetrahydrofuran (THF) (75 mL) followed by benzoic acid (2.72 g, 22.24 mmol). The reaction mixture cleared to a yellow solution and was stirred for 2 h. LCMS analysis showed product formation, however the SM peak was obscured by-product so it was difficult to confirm reaction had gone to completion. The reaction was left to stir overnight (20 h). The reaction mixture was concentrated under vacuum. The residue was purified by silica chromatography. The residue was loaded in DCM on a 340 g silica cartridge and purified using a 0-40% EtOAc/cyclohexane gradient. The appropriate fractions were combined and the solvent evaporated in vacuo to give the crude product cis-benzyl 4-(benzoyloxy)-3-((tert-butoxycarbonyl)amino) piperidine-1-carboxylate (8.11 g, 17.84 mmol, 96% yield) as a pale yellow oil.

LCMS (Method B): Rt=1.27 min, MH$^+$=455.3.

Intermediate 76: cis-Benzyl 3-((tert-butoxycarbonyl)amino)-4-hydroxypiperidine-1-carboxylate

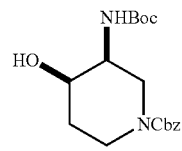 [SMILES: CC(C)(C)OC(=O)N[C@H]1CN(C(=O)OCc2ccccc2)CC[C@H]1O]

Intermediate 77: (3S,4R)-Benzyl 3-((tert-butoxycarbonyl)amino)-4-hydroxypiperidine-1-carboxylate

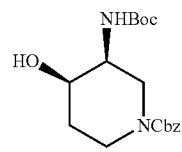

Intermediate 78: (3R,4S)-Benzyl 3-((tert-butoxycarbonyl)amino)-4-hydroxypiperidine-1-carboxylate

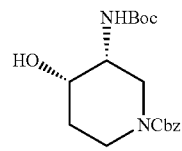

A solution of potassium carbonate (3.70 g, 26.8 mmol) in water (80 mL) was added to a solution of cis-benzyl 4-(benzoyloxy)-3-((tert-butoxycarbonyl)amino)piperidine-1-carboxylate (8.11 g, 17.84 mmol) in ethanol (160 mL) and the mixture was stirred at 70° C. for 20 h. The reaction mixture was concentrated in vacuo to ⅓ volume and the resultant suspension was diluted with water (50 mL) and extracted using DCM (3×70 mL). The collected organics were combined and dried (Na$_2$SO$_4$) and concentrated in vacuo to afford the crude product as a colourless oil. The crude product was then purified by column chromatography on a silica cartridge (340 g) using a 0-100% ethyl acetate/cyclohexane gradient. The appropriate fractions were combined and evaporated in vacuo to give the required product cis-benzyl 3-((tert-butoxycarbonyl)amino)-4-hydroxypiperidine-1-carboxylate (5.54 g, 15.81 mmol, 89% yield) as a white foam.

LCMS (Method B): Rt=0.98 min, MH$^+$=351.2

1 g of the racemic product was submitted for chiral purification chromatography using Chiral HPLC Method B. The isomers were successfully resolved:

Isomer 1, was obtained as a colourless oil—(3S,4R)-benzyl 3-((tert-butoxycarbonyl)amino)-4-hydroxypiperidine-1-carboxylate (405 mg, 1.156 mmol, 6.48% yield).

LCMS (Method B): Rt=0.97 min, MH$^+$=351.2

Chiral HPLC (Method A): 100% ee.

Isomer 2, was obtained as a colourless oil—(3R,4S)-benzyl 3-((tert-butoxycarbonyl)amino)-4-hydroxypiperidine-1-carboxylate (411 mg, 1.173 mmol, 6.57% yield).

LCMS (Method B): Rt=0.99 min, MH$^+$=351.2

Chiral HPLC (Method A): 95% ee.

The remaining 4.5 g of racemate was also submitted for chiral purification using Chiral HPLC Method C. The isomers were successfully resolved:

Isomer 1, was obtained as a colourless oil—(3S,4R)-benzyl 3-((tert-butoxycarbonyl)amino)-4-hydroxypiperidine-1-carboxylate (1.94 g, 5.54 mmol, 31.0% yield).

LCMS (Method B): Rt=0.98 min, MH$^+$=351.2

Chiral HPLC (Method A): 98.7% ee.

Isomer 2, obtained as a colourless oil—(3R,4S)-benzyl 3-((tert-butoxycarbonyl)amino)-4-hydroxypiperidine-1-carboxylate (1.92 g, 5.48 mmol, 30.7% yield).

LCMS (Method B): Rt=0.97 min, MH$^+$=351.1

Chiral HPLC (Method A): 96.3% ee.

Intermediate 79: tert-Butyl ((3S,4R)-4-hydroxypiperidin-3-yl)carbamate

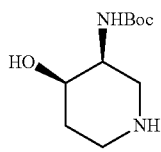

A solution of (3S,4R)-benzyl 3-((tert-butoxycarbonyl)amino)-4-hydroxypiperidine-1-carboxylate (1.94 g, 5.54 mmol) in ethanol (48 mL) was added to a hydrogenation flask containing 10% Pd/C (0.059 g, 0.554 mmol) that had been evacuated and back-filled with N$_2$ (×3). The flask was again evacuated and then back-filled with H$_2$ (×3). Enough H$_2$ to allow complete reaction was then introduced to a burette and the system closed and the flask allowed to stir under a H$_2$ atmosphere overnight. The reaction mixture was filtered through Celite and washed with EtOH (2×20 mL) and ethyl acetate (2×20 mL). The combined filtrate was concentrated in vacuo to afford the product as a cream oily solid—tert-butyl ((3S,4R)-4-hydroxypiperidin-3-yl)carbamate (1.13 g, 5.22 mmol, 94% yield).

LCMS (Method B): Rt=0.40 min, MH$^+$=217.1

Intermediate 80: tert-Butyl ((3R,4S)-4-hydroxypiperidin-3-yl)carbamate

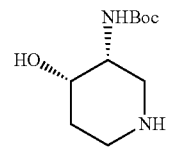

A solution of benzyl 3-((tert-butoxycarbonyl)amino)-4-hydroxypiperidine-1-carboxylate (141 mg, 0.402 mmol) in methanol (8.05 mL) was hydrogenated using the H-cube (settings: 25° C., full H$_2$ mode, 1 mL/min flow rate) and 10% Pd/C CatCart 30 as the catalyst. The eluent was evaporated in vacuo to give the required tert-butyl (4-hydroxypiperidin-3-yl)carbamate (85.1 mg, 0.393 mmol, 98% yield) as a clear oil.

$^1$H NMR (DMSO-d$_6$, 393K): 5.60 (1H, br s, NH), 3.77 (1H, dt, CH), 3.45 (1H, ddd, CH), 2.80 (1H, ddd, C$\underline{H}_A$H$_B$), 2.72 (1H, dd, C$\underline{H}_A$H$_B$), 2.63 (1H, dd, CH$_A\underline{H}_B$), 2.55-2.48 (1H, obs, CH$_A\underline{H}_B$), 1.59-1.53 (2H, m, CH$_2$), 1.42 (9H, s, 3×CH$_3$).

Proof of Absolute Stereochemistry for Intermediates 79 and 80

The absolute configuration of intermediates 79 and 80 was assigned using ab initio VCD analysis. The confidence level for this assignment was estimated to be >99%.

Theoretical Analysis:

Conformational Search: MOE stochastic csearch using MMFF94x force field

Model Chemistry: # opt freq=(noraman,vcd) b3lyp/dgdzvp

Conformational Analysis: Fractional populations estimated using Boltzmann statistics Lorentzian band width: 6 cm$^{-1}$ Frequency scale factor: 0.975

Estimation of Confidence Limit: CompareVOA (BioTools, Inc.) analysis

Experimental:

Spectrometer: BioTools ChiralIR-2X FT-VCD spectrometer operated at 4 cm$^{-1}$

Frequency Range: 2000-800 cm$^{-1}$

PEM Calibration: PEM calibrated at 1400 cm$^{-1}$

PEM Retardation Settings: PEM1=0.250*λ; PEM2=0.260*λ

Scan Method: single 4 h scan; total #=3120×4=12480 scans) scans; t~6 h.)

Solvent: CDCl$_3$

Concentrations: ~10 mg/250 uL

Baseline Correction Method: modified half-difference (VCDE1 (corr'd)=VCDE1 minus VCDE2; VCDE2 (corr'd)=VCDE2 minus VCDE1)

Additional Processing: Savitsky-Golay 9-point smooth

Estimated Level of Reliability

The confidence limit in this study was estimated using CompareVOA™ (BioTools, Inc.), an automated tool for quantifying the level of agreement between two sets of spectral data.

The degree of reliability (the confidence limit) is assessed using the absolute values of two parameters: total neighborhood similarity for the VCD correlation (TNS (VCD)) and the enantiomeric similarity index (ESI).

The degrees of reliability based on CompareVOA analysis are as follows:

| Reliability | *TNS (VCD) (range) | *ESI (range) | Confidence Limit (CL) (range) |
|---|---|---|---|
| High | ≥70 | ≥60 | >99% |
| Medium | 60-70 | 50-60 | 95-99% |
| Low | 50-60 | 40-50 | 90-95% |
| Unreliable | <50 | <40 | <90% |

*absolute value

CompareVOA Results:

Spectral range: 1760-950 cm$^{-1}$

Region omitted: none

Range of statistical analysis (minimum 400 cm$^{-1}$): 810 cm$^{-1}$

Width of triangular weighting function: 20 cm$^{-1}$

TNS (VCD): 85.1 (absolute value)

ESI: 82.8 (absolute value)

Optimized scale factor: 0.975

Estimated confidence level: >99%

Intermediate 81: (+/−)-tert-Butyl (cis-4-hydroxypiperidin-3-yl)carbamate

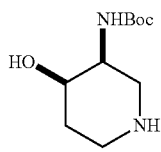 [SMILES: CC(C)(C)OC(=O)N[C@H]1CNCC[C@H]1O]

Prepared in a similar manner to Intermediate 80, from, cis-benzyl 3-((tert-butoxycarbonyl)amino)-4-hydroxypiperidine-1-carboxylate.

$^1$H NMR (CDCl$_3$): 5.31 (1H, br s, NH), 4.00-3.75 (2H, m, 2×CH), 3.04-2.89 (2H, m, 2×C$\underline{H}_A$H$_B$), 2.81 (1H, dd, CH$_A$$\underline{H}_B$), 2.64 (1H, ddd, CH$_A$$\underline{H}_B$), 1.83-1.60 (2H, m, CH$_2$), 1.50 (9H, s, 3×CH$_3$).

Intermediate 82: (+/−)-tert Butyl (trans-4-hydroxypiperidin-3-yl)carbamate

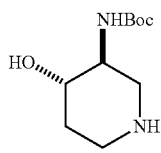

Prepared in a similar manner to Intermediate 80, from, trans-benzyl 3-((tert-butoxycarbonyl)amino)-4-hydroxypiperidine-1-carboxylate.

$^1$H NMR (CDCl$_3$): 4.74 (1H, br d, NH), 3.48 (1H, ddd, CH), 3.42-3.31 (1H, m, CH), 3.24 (1H, dd, C$\underline{H}_A$H$_B$), 3.04 (1H, dt, C$\underline{H}_A$H$_B$), 2.58 (1H, ddd, CH$_A$$\underline{H}_B$), 2.38 (1H, dd, CH$_A$$\underline{H}_B$), 2.02 (1H, dq, C$\underline{H}_A$H$_B$), 1.53-1.40 (10H, m, CH$_A$$\underline{H}_B$, 3×CH$_3$).

Intermediate 83: (+/−)-(cis)-Benzyl 3-((tert-butoxycarbonyl)amino)-4-ethoxypiperidine-1-carboxylate

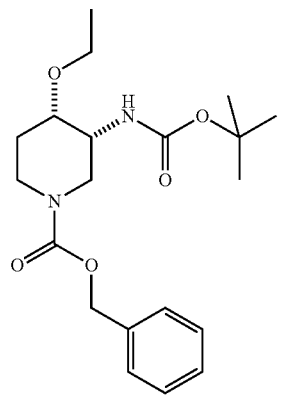

A suspension of sodium hydride (32.3 mg, 1.346 mmol) in THF (9 mL) was stirred under nitrogen in an ice-water-bath at 0° C. A solution of benzyl 3-((tert-butoxycarbonyl)amino)-4-hydroxypiperidine-1-carboxylate (393 mg, 1.122 mmol) in THF (5 mL) was added and the reaction mixture was stirred for 45 min at 0° C. The reaction mixture was placed in an ice-NaCl bath at −25° C. before ethyl trifluoromethanesulfonate (0.159 mL, 1.234 mmol) was added dropwise. After 10 min, the ice-NaCl bath was replaced with an ice-water bath, and reaction mixture was stirred for 1.5 h. The reaction mixture was then stirred at rt for 4.5 h and kept in the freezer overnight. The reaction mixture was neutralised with glacial acetic acid (15 drops) and the solvent was evaporated under reduced pressure to give a clear oil. The residue was dissolved in EtOAc (50 mL), extracted with NaHCO$_3$ (3×70 mL) and washed with brine (70 mL). The organic extracts were combined and dried through a hydrophobic frit. The solvent was evaporated under reduced pressure to give a clear oil. The residue was loaded onto a 50 g SNAP silica column and purified by SP4, eluting with a gradient of 0-50% EtOAc in cyclohexane (15 CVs). The appropriate fractions were combined and concentrated under reduced pressure to give the crude product benzyl 3-((tert-butoxycarbonyl)amino)-4-ethoxypiperidine-1-carboxylate (60 mg, 0.159 mmol, 14.14% yield) as a clear oil. This was used without further purification in the subsequent reaction.

Intermediate 84: (+/−)-(trans)-Benzyl 3-((tert-butoxycarbonyl)amino)-4-methoxypiperidine-1-carboxylate

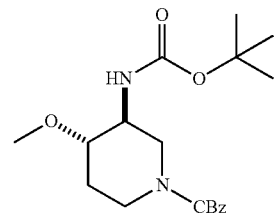

To an ice-cooled solution of (trans)-benzyl 3-((tert-butoxycarbonyl)amino)-4-hydroxypiperidine-1-carboxylate (553 mg, 1.578 mmol) in tetrahydrofuran (THF) (20 mL)

was added sodium hydride (60% in mineral oil) (76 mg, 1.894 mmol) in portions. After addition the resulting mixture was stirred at 0° C. for 1 h. Then methyl iodide (0.118 mL, 1.894 mmol) was added dropwise at 0° C. After addition the mixture was allowed to warm to rt and stirred for 20 h, then the mixture was concentrated in vacuo. The residue was taken up in DCM and loaded onto a Biotage SNAP cartridge (100 g). This was eluted with EtOAc in cyclohexane 0-60%, 20 CV. One major product, and a slightly more polar minor product—both visualised by TLC spraying with Vanillin. The major product was collected to afford the desired product (336.3 mg) as a white solid.

LCMS (Method B): Rt=1.11 min, MH$^+$=365.1

Intermediate 85: (+/−)-(cis)-tert-Butyl (4-ethoxypiperidin-3-yl)carbamate

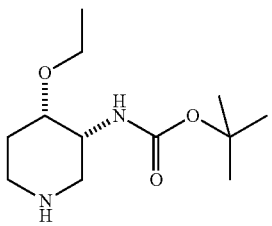 [SMILES: CCO[C@H]1CCNC[C@H]1NC(=O)OC(C)(C)C]

A solution of benzyl 3-((tert-butoxycarbonyl)amino)-4-ethoxypiperidine-1-carboxylate (54 mg, 0.143 mmol) in MeOH (3 mL) was hydrogenated using the H-cube (settings: 25° C., full H$_2$ mode, 1 mL/min flow rate) and 10% Pd/C CatCart 30 cartridge. The solvent was evaporated under reduced pressure to give the required product tert-butyl (4-ethoxypiperidin-3-yl)carbamate (30 mg, 0.123 mmol, 86% yield) as a clear oil. This was used without purification in the subsequent step.

Intermediate 86: (+/−)-tert-Butyl ((trans)-4-methoxypiperidin-3-yl)carbamate

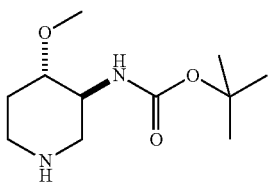 [SMILES: CO[C@H]1CCNC[C@@H]1NC(=O)OC(C)(C)C]

Prepared in a similar manner to Intermediate 85, from (3S,4S)-benzyl 3-((tert-butoxycarbonyl)amino)-4-methoxypiperidine-1-carboxylate Intermediate 87: (R)-3-Azido-1,2,3,6-tetrahydropyridine

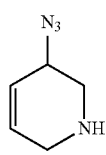

To a solution of tert-butyl 5-azido-5,6-dihydropyridine-1(2H)-carboxylate (the preparation of this intermediate is reported in Synlett, 2006, 13, 2109-2113) (56 mg, 0.250 mmol) in DCM (5 mL) under nitrogen at rt was added trifluoroacetic acid (1 mL, 12.98 mmol). The mixture was stirred for 40 min then concentrated in vacuo. The residue which remained was taken up in DCM and washed with NaHCO$_3$ (sat). The organic layer was dried (Na$_2$SO$_4$), filtered, and concentrated to low volume. The material so obtained was carried on to the next step without further purification.

LCMS (Method B): Rt=0.21 min, MH$^+$=125.0

Intermediate 88: Methyl 4-(methylamino)-3-nitrobenzoate

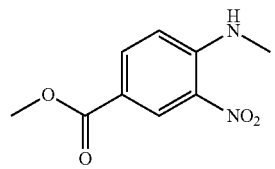

Methylamine (2M in THF) (23.19 mL, 46.4 mmol) was added to a solution of methyl 4-chloro-3-nitrobenzoate (5 g, 23.19 mmol) (available, for example, from Lancaster Synthesis Ltd.) in N,N-dimethylformamide (DMF) (8 mL) at rt under nitrogen. The reaction mixture was heated to 80° C. and stirred overnight. LCMS showed major peak product, but reaction had not gone to completion. Further methylamine (2M in THF, 10 mL) was added and the reaction heated to 90° C. for 6 h. Further methylamine (2M in THF, 6 mL) was added and the reaction stirred for 1 h at rt and 72 h at 70° C. Further methylamine (2M in THF, 10 mL) was added and the reaction heated to 80° C. for 3 h. The reaction was allowed to cool to rt and then the product was precipitated by the addition of water (50 mL). The resultant suspension was cooled to 0° C. and then filtered. The residue was washed with further water (3×25 mL) and allowed to dry on the filter pad for ~15 mins. The solid was collected and dried in vacuo to afford the title compound as a yellow solid (4.54 g, 21.60 mmol, 93% yield).

LCMS (Method B): Rt=0.69 min, MH$^+$=197.2

Intermediate 89: 4-(Methylamino)-3-nitrobenzoic Acid

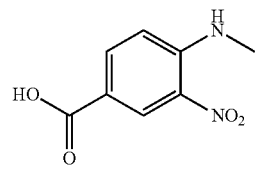

Methyl 4-(methylamino)-3-nitrobenzoate (1.82 g, 8.66 mmol) was dissolved in a 1:1 ratio of tetrahydrofuran (THF) (41.4 mL) and water (41.4 mL). To this was added lithium hydroxide (1.817 g, 43.3 mmol) and the reaction stirred at rt for 16 h. The reaction mixture was cooled to 0° C. and acidified by the addition of 5M HCl (~20 mL), until the pH reached ~5)—a bright yellow precipitate formed, the slurry was filtered and the residue washed with distilled H$_2$O (2×30 mL). The residue was collected and dried in vacuo at 50° C. to afford the product as a yellow solid—4-(methylamino)-3-nitrobenzoic acid (1.43 g, 7.29 mmol, 84% yield). This was used without further purification in the subsequent reactions.

LCMS (Formic): Rt=0.69 min, MH+=197.2

Intermediate 90: 4-Chloro-2-methyl-5-nitrobenzoic Acid

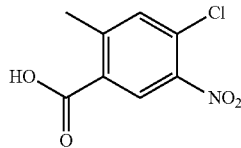

To 4-chloro-2-methylbenzoic acid (2.4 g, 14.07 mmol, commercially available, for example, from Sigma-Aldrich) was added conc. sulfuric acid (12 mL, 225 mmol) and the reaction mixture cooled to ~20° C. Fuming nitric acid (0.754 mL, 16.88 mmol) was added at this temperature, then the reaction mixture allowed to warm to rt. Stirring was continued for another 2 h at rt. The reaction mixture was partitioned between water (50 mL) and ethyl acetate (2×50 mL). The ethyl acetate layer was stood overnight, whereupon crystals had formed. These were removed by filtration to give 4-chloro-2-methyl-5-nitrobenzoic acid (389 mg, 1.804 mmol, 12.83% yield).

LCMS (Method C): Rt 0.91 min, MH+ not seen.

Intermediate 91: Methyl 4-chloro-2-methyl-5-nitrobenzoate

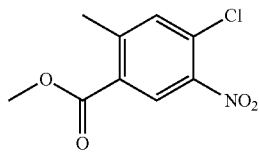

To 4-chloro-2-methyl-5-nitrobenzoic acid (430 mg, 1.995 mmol) in methanol (10 mL) was added 2M aqueous hydrochloric acid (10 mL, 20.00 mmol) and the reaction mixture heated at 80° C. overnight. Concentrated hydrochloric acid (200 □L) was added, and the reaction heated at 80° C. for 1 h. The reaction mixture was cooled to rt. Water (100 mL) was added, and the aqueous layer basified to pH 14 using 2M aqueous sodium hydroxide solution and extracted with ethyl acetate (3×100 mL). These organic layers were kept to one side and used later.

The aqueous layer was acidified with concentrated hydrochloric acid and extracted with ethyl acetate (3×100 mL) and these organics were combined, dried using a hydrophobic frit and evaporated under vacuum to give recovered starting material. To the recovered starting material in methanol (10 mL) was added 2M aqueous hydrochloric acid (10 mL, 20.00 mmol) and the reaction mixture stirred at 80° C. for 1 h, and then stood at rt over the weekend. The reaction mixture was cooled to rt. Water (100 mL) was added, and the aqueous layer basified to pH 14 using 2M aqueous sodium hydroxide solution and extracted with ethyl acetate (3×100 mL).

The organics were combined, the organics from previously added, dried using a hydrophobic frit and evaporated under vacuum to leave methyl 4-chloro-2-methyl-5-nitrobenzoate (326 mg, 1.420 mmol, 71.2% yield).

LCMS (Method B): Rt 1.11 min, MH+ not seen.

Intermediate 92: Methyl 2-methyl-4-(methylamino)-5-nitrobenzoate

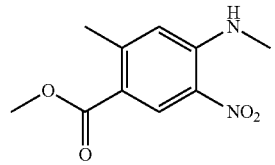

To methyl 4-chloro-2-methyl-5-nitrobenzoate (321 mg, 1.398 mmol) in N,N-dimethylformamide (2.5 mL) was added 2M methylamine in THF (2.80 mL, 5.59 mmol) and the reaction mixture stirred at 80° C. overnight. The reaction mixture was blown down under a stream of nitrogen. Methanol (5 mL) and water (5 mL) were added, and the solid formed removed by filtration and dried in a vacuum oven to give methyl 2-methyl-4-(methylamino)-5-nitrobenzoate (264 mg, 1.177 mmol, 84% yield) as a yellow solid.

LCMS (Method B): Rt 1.02 min, MH+=225.

Intermediate 93: Methyl 3,4-diamino-5-methylbenzoate

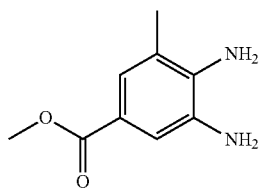

To 3,4-diamino-5-methylbenzoic acid (1 g, 6.02 mmol) (available from, for example, Parkway Scientific LLC) in methanol (30 mL) was added 2M aqueous hydrochloric acid (30.1 mL, 60.2 mmol) and the reaction mixture heated at 65° C. for two nights. The reaction mixture was concentrated under reduced pressure, and applied to 2×2 g Isolute Sorbent 103 cartridges. The cartridges were washed with water and eluted using methanol. The methanol fractions were evaporated under reduced pressure. The residue was loaded in dichloromethane/methanol and purified by SPE (aminopropyl, 20 g), and eluted using 10% methanol in dichloromethane. The appropriate fractions were combined and evaporated under reduced pressure to give the required product methyl 3,4-diamino-5-methylbenzoate (620 mg, 3.44 mmol, 57.2% yield) as an off-white solid.

LCMS (Method B): Rt 0.50 min, MH+ 181.

Intermediate 94: (R)-tert-Butyl (1-(4-chloro-3-nitrobenzoyl)piperidin-3-yl)carbamate

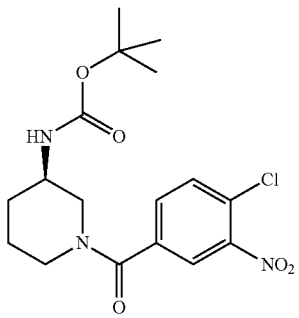 [SMILES: CC(C)(C)OC(=O)N[C@@H]1CCCN(C(=O)c2ccc(Cl)c([N+](=O)[O-])c2)C1]

4-Chloro-3-nitrobenzoic acid (30 g, 149 mmol, available from, for example, Apollo Scientific) was mixed with SOCl$_2$ (200 mL, 2756 mmol) and stirred at 80° C. for 2 h. Toluene (500 mL) was added. The solution containing the product was used directly in the next step, after evaporation of the solvents. 4-Chloro-3-nitrobenzoyl chloride (29 g, 132 mmol), (R)-tert-butyl piperidin-3-ylcarbamate (25 g, 124 mmol) and DIPEA (66 g, 512 mmol) were stirred in DCM (300 mL) under N$_2$ at 0° C. to 20° C. for 3 h. The reaction was quenched into ice/H$_2$O (~100 g) and HCl was added (to pH 1). The organic phase was washed with NaHCO$_3$ (aq., 100 mL, to pH 8), dried (Na$_2$SO$_4$) and evaporated in vacuo. The crude product was purified by silica chromatography eluting with DCM/MeOH=80:1. This afforded the title compound (30 g).

LCMS (Method B): Rt=1.06 min, M+H$^+$=384.1

Intermediate 95: 1,1-Dimethylethyl ((3R)-1-{[4-(methylamino)-3-nitrophenyl]carbonyl}-3-piperidinyl)carbamate

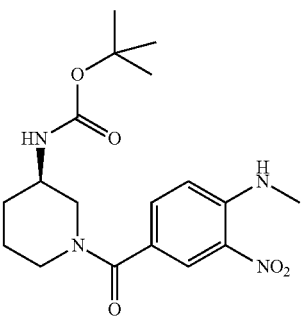 [SMILES: CNc1ccc(C(=O)N2CCC[C@@H](NC(=O)OC(C)(C)C)C2)cc1[N+](=O)[O-]]

To a solution of 1,1-dimethylethyl (3R)-3-piperidinylcarbamate (1.460 g, 7.29 mmol, available from, for example Apollo Scientific Ltd.), 4-(methylamino)-3-nitrobenzoic acid (1.43 g, 7.29 mmol) and HATU (2.77 g, 7.29 mmol) in N,N-dimethylformamide (DMF) (50 mL) was added DIPEA (2.55 mL, 14.58 mmol) and the reaction stirred at rt for 16 h. Water (200 mL) and Et$_2$O (200 mL) were added and the layers separated. The aqueous layer was extracted with further Et$_2$O (2×200 mL) and the combined organics washed with water (2×50 mL), dried (Na$_2$SO$_4$) and concentrated in vacuo to afford a bright yellow oil. The crude product was purified on silica (100 g) using a gradient of 40% EtOAc/cyclohexane→100% ethyl acetate/cyclohexane. The appropriate fractions were combined and evaporated under vacuum to give the product as an orange-gold solid—1,1-dimethylethyl ((3R)-1-{[4-(methylamino)-3-nitrophenyl]carbonyl}-3-piperidinyl)carbamate (2.76 g, 7.29 mmol, 100% yield)

LCMS (Method B): Rt=0.96 min, MH$^+$=379.3

Intermediate 96: 1,1-Dimethylethyl (1-{[4-(methylamino)-3-nitrophenyl]carbonyl}-3-piperidinyl)carbamate

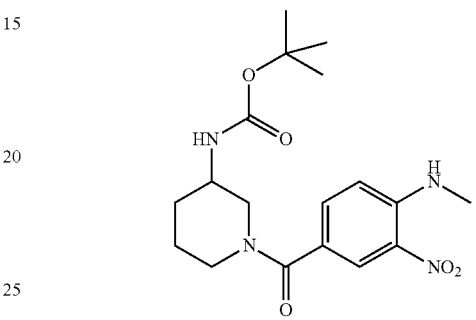

Prepared in a similar manner to Intermediate 95, from 1,1-dimethylethyl (+/−)-3-piperidinylcarbamate (1.460 g, 7.29 mmol, available from, for example, Apollo Scientific Ltd.) and 4-(methylamino)-3-nitrobenzoic acid in 57% yield LCMS (Method B): Rt=0.96 min, MH$^+$=379.2

Intermediate 97: (R)-tert-Butyl (1-(3-amino-4-(methylamino)benzoyl)piperidin-3-yl)carbamate

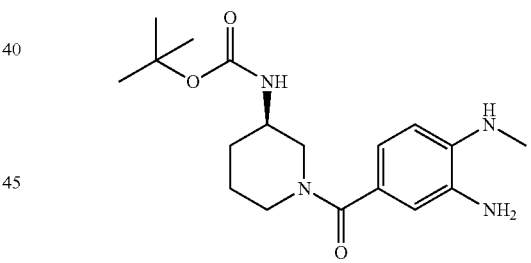

This Intermediate was made according to one of the following method A or B:

Method A:

(R)-tert-Butyl (1-(4-(methylamino)-3-nitrobenzoyl)piperidin-3-yl)carbamate (400 mg) was dissolved in methanol (ca. 18 mL) and the solution hydrogenated over a 5% palladium on carbon CatCart or a 10% palladium on carbon Catcart using a flow hydrogenation apparatus (H-Cube, settings: full hydrogen, atm pressure, ambient temperature) in one or two run. The solution was washed through with further methanol (60 mL) and the solution reduced to dryness in vacuo to give (R)-tert-butyl (1-(3-amino-4-(methylamino)benzoyl)piperidin-3-yl)carbamate as a pale brown gum (360 mg).

LCMS (Method B): Rt=0.71 min, MH$^+$=349

Method B:

(R)-tert-Butyl (1-(4-(methylamino)-3-nitrobenzoyl)piperidin-3-yl)carbamate (2 g, 5.29 mmol) in ethanol (30 mL)

was added to a flushed hydrogenation flask containing palladium on carbon (0.400 g, 3.76 mmol), the resulting mixture was flushed with nitrogen/vacuum three times, then stirred under an atmosphere of hydrogen for 44 h. The reaction mixture was flushed from hydrogen atmosphere with nitrogen/vacuum three times, and filtered on a pre-packed 10 g celite (dark green solution obtained). The appropriate fractions were concentrated under reduced pressure to afford 1.955 g of a dark green solid. The residue was dissolved in DCM and purified by silica chromatography, eluting with a 0% to 6% 2M NH$_3$/MeOH in DCM gradient over 24CV. The relevant fractions were combined and concentrated in vacuo before being azeotroped to give the required product, 1.916 g as a grey solid.

LCMS (Method A): Rt=0.85 min, MH$^+$=349

Intermediate 98: (R)-tert-Butyl (1-(4-(ethylamino)-3-nitrobenzoyl)piperidin-3-yl)carbamate

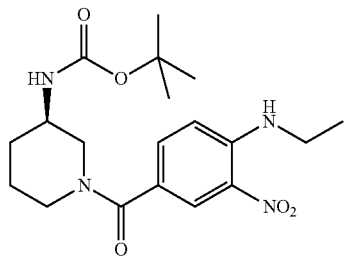 [SMILES: CCNc1ccc(C(=O)N2CCC[C@@H](NC(=O)OC(C)(C)C)C2)cc1[N+](=O)[O-]]

2M Ethylamine in THF (5.21 mL, 10.42 mmol) was added to 1,1-dimethylethyl {(3R)-1-[(4-chloro-3-nitrophenyl)carbonyl]-3-piperidinyl}carbamate (500 mg, 1.303 mmol) in N,N-dimethylformamide (5 mL) and the reaction stirred under nitrogen, at 80° C. After 30 min, further 2M ethylamine in THF (5.21 mL, 10.42 mmol) was added and the reaction stirred under nitrogen, at 80° C., for 24 h. The reaction mixture was partitioned between saturated aqueous sodium bicarbonate (70 mL) and DCM (3×70 mL). The organics were combined, dried using a hydrophobic frit and dried under a stream of nitrogen. The sample was loaded in dichloromethane and purified by Biotage SP4 chromatography (SNAP 100 g silica) using a gradient of 0-100% cyclohexane-ethyl acetate. The appropriate fractions were combined and evaporated under vacuum to give the required product (R)-tert-butyl (1-(4-(ethylamino)-3-nitrobenzoyl)piperidin-3-yl)carbamate (225 mg, 0.573 mmol, 44.0% yield) as a bright yellow glass.

LCMS (Method B): Rt=1.04 min, MH+ 393.

Intermediate 99: 1,1-Dimethylethyl {(3R)-1-[(4-{[3-({[(9H-fluoren-9-ylmethyl)oxy]carbonyl}amino)propyl]amino}-3-nitrophenyl)carbonyl]-3-piperidinyl}carbamate

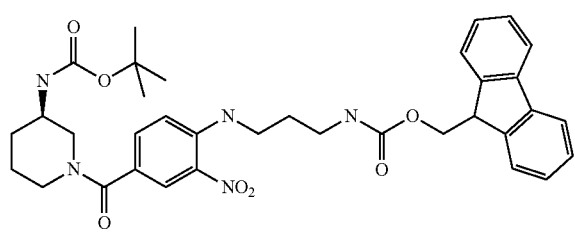 [SMILES: CC(C)(C)OC(=O)N[C@@H]1CCCN(C(=O)c2ccc(NCCCNC(=O)OCC3c4ccccc4-c4ccccc43)c([N+](=O)[O-])c2)C1]

To a mixture of (R)-tert-butyl (1-(4-((3-aminopropyl)amino)-3-nitrobenzoyl)piperidin-3-yl)carbamate (2.1 g, 4.98 mmol), DIPEA (1.740 mL, 9.96 mmol) and DCM (20 mL) was added, with stirring and ice-bath cooling, (9H-Fluoren-9-yl)methyl carbonochloridate (1.289 g, 4.98 mmol) in DCM (10 mL) over a period of 30 min. The reaction was then left to stir under nitrogen, at ambient temperature, for 15 min. The reaction mixture was diluted with DCM (50 mL) washed with 2M aqueous hydrochloric acid (40 mL), followed by saturated aqueous sodium bicarbonate (50 mL) and brine (40 mL) before being dried with a hydrophobic frit and evaporated under vacuum. The sample was loaded in dichloromethane and purified by Biotage SP4 (2×SNAP 100 g silica) using a gradient of 0-100% cyclohexane-ethyl acetate over 10 column volumes followed by holding at 100% cyclohexane-ethyl acetate for 5 column volumes. The appropriate fractions were combined and evaporated under vacuum to give the required product 1,1-dimethylethyl {(3R)-1-[(4-{[3-({[(9H-fluoren-9-ylmethyl)oxy]carbonyl}amino)propyl]amino}-3-nitrophenyl)carbonyl]-3-piperidinyl}carbamate (3.09 g, 4.80 mmol, 96% yield) as a yellow foam.

LCMS (Method B): Rt 1.27 min, MH+ 644.

Intermediate 100: (R)-tert-Butyl (1-(4-((3-aminopropyl)amino)-3-nitrobenzoyl)piperidin-3-yl)carbamate

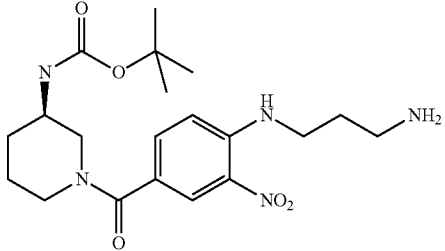 [SMILES: CC(C)(C)OC(=O)N[C@@H]1CCCN(C(=O)c2ccc(NCCCN)c([N+](=O)[O-])c2)C1]

Propane-1,3-diamine (10.97 mL, 130 mmol) was added to 1,1-dimethylethyl {(3R)-1-[(4-chloro-3-nitrophenyl)carbonyl]-3-piperidinyl)}carbamate (2 g, 5.21 mmol) and the mixture heated, while being stirred under nitrogen, at 100° C. for 1 h. The reaction mixture was concentrated in vacuo. The sample was then acidified to pH 6 by addition of 2M hydrochloric acid, dissolved in water (40 mL) and basified to pH 12 with 2M sodium hydroxide. The mixture was then extracted with DCM (3×50 mL). The organics were combined, dried using a hydrophobic frit and evaporated under vacuum to leave (R)-tert-butyl (1-(4-((3-aminopropyl)amino)-3-nitrobenzoyl)piperidin-3-yl)carbamate (2.18 g, 5.17 mmol, 99% yield).

LCMS (Method B): Rt 0.71 min, MH+ 422

Intermediate 101: 1,1-Dimethylethyl {(3R)-1-[(4-{[2-({[(1,1-dimethylethyl)oxy]carbonyl}amino)ethyl]amino}-3-nitrophenyl)carbonyl]-3-piperidinyl)}carbamate

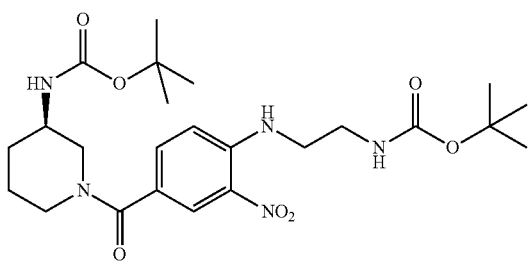 [SMILES: CC(C)(C)OC(=O)NCCNc1ccc(C(=O)N2CCC[C@@H](NC(=O)OC(C)(C)C)C2)cc1[N+](=O)[O-]]

Tert-butyl (2-aminoethyl)carbamate (2.06 mL, 13.03 mmol) was added to a solution of 1,1-dimethylethyl {(3R)-1-[(4-chloro-3-nitrophenyl)carbonyl]-3-piperidinyl}carbamate (500 mg, 1.30 mmol) in 1,4-dioxane (5 mL). After 21 h of stirring at 100° C., the reaction mixture was concentrated under reduced pressure to give the crude product as a dark orange oil. The residue was loaded in DCM onto a 100 g SNAP silica column and purified by SP4, eluting with a gradient of 0-5% MeOH in DCM (15 CVs). The appropriate fractions were combined and evaporated under reduced pressure to give the crude product 1,1-dimethylethyl {(3R)-1-[(4-{[2-({[(1,1-dimethylethyl)oxy]carbonyl}amino)ethyl]amino}-3-nitrophenyl)carbonyl]-3-piperidinyl}carbamate (682.4 mg, 1.344 mmol, 103% yield) as a dark yellow solid. This was used without further purification in the subsequent reactions.

LCMS (Method B): Rt=1.06 mins, MH+=508.3

Intermediate 102: (R)-tert-Butyl (1-(4-fluoro-3-nitro-5-(trifluoromethyl)benzoyl)piperidin-3-yl)carbamate

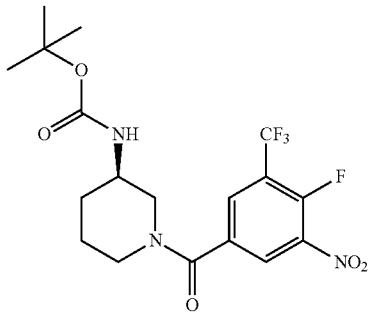 [SMILES: CC(C)(C)OC(=O)N[C@@H]1CCCN(C(=O)c2cc([N+](=O)[O-])c(F)c(C(F)(F)F)c2)C1]

A solution of 4-fluoro-3-nitro-5-(trifluoromethyl)benzoic acid (300 mg, 1.185 mmol, commercially available from, for example, Fluorochem) in DCM (12 mL) was evacuated 9 times before oxalyl chloride (0.208 mL, 2.371 mmol) was added dropwise, followed by DMF (0.075 mL, 0.968 mmol). Initial bubbling of the reaction mixture was observed. After 4.5 h of stirring under nitrogen, oxalyl chloride (0.052 mL, 0.593 mmol) was added to the reaction mixture, followed by DMF (18 µL, 0.232 mmol). After 2 h of stirring at rt, the reaction mixture was concentrated under reduced pressure to give an off-white solid. The residue was dissolved in DCM (12 mL) and (R)-tert-butyl piperidin-3-ylcarbamate (261 mg, 1.304 mmol, commercially available from, for example, Apollo Scientific) and DIPEA (0.414 mL, 2.370 mmol) were added. After 18 h of stirring at rt, (R)-tert-butyl piperidin-3-ylcarbamate (119 mg, 0.593 mmol) was added to the reaction mixture followed by DIPEA (0.104 mL, 0.593 mmol). After 1 h of stirring at rt, the reaction mixture was diluted with DCM (20 mL), sodium bicarbonate was added (50 mL) and the layers were separated. The organic layer was washed with sodium bicarbonate (3×50 mL), passed through a hydrophobic frit and the solvent was evaporated under reduced pressure to give a dark orange oil. The residue was loaded in DCM onto a 25 g SNAP silica column and purified by SP4, eluting with a gradient of 0-50% EtOAc in cyclohexane (15 CVs). The appropriate fractions were combined and evaporated under reduced pressure to give the required product (R)-tert-butyl (1-(4-fluoro-3-nitro-5-(trifluoromethyl)benzoyl)piperidin-3-yl)carbamate (419 mg, 0.962 mmol, 81% yield) as a yellow solid.

LCMS (Method A): Rt=1.21 min, MH+=436.0

Intermediate 103: (R)-tert-Butyl (1-(4-(methylamino)-3-nitro-5-(trifluoromethyl)benzoyl)piperidin-3-yl)carbamate

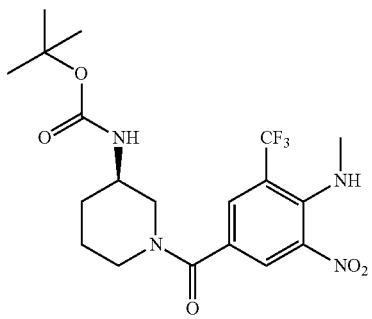 [SMILES: CNc1c([N+](=O)[O-])cc(C(=O)N2CCC[C@@H](NC(=O)OC(C)(C)C)C2)cc1C(F)(F)F]

Methanamine (1.925 mL of a 2 M solution in THF, 3.85 mmol) was added to a solution of (R)-tert-butyl (1-(4-fluoro-3-nitro-5-(trifluoromethyl)benzoyl)piperidin-3-yl)carbamate (419 mg, 0.96 mmol) in DMF (15 mL). After 2 h of stirring at 80° C., the solution was allowed to cool to rt. The reaction mixture was concentrated under reduced pressure and the residue was taken up in water (50 mL). EtOAc (50 mL) was added and the layers were separated. The aqueous layer was further extracted with EtOAc (4×50 mL). The organic extracts were combined, passed through a hydrophobic frit and the solvent was removed under reduced pressure. The residue was loaded in DCM onto a 50 g SNAP silica column and purified by SP4, eluting with a gradient of 0-50% EtOAc in cyclohexane gradient (15 CVs). The appropriate fractions were combined and evaporated under reduced pressure to give the required product (R)-tert-butyl (1-(4-(methylamino)-3-nitro-5-(trifluoromethyl)benzoyl)piperidin-3-yl)carbamate (400 mg, 0.90 mmol, 93% yield) as a yellow solid.

LCMS (Method A): Rt=1.15 min, MH+=447.05.

Intermediate 104: Methyl 3-methoxy-4-(methylamino)-5-nitrobenzoate

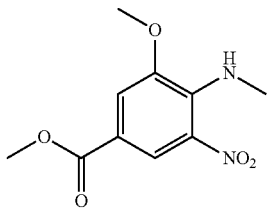

Methyl 4-chloro-3-methoxy-5-nitrobenzoate (available from, for example, Apollo Scientific Ltd) (14 g, 57.0 mmol) was dissolved in N,N-dimethylformamide (DMF) (140 mL) and cooled to ~0° C. in an ice/water bath. Methanamine (2M in THF) (114 mL, 228 mmol) was added dropwise with vigorous stirring using a dropping funnel and the mixture was flushed with nitrogen and heated at 80° C. for 3 h. The mixture was allowed to cool to rt over the weekend. The reaction mixture was diluted with water (500 mL), and filtered under vacuum to give the title compound as an orange solid (13.69 g).

LCMS (Method A): Rt=1.04 min, MH+=241.05

Intermediate 105:
3-Methoxy-4-(methylamino)-5-nitrobenzoic Acid

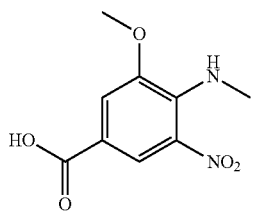 [SMILES: CNc1c(OC)cc(C(=O)O)cc1[N+](=O)[O-]]

To a solution of methyl 3-methoxy-4-(methylamino)-5-nitrobenzoate (13.69 g, 57.0 mmol) in tetrahydrofuran (THF) (100 mL) and water (50.0 mL) was added a single portion of lithium hydroxide (4.09 g, 171 mmol). The resulting suspension was stirred for 19 h at rt. The reaction was acidified with aq. 2N HCl (~50 mL), until pH reached ~4. The resultant suspension was filtered and the orange solid dried on the high vacuum line overnight to give the title compound as an orange solid (11.09 g).

LCMS (Method A): Rt=0.51 min, MH+=227.0

Intermediate 106: (R)-tert-Butyl (1-(3-methoxy-4-(methylamino)-5-nitrobenzoyl)piperidin-3-yl)carbamate

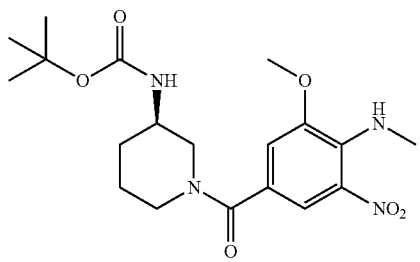 [SMILES: CNc1c(OC)cc(C(=O)N2CCC[C@@H](NC(=O)OC(C)(C)C)C2)cc1[N+](=O)[O-]]

To a solution of 3-methoxy-4-(methylamino)-5-nitrobenzoic acid (11.09 g, 49.0 mmol) and HATU (18.64 g, 49.0 mmol) in N,N-dimethylformamide (DMF) (300 mL) was added DIPEA (17.13 mL, 98 mmol) and the mixture stirred for 30 min. Upon addition of the DIPEA the mixture went cloudy after ~1 min with stirring. (R)-tert-Butyl piperidin-3-ylcarbamate (9.82 g, 49.0 mmol) was then added and stirred for 1.5 h, after which time LCMS showed the reaction was complete. To 5 mL of the reaction mixture was added sat.aq. LiCl solution (5 mL) and Et₂O (10 mL) and the layers separated. The aqueous layer was re-extracted with Et₂O (2×10 mL), the combined organics were backwashed with water (10 mL), dried with Na₂SO₄, filtered and concentrated in vacuo to give the crude product as an orange gum. The gum was dissolved in the minimum amount of DCM and purified by Si SNAP 25 g column using a 50-100% ethyl acetate/cyclohexane. The appropriate fractions were combined and evaporated in vacuo before being azeotroped with cyclohexane and dried under vacuum to give the required product, 281 mg as an orange solid. The remaining reaction mixture was concentrated in vacuo to remove some of the DMF. Saturated aq. LiCl solution (300 mL) and Et₂O (700 mL) were added and the mixture separated. The aqueous layer was re-extracted with Et₂O (2×700 mL), the combined organic layers were backwashed with water (1 L), dried with Na₂SO₄, filtered and concentrated in vacuo to give the crude product as an orange gum. This was purified on a 340 g SNAP silica cartridge eluting with 30%-60% ethyl acetate in cyclohexane. The appropriate fractions were combined and concentrated in vacuo to yield the title compound as an orange solid (19.4 g).

LCMS: (Method B): Rt=1.02 min, MH+=409.1

Intermediate 107: tert-Butyl (1-(3-methoxy-4-(methylamino)-5-nitrobenzoyl)pyrrolidin-3-yl)carbamate

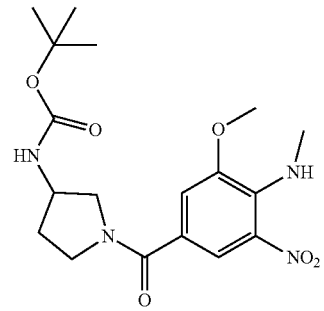 [SMILES: CNc1c(OC)cc(C(=O)N2CCC(NC(=O)OC(C)(C)C)C2)cc1[N+](=O)[O-]]

Prepared in a similar manner to Intermediate 106, from 3-methoxy-4-(methylamino)-5-nitrobenzoic acid and tert-butyl pyrrolidin-3-ylcarbamate (commercially available from, for example, TCI Europe).

LCMS (Method B): Rt=0.98 min, MH+=395.2,

Intermediate 108: Methyl 6-(methylamino)-5-nitronicotinate

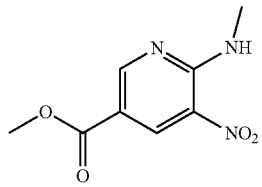

A solution of methyl 6-chloro-5-nitronicotinate (500 mg, 2.309 mmol, commercially available from, for example, ButtPark) in anhydrous DMF (2.5 mL) was treated with methylamine (2M in THF, 2.5 mL, 5 mmol)—instant dark yellow colour warming and ppt. The reaction was stirred at ambient temperature (air atm.—loosely capped vial) for ~20 min. A further portion of methylamine (2M in THF, 1.0 mL, 2 mmol) was added and stirring continued for ~40 min. Most of the solvent was evaporated under a stream of nitrogen and the residue (semi-solid) diluted with water and treated with DIPEA (~2 mL). The mixture was extracted repeatedly with ethyl acetate (solid not particularly soluble in ethyl acetate). The organic extracts were combined, dried (hydrophobic frit) and reduced to dryness under a stream of nitrogen to give a yellow crystalline solid (436 mg).

LCMS (Method B): Rt=0.84 min, MH+=212.1.

Intermediate 109: Methyl 1-methyl-2-[1-(phenylmethyl)-1H-indol-2-yl]-1H-benzimidazole-5-carboxylate

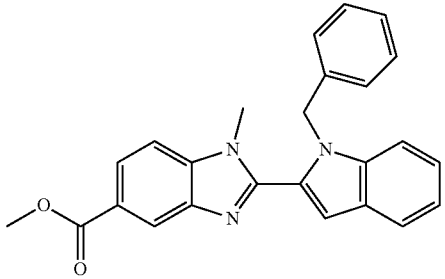 [SMILES: COC(=O)c1ccc2c(c1)nc(-c1cc3ccccc3n1Cc1ccccc1)n2C]

Sodium hydrosulfite (2339 mg, 11.42 mmol) dissolved in water (4.0 mL) was added to a solution of methyl 4-(methylamino)-3-nitrobenzoate (800 mg, 3.81 mmol) and 1-(phenylmethyl)-1H-indole-2-carbaldehyde (896 mg, 3.81 mmol) in ethanol (8 mL) at rt under nitrogen. The reaction mixture was heated to 80° C. and stirred overnight. The reaction was allowed to cool to rt. Water (50 mL) and DCM (50 mL) were added, an inseparable suspension resulted so 1N HCl (20 mL) was added and the layers separated. The aqueous layer was further extracted with 10% MeOH/DCM (2×25 mL) and the combined organics diluted with MeOH (20 mL), dried (MgSO₄) and concentrated in vacuo to afford the crude product as an orange solid. The crude product was purified on silica (100 g) using a gradient of cyclohexane→50% ethyl acetate/cyclohexane. The appropriate fractions were combined and evaporated under vacuum to give the product as a yellow solid—methyl 1-methyl-2-[1-(phenylmethyl)-1H-indol-2-yl]-1H-benzimidazole-5-carboxylate (621 mg, 1.570 mmol, 41.3% yield).

LCMS (Method B): Rt=1.30 mins, MH$^+$=396.2

Intermediate 110: Methyl 2-(1-ethyl-1H-indol-2-yl)-1-methyl-1H-benzo[d]imidazole-5-carboxylate

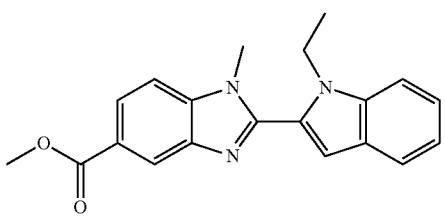 [SMILES: CCn1c(-c2nc3cc(C(=O)OC)ccc3n2C)cc2ccccc21]

Prepared in a similar manner to Intermediate 109 from 1-ethyl-1H-indole-2-carbaldehyde and methyl 4-(methylamino)-3-nitrobenzoate (8 g, 38.1 mmol)

LCMS (Method B): Rt: 1.20 min, MH$^+$ 334.

Intermediate 111: 1-Methyl-2-[1-(phenylmethyl)-1H-indol-2-yl]-1H-benzimidazole-5-carboxylic Acid

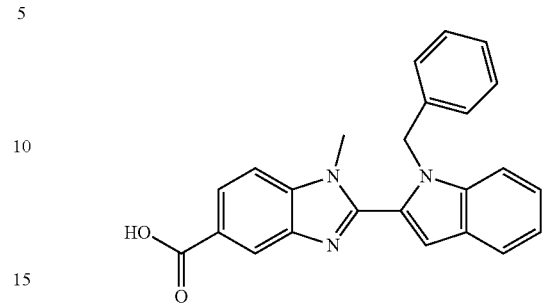

Methyl 1-methyl-2-[1-(phenylmethyl)-1H-indol-2-yl]-1H-benzimidazole-5-carboxylate (621 mg, 1.570 mmol) was dissolved in a 1:1 ratio of tetrahydrofuran (THF) (7.5 mL) and water (7.5 mL). To this was added lithium hydroxide (329 mg, 7.85 mmol) and the reaction stirred at rt for 1 h. The reaction was allowed to stir for a further 16 h at rt. The reaction mixture was acidified by the addition of 2M HCl (20 mL) and the organics extracted into 10% MeOH/DCM (20 mL). The aqueous layer was washed with 10% MeOH/DCM (2×20 mL) and the combined organics dried (Na₂SO₄) and concentrated in vacuo to afford a yellow solid—1-methyl-2-[1-(phenylmethyl)-1H-indol-2-yl]-1H-benzimidazole-5-carboxylic acid (607 mg, 1.591 mmol, 101% yield). This was used without further purification in the subsequent reactions.

LCMS (Method B): Rt=1.13 mins, MH$^+$=382.2

Intermediate 112: 2-(1-Ethyl-1H-indol-2-yl)-1-methyl-1H-benzo[d]imidazole-5-carboxylic Acid

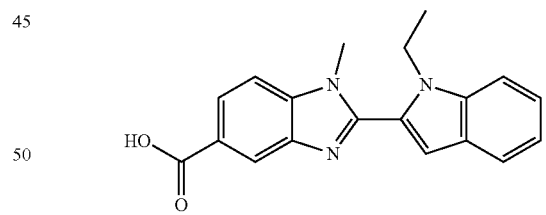

To a solution of methyl 2-(1-ethyl-1H-indol-2-yl)-1-methyl-1H-benzimidazole-5-carboxylate (8 g, 24.00 mmol) in THF (50 mL) was added lithium hydroxide monohydrate (5 g, 119 mmol) then water (50 mL). The mixture was stirred at rt in a stoppered vessel for 16 h. The reaction mixture was then stirred at 80° C. for 8 h. The reaction mixture was allowed to cool to rt and the volatiles evaporated under vacuum. The remaining slight suspension was acidified to pH=1 with 2 M HCl (aq). A precipitate formed which was filtered and the solid washed with water (400 mL). The solid was dried in a vacuum oven to give the title compound as a grey solid (7.4 g, 23.17 mmol, 97%).

LCMS (Method B): Rt 1.02 min; MH+ 320.

Intermediate 113: Methyl 2-(1-ethyl-1H-indol-2-yl)-1,6-dimethyl-1H-benzo[d]imidazole-5-carboxylate

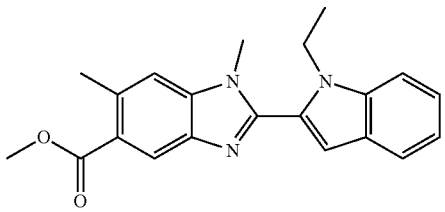 [SMILES: CCn1c(-c2nc3cc(C(=O)OC)c(C)cc3n2C)cc2ccccc21]

Methyl 2-methyl-4-(methylamino)-5-nitrobenzoate (260 mg, 1.160 mmol), 1-ethyl-1H-indole-2-carbaldehyde (201 mg, 1.160 mmol) and sodium hydrosulfite (606 mg, 3.48 mmol) were combined in ethanol (3 mL) and water (1.5 mL) and the reaction mixture heated at 80° C. for 2 h. The reaction mixture was partitioned between saturated aqueous ammonium chloride solution (75 mL) and ethyl acetate (3×75 mL). The organics were combined, dried using a hydrophobic frit and evaporated under vacuum. The sample was loaded in methanol/dichloromethane (and the column dried in a vacuum oven) and purified by SPE (silica, 50 g) using 0-50% ethyl acetate/cyclohexane. The appropriate fractions were combined and dried under a stream of nitrogen to give the required product methyl 2-(1-ethyl-1H-indol-2-yl)-1,6-dimethyl-1H-benzimidazole-5-carboxylate (249 mg, 0.717 mmol, 61.8% yield) as a yellow solid.

LCMS (Method B): Rt 1.25 min, MH+=348.

Intermediate 114: 2-(1-Ethyl-1H-indol-2-yl)-1,6-dimethyl-1H-benzo[d]imidazole-5-carboxylic Acid

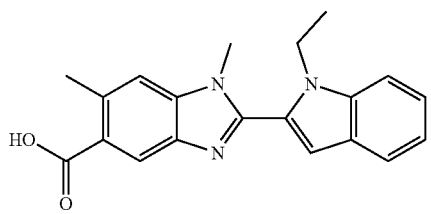 [SMILES: CCn1c(-c2nc3cc(C(=O)O)c(C)cc3n2C)cc2ccccc21]

Methyl 2-(1-ethyl-1H-indol-2-yl)-1,6-dimethyl-1H-benzimidazole-5-carboxylate (245 mg, 0.705 mmol) and lithium hydroxide monohydrate (34 mg) were stirred in methanol (2 mL) and water (1 mL) at rt overnight. Further lithium hydroxide monohydrate (34 mg) was added and the reaction mixture heated at 70° C. for 2.5 days. The reaction mixture was partitioned between saturated aqueous ammonium chloride solution (15 mL) and dichloromethane (3×15 mL). The organics were combined, dried using a hydrophobic frit and dried under a stream of nitrogen to give 2-(1-ethyl-1H-indol-2-yl)-1,6-dimethyl-1H-benzimidazole-5-carboxylic acid (242 mg, 0.726 mmol, 103% yield).

LCMS (Method B): Rt 1.05 min, MH+=334.

Intermediate 115: Methyl 4-amino-3-(1-ethyl-1H-indole-2-carboxamido)-5-methylbenzoate

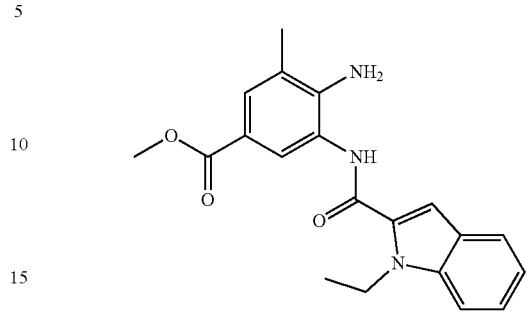

To a mixture of 1-ethyl-1H-indole-2-carboxylic acid (358 mg, 1.892 mmol, commercially available from, for example, Enamine building blocks) and HATU (785 mg, 2.064 mmol) in N,N-dimethylformamide (DMF) (2 mL) was added DIPEA (0.901 mL, 5.16 mmol) and the reaction mixture stirred at rt for 15 min. Methyl 3,4-diamino-5-methylbenzoate (310 mg, 1.720 mmol) was added and stirring continued for a further 2 h. The reaction mixture was blown down under a stream of nitrogen and the residue loaded in dichloromethane and purified by SPE (aminopropyl, 20 g), eluted using 10% methanol in dichloromethane. The appropriate fractions were combined and dried under a stream of nitrogen. The sample was loaded in dichloromethane and purified by Biotage SP4 (SNAP 100 g silica) using a gradient of 0-10% 2M ammonia in methanol-dichloromethane. The appropriate fractions were combined and evaporated under reduced pressure to give the required product methyl 4-amino-3-(1-ethyl-1H-indole-2-carboxamido)-5-methylbenzoate (379 mg, 1.079 mmol, 62.7% yield) as a brown solid.

LCMS (Method B): Rt 1.10 min, MH+ 352.

Intermediate 116: Methyl 2-(1-ethyl-1H-indol-2-yl)-7-methyl-1H-benzo[d]imidazole-5-carboxylate

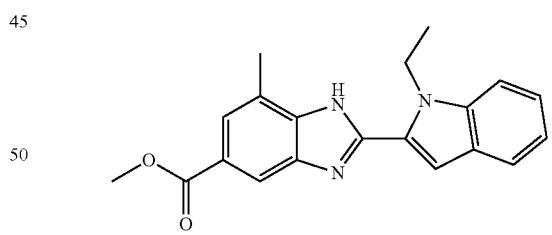

Methyl 4-amino-3-(1-ethyl-1H-indole-2-carboxamido)-5-methylbenzoate (375 mg, 1.067 mmol) and p-toluenesulfonic acid monohydrate (223 mg, 1.174 mmol) were combined in toluene (30 mL) and the reaction mixture heated at 100° C. overnight. The reaction mixture was evaporated under vacuum and the residue loaded in methanol/dichloromethane (and the column dried in a vacuum oven) and purified by Biotage SP4 (SNAP 50 g silica) using a gradient of 0-100% cyclohexane-ethyl acetate over 10 column volumes followed by holding at 100% cyclohexane-ethyl acetate for 5 column volumes. The appropriate fractions were combined and evaporated under reduced pressure to give the required product methyl 2-(1-ethyl-1H-indol-2-yl)-

7-methyl-1H-benzo[d]imidazole-5-carboxylate (105 mg, 0.315 mmol, 29.5% yield) as a yellow solid.

LCMS (Method B): Rt 1.27 min, MH+ 334.

Intermediate 117: 2-(1-Ethyl-1H-indol-2-yl)-1,4-dimethyl-1H-benzo[d]imidazole-6-carboxylic Acid

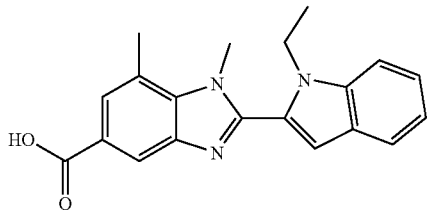 [SMILES: CCn1c(-c2nc3cc(C(=O)O)cc(C)c3n2C)cc2ccccc21]

To methyl 2-(1-ethyl-1H-indol-2-yl)-7-methyl-1H-benzo[d]imidazole-5-carboxylate (101 mg, 0.303 mmol) in N,N-dimethylformamide (1 mL) was added 60% sodium hydride in mineral oil (18.18 mg, 0.454 mmol), the reaction mixture was cooled in an ice/water bath, and stirred for 90 min. Methyl iodide (0.022 mL, 0.348 mmol) was added and the reaction mixture allowed to warm to rt and stirred overnight. Further 60% sodium hydride in mineral oil (18.18 mg, 0.454 mmol) was added, followed by methyl iodide (0.022 mL, 0.348 mmol), and the reaction mixture stirred overnight. Lithium hydroxide (14.51 mg, 0.606 mmol) and water (0.5 mL) were added, and the reaction mixture stirred overnight. The reaction mixture was blown down under a stream of nitrogen. HATU (173 mg, 0.454 mmol) and N,N-dimethylformamide (1 mL) were added to the resulting solid, followed by DIPEA (0.159 ml, 0.909 mmol) and then, after stirring at rt for 10 mins, (R)-tert-butyl piperidin-3-ylcarbamate (91 mg, 0.454 mmol). The reaction mixture was stirred at rt overnight. The reaction mixture was blown down under a stream of nitrogen and partitioned between saturated aqueous sodium hydrogen carbonate solution (10 mL) and ethyl acetate (3×10 mL). The organic layers were combined, dried using a hydrophobic frit and dried under a stream of nitrogen.

No amide formation had occurred, instead the desired carboxylic acid product and its alkylated benzimidazole regioisomer were isolated: Accordingly, the residue was dissolved in DMSO (2×1 mL) and purified by MDAP (Method B). The solvent was dried under a stream of nitrogen to give the desired product (6 mg) and the regioisomeric product (26 mg). The desired product was used in the subsequent reaction without further analysis at this stage.

Intermediate 118: 4-Bromo-N-methyl-2-nitro-6-(trifluoromethoxy)aniline

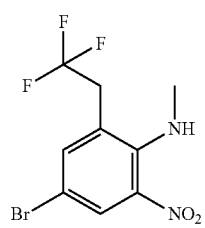 [SMILES: CNc1c(CC(F)(F)F)cc(Br)cc1[N+](=O)[O-]]

A solution of 4-bromo-2-nitro-6-(trifluoromethoxy)aniline (1 g, 3.32 mmol, commercially available from, for example, Apollo Scientific) in DMF (40 mL) was cooled using an ice/water bath for 10 min then cesium carbonate (2.17 g, 6.64 mmol) was added. The reaction mixture was stirred for 10 min then iodomethane (0.208 mL, 3.32 mmol) was added and the mixture allowed warm to rt under nitrogen over 67 h. Further iodomethane (0.208 mL, 3.32 mmol) was added to the reaction mixture was stirred for a further 6 h then partitioned using EtOAc and water (200 mL each). The aqueous layer was re-extracted with EtOAc (2×200 mL) then the combined organics were washed with water (200 mL) then passed through a hydrophobic frit and concentrated under reduced pressure to give the crude product as a brown gum. The material was purified by silica column chromatography, eluting with a DCM/cyclohexane solvent system (0 to 30%) to give the title product as an orange solid (404 mg, 39% yield).

LCMS (Method A): Rt=1.33 min, M+NH$_4$$^+$=332.7

Intermediate 119: 5-Bromo-2-(1-ethyl-1H-indol-2-yl)-1-methyl-7-(trifluoromethoxy)-1H-benzo[d]imidazole

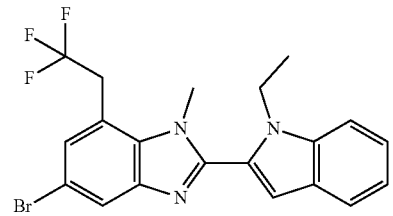 [SMILES: CCn1c(-c2nc3cc(Br)cc(CC(F)(F)F)c3n2C)cc2ccccc21]

A solution of sodium dithionate (780 mg, 3.81 mmol) in water (6.0 mL) was added to a microwave vial which was equipped with a stirrer and a solution of 4-bromo-N-methyl-2-nitro-6-(trifluoromethoxy)aniline (400 mg, 1.27 mmol) and 1-ethyl-1H-indole-2-carbaldehyde (220 mg, 1.270 mmol) in EtOH (12 mL). The reaction vessel was sealed and heated using a microwave to 100° C. for 5 h then allowed to cool. The reaction mixture was diluted with DCM (40 mL) then sodium sulphate added and the mixture filtered then concentrated under reduced pressure. The resulting crude product was purified using silica column chromatography, eluting with a DCM/cyclohexane solvent system (40 to 100%) to give the title compound as a colourless gum (309 mg, 56% yield).

LCMS (Method A): Rt=1.58 min, MH$^+$=438.1/440.1

Intermediate 120: Methyl 2-(1-ethyl-1H-indol-2-yl)-1-methyl-7-(trifluoromethoxy)-1H-benzo[d]imidazole-5-carboxylate

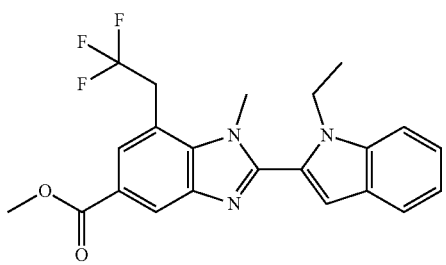 [SMILES: CCn1c(-c2nc3cc(C(=O)OC)cc(CC(F)(F)F)c3n2C)cc2ccccc21]

5-Bromo-2-(1-ethyl-1H-indol-2-yl)-1-methyl-7-(trifluoromethoxy)-1H-benzo[d]imidazole (149 mg, 0.34 mmol), MeOH (0.206 mL, 5.10 mmol), DIPEA (0.119 mL, 0.680 mmol), DMAP (83 mg, 0.680 mmol), molybdenum hexacarbonyl (47 mg, 0.178 mmol) and acetoxy(2-(di-o-tolyl-phosphino)benzyl)palladium (17 mg, 0.018 mmol) were dissolved in 1,4-dioxane (12 mL) in a microwave vial. The reaction vessel was sealed and heated using a microwave to 180° C. for 3 h, then allowed to cool. The reaction mixture was concentrated under reduced pressure to give the crude title compound (210 mg, >99% yield).

LCMS (Method A): Rt=1.46 min, MH$^+$=418.2

Intermediate 121: 2-(1-Ethyl-1H-indol-2-yl)-1-methyl-7-(trifluoromethoxy)-1H-benzo[d]imidazole-5-carboxylic Acid

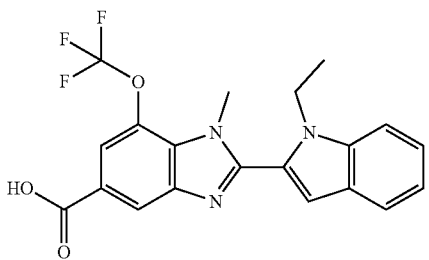 [SMILES: CCn1c(-c2nc3cc(C(=O)O)cc(OC(F)(F)F)c3n2C)cc2ccccc21]

To a stirred solution of methyl 2-(1-ethyl-1H-indol-2-yl)-1-methyl-7-(trifluoromethoxy)-1H-benzo[d]imidazole-5-carboxylate (444 mg, 1.06 mmol) in a mixture of THF (12 mL) and water (6 mL) was added lithium hydroxide (76 mg, 3.19 mmol). The mixture was stirred under nitrogen for 68 h at rt then filtered through a hydrophobic frit and acidified to around pH 4 using HCl (2N). The reaction mixture was partitioned between EtOAc (50 mL) and water (50 mL), the layers separated and the aqueous layer re-extracted with EtOAc (2×50 mL). The combined organics were passed through a hydrophobic frit and concentrated under reduced pressure to give the crude product. The material was loaded in IPA onto a 10 g aminopropyl SPE column which was eluted with IPA then a 10% HCl in IPA. Fractions containing product were combined then concentrated under reduced pressure to give the crude title compound as a brown solid (121 mg, 28% yield).

LCMS (Method A): Rt=0.93 mins, MH$^+$=404.1

Intermediate 122: Methyl 7-bromo-2-(1-ethyl-1H-indol-2-yl)-1-methyl-1H-benzo[d]imidazole-5-carboxylate

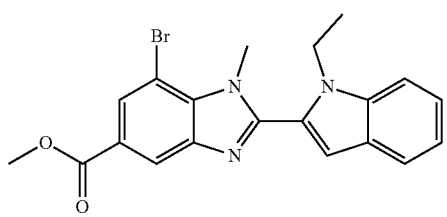 [SMILES: CCn1c(-c2nc3cc(C(=O)OC)cc(Br)c3n2C)cc2ccccc21]

To a solution of methyl methyl 3-bromo-4-(methylamino)-5-nitrobenzoate (2.65 g, 9.17 mmol, preparation described in PCT Int. Appl. WO2010034796A1) and 1-ethyl-1H-indole-2-carbaldehyde (2.16 g, 12.5 mmol, commercially available from, for example, Sigma Aldrich) in EtOH (70 mL) was added dropwise a solution of sodium dithionite (3.4 g, 16.6 mmol) in water (35.0 mL). The mixture was flushed with nitrogen then heated at 100° C. overnight for 16 h. The reaction mixture was concentrated under reduced pressure then partitioned between DCM (100 mL) and water (100 mL). After leaving the layers to separate for approximately 1 h, the organic layer was isolated then the aqueous layer re-extracted with DCM (3×100 mL). The organic layers were combined, dried over sodium sulphate, filtered through a hydrophobic frit and then concentrated under reduced pressure. The resulting brown solid was purified by silica column chromatography, eluting with a EtOAc/cyclohexane solvent system (0 to 20%) to give the title compound as a yellow solid (1.2 g, 32% yield).

LCMS (Method B): Rt=1.40 min, MH$^+$=412.0/414.0

Intermediate 123: 7-Bromo-2-(1-ethyl-1H-indol-2-yl)-1-methyl-1H-benzo[d]imidazole-5-carboxylic Acid

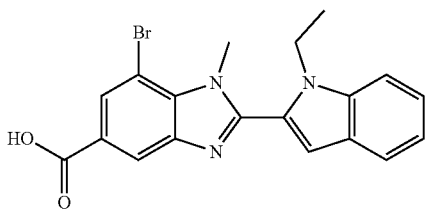 [SMILES: CCn1c(-c2nc3cc(C(=O)O)cc(Br)c3n2C)cc2ccccc21]

To a stirred suspension of methyl 7-bromo-2-(1-ethyl-1H-indol-2-yl)-1-methyl-1H-benzo[d]imidazole-5-carboxylate (1.97 g, 4.78 mmol) in a mixture of THF (40 mL) and water (20 mL) was added lithium hydroxide (229 mg, 9.56 mmol). The mixture was stirred at rt over the weekend then acidified by addition of HCl (2M, 40 mL). The mixture was partitioned with 10% MeOH/90% DCM (50 mL) then the aqueous layer re-extracted with 10% MeOH/90% DCM (50 mL). The combined organics were dried over sodium sulphate then passed through a hydrophobic frit and concentrated under reduced pressure to yield the title compound as a yellow/white solid (1.67 g, 88% yield).

LCMS (Method B): Rt=1.20 min, MH$^+$=398.0/400.1

Intermediate 124: Methyl 2-(1-(cyclopropylmethyl)-1H-indol-2-yl)-1-methyl-1H-benzo[d]imidazole-5-carboxylate

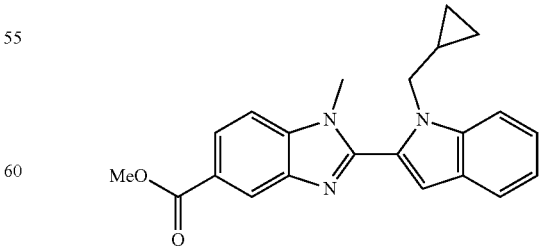

To a solution of methyl 4-(methylamino)-3-nitrobenzoate (6.6 g, 31.4 mmol) and 1-(cyclopropylmethyl)-1H-indole-2-carbaldehyde (7.0 g, 35.2 mmol) in EtOH/H$_2$O (100 mL/50 mL) was added Na$_2$SO$_4$ (16.4 g, 94.2 mmol), the mixture was stirred overnight at 80° C. under N$_2$, the mixture was monitored by LCMS which showed methyl 4-(methylamino)-3-nitrobenzoate had been completely consumed. Water and DCM were added, and the obtained organic phase was dried over Na$_2$SO$_4$ and then purified by silica chromatography eluting with petroleum ether/ethyl acetate=5:1. This gave the title compound (7.0 g, 62%)

LCMS (Method D): Rt=1.78 mins, MH$^+$=360.2

Intermediate 125: 2-(1-(Cyclopropylmethyl)-1H-indol-2-yl)-1-methyl-1H-benzo[d]imidazole-5-carboxylic Acid

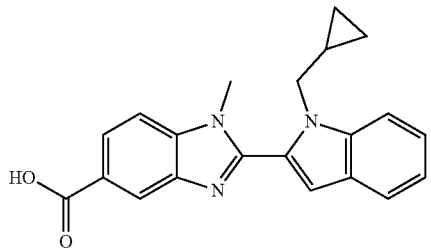 [SMILES: Cn1c(-c2cc3ccccc3n2CC2CC2)nc2cc(C(=O)O)ccc21]

To a solution of methyl 2-(1-(cyclopropylmethyl)-1H-indol-2-yl)-1-methyl-1H-benzo[d]imidazole-5-carboxylate (7.0 g, 195 mmol) in THF/water (150 mL/150 mL) was added LiOH (4.10 g, 975 mmol). The mixture was stirred overnight at 50° C., then concentrated and water (10 mL) added. The mixture was neutralised with 2N HCl (50 mL), filtered and washed with water and Et$_2$O. The solid was dried to give the title compound (5.2 g, 78%)

LCMS (Method D): Rt=1.62 mins, MH$^+$=346.2.

Intermediate 126: Methyl 7-methoxy-1-methyl-2-(1-(2,2,2-trifluoroethyl)-1H-indol-2-yl)-1H-benzo[d]imidazole-5-carboxylate

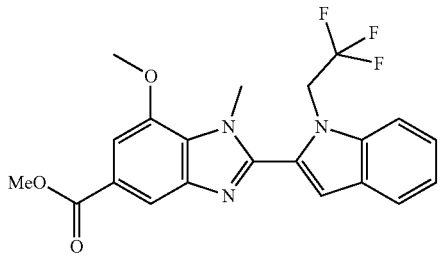 [SMILES: COC(=O)c1cc(OC)c2c(c1)nc(-c1cc3ccccc3n1CC(F)(F)F)n2C]

A suspension of sodium hydrosulfite (541 mg, 2.64 mmol) in water (1.5 mL) was added to a solution of methyl 3-methoxy-4-(methylamino)-5-nitrobenzoate (235 mg, 0.978 mmol) and 1-(2,2,2-trifluoroethyl)-1H-indole-2-carbaldehyde (200 mg, 0.880 mmol) in ethanol (3.5 mL) in a 5 mL microwave vial. The reaction mixture was heated in the microwave for 5 h at 100° C. The reaction mixture was concentrated in vacuo. The pale yellow residue was taken up in diethyl ether. The resulting suspension was filtered in vacuo. NMR and LCMS analysis of the collected solid showed the product as the main component. The solid was dried on the vacuum line overnight to give the crude product as an off-white solid—methyl 7-methoxy-1-methyl-2-(1-(2, 2,2-trifluoroethyl)-1H-indol-2-yl)-1H-benzo[d]imidazole-5-carboxylate (700 mg, 0.755 mmol, 86% yield) which was suitable for the subsequent reaction.

However, LCMS and NMR of the filtrate liquid showed some product and impurities present. The filtrate was concentrated in vacuo. The residue was loaded in dichloromethane and purified by column chromatography on silica (10 g) using a 0-30% ethyl acetate/cyclohexane gradient. The appropriate fractions were combined and evaporated in vacuo to give the required product—methyl 7-methoxy-1-methyl-2-(1-(2,2,2-trifluoroethyl)-1H-indol-2-yl)-1H-benzo[d]imidazole-5-carboxylate (49 mg, 0.117 mmol, 13.35% yield) as a yellow solid.

LCMS (Method B): Rt=1.29 mins, MH$^+$=418.1

Intermediate 127: 7-Methoxy-1-methyl-2-(1-(2,2,2-trifluoroethyl)-1H-indol-2-yl)-1H-benzo[d]imidazole-5-carboxylic Acid

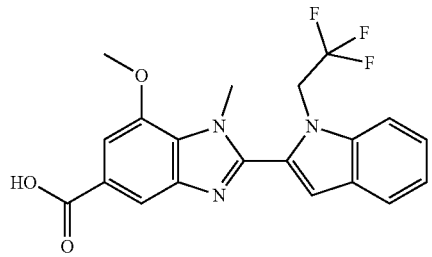 [SMILES: COc1cc(C(=O)O)cc2nc(-c3cc4ccccc4n3CC(F)(F)F)n(C)c12]

A mixture of methyl 7-methoxy-1-methyl-2-(1-(2,2,2-trifluoroethyl)-1H-indol-2-yl)-1H-benzo[d]imidazole-5-carboxylate (318 mg, 0.762 mmol) and lithium hydroxide monohydrate (63.9 mg, 1.524 mmol) in tetrahydrofuran (THF) (5 mL) and water (3 mL) was stirred at rt for 2 h. LCMS analysis showed no product formation. Therefore, lithium hydroxide monohydrate (63.9 mg, 1.524 mmol) was added and the reaction mixture was left stirring for a further 2 h. Product formation failed to take place as shown by LCMS. Therefore, further lithium hydroxide monohydrate (128 mg, 3.05 mmol) was added to the reaction mixture. The reaction mixture was left stirring overnight at rt. LCMS analysis showed the reaction had not progressed. Therefore, the reaction mixture was concentrated and the residue was taken up in water (40 mL). The organics were extracted using DCM (4×40 mL). The aqueous layer was further extracted using a 10% MeOH/DCM solution (3×30 mL). The combined collected DCM layers and MeOH/DCM layers were concentrated individually. NMR analysis showed both the DCM and 10% MeOH/DCM batches contained the unreacted starting material ester as the main component. The two batches were combined and dried over the weekend in the vacuum oven.

The hydrolysis reaction was restarted: A mixture of methyl 7-methoxy-1-methyl-2-(1-(2,2,2-trifluoroethyl)-1H-indol-2-yl)-1H-benzo[d]imidazole-5-carboxylate (230 mg, 0.551 mmol) and lithium hydroxide monohydrate (46.2 mg, 1.102 mmol) in tetrahydrofuran (THF) (4 mL) and water (3 mL) was stirred at rt overnight for 24 h. LCMS analysis showed completion of the reaction. The reaction mixture was concentrated in vacuo. The residue was dissolved in water (7 mL) and 2M HCl (aq.) was added dropwise until pH 2. The resulting solid was collected by filtration in vacuo, washed with water and subsequently dried in the vacuum oven to give the required product -7-methoxy-1-methyl-2-

(1-(2,2,2-trifluoroethyl)-1H-indol-2-yl)-1H-benzo[d]imidazole-5-carboxylic acid (210.5 mg, 0.522 mmol, 68.5% yield) as an off-white solid.

LCMS (Method B): Rt=1.13 mins, MH+=404.1.

Intermediate 128: Methyl 2-(1-ethyl-1H-indol-2-yl)-7-methoxy-1-methyl-1H-benzo[d]imidazole-5-carboxylate

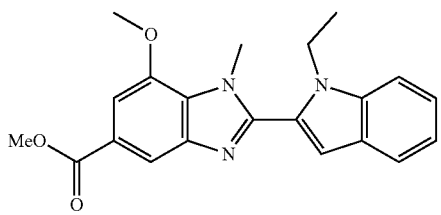 [SMILES: CCn1c(-c2nc3cc(C(=O)OC)cc(OC)c3n2C)cc2ccccc21]

A solution of sodium hydrosulfite (1.56 g, 7.62 mmol) in water (6 mL) was added to a suspension of methyl 3-methoxy-4-(methylamino)-5-nitrobenzoate (610 mg, 2.54 mmol) and 1-ethyl-1H-indole-2-carbaldehyde (440 mg, 2.54 mmol) in ethanol (12 mL) in a 10-20 mL microwave vial. The reaction mixture was heated to 100° C. for 5 h. The reaction mixture was diluted with DCM (50 mL), dried (Na$_2$SO$_4$), filtered and concentrated in vacuo to afford the crude product as an off white solid. The crude product was purified by flash chromatography on silica (100 g) eluting with 60%-100% ethyl acetate/cyclohexane. The product initially eluted near the solvent front and then tailed through a large number of fractions, suggesting low solubility. Further elution with 50% (20% MeOH/DCM)/DCM provided more fractions containing products. The appropriate fractions from both columns were combined together and concentrated in vacuo to afford the product as an off white solid—methyl 2-(1-ethyl-1H-indol-2-yl)-7-methoxy-1-methyl-1H-benzo[d]imidazole-5-carboxylate (761 mg, 2.094 mmol, 82% yield), this was used without further purification.

LCMS (Method B): Rt=1.26 mins, MH+=364.3.

Intermediate 129: 2-(1-Ethyl-1H-indol-2-yl)-7-methoxy-1-methyl-1H-benzo[d]imidazole-5-carboxylic Acid

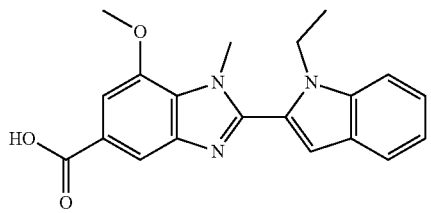 [SMILES: CCn1c(-c2nc3cc(C(=O)O)cc(OC)c3n2C)cc2ccccc21]

Methyl 2-(1-ethyl-1H-indol-2-yl)-7-methoxy-1-methyl-1H-benzo[d]imidazole-5-carboxylate (761 mg, 2.094 mmol) was dissolved in a 1:1 ratio of tetrahydrofuran (THF) (12 mL) and water (12 mL). To this was added lithium hydroxide (60.2 mg, 2.51 mmol) and the reaction stirred at rt for 16 h. LCMS showed only a small amount of conversion. Further lithium hydroxide (60.2 mg, 2.51 mmol) was added and the reaction stirred for a further 24 h. The reaction was progressing slowly. A further portion of lithium hydroxide (180 mg, 7.53 mmol) was added and the reaction stirred for a further 24 h. Reaction has still not gone to completion, so a further portion of lithium hydroxide (180 mg, 7.53 mmol) was added and the reaction mixture stirred over the weekend—reaction now complete by LCMS. The reaction mixture was acidified (to pH ~5) by the addition of 2M HCl (~20 mL) and the organics extracted into 10% MeOH/DCM (20 mL). The aqueous layer was washed with 10% MeOH/DCM (2×20 mL) and the combined organics (as a suspension) were concentrated in vacuo to afford a yellow solid—2-(1-ethyl-1H-indol-2-yl)-7-methoxy-1-methyl-1H-benzo[d]imidazole-5-carboxylic acid (728 mg, 2.084 mmol, 100% yield). This was used without further purification in the subsequent reactions.

LCMS (Method B): Rt=1.08 mins, MH+=350.3.

Intermediate 130: Methyl 2-(1-(cyclopropylmethyl)-1H-indol-2-yl)-7-methoxy-1-methyl-1H-benzo[d]imidazole-5-carboxylate

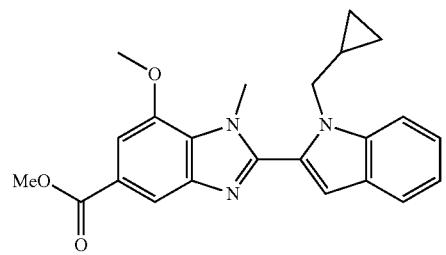 [SMILES: COC(=O)c1cc(OC)c2c(c1)nc(-c1cc3ccccc3n1CC1CC1)n2C]

A solution of sodium hydrosulfite (5.27 g, 25.7 mmol) in water (32.5 mL) was added to a suspension of methyl 3-methoxy-4-(methylamino)-5-nitrobenzoate (2.06 g, 8.58 mmol) and 1-(cyclopropylmethyl)-1H-indole-2-carbaldehyde (1.709 g, 8.58 mmol) in ethanol (65 mL). The reaction mixture was heated to reflux for 16 h. The reaction mixture was diluted with DCM (100 mL), dried (Na$_2$SO$_4$), filtered and concentrated in vacuo to afford the crude product as an orange solid. The crude product was purified by column chromatography on a silica cartridge (100 g) using a gradient of 60% EtOAc/cyclohexane→100% EtOAc/cyclohexane. The product eluted very quickly and then tailed through a number of fractions, suggesting poor solubility in EtOAc/cyclohexane mixtures. The appropriate fractions were combined and evaporated under vacuum to give the product as an orange solid which was still impure. The crude product was then purified by column chromatography on a silica cartridge (100 g) using a gradient of 0% EtOAc/DCM→10% EtOAc/DCM. The appropriate fractions were collected and concentrated in vacuo to afford the desired product as a cream solid—methyl 2-(1-(cyclopropylmethyl)-1H-indol-2-yl)-7-methoxy-1-methyl-1H-benzo[d]imidazole-5-carboxylate (2.185 g, 5.61 mmol, 65.4% yield)

LCMS (Method B): Rt=1.29 mins, MH+=390.1.

Intermediate 131: 2-(1-(Cyclopropylmethyl)-1H-indol-2-yl)-7-methoxy-1-methyl-1H-benzo[d]imidazole-5-carboxylic Acid

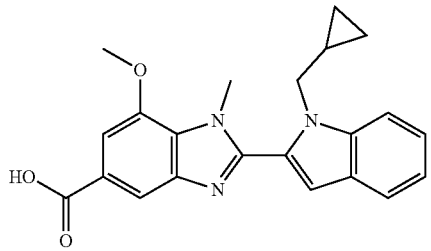 [SMILES: COc1cc(C(=O)O)cc2nc(-c3cc4ccccc4n3CC3CC3)n(C)c12]

Methyl 2-(1-(cyclopropylmethyl)-1H-indol-2-yl)-7-methoxy-1-methyl-1H-benzo[d]imidazole-5-carboxylate (2.185 g, 5.61 mmol) was dissolved in a 1:1 ratio of tetrahydrofuran (THF) (32 mL) and water (32.0 mL). To this was added lithium hydroxide anhydrous (1.177 g, 28.1 mmol) and the reaction stirred at rt for 16 h. The reaction mixture was acidified by the addition of 2M HCl(aq) (50 mL) and the organics extracted into 10% MeOH/DCM (20 mL). The aqueous layer was washed with 10% MeOH/DCM (2×20 mL) and the combined organics dried (Na$_2$SO$_4$) and concentrated in vacuo. LCMS confirmed the presence of product. A large amount of insoluble material remained in the aqueous layer and this was filtered and the residue analysed. This was also pure product by LCMS. The two batches were combined to afford the product as an off white solid—2-(1-(cyclopropylmethyl)-1H-indol-2-yl)-7-methoxy-1-methyl-1H-benzo[d]imidazole-5-carboxylic acid (1.86 g, 4.95 mmol, 88% yield).

LCMS (Method B): Rt=1.12 mins, MH$^+$=376.1

Intermediate 132: Methyl 1-methyl-2-(1-methyl-1H-indol-2-yl)-1H-benzo[d]imidazole-5-carboxylate

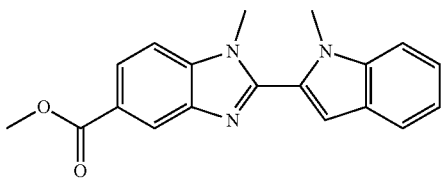 [SMILES: COC(=O)c1ccc2c(c1)nc(-c1cc3ccccc3n1C)n2C]

Sodium hydrosulfite (585 mg, 2.85 mmol) dissolved in water (1 mL) was added to a solution of methyl 4-(methylamino)-3-nitrobenzoate (200 mg, 0.952 mmol) and 1-methyl-1H-indole-2-carbaldehyde (151 mg, 0.952 mmol, commercially available from, for example, Sigma-Aldrich) in ethanol (2 mL) at rt under nitrogen. The reaction mixture was heated to 80° C. and stirred overnight. The reaction was allowed to cool to rt. Water (50 mL) and DCM (50 mL) were added and the layers separated. The aqueous layer was further extracted with DCM (2×25 mL) and the combined organics dried (MgSO$_4$) and concentrated in vacuo to afford the crude product as a yellow solid. The crude product was purified by Biotage SP4 flash chromatography on a SNAP 25 g silica cartridge using a gradient of cyclohexane→50% ethyl acetate/cyclohexane. The appropriate fractions were combined and evaporated under vacuum to give the product as a yellow solid—methyl 1-methyl-2-(1-methyl-1H-indol-2-yl)-1H-benzimidazole-5-carboxylate (133 mg, 0.416 mmol, 43.8% yield).

LCMS (Method B): Rt=1.12 min, MH+=320.1.

Intermediate 133: 1-Methyl-2-(1-methyl-1H-indol-2-yl)-1H-benzo[d]imidazole-5-carboxylic Acid

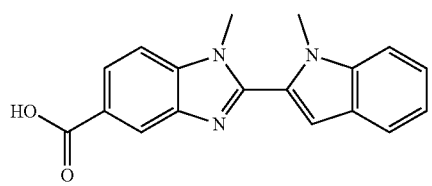 [SMILES: Cn1c(-c2nc3cc(C(=O)O)ccc3n2C)cc2ccccc21]

Methyl 1-methyl-2-(1-methyl-1H-indol-2-yl)-1H-benzimidazole-5-carboxylate (133 mg, 0.416 mmol) was dissolved in a 1:1 ratio of tetrahydrofuran (THF) (2 mL) and water (2 mL). To this was added lithium hydroxide (87 mg, 2.082 mmol) and the reaction stirred at rt for 1 h. LCMS showed mostly starting material. The reaction was allowed to stir for a further 16 h at rt. The reaction mixture was acidified by the addition of 2M HCl (20 mL) and the organics extracted into EtOAc (20 mL). The desired product appeared sparingly soluble in EtOAc and the layer was collected as a suspension. The aqueous layer was washed with DCM (2×20 mL) and the combined organics (as a suspension) were concentrated in vacuo to afford a yellow solid—1-methyl-2-(1-methyl-1H-indol-2-yl)-1H-benzimidazole-5-carboxylic acid (148 mg, 0.485 mmol, 116% yield). This was used without further purification in the subsequent reactions.

LCMS (Method B): Rt=0.94 min, MH+=306.1.

Intermediate 134: Methyl 7-((tert-butoxycarbonyl)amino)-2-(1-ethyl-1H-indol-2-yl)-1-methyl-1H-benzo[d]imidazole-5-carboxylate

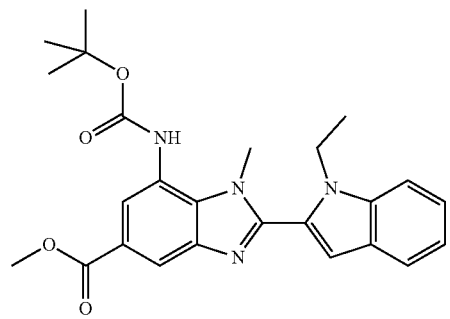 [SMILES: CCn1c(-c2nc3cc(C(=O)OC)cc(NC(=O)OC(C)(C)C)c3n2C)cc2ccccc21]

To a microwave vial fitted with a septa, was added methyl 7-bromo-2-(1-ethyl-1H-indol-2-yl)-1-methyl-1H-benzo[d]imidazole-5-carboxylate (500 mg, 1.213 mmol), tert-butyl carbamate (170 mg, 1.455 mmol), Pd$_2$(dba)$_3$ (44.4 mg, 0.049 mmol), Xantphos (112 mg, 0.194 mmol) and cesium carbonate (553 mg, 1.698 mmol). 1,4-Dioxane (5 mL) was added and N$_2$ bubbled through the resultant suspension for 2 min. The vial was sealed and heated in a microwave at 110° C. for 5 h. The reaction was quenched by the addition of H$_2$O (50 mL). EtOAc (40 mL) was added and the layers separated. The aqueous layer was further extracted with EtOAc (2×40 mL) and the combined organics dried (Na₂SO₄) and concentrated in vacuo to afford the crude product as an orange oil. The crude product was purified by Biotage SP4 flash chromatography on a SNAP 25 g silica cartridge using a gradient of 0% EtOAc/cyclohexane→30% ethyl acetate/cyclohexane. The appropriate fractions were combined and evaporated under vacuum to give the product as a cream foam—methyl 7-((tert-butoxycarbonyl)amino)-2-(1-ethyl-1H-indol-2-yl)-1-methyl-1H-benzo[d]imidazole-5-carboxylate (398 mg, 0.887 mmol, 73.2% yield)

LCMS (Method B): Rt=1.27 min, MH+=449.3

Intermediate 135: Methyl 7-((tert-butoxycarbonyl)(methyl)amino)-2-(1-ethyl-1H-indol-2-yl)-1-methyl-1H-benzo[d]imidazole-5-carboxylate

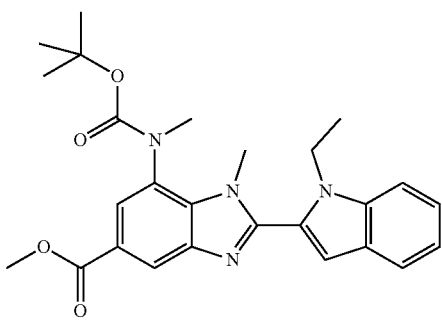 [SMILES: CCn1c(-c2nc3cc(C(=O)OC)cc(N(C)C(=O)OC(C)(C)C)c3n2C)cc2ccccc21]

To a dry flask, was added methyl 7-((tert-butoxycarbonyl)amino)-2-(1-ethyl-1H-indol-2-yl)-1-methyl-1H-benzo[d]imidazole-5-carboxylate (398 mg, 0.887 mmol) in N,N-dimethylformamide (DMF) (4 mL) and the reaction mixture cooled to 0° C. Sodium hydride (60% dispersion in mineral oil) (39.0 mg, 0.976 mmol) was added and the resultant suspension stirred for 30 min at 0° C. and 30 min at rt. The solution was recooled to 0° C. and methyl iodide (0.083 mL, 1.331 mmol) added. The reaction was allowed to warm to rt and stirred for ~1 h. Further MeI (40 µL) was added and the reaction stirred for a further 15 min. A further portion of NaH (10 mg, 60% dispersion in oil) was added and the reaction stirred for a further 15 min. The reaction was quenched by the addition of water (10 mL) and the organics extracted into Et₂O (20 mL). The aqueous layer was washed with further Et₂O (2×20 mL) and the combined organics then back-extracted with water (2×20 mL). The organic layer was dried (Na₂SO₄) and concentrated in vacuo to afford the crude product as an off white glass. The crude product was purified by Biotage SP4 flash chromatography on a SNAP 25 g silica cartridge using a gradient of 0% EtOAc/cyclohexane→30% ethyl acetate/cyclohexane. The appropriate fractions were combined and evaporated under vacuum to give the product as a white foam—methyl 7-((tert-butoxycarbonyl)(methyl)amino)-2-(1-ethyl-1H-indol-2-yl)-1-methyl-1H-benzo[d]imidazole-5-carboxylate (324 mg, 0.700 mmol, 79% yield).

LCMS (Method B): Rt=1.37 min, MH+=463.3

Intermediate 136: 7-((tert-Butoxycarbonyl)(methyl)amino)-2-(1-ethyl-1H-indol-2-yl)-1-methyl-1H-benzo[d]imidazole-5-carboxylic Acid

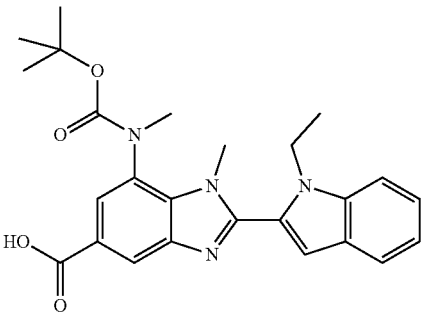 [SMILES: CCn1c(-c2nc3cc(C(=O)O)cc(N(C)C(=O)OC(C)(C)C)c3n2C)cc2ccccc21]

Lithium hydroxide (17.60 mg, 0.735 mmol) was added to a stirred suspension of methyl 7-((tert-butoxycarbonyl)(methyl)amino)-2-(1-ethyl-1H-indol-2-yl)-1-methyl-1H-benzo[d]imidazole-5-carboxylate (170 mg, 0.368 mmol) in tetrahydrofuran (THF) (2 mL)/water (1 mL) and the reaction stirred at rt overnight. The reaction mixture was acidified by the addition of 2M HCl (5 mL) and the organics extracted into 10% MeOH/DCM (10 mL). The aqueous layer was washed with 10% MeOH/DCM (2×10 mL) and the combined organics dried (Na₂SO₄) and concentrated in vacuo to afford 7-((tert-butoxycarbonyl)(methyl)amino)-2-(1-ethyl-1H-indol-2-yl)-1-methyl-1H-benzo[d]imidazole-5-carboxylic acid (162 mg, 0.361 mmol, 98% yield).

LCMS (Method B): Rt=1.22 min, MH+=449.2.

Intermediate 137: Methyl 2-(1-ethyl-1H-indol-2-yl)-1-methyl-7-(methylamino)-1H-benzo[d]imidazole-5-carboxylate

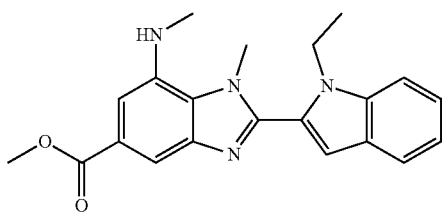 [SMILES: CCn1c(-c2nc3cc(C(=O)OC)cc(NC)c3n2C)cc2ccccc21]

To a flask containing methyl 7-((tert-butoxycarbonyl)(methyl)amino)-2-(1-ethyl-1H-indol-2-yl)-1-methyl-1H-benzo[d]imidazole-5-carboxylate (154 mg, 0.333 mmol) in dichloromethane (DCM) (2 mL) was added TFA (0.410 mL, 5.33 mmol) and the reaction was stirred for 30 min. The reaction was stirred for a further 1.5 h. The reaction was quenched by the cautious addition of the reaction mixture into a stirred NaHCO₃ solution (50 mL). DCM (30 mL) was added and the layers separated. The aqueous layer was further extracted with DCM (2×30 mL) and the combined organics dried (Na₂SO₄) and concentrated in vacuo to afford the crude product as a white solid. The crude product was purified by Biotage SP4 flash chromatography on a SNAP 25 g silica cartridge using a gradient of 5% EtOAc/cyclohexane→40% ethyl acetate/cyclohexane. The appropriate fractions were combined and evaporated in vacuo to give the product as a cream solid—methyl 2-(1-ethyl-1H-indol-2- yl)-1-methyl-7-(methylamino)-1H-benzo[d]imidazole-5-carboxylate (120 mg, 0.331 mmol, 99% yield).

LCMS (Method B): Rt=1.13 min, MH+=363.2.

Intermediate 138: Methyl 7-(dimethylamino)-2-(1-ethyl-1H-indol-2-yl)-1-methyl-1H-benzo[d]imidazole-5-carboxylate

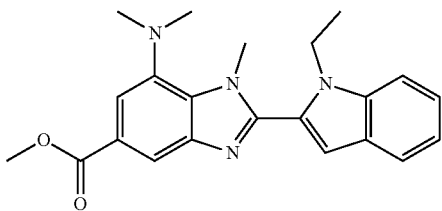 [SMILES: CCn1c(-c2nc3cc(C(=O)OC)cc(N(C)C)c3n2C)cc2ccccc21]

A stock solution of MeI (58 µL, 0.93 mmol) in DMF (1 mL) was prepared in a dry flask. To a second dry flask, was added methyl 2-(1-ethyl-1H-indol-2-yl)-1-methyl-7-(methylamino)-1H-benzo[d]imidazole-5-carboxylate (30.5 mg, 0.084 mmol) in N,N-dimethylformamide (DMF) (0.7 mL) at rt. Sodium hydride (60% dispersion in mineral oil) (6.73 mg, 0.168 mmol) was added and the resultant orange solution stirred for 20 min at rt by which time the solution had turned brown. An aliquot of the MeI stock solution was added (100 µL, 0.093 mmol) and the reaction mixture allowed to stir for 1 h. A further aliquot of the MeI stock solution was added (20 µL) and the reaction mixture stirred for a further 30 min. A small amount of NaH (2 mg) was added and the reaction stirred for a further 1 h. The reaction was quenched by the addition of water (10 mL) and the organics extracted into Et$_2$O (20 mL). The aqueous layer was washed with further Et$_2$O (2×20 mL) and the combined organics then back-extracted with water (2×20 mL). The organic layer was dried (Na$_2$SO$_4$) and concentrated in vacuo to afford the crude product as a white solid. This was combined with a second batch of the same compound from a different experiment for purification: The combined crude products were purified by Biotage SP4 flash chromatography on a SNAP 10 g silica cartridge using a gradient of 5% EtOAc/cyclohexane→60% ethyl acetate/cyclohexane. the appropriate fractions were combined and evaporated in vacuo and afforded the desired product as a white solid—methyl 7-(dimethylamino)-2-(1-ethyl-1H-indol-2-yl)-1-methyl-1H-benzo[d]imidazole-5-carboxylate (38 mg, 0.101 mmol). Yield based on both reactions=67%.

LCMS (Method B): Rt=1.32 min, MH$^+$=377.2.

Intermediate 139: 7-(Dimethylamino)-2-(1-ethyl-1H-indol-2-yl)-1-methyl-1H-benzo[d]imidazole-5-carboxylic Acid

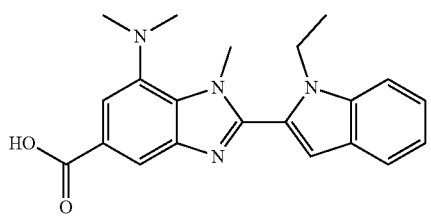 [SMILES: CCn1c(-c2nc3cc(C(=O)O)cc(N(C)C)c3n2C)cc2ccccc21]

Lithium hydroxide (6.23 mg, 0.260 mmol) was added to a stirred suspension of methyl 7-(dimethylamino)-2-(1-ethyl-1H-indol-2-yl)-1-methyl-1H-benzo[d]imidazole-5-carboxylate (49 mg, 0.130 mmol) in tetrahydrofuran (THF) (1 mL)/water (0.5 mL) and the reaction stirred at rt overnight. The reaction mixture was then allowed to stand for 72 h during which time some of the THF evaporated. 2M HCl (aq) (10 mL) and 10% MeOH/DCM (10 mL) were added and the layers separated. The aqueous layer was further extracted with 10% MeOH/DCM (2×20 mL). The combined organics were dried (Na$_2$SO$_4$) and concentrated in vacuo. LCMS showed only 30% product and 70% SM. The crude product was redissolved in tetrahydrofuran (THF) (1 mL)/Water (0.5 mL) and lithium hydroxide (6.23 mg, 0.260 mmol) added and the resultant suspension stirred for 3 h. The reaction was allowed to stir overnight and LCMS then showed only 7% SM remaining. The reaction was quenched by the addition of 2M HCl (aq) (10 mL) and the organics extracted into 10% MeOH/DCM (3×20 mL). The combined organics were dried (Na$_2$SO$_4$) and concentrated in vacuo to afford the product as a pale yellow solid—7-(dimethylamino)-2-(1-ethyl-1H-indol-2-yl)-1-methyl-1H-benzo[d]imidazole-5-carboxylic acid (48 mg, 0.132 mmol, 102% yield).

LCMS (Method B): Rt=1.13 min, MH+=363.2.

Intermediate 140: Methyl 2-(1-ethyl-1H-indol-2-yl)-3-methyl-3H-imidazo[4,5-b]pyridine-6-carboxylate

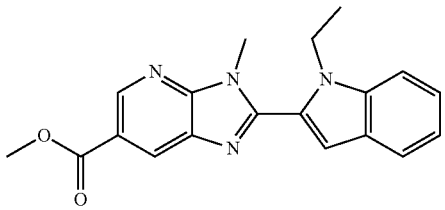 [SMILES: CCn1c(-c2nc3cc(C(=O)OC)cnc3n2C)cc2ccccc21]

Methyl 6-(methylamino)-5-nitro-3-pyridinecarboxylate (400 mg, 1.894 mmol) and 1-ethyl-1H-indole-2-carbaldehyde (328 mg, 1.894 mmol) were suspended in ethanol (4.0 mL). The suspension was treated with sodium hydrosulfite (1.16 g, 5.66 mmol) and water (2.0 mL) and the resulting suspension heated at 80° C. (thermal, air atm.) for ~48 h. The reaction was allowed to cool, and partitioned between water and DCM. The aqueous layer was extracted with DCM (×2). The combined organic extracts were dried (hydrophobic frit) and reduced to dryness under a stream of nitrogen to give the crude product as an orange oil. This was triturated with diethyl ether and the solid isolated by filtration (still sticky). The solid was retriturated with ethyl acetate. All three fractions (ether solution, solid and ethyl acetate solution) contain the desired product by LCMS. The fractions were therefore dissolved in ethyl acetate/acetone and absorbed onto silica in vacuo. The silica was applied to 1×20 g silica cartridge and eluted with an ethyl acetate/cyclohexane gradient (0-16%). The product fractions were combined and reduced to dryness in vacuo to give the desired product as a cream solid (110 mg).

LCMS (Method B): Rt=1.21 min, MH+=335.1.

Intermediate 141: 2-(1-Ethyl-1H-indol-2-yl)-3-methyl-3H-imidazo[4,5-b]pyridine-6-carboxylic Acid, Lithium Salt

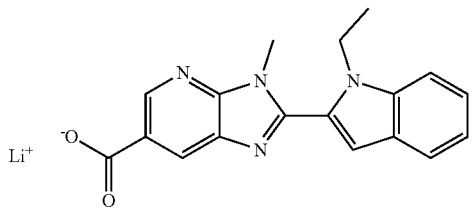

Methyl 3-methyl-2-[1-(phenylmethyl)-1H-indol-2-yl]-3H-imidazo[4,5-b]pyridine-6-carboxylate (275 mg, 0.822 mmol) and lithium hydroxide.H$_2$O (20 mg, 0.477 mmol) were combined in THF (10.0 mL) and water (3.0 mL), the resulting suspension was stirred at ambient temperature (air atm.) for ~4 h—50% reaction by LCMS—unchanged from 2.5 h sample. A further portion of lithium hydroxide.H$_2$O (20 mg, 0.477 mmol) was added and stirring continued for ~2 h (87% by LCMS). The solvents were evaporated under a stream of nitrogen to give the title compound as a pale yellow solid (314 mg).

LCMS (Method B): Rt=1.02 min, MH+=321.1.

Intermediate 142: 1,1-Dimethylethyl [(3R)-1-({2-[1-ethyl-6-(methyloxy)-1H-indol-2-yl]-1-methyl-1H-benzimidazol-5-yl}carbonyl)-3-piperidinyl]carbamate

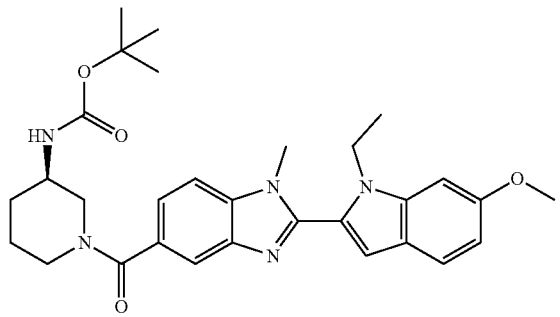 [SMILES: CCn1c(-c2nc3cc(C(=O)N4CCC[C@@H](NC(=O)OC(C)(C)C)C4)ccc3n2C)cc2ccc(OC)cc21]

HATU (860 mg, 1.397 mmol) was added to a solution of 1-ethyl-6-methoxy-1H-indole-2-carboxylic acid (201.8 mg, 0.792 mmol) in N,N-dimethylformamide (DMF) (5 mL) and left stirring at rt for 5 min. A solution of DIPEA (0.41 mL, 2.354 mmol) and (R)-tert-butyl (1-(3-amino-4-(methylamino)benzoyl)piperidin-3-yl)carbamate (457.5 mg, 1.313 mmol) in N,N-dimethylformamide (DMF) (5 mL) was added to the reaction mixture and left stirring under nitrogen at rt overnight (16 h). (R)-tert-Butyl (1-(3-amino-4-(methylamino)benzoyl)piperidin-3-yl)carbamate (148.3 mg) was added to the reaction mixture and left to stir at rt under nitrogen for 2 h. DIPEA (0.5 mL) was added to the reaction mixture and left stirring under nitrogen at rt for 1.5 h. The reaction mixture was left stirring overnight at rt under nitrogen. Distilled water (40 mL) was added to the reaction mixture and the organic product extracted using Et$_2$O (40 mL) and the layers separated. The aqueous layer was further extracted with Et$_2$O (2×40 mL). The organic layers were collected and back extracted using water (2×30 mL). The organic layers were collected, dried with Na$_2$SO$_4$, passed through a hydrophobic frit and concentrated under vacuum to give a blue solid. The blue solid was dried under high vacuum overnight to provide the desired amide intermediate.

LCMS (Method A) Rt=1.20 mins, MH+=550.3.

The amide intermediate was dissolved in toluene (10 mL). acetic acid (0.04 mL, 0.699 mmol) was added to the solution and refluxed for 1.5 h. Sodium bicarbonate (40 mL) was added to the reaction mixture and the layers separated. The aqueous layer was further washed with toluene (3×30 mL). The organic layers were collected, dried with Na$_2$SO$_4$, passed through a hydrophobic frit and concentrated under vacuum. The product was purified on silica (25 g). The column was eluted with a gradient of 60-100% ethyl acetate/cyclohexane. The appropriate fractions were collected and concentrated under vacuum to afford—1,1-Dimethylethyl [(3R)-1-({2-[1-ethyl-6-(methyloxy)-1H-indol-2-yl]-1-methyl-1H-benzimidazol-5-yl}carbonyl)-3-piperidinyl]carbamate (102 mg, 24%).

LCMS (Method B): Rt=1.10 mins, MH+=532.3

Intermediate 143: (R)-tert-Butyl (1-(2-(6-ethoxy-1-ethyl-1H-indol-2-yl)-1-methyl-1H-benzo[d]imidazole-5-carbonyl)piperidin-3-yl)carbamate

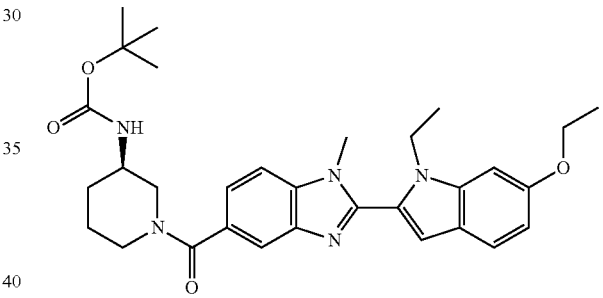

Prepared in a similar manner to Intermediate 142, from 6-ethoxy-1-ethyl-1H-indole-2-carboxylic acid and (R)-tert-butyl (1-(3-amino-4-(methylamino)benzoyl)piperidin-3-yl) carbamate.

LCMS (Method B): Rt=1.17 min, MH+=546.4

Intermediate 144: 1,1-Dimethylethyl ((3R)-1-{[2-(1-ethyl-6-fluoro-1H-indol-2-yl)-1-methyl-1H-benzimidazol-5-yl]carbonyl}-3-piperidinyl)carbamate

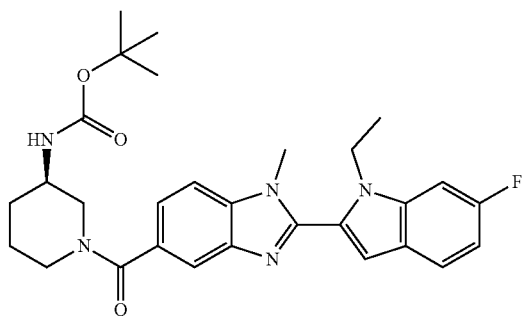 [SMILES: CCn1c(-c2nc3cc(C(=O)N4CCC[C@@H](NC(=O)OC(C)(C)C)C4)ccc3n2C)cc2ccc(F)cc21]

Prepared in a similar manner to Intermediate 142, from 1-ethyl-6-fluoro-1H-indole-2-carboxylic acid and (R)-tert-butyl (1-(3-amino-4-(methylamino)benzoyl)piperidin-3-yl)carbamate LCMS (Method A): Rt=1.23 mins, MH⁺=520.2

Intermediate 145: 1,1-Dimethylethyl [(3S)-1-({1-methyl-2-[1-(phenylmethyl)-1H-indol-2-yl]-1H-benzimidazol-5-yl}carbonyl)-3-piperidinyl]carbamate

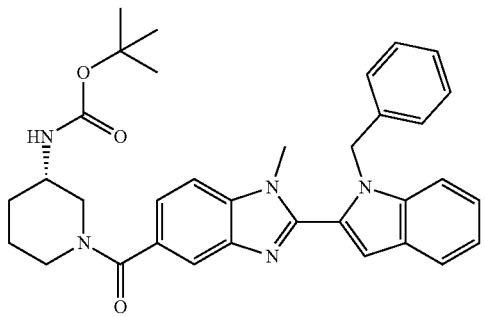 [SMILES: Cn1c(-c2cc3ccccc3n2Cc2ccccc2)nc2cc(C(=O)N3CCC[C@H](NC(=O)OC(C)(C)C)C3)ccc21]

To a solution of (S)-tert-butyl piperidin-3-ylcarbamate (47.3 mg, 0.236 mmol, commercially available from, for example, Sigma-Aldrich), 1-methyl-2-[1-(phenylmethyl)-1H-indol-2-yl]-1H-benzimidazole-5-carboxylic acid (90 mg, 0.236 mmol) and HATU (90 mg, 0.236 mmol) in N,N-dimethylformamide (DMF) (3 mL) was added DIPEA (0.082 mL, 0.472 mmol) and the reaction stirred at rt for 16 h. Water (20 mL) and EtOAc (20 mL) were added and the layers separated. The aqueous layer was extracted with further EtOAc (2×20 mL) and the combined organics washed with water (2×20 mL), dried (MgSO₄) and concentrated in vacuo to afford a yellow oil. The crude product was purified on silica (25 g) using a gradient of 40% EtOAc/cyclohexane→100% ethyl acetate/cyclohexane. The appropriate fractions were combined and evaporated under vacuum to give the product as a yellow oil—1,1-dimethylethyl [(3S)-1-({1-methyl-2-[1-(phenylmethyl)-1H-indol-2-yl]-1H-benzimidazol-5-yl}carbonyl)-3-piperidinyl]carbamate (115 mg, 0.204 mmol, 86% yield).

LCMS (Method B): Rt=1.25 min, MH⁺=564.3 Other examples indicated in the following table were prepared in a similar manner to Intermediate 145:

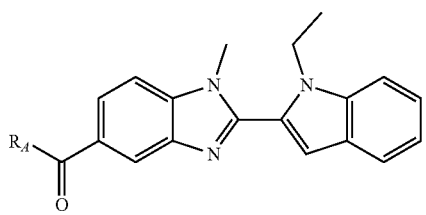

| Intermediate | R$_A$ | Yield/% | LCMS |
|---|---|---|---|
| 146: 1,1-Dimethylethyl ((1R,5S)-3-{[2-(1-ethyl-1H-indol-2-yl)-1-methyl-1H-benzimidazol-5-yl]carbonyl}-3-azabicyclo[3.1.0]hex-1-yl)carbamate (prepared from tert-butyl (1R)-3-azabicyclo[3.1.0]hexan-1-ylcarbamate (commercially available from, for example, Chemstep) and 2-(1-ethyl-1H-indol-2-yl)-1-methyl-1H-benzo[d]imidazole-5-carboxylic acid). | (structure) | 96 | LCMS (Method B): Rt = 1.14 min, MH+ = 500.3 |
| 147: trans (+/−) tert-Butyl (1-(2-(1-ethyl-1H-indol-2-yl)-1-methyl-1H-benzo[d]imidazole-5-carbonyl)-4-fluoropiperidin-3-yl)carbamate (prepared from 2-(1-ethyl-1H-indol-2-yl)-1-methyl-1H-benzimidazole-5-carboxylic acid and trans-(+/−)-tert-butyl 4-fluoropiperidin-3-ylcarbamate (this intermediate is prepared in patent: Fink, B. E. et al. WO 2005/066176)). | (structure) | 43 | .LCMS (Method B): Rt: 1.15 min MH⁺ 520. |
| 148: cis (+/−)-tert-Butyl (1-(2-(1-ethyl-1H-indol-2-yl)-1-methyl-1H-benzo[d]imidazole-5-carbonyl)-4-hydroxypiperidin-3-yl)carbamate (prepared from 2-(1-ethyl-1H-indol-2-yl)-1-methyl-1H-benzimidazole-5-carboxylic acid and cis-(+/−) tert-butyl-4-hydroxypiperidin-3-yl carbamate). | (structure) | 74 | LCMS (Method B): Rt: 1.03 min, MH⁺ 518. |

-continued

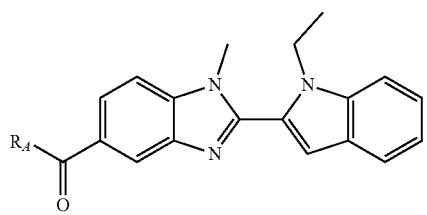

| Intermediate | R$_A$ | Yield/% | LCMS |
|---|---|---|---|
| 149: tert-Butyl (trans-(+/−))-1-(2-(1-ethyl-1H-indol-2-yl)-1-methyl-1H-benzo[d]imidazole-5-carbonyl)-4-hydroxypiperidin-3-yl)carbamate (prepared from 2-(1-ethyl-1H-indol-2-yl)-1-methyl-1H-benzimidazole-5-carboxylic acid and trans-(+/−) tert-butyl-4-hydroxypiperidin-3-yl carbamate). | | 100 | LCMS (Method B): Rt = 1.02 mins, MH$^+$ = 518.4 |
| 150: cis (+/−)-tert-butyl (4-ethoxy-1-(2-(1-ethyl-1H-indol-2-yl)-1-methyl-1H-benzo[d]imidazole-5-carbonyl)piperidin-3-yl)carbamate (prepared from 2-(1-ethyl-1H-indol-2-yl)-1-methyl-1H-benzo[d]imidazole-5-carboxylic acid and (+/−)-tert-butyl ((trans)-4-ethoxypiperidin-3-yl)carbamate). | | 45 | LCMS (Method B): Rt = 1.23 min, MH$^+$ = 546.4 |
| 151: (+/−)-tert-Butyl ((trans)-1-(2-(1-ethyl-1H-indol-2-yl)-1-methyl-1H-benzo[d]imidazole-5-carbonyl)-4-methoxypiperidin-3-yl)carbamate (prepared from 2-(1-ethyl-1H-indol-2-yl)-1-methyl-1H-benzo[d]imidazole-5-carboxylic acid and (+/−)-tert-butyl ((trans)-4-methoxypiperidin-3-yl)carbamate). | | 54 | LCMS (Method B): Rt = 1.14 min, MH$^+$ = 532.32 |
| 152: tert-Butyl 3-(2-(1-ethyl-1H-indol-2-yl)-1-methyl-1H-benzo[d]imidazole-5-carboxamido)azepane-1-carboxylate (prepared from 2-(1-ethyl-1H-indol-2-yl)-1-methyl-1H-benzo[d]imidazole-5-carboxylic acid and tert-butyl 3-aminoazepane-1-carboxylate (commercially available from, fro example, Ark Pharm Inc)). | | 64 | LCMS (Method A): Rt = 1.36 mins, MH$^+$ = 516.34. |
| 153: (R)-(5-azido-5,6-dihydropyridin-1(2H)-yl)(2-(1-ethyl-1H-indol-2-yl)-1-methyl-1H-benzo[d]imidazol-5-yl)methanone (prepared from 2-(1-ethyl-1H-indol-2-yl)-1-methyl-1H-benzo[d]imidazole-5-carboxylic acid and (R)-3-azido-1,2,3,6-tetrahydropyridine). | | 38 | LCMS (Method B): Rt = 1.12 min, MH$^+$ = 426.1 |
| 154: tert-Butyl-cis-(1-(2-(1-ethyl-1H-indol-2-yl)-1-methyl-1H-benzo[d]imidazole-5-carbonyl)-2-methylpiperidin-3-yl)carbamate single unknown enantiomer with known relative stereochemistry (prepared from 2-(1-ethyl-1H-indol-2-yl)-1-methyl-1H-benzo[d]imidazole-5-carboxylic acid and tert-butyl (2-methylpiperidin-3-yl)carbamate, commercially available from, for example, ISPharm). | | 5 | LCMS (Method B): Rt = 1.17 min, MH+ = 516.3. |

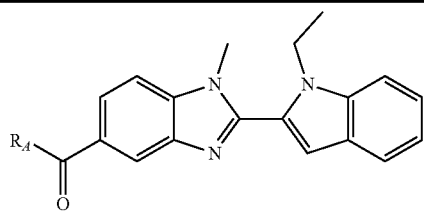

| Intermediate | $R_A$ | Yield/% | LCMS |
|---|---|---|---|
| 155: tert-Butyl 6-(2-(1-ethyl-1H-indol-2-yl)-1-methyl-1H-benzo[d]imidazole-5-carboxamido)-1,4-oxazepane-4-carboxylate (prepared from 2-(1-ethyl-1H-indol-2-yl)-1-methyl-1H-benzo[d]imidazole-5-carboxylic acid and tert-butyl 6-amino-1,4-oxazepane-4-carboxylate, commercially available from, for example, Amatek Chemical). | 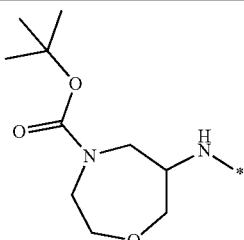 | 82 | LCMS (Method B): MH+ = Rt = 1.17 min, 518.4. |

Intermediate 156: (R)-tert-Butyl (1-(2-(1-ethyl-1H-indol-2-yl)-1,6-dimethyl-1H-benzo[d]imidazole-5-carbonyl)piperidin-3-yl)carbamate

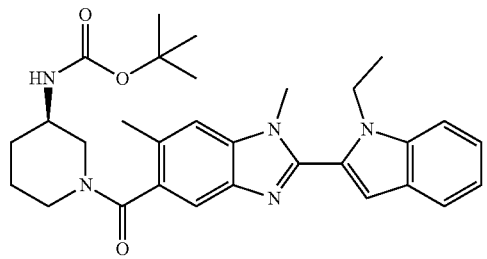 [SMILES: CCn1c(-c2nc3cc(C(=O)N4CCC[C@@H](NC(=O)OC(C)(C)C)C4)c(C)cc3n2C)cc2ccccc21]

Prepared in a similar manner to Intermediate 145 from 2-(1-ethyl-1H-indol-2-yl)-1,6-dimethyl-1H-benzo[d]imidazole-5-carboxylic acid and (R)-tert-butyl piperidin-3-ylcarbamate.

LCMS (Method B): Rt 1.15 min, MH$^+$=516.4

Intermediate 157: 1,1-Dimethylethyl {2-[({1-methyl-2-[1-(phenylmethyl)-1H-indol-2-yl]-1H-benzimidazol-5-yl}carbonyl)amino]ethyl}carbamate

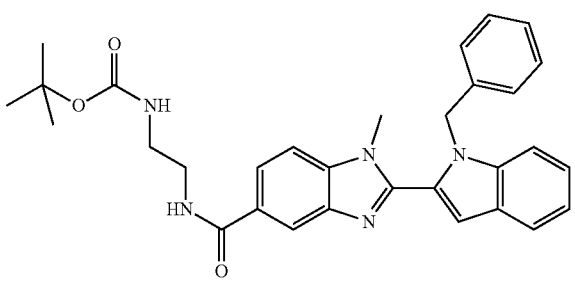 [SMILES: Cn1c(-c2cc3ccccc3n2Cc2ccccc2)nc2cc(C(=O)NCCNC(=O)OC(C)(C)C)ccc21]

Prepared in a similar manner to Intermediate 145 from 1-methyl-2-[1-(phenylmethyl)-1H-indol-2-yl]-1H-benzimidazole-5-carboxylic acid and 1,1-dimethylethyl (2-aminoethyl)carbamate (commercially available from, for example, Sigma-Aldrich)

LCMS (Method B): Rt 1.20 min, MH$^+$ 524

Intermediate 158: tert-Butyl ((3S,4R)-4-hydroxy-1-(7-methoxy-1-methyl-2-(1-(2,2,2-trifluoroethyl)-1H-indol-2-yl)-1H-benzo[d]imidazole-5-carbonyl)piperidin-3-yl)carbamate

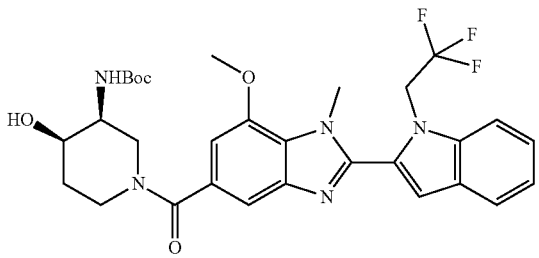 [SMILES: COc1cc(C(=O)N2CC[C@@H](O)[C@@H](NC(=O)OC(C)(C)C)C2)cc2nc(-c3cc4ccccc4n3CC(F)(F)F)n(C)c12]

Prepared in a similar manner to Intermediate 145 from 7-methoxy-1-methyl-2-(1-(2,2,2-trifluoroethyl)-1H-indol-2-yl)-1H-benzo[d]imidazole-5-carboxylic acid and tert-butyl ((3S,4R)-4-hydroxypiperidin-3-yl)carbamate LCMS (Method B): Rt=1.15 mins, MH$^+$=602.5.

Intermediate 159: tert-Butyl ((3S,4R)-1-(2-(1-(cyclopropylmethyl)-1H-indol-2-yl)-1-methyl-1H-benzo[d]imidazole-5-carbonyl)-4-hydroxypiperidin-3-yl)carbamate

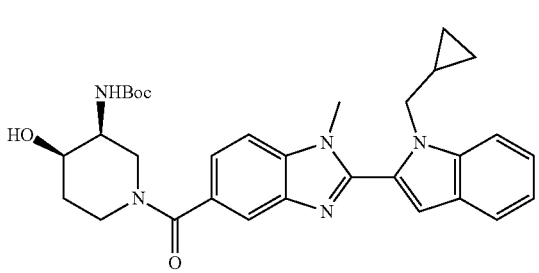 [SMILES: Cn1c(-c2cc3ccccc3n2CC2CC2)nc2cc(C(=O)N3CC[C@@H](O)[C@@H](NC(=O)OC(C)(C)C)C3)ccc21]

Prepared in a similar manner to Intermediate 145 from 2-(1-(cyclopropylmethyl)-1H-indol-2-yl)-1-methyl-1H-benzo[d]imidazole-5-carboxylic acid and tert-butyl ((3S,4R)-4-hydroxypiperidin-3-yl)carbamate.
LCMS (Method B): Rt=1.07 mins, MH⁺=544.2

Intermediate 160: tert-Butyl ((3S,4R)-1-(2-(1-(cyclopropylmethyl)-1H-indol-2-yl)-7-methoxy-1-methyl-1H-benzo[d]imidazole-5-carbonyl)-4-hydroxypiperidin-3-yl)carbamate

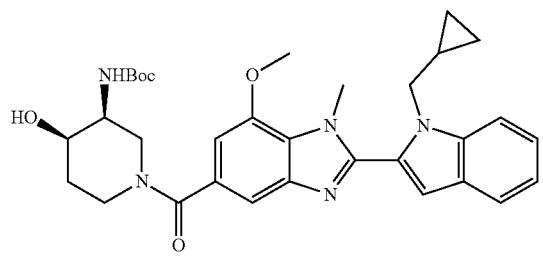 [SMILES: COc1cc(C(=O)N2CC[C@@H](O)[C@@H](NC(=O)OC(C)(C)C)C2)cc2nc(-c3cc4ccccc4n3CC3CC3)n(C)c12]

Prepared in a similar manner to Intermediate 145 from 2-(1-(cyclopropylmethyl)-1H-indol-2-yl)-7-methoxy-1-methyl-1H-benzo[d]imidazole-5-carboxylic acid and tert-butyl ((3S,4R)-4-hydroxypiperidin-3-yl)carbamate.
LCMS (Method B): Rt=1.13 min, MH⁺=574.2

Intermediate 161: tert-Butyl ((3S,4R)-1-(2-(1-ethyl-1H-indol-2-yl)-7-methoxy-1-methyl-1H-benzo[d]imidazole-5-carbonyl)-4-hydroxypiperidin-3-yl)carbamate

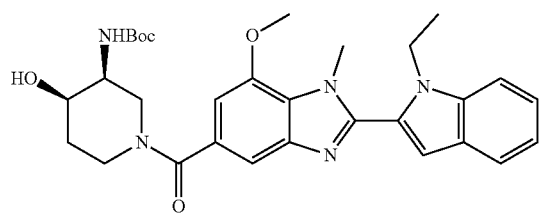 [SMILES: CCn1c(-c2nc3cc(C(=O)N4CC[C@@H](O)[C@@H](NC(=O)OC(C)(C)C)C4)cc(OC)c3n2C)cc2ccccc21]

Prepared in a similar manner to Intermediate 145 from 2-(1-ethyl-1H-indol-2-yl)-7-methoxy-1-methyl-1H-benzo[d]imidazole-5-carboxylic acid and tert-butyl ((3S,4R)-4-hydroxypiperidin-3-yl)carbamate.
LCMS (Method B): Rt=1.09 min, MH+=548.4

Intermediate 162: tert-Butyl ((3R,4S)-4-hydroxy-1-(7-methoxy-1-methyl-2-(1-(2,2,2-trifluoroethyl)-1H-indol-2-yl)-1H-benzo[d]imidazole-5-carbonyl)piperidin-3-yl)carbamate

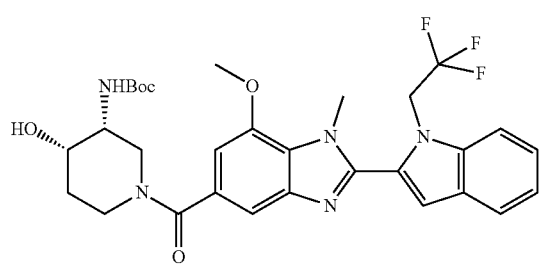

Prepared in a similar manner to Intermediate 145 from 7-methoxy-1-methyl-2-(1-(2,2,2-trifluoroethyl)-1H-indol-2-yl)-1H-benzo[d]imidazole-5-carboxylic acid and tert-butyl (4-hydroxypiperidin-3-yl)carbamate.
LCMS (Method B): Rt=1.15 mins, MH⁺=602.5

Intermediate 163: (S)-tert-Butyl (1-(1-methyl-2-(1-methyl-1H-indol-2-yl)-1H-benzo[d]imidazole-5-carbonyl)piperidin-3-yl)carbamate

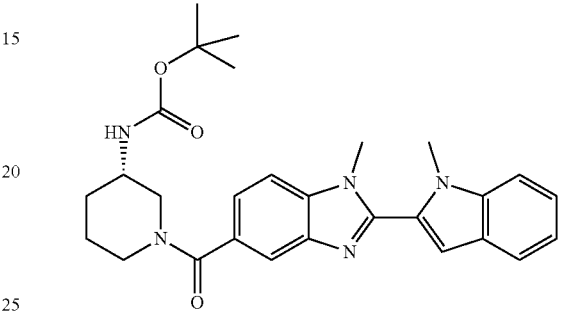

Prepared in a similar manner to Intermediate 145 from (S)-3-(Boc-amino)-piperidine (commercially available from, for example, Acros Organics) and 1-methyl-2-(1-methyl-1H-indol-2-yl)-1H-benzimidazole-5-carboxylic acid.
LCMS (Method B): Rt=1.08 min, MH+=488.4

Intermediate 164: (R)-tert-Butyl (1-(1-methyl-2-(1-methyl-1H-indol-2-yl)-1H-benzo[d]imidazole-5-carbonyl)piperidin-3-yl)carbamate

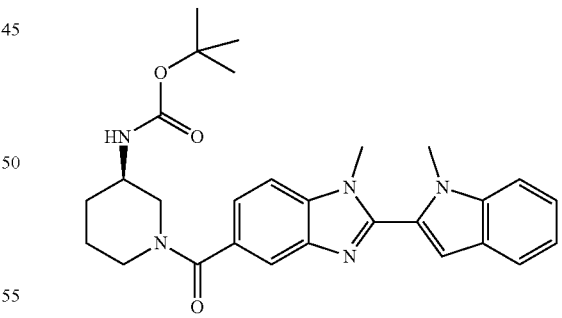

Prepared in a similar manner to Intermediate 145 from 1,1-dimethylethyl (3R)-3-piperidinylcarbamate (commercially available from, for example, Apollo Scientific) and 1-methyl-2-(1-methyl-1H-indol-2-yl)-1H-benzimidazole-5-carboxylic acid.
LCMS (Method B): Rt=1.04 min, MH+=488.4

Intermediate 165: tert-Butyl (3-(2-(1-benzyl-1H-indol-2-yl)-1-methyl-1H-benzo[d]imidazole-5-carbonyl)cyclopentyl)carbamate

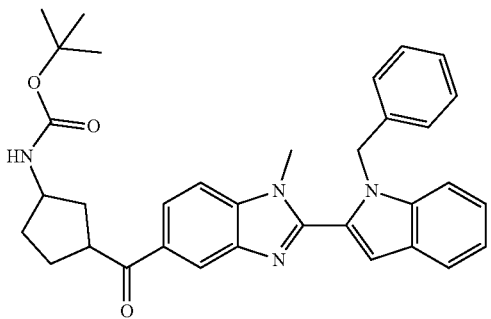 [SMILES: Cn1c(-c2cc3ccccc3n2Cc2ccccc2)nc2cc(C(=O)C3CCC(NC(=O)OC(C)(C)C)C3)ccc21]

Prepared in a similar manner to Intermediate 145 from 1,1-dimethylethyl 3-pyrrolidinylcarbamate (commercially available from, for example, Sigma-Aldrich) and 1-methyl-2-[1-(phenylmethyl)-1H-indol-2-yl]-1H-benzimidazole-5-carboxylic acid.

LCMS (Method B): Rt=1.22 min, MH+=550.6.

Intermediate 166: (R)-tert-Butyl (5-(3-((tert-butoxycarbonyl)amino)piperidine-1-carbonyl)-2-(1-ethyl-1H-indol-2-yl)-1-methyl-1H-benzo[d]imidazol-7-yl)(methyl)carbamate

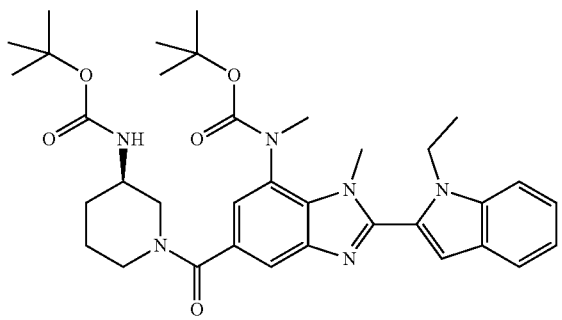 [SMILES: CCn1c(-c2nc3cc(C(=O)N4CCC[C@@H](NC(=O)OC(C)(C)C)C4)cc(N(C)C(=O)OC(C)(C)C)c3n2C)cc2ccccc21]

Prepared in a similar manner to Intermediate 145 from 7-((tert-butoxycarbonyl)(methyl)amino)-2-(1-ethyl-1H-indol-2-yl)-1-methyl-1H-benzo[d]imidazole-5-carboxylic acid and (R)-tert-butyl piperidin-3-ylcarbamate (commercially available from, for example, Apollo Scientific).

LCMS (Method B): Rt=1.30 min, MH+=631.5

Intermediate 167: (R)-tert-Butyl (1-(2-(1-ethyl-1H-indol-2-yl)-3-methyl-3H-imidazo[4,5-b]pyridine-6-carbonyl)piperidin-3-yl)carbamate

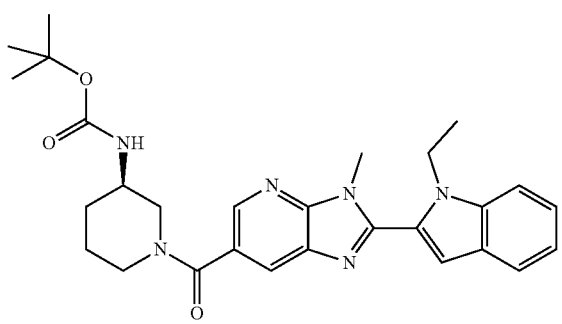 [SMILES: CCn1c(-c2nc3cc(C(=O)N4CCC[C@@H](NC(=O)OC(C)(C)C)C4)cnc3n2C)cc2ccccc21]

Prepared in a similar manner to Intermediate 145 from 2-(1-ethyl-1H-indol-2-yl)-3-methyl-3H-imidazo[4,5-b]pyridine-6-carboxylic acid lithium salt and (R)-tert-butyl piperidin-3-ylcarbamate (commercially available from, for example, Apollo Scientific).

LCMS (Method B): Rt=1.16 min, MH+=503.3.

Intermediate 168: (R)-tert-Butyl (1-(7-(dimethylamino)-2-(1-ethyl-1H-indol-2-yl)-1-methyl-1H-benzo[d]imidazole-5-carbonyl)piperidin-3-yl)carbamate

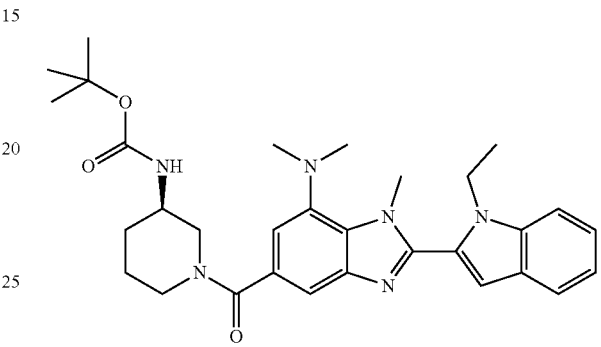

Prepared in a similar manner to Intermediate 145 from 7-(dimethylamino)-2-(1-ethyl-1H-indol-2-yl)-1-methyl-1H-benzo[d]imidazole-5-carboxylic acid and (R)-tert-butyl piperidin-3-ylcarbamate (commercially available from, for example, Apollo Scientific).

LCMS (Method B): Rt=1.25 min, MH+=545.5.

Intermediate 169: (R)-tert-Butyl (1-(7-bromo-2-(1-ethyl-1H-indol-2-yl)-1-methyl-1H-benzo[d]imidazole-5-carbonyl)piperidin-3-yl)carbamate

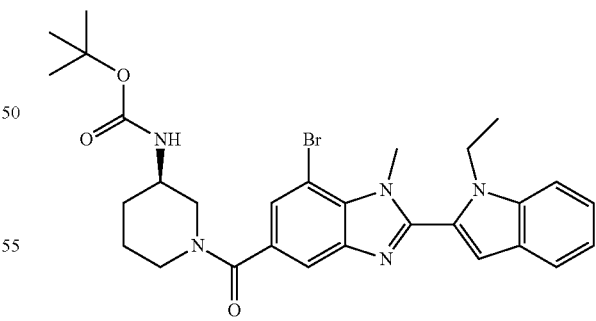

Prepared in a similar manner to Intermediate 145, from 7-bromo-2-(1-ethyl-1H-indol-2-yl)-1-methyl-1H-benzo[d]imidazole-5-carboxylic acid and (R)-tert-butyl piperidin-3-ylcarbamate.

LCMS (Method B): Rt=1.32 min, MH+=580.3/582.3

Intermediate 170: (R)-tert-Butyl (1-(2-(1-ethyl-1H-indol-2-yl)-1-methyl-7-(trifluoromethoxy)-1H-benzo[d]imidazole-5-carbonyl)piperidin-3-yl)carbamate

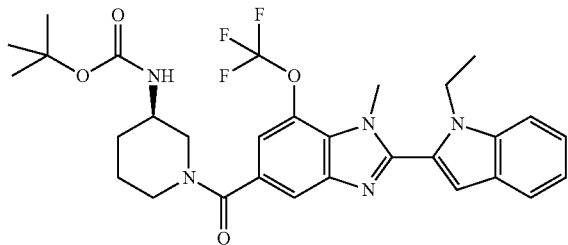 [SMILES: CCn1c(-c2nc3cc(C(=O)N4CCC[C@@H](NC(=O)OC(C)(C)C)C4)cc(OC(F)(F)F)c3n2C)cc2ccccc21]

Prepared in a similar manner to Intermediate 145, from 2-(1-ethyl-1H-indol-2-yl)-1-methyl-7-(trifluoromethoxy)-1H-benzo[d]imidazole-5-carboxylic acid and (R)-tert-butyl piperidin-3-ylcarbamate.

LCMS (Method A): Rt=1.40 min, MH$^+$=586.4

Intermediate 171: 1,1-Dimethylethyl ((3R)-1-{[2-(6-cyano-1-ethyl-1H-indol-2-yl)-1-methyl-1H-benzimidazol-5-yl]carbonyl}-3-piperidinyl)carbamate

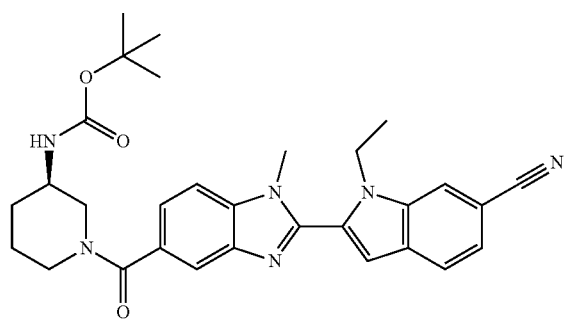 [SMILES: CCn1c(-c2nc3cc(C(=O)N4CCC[C@@H](NC(=O)OC(C)(C)C)C4)ccc3n2C)cc2ccc(C#N)cc21]

Zinc cyanide (9.1 mg, 0.078 mmol) was added to a stirred solution of (R)-tert-butyl (1-(2-(6-bromo-1-ethyl-1H-indol-2-yl)-1-methyl-1H-benzo[d]imidazole-5-carbonyl)piperidin-3-yl)carbamate (50.2 mg, 0.086 mmol) in N,N-dimethylformamide (DMF) (1 mL) in a dried 2 mL microwave vial under nitrogen and left stirring for 20 min. Palladium tetrakis (5.6 mg, 4.85 µmol) was added to the reaction mixture and the vial heated in the microwave for 1 h at 95° C. The reaction mixture was heated to 105° C. in the microwave for 1 h. Further zinc cyanide (10.5 mg) was added to the reaction mixture and this then stirred under nitrogen for 15 min. Palladium tetrakis (10.2 mg) was added and the reaction heated in the microwave at 95° C.

The reaction was re-heated to 95° C. for a further 2 h in the microwave. The reaction mixture was poured into aqueous saturated Na$_2$CO$_3$ solution (50 mL) and extracted with EtOAc (50 mL). The aqueous layer was further extracted with EtOAc (2×50 mL). The combined organic fractions were washed with water (50 mL) and then brine (50 mL). The washed organic fractions were dried using Na$_2$SO$_4$ and passed through a hydrophobic frit. The combined organics were concentrated under vacuum to give a yellow oil. The crude product was purified on silica (25 g). The column was eluted with a gradient of 50-100% ethyl acetate/cyclohexane. The appropriate fractions were collected and concentrated under vacuum to afford the desired product as two batches, both of which were still impure. These were further purified using MDAP (Method A). Product fractions were collected and concentrated under vacuum to afford 1,1-dimethylethyl ((3R)-1-{[2-(6-cyano-1-ethyl-1H-indol-2-yl)-1-methyl-1H-benzimidazol-5-yl]carbonyl}-3-piperidinyl)carbamate (19.2 mg, 42%) which was still impure by NMR and used as such in the subsequent reaction.

LCMS (Method B): Rt=1.12 mins, MH$^+$=527.3

Intermediate 172: N,N-((3,4-cis)-1-{[2-(1-Ethyl-H-indol-2-yl)-1-methyl-1H-benzimidazol-5-yl]carbonyl}-3,4-piperidinediyl)bis(2,2,2-trifluoroacetamide)

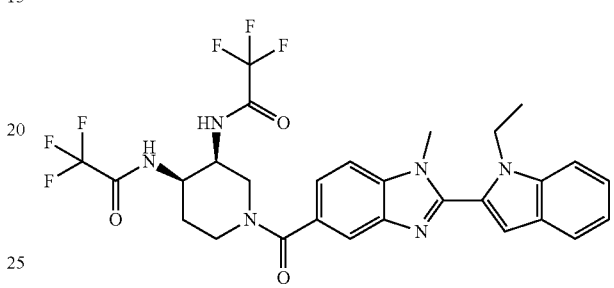

To a solution of 2-(1-ethyl-1H-indol-2-yl)-1-methyl-1H-benzo[d]imidazole-5-carboxylic acid (200 mg, 0.626 mmol) and HATU (238 mg, 0.626 mmol) in N,N-dimethylformamide (DMF) (4 mL) was added DIPEA (0.547 mL, 3.13 mmol) and the reaction stirred at rt for 30 min. N,N'-(piperidine-3,4-diyl)bis(2,2,2-trifluoroacetamide), acetic acid salt (402 mg, 1.096 mmol) in N,N-dimethylformamide (DMF) (2 mL) was added and the reaction stirred at rt for 1 h. The reaction was left stirring overnight. Water (50 mL) and Et$_2$O (50 mL) were added and the layers separated. The aqueous layer was extracted with further Et$_2$O (2×30 mL) and the combined organics washed with water (2×20 mL), dried (Na$_2$SO$_4$) and concentrated in vacuo to afford a brown oil. The crude product was purified on silica (100 g) using a gradient of 0% EtOAc/cyclohexane→100% ethyl acetate/cyclohexane. Some separation of the diastereomers was observed. Three sets of fractions were collected and concentrated in vacuo to afford: Trans-diastereomer (racemic)—(20.4 mg, 5%); diastereomeric mixture—(119 mg, 31%); cis-diastereomer (racemic)—(55.3 mg, 14%)

The unseparated diastereomeric mixture (119 mg) was submitted for preparative chiral HPLC (Method E) to resolve the 4 components. This afforded: N,N'-((3,4-trans)-1-(2-(1-ethyl-1H-indol-2-yl)-1-methyl-1H-benzo[d]imidazole-5-carbonyl)piperidine-3,4-diyl)bis(2,2,2-trifluoroacetamide) (11 mg, 0.018 mmol, 2.89% yield); Single enantiomer, trans-diastereomer;

Chiral HPLC (Method D): Rt=6.55 mins.

N,N'-((3,4-trans)-1-(2-(1-ethyl-1H-indol-2-yl)-1-methyl-1H-benzo[d]imidazole-5-carbonyl)piperidine-3,4-diyl)bis(2,2,2-trifluoroacetamide) (10 mg, 0.016 mmol, 2.62% yield);

Single enantiomer, trans-diastereomer;

Chiral HPLC (Method D): Rt=8.58 mins.

N,N'-((3,4-cis)-1-(2-(1-ethyl-1H-indol-2-yl)-1-methyl-1H-benzo[d]imidazole-5-carbonyl)piperidine-3,4-diyl)bis(2,2,2-trifluoroacetamide) (37 mg, 0.061 mmol, 9.71% yield);

Single enantiomer, cis-diastereomer;

Chiral HPLC (Method D): Rt=14.24 mins.

N,N'-((3,4-cis)-1-(2-(1-ethyl-1H-indol-2-yl)-1-methyl-1H-benzo[d]imidazole-5-carbonyl)piperidine-3,4-diyl)bis(2,2,2-trifluoroacetamide) (37 mg, 0.061 mmol, 9.71% yield);

Single enantiomer, cis-diastereomer;

Chiral HPLC (Method D): Rt=23.14 mins. CL Intermediate 173 and 174: tert-Butyl-((cis)-1-(2-(1-ethyl-1H-indol-2-yl)-1-methyl-1H-benzo[d]imidazole-5-carbonyl)-6-methylpiperidin-3-yl)carbamate, Single Unknown Enantiomers with Known Relative Stereochemistry

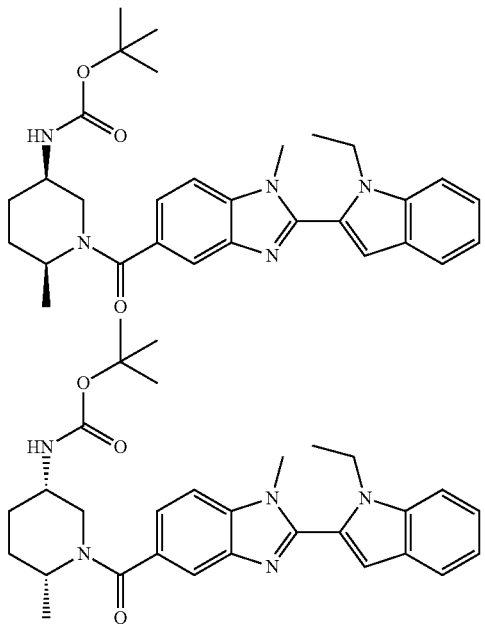

To tert-butyl (6-methylpiperidin-3-yl)carbamate (512 mg, 2.389 mmol, commercially available from, for example, ISPharm) and 2-(1-ethyl-1H-indol-2-yl)-1-methyl-1H-benzo[d]imidazole-5-carboxylic acid (763 mg, 2.389 mmol) in N,N-dimethylformamide (DMF) (10 mL) was added HATU (908 mg, 2.389 mmol) and Et$_3$N (0.666 mL, 4.78 mmol) and the reaction stirred at ambient temperature for 48 h. The reaction was then heated in a microwave at 60° C. for 1 h. Additional HATU (908 mg, 2.389 mmol) was then added and the reaction microwaved at 60° C. for 1 h followed by 1 h at 100° C. The reaction mixture was partitioned between DCM and water (×3) and the combined organics washed with water and then evaporated. The residue was redissolved in DCM and loaded onto a 25 g silica SNAP column and purified on the SP4 eluting with 0-10% methanol in DCM. After evaporation the material was subjected to additional purification by MDAP (Method B). The appropriate fractions were combined and the solvent removed. The residue was dried under high vacuum overnight to give a yellow film which was then separated by chiral preparative HPLC (Method F) to give the title compounds.

Intermediate 173

LCMS (Method B): Rt=1.20 min, MH+=516.3.

Intermediate 174

LCMS (Method B): Rt=1.19 min, MH+=516.3.

Intermediate 175: tert-Butyl 3-(2-(1-(cyclopropylmethyl)-1H-indol-2-yl)-1-methyl-1H-benzo[d]imidazole-5-carboxamido)azepane-1-carboxylate

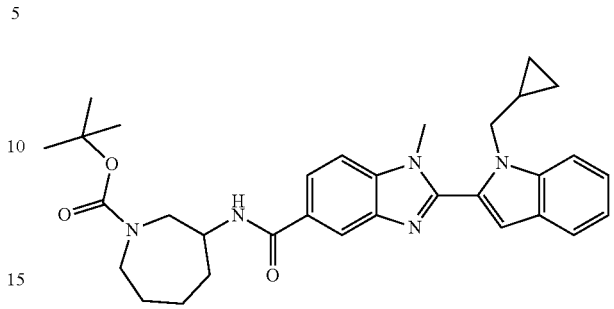

To 2-(1-(cyclopropylmethyl)-1H-indol-2-yl)-1-methyl-1H-benzo[d]imidazole-5-carboxylic acid (200 mg, 0.579 mmol) in N,N-dimethylformamide (DMF) (6 mL) was added tert-butyl 3-aminoazepane-1-carboxylate (124 mg, 0.579 mmol, commercially available from, for example, J&W Pharmlab) and HATU (264 mg, 0.695 mmol) and Et$_3$N (0.242 mL, 1.737 mmol) and the reaction stirred over the weekend at rt. Additional tert-butyl 3-aminoazepane-1-carboxylate (50 mg, 0.23 mmol), Et$_3$N (0.2 mL, 1.44 mmol) and HATU (200 mg, 0.53 mmol) were added and the reaction stirred for 4 h. The reaction mixture was partitioned between DCM and water (×3), the combined organic layers were then washed with water (×2) and the solvent removed. The residue was dissolved in DCM and loaded onto a 25 g silica SNAP column and purified by flash chromatography on the SP4 eluting with 0-50% ethyl acetate in cyclohexane. The appropriate fractions were combined and the solvent removed to give a clear film residue (123 mg, 39%).

LCMS (Method B): Rt=0.84 min, MH+=442.3.

Intermediate 176: N-(1-(2-(1-Ethyl-1H-indol-2-yl)-1-methyl-1H-benzo[d]imidazole-5-carbonyl)-5-methylpiperidin-3-yl)-2,2,2-trifluoroacetamide, Diastereomeric Mixture

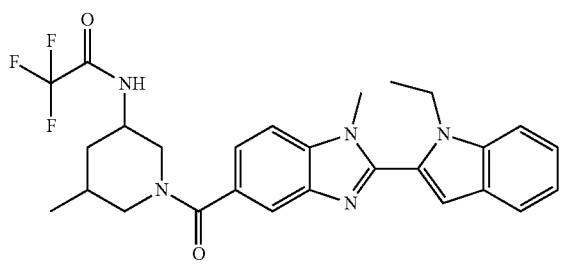 [SMILES: CCn1c(-c2nc3cc(C(=O)N4CC(C)CC(NC(=O)C(F)(F)F)C4)ccc3n2C)cc2ccccc21]

To 2-(1-ethyl-1H-indol-2-yl)-1-methyl-1H-benzo[d]imidazole-5-carboxylic acid (185 mg, 0.579 mmol) in N,N-dimethylformamide (DMF) (6 mL) was added HATU (264 mg, 0.695 mmol) and Et$_3$N (0.404 mL, 2.90 mmol) followed by 2,2,2-trifluoro-N-(5-methylpiperidin-3-yl)acetamide, acetic acid salt (220 mg, 0.814 mmol) and the reaction stirred overnight at rt under nitrogen. Additional Et$_3$N (1 mL) and 2,2,2-trifluoro-N-(5-methylpiperidin-3-yl)acetamide (220 mg, 1.047 mmol) in DMF (1 mL) were added and the reaction stirred for 1 h. Additional HATU (264 mg, 0.695 mmol) was added and the reaction stirred for 90 min. 2,2,2-Trifluoro-N-(5-methylpiperidin-3-yl)acetamide was then added (~100 mg) and the reaction left overnight. The solvent was removed and the residue dried under high vacuum for 1 h. HATU (1 g), Et₃N (1 mL) and DMF (6 mL) were added and the reaction left to stir overnight. Water was added and the organics extracted into DCM (×3). The combined organic layers were washed with water and the solvent removed. The residue was dissolved in DCM and purified on silica eluting with 0-100% ethyl acetate in cyclohexane. The appropriate fractions were combined and the solvent removed to give the title compound as a brown oil (42 mg, 11%).

LCMS (Method B): Rt=1.14 min, MH+=512.2.

Intermediate 177: N-(1-(2-(1-Ethyl-1H-indol-2-yl)-1-methyl-1H-benzo[d]imidazole-5-carbonyl)-5-fluoropiperidin-3-yl)-2,2,2-trifluoroacetamide, Diastereomeric Mixture

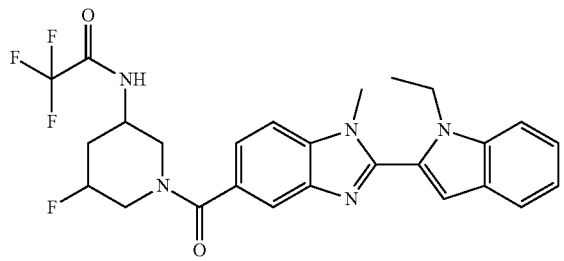 [SMILES: CCn1c(-c2nc3cc(C(=O)N4CC(F)CC(NC(=O)C(F)(F)F)C4)ccc3n2C)cc2ccccc21]

To 2-(1-ethyl-1H-indol-2-yl)-1-methyl-1H-benzo[d]imidazole-5-carboxylic acid (522 mg, 1.636 mmol) in N,N-dimethylformamide (DMF) (12 mL) was added HATU (745 mg, 1.961 mmol) and Et₃N (1.139 mL, 8.20 mmol). The reaction was left for 15 min. 2,2,2-Trifluoro-N-(5-fluoropiperidin-3-yl)acetamide, acetic acid salt (567 mg, 2.07 mmol) was then added and the reaction mixture stirred overnight at rt under nitrogen. Water was added and the mixture partitioned between DCM and water (×3). The combined organic layers were evaporated to give a beige solid which was dissolved in DCM/MeOH and loaded onto silica and dried in the vacuum oven for 1 h, before being eluted with 0-100% ethyl acetate in cyclohexane. The appropriate fractions were combined and the solvent removed to give a beige solid which was suspended in methanol (2 mL) and the precipitate filtered off. The liquors were purified by MDAP (Method B)—the appropriate fractions were combined and the solvent removed to give a white solid which was dried under high vacuum for 3 h to afford the title compound (11 mg, 1%).

LCMS (Method B): Rt=1.10 min, MH+=516.2.

Intermediate 178: cis-N,N'-(-1-(2-(1-Ethyl-1H-indol-2-yl)-1-methyl-1H-benzo[d]imidazole-5-carbonyl)piperidine-3,5-diyl)bis(2,2,2-trifluoroacetamide)

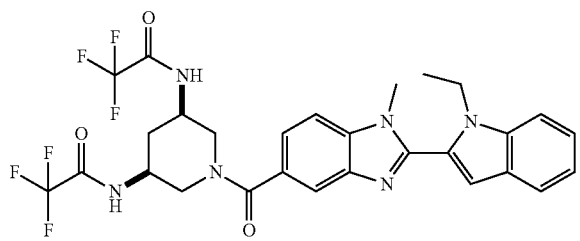 [SMILES: CCn1c(-c2nc3cc(C(=O)N4C[C@H](NC(=O)C(F)(F)F)C[C@H](NC(=O)C(F)(F)F)C4)ccc3n2C)cc2ccccc21]

To 2-(1-ethyl-1H-indol-2-yl)-1-methyl-1H-benzo[d]imidazole-5-carboxylic acid (0.870 g, 2.72 mmol) in N,N-dimethylformamide (DMF) (6 mL) was added HATU (1.242 g, 3.27 mmol) and Et₃N (1.898 mL, 13.61 mmol) and the reaction stirred for 1 h. N,N'-(Piperidine-3,5-diyl)bis(2,2,2-trifluoroacetamide), acetic acid salt (1 g, 2.72 mmol) was added and the reaction stirred overnight. The solution was partitioned between DCM and water (×3), and the combined organic layers washed with water (×2) and the solvent removed. The crude product was purified on silica eluting with 0-100% ethyl acetate in cyclohexane. The appropriate fractions were combined and the solvent removed to give a yellow oil which was dried under high vacuum overnight, then separated by chiral preparative HPLC (Method G) to give the title compound as a white solid (413 mg, 24%).

LCMS (Method B): Rt=1.11 min, MH+=609.4.

Intermediate 179: (+/−)-N-((trans)-1-(2-(1-Ethyl-1H-indol-2-yl)-1-methyl-1H-benzo[d]imidazole-5-carbonyl)-5-methoxypiperidin-3-yl)-2,2,2-trifluoroacetamide

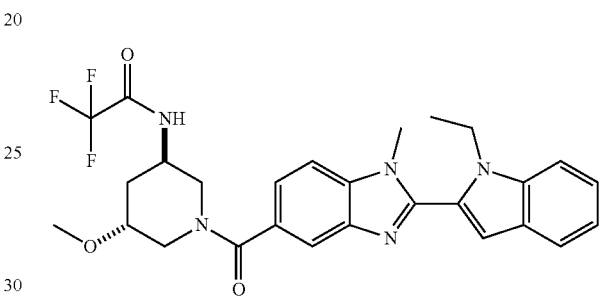

To 2-(1-ethyl-1H-indol-2-yl)-1-methyl-1H-benzo[d]imidazole-5-carboxylic acid (1116 mg, 3.49 mmol) in N,N-dimethylformamide (DMF) (6 mL) was added HATU (1594 mg, 4.19 mmol) and Et₃N (2.435 mL, 17.47 mmol) and the reaction stirred for 1 h. 2,2,2-Trifluoro-N-(5-methoxypiperidin-3-yl)acetamide, acetic acid salt (1000 mg, 3.49 mmol) was added and the reaction stirred overnight. The residue was partitioned between DCM and water (×3) and combined organic layers washed with water (×2). The solvent was removed and the residue dissolved in DCM and loaded onto silica and eluted with 0-100% ethyl acetate in cyclohexane. The appropriate fractions were combined and solvent removed. Further purification was achieved by MDAP (Method B). The appropriate fractions were combined and the solvent was removed. The residue was dried under high vacuum overnight to afford the product as a yellow film (13 mg, 1%) (and a by-product, Intermediate 180).

LCMS (Method B): Rt=1.05 min, MH+=528.3.

Intermediate 180: N-(1-(2-(1-Ethyl-1H-indol-2-yl)-1-methyl-1H-benzo[d]imidazole-5-carbonyl)-5-hydroxypiperidin-3-yl)-2,2,2-trifluoroacetamide

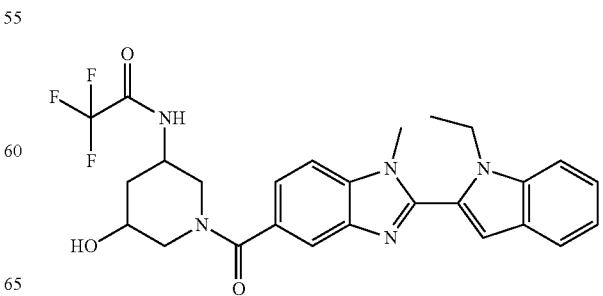

Prepared as a by-product in the preparation of intermediate 179 (6 mg, 0.3%).

LCMS (Method B): Rt=0.99 min, MH+=514.3.

Intermediate 181: (+/−)-N-((cis)-1-(2-(1-Ethyl-1H-indol-2-yl)-1-methyl-1H-benzo[d]imidazole-5-carbonyl)-5-methylpyrrolidin-3-yl)-2,2,2-trifluoroacetamide

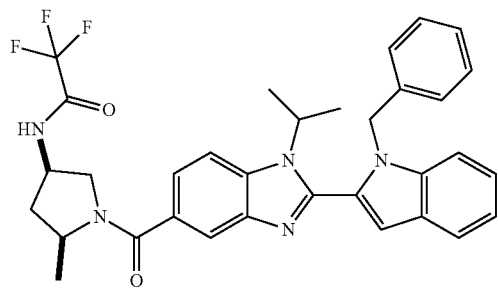 [SMILES: CC(C)n1c(-c2cc3ccccc3n2Cc2ccccc2)nc2cc(C(=O)N3C[C@H](NC(=O)C(F)(F)F)C[C@@H]3C)ccc21]

To 2-(1-ethyl-1H-indol-2-yl)-1-methyl-1H-benzo[d]imidazole-5-carboxylic acid (98 mg, 0.307 mmol) and 2,2,2-trifluoro-N-((cis)-5-methylpyrrolidin-3-yl)acetamide, trifluoroacetic acid salt (60 mg, 0.193 mmol) in N,N-dimethylformamide (DMF) (6 mL) was added HATU (140 mg, 0.368 mmol) and Et₃N (0.128 mL, 0.919 mmol) and the reaction left to stir over the weekend under nitrogen. The reaction was then partitioned between DCM and water (×3), the combined organic layers washed with water (×2) and the solvent removed. The residue was dissolved in DCM and loaded onto a 10 g silica SNAP column and purified by SP4 flash chromatography eluting with 0-100% ethyl acetate in cyclohexane. The appropriate fractions were combined, the solvent removed and the residue dried under high vacuum overnight to afford a clear oil (33 mg).

LCMS (Method B): Rt=1.07 min, MH+=498.2.

Intermediate 182 and Intermediate 183: N-(1-(2-(1-Ethyl-1H-indol-2-yl)-1-methyl-1H-benzo[d]imidazole-5-carbonyl)-4-methylpiperidin-3-yl)-2,2,2-trifluoroacetamide Trans and Cis Isomers

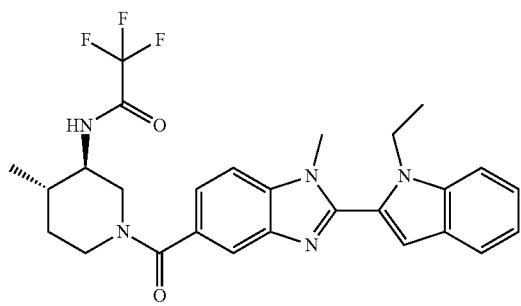

-continued

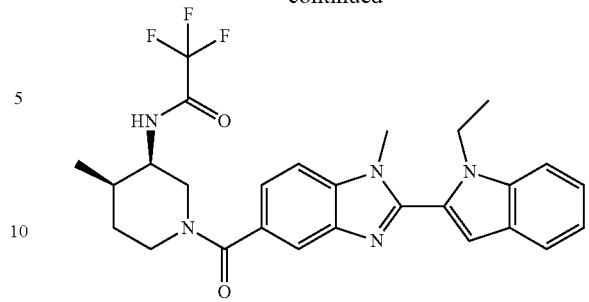

T3P (1.12 mL, 1.88 mmol, 50% in ethyl acetate) and DIPEA (0.436 mL, 2.51 mmol) were added to a solution of 2-(1-ethyl-1H-indol-2-yl)-1-methyl-1H-benzo[d]imidazole-5-carboxylic acid (400 mg, 1.25 mmol) in DMF (3 mL). After 5 min. 2,2,2-trifluoro-N-(4-methylpiperidin-3-yl)acetamide (263 mg, 1.25 mmol) was added and the resulting mixture was stirred at rt for 4 h. Another 1 eq of T3P (0.746 mL, 1.25 mmol, 50% in ethyl acetate) and DIPEA (0.218 mL, 1.25 mmol) were added and the reaction was left on at rt overnight. The addition of T3P and DIPEA was repeated twice and after 48 h the reaction was stopped. The reaction mixture was partitioned between water and ethyl acetate and the aqueous layer was further extracted with ethyl acetate. The organics were combined, passed through a hydrophobic cartridge and concentrated under vacuum. The residue was purified by Biotage SP4 chromatography on a 25 g silica SNAP cartridge, eluting with methanol in DCM 0 to 3% over 20 column volumes.

The earlier fractions were combined and concentrated under vacuum to give N-(1-(2-(1-ethyl-1H-indol-2-yl)-1-methyl-1H-benzo[d]imidazole-5-carbonyl)-4-methylpiperidin-3-yl)-2,2,2-trifluoroacetamide:

Intermediate 182: Trans-Isomer as a Pale Yellow Oil (143 mg, 22%)

LCMS (Method B): Rt 1.12 min, m/z 512.2 (MH⁺).

The later fractions were combined and concentrated under vacuum to give N-(1-(2-(1-ethyl-1H-indol-2-yl)-1-methyl-1H-benzo[d]imidazole-5-carbonyl)-4-methylpiperidin-3-yl)-2,2,2-trifluoroacetamide.

Intermediate 183: Cis-Isomer as a Yellow Oil (524 mg, 82%)

LCMS (Method B): Rt 1.14 min, m/z 512.2 (MH⁺).

Intermediate 184: Methyl 1-(2-(1-ethyl-1H-indol-2-yl)-1-methyl-1H-benzo[d]imidazole-5-carbonyl)-5-(2,2,2-trifluoroacetamido)piperidine-3-carboxylate

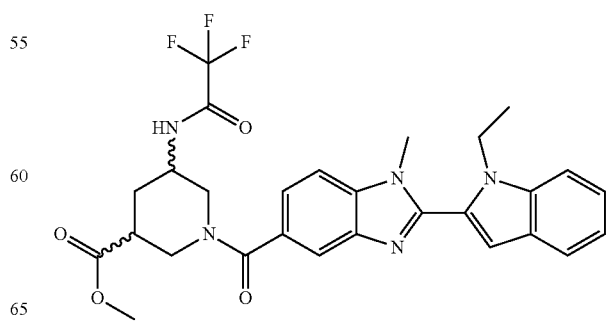

Prepared in a similar manner to Intermediate 182, from methyl 5-(2,2,2-trifluoroacetamido)piperidine-3-carboxylate and 2-(1-ethyl-1H-indol-2-yl)-1-methyl-1H-benzo[d]imidazole-5-carboxylic acid.

LCMS (Method B): Rt=1.09 mins, MH+=556.2

Intermediate 185: (+/−)-1-(2-(1-Ethyl-1H-indol-2-yl)-1-methyl-1H-benzo[d]imidazole-5-carbonyl)-5-(2,2,2-trifluoroacetamido)piperidine-3-carboxylic Acid, Cis-Isomer

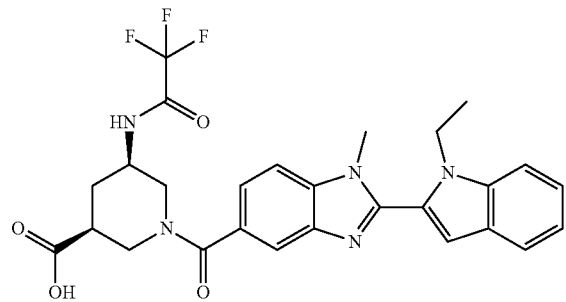 [SMILES: CCn1c(-c2nc3cc(C(=O)N4C[C@H](NC(=O)C(F)(F)F)C[C@H](C(=O)O)C4)ccc3n2C)cc2ccccc21]

Methyl 1-(2-(1-ethyl-1H-indol-2-yl)-1-methyl-1H-benzo[d]imidazole-5-carbonyl)-5-(2,2,2-trifluoroacetamido)piperidine-3-carboxylate (mixture of diastereoisomers) (1.61 g, 2.90 mmol) was stirred in tetrahydrofuran (10 mL) and water (5 mL) with lithium hydroxide (0.083 g, 3.48 mmol) at 40° C. for 70 h. The mixture was concentrated under vacuum and the residue was purified by biotage SP4 chromatography on a 100 g silica gel SNAP cartridge, eluting with 2M NH$_3$/MeOH in DCM 0 to 20% over 20 column volumes, then with 20% 2M NH$_3$/MeOH in DCM over 10 column volumes to afford the desired cis-product as a colourless oil (237 mg, 15%).

LCMS (Method B): Rt 1.00 min, m/z 542.2 (MH+)

Intermediate 186: (+/−)-cis-1-(2-(1-Ethyl-1H-indol-2-yl)-1-methyl-1H-benzo[d]imidazole-5-carbonyl)-5-(2,2,2-trifluoroacetamido)piperidine-3-carboxamide

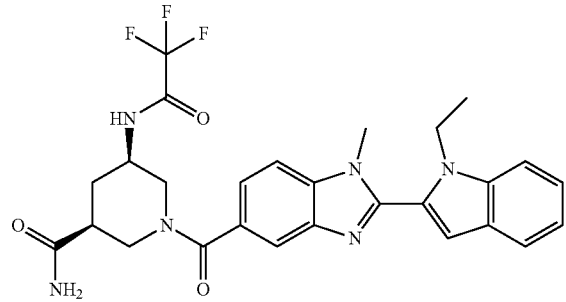 [SMILES: CCn1c(-c2nc3cc(C(=O)N4C[C@H](NC(=O)C(F)(F)F)C[C@H](C(N)=O)C4)ccc3n2C)cc2ccccc21]

DIPEA (0.222 mL, 1.274 mmol) and ammonia (2.55 mL, 1.27 mmol, 0.5 M in 1,4-dioxane) were added to a suspension of cis-1-(2-(1-ethyl-1H-indol-2-yl)-1-methyl-1H-benzo[d]imidazole-5-carbonyl)-5-(2,2,2-trifluoroacetamido)piperidine-3-carboxylic acid (230 mg, 0.425 mmol) in 1,4-dioxane (3 ml) with T3P (0.506 mL, 0.85 mmol, 50% in ethyl acetate). The resulting mixture was stirred at 70° C. for 2 h then an extra eq of DIPEA (0.074 mL, 0.425 mmol) and T3P 50% in ethyl acetate (0.253 mL, 0.425 mmol) were added. After 1 h the addition of DIPEA and T3P was repeated and the reaction was left on at 70° C. for 20 h. The reaction was allowed to cool down and the mixture was partitioned between ethyl acetate and water. The aqueous layer was further extracted with ethyl acetate. The organics were combined, washed with brine, passed though a hydrophobic cartridge and concentrated under vacuum. The residue was purified by Biotage SP4 chromatography on a 25 g silica gel SNAP cartridge, eluting with 2M NH$_3$/MeOH in DCM 0 to 20% over 15 column volumes, then with 20% 2M NH$_3$/MeOH in DCM over 5 column volumes to afford the desired product as a pale yellow oil (128 mg, 56%).

LCMS (Method B): Rt 0.95 min, m/z 541.3 (MH+)

Intermediate 187: cis-Methyl 1-(2-(1-ethyl-1H-indol-2-yl)-1-methyl-1H-benzo[d]imidazole-5-carbonyl)-3-(2,2,2-trifluoroacetamido)piperidine-4-carboxylate, Single Unknown Enantiomer

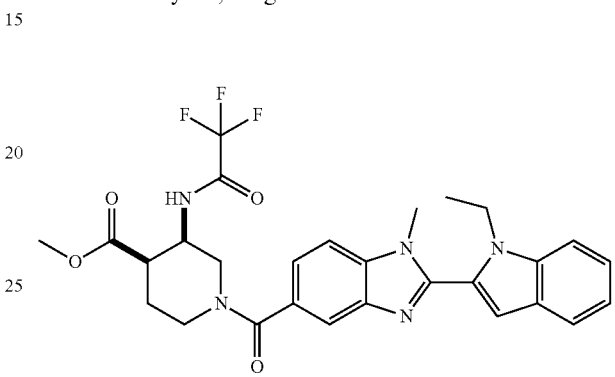

To 2-(1-ethyl-1H-indol-2-yl)-1-methyl-1H-benzo[d]imidazole-5-carboxylic acid (900 mg, 2.821 mmol) in N,N-dimethylformamide (DMF) (10 mL) was added HATU (1286 mg, 3.384 mmol) and Et$_3$N (1.964 mL, 14.1 mmol). The reaction was stirred for 15 min. Methyl 3-(2,2,2-trifluoroacetamido)piperidine-4-carboxylate, acetic acid salt (850 mg, 2.707 mmol) was added and the reaction stirred for 3 h under nitrogen. Water was added and a cream precipitate filtered off and washed with water and dried under high vacuum overnight (pale yellow solid turning into golden brown oil on standing). This was dissolved in DCM and loaded onto silica and eluted with 0-100% ethyl acetate in cyclohexane. The appropriate fractions were combined and the solvent removed to give a clear film which was dried under high vacuum overnight. The 4 components were separated by chiral preparative HPLC (Method H1/H2) to give the title compound (239 mg, 16%).

LCMS (Method B): Rt=1.10 min, MH+=556.4.

Intermediate 188: cis-1-(2-(1-Ethyl-1H-indol-2-yl)-1-methyl-1H-benzo[d]imidazole-5-carbonyl)-3-(2,2,2-trifluoroacetamido)piperidine-4-carboxylic Acid, Single Unknown Enantiomer

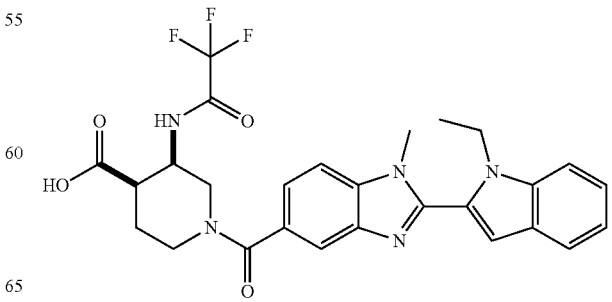

To cis-methyl 1-(2-(1-ethyl-1H-indol-2-yl)-1-methyl-1H-benzo[d]imidazole-5-carbonyl)-3-(2,2,2-trifluoroacetamido)piperidine-4-carboxylate (160 mg, 0.288 mmol) in tetrahydrofuran (THF) (2 mL) and water (1 mL) was added LiOH (6.90 mg, 0.288 mmol) and the reaction left to stir overnight at rt. The solvent was removed and the residue dissolved in DCM/MeOH and loaded onto silica, eluting with 0-20% methanol in DCM, then 20-50% methanol in DCM. The appropriate fractions were combined and the solvent removed to give a clear film which was dried under high vacuum overnight to afford an off white solid (46 mg, 30%).

LCMS (Method B): Rt=0.99 min, MH+=542.4.

Intermediate 189: cis-1-(2-(1-Ethyl-1H-indol-2-yl)-1-methyl-1H-benzo[d]imidazole-5-carbonyl)-3-(2,2,2-trifluoroacetamido)piperidine-4-carboxamide, Single Unknown Enantiomer

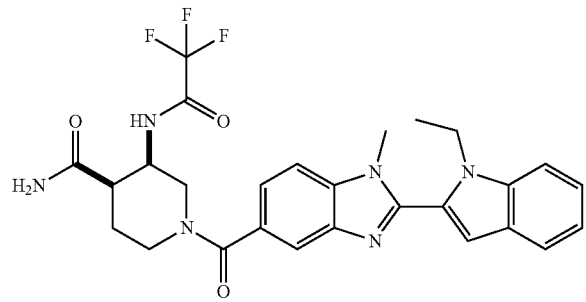 [SMILES: CCn1c(-c2nc3cc(C(=O)N4CC[C@@H](C(N)=O)[C@@H](NC(=O)C(F)(F)F)C4)ccc3n2C)cc2ccccc21]

To cis-1-(2-(1-ethyl-1H-indol-2-yl)-1-methyl-1H-benzo[d]imidazole-5-carbonyl)-3-(2,2,2-trifluoroacetamido)piperidine-4-carboxylic acid (46 mg, 0.085 mmol) and HATU (38.8 mg, 0.102 mmol) in 1,4-dioxane (1 mL) was added Et₃N (0.036 mL, 0.255 mmol) and then 0.5M ammonia in dioxane (1 mL, 0.500 mmol) and the reaction left to stir overnight. Additional HATU (38.8 mg, 0.102 mmol), Et₃N (0.036 mL, 0.255 mmol) and ammonia 0.5M in dioxane (1 mL, 0.500 mmol) were added and the reaction stirred overnight at 70° C. Additional HATU (38.8 mg, 0.102 mmol), Et₃N (0.036 mL, 0.255 mmol) and 0.5M ammonia in dioxane (1 mL, 0.500 mmol) were added and the reaction stirred overnight at 70° C. The reaction mixture was allowed to cool and the solvent removed. The crude product was partitioned between ethyl acetate and water (×3) and the combined organic layers washed with water (×2). The solvent was removed and the residue dissolved in DCM and loaded onto silica eluting with 0-10% 2M methanolic ammonia in DCM. The appropriate fractions were combined and the solvent removed. The residue was dried under high vacuum for 3 h to give a white solid (8 mg, 17%).

LCMS (Method B): Rt=0.94 min, MH+=541.3.

Intermediate 190: 1,1-Dimethylethyl [(3R)-1-({2-(1-ethyl-1H-indol-2-yl)-1-[3-({[(9H-fluoren-9-ylmethyl)oxy]carbonyl}amino)propyl]-1H-benzimidazol-5-yl}carbonyl)-3-piperidinyl]carbamate

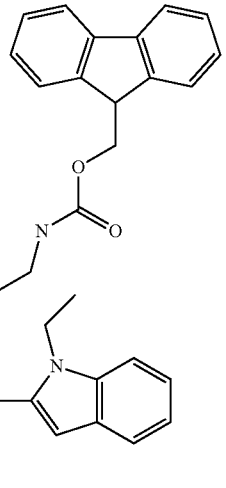

In two equal batches, 1,1-dimethylethyl {(3R)-1-[(4-{[3-({[(9H-fluoren-9-ylmethyl)oxy]carbonyl}amino)propyl]amino}-3-nitrophenyl)carbonyl]-3-piperidinyl}carbamate (6 g, 9.32 mmol), 1-ethyl-1H-indole-2-carbaldehyde (7.844 g, 27.96 mmol) and sodium hydrosulfite (4.868 g, 27.96 mmol) were combined in ethanol (40 mL) and water (20 mL) and heated in a Biotage Initiator microwave using initial high absorption setting to 100° C. for 6 h. The reaction mixtures were combined and then partitioned between DCM (150 mL) and water (150 mL). The ethanol from the reaction mixture led to poor separation of the two layers, so the whole mixture was evaporated under vacuum—to the point where it was assumed most of the ethanol had evaporated and only the aqueous layer remained. The aqueous layer was then extracted with DCM (3×100 mL). The organics were combined, dried using a hydrophobic frit and evaporated under vacuum. The sample was loaded in dichloromethane and purified by Biotage SP4 (2×SNAP 100 g silica) using a gradient of 50-100% cyclohexane-ethyl acetate. The appropriate fractions were combined and evaporated under vacuum to give the required product 1,1-dimethylethyl [(3R)-1-({2-(1-ethyl-1H-indol-2-yl)-1-[3-({[(9H-fluoren-9-ylmethyl)oxy]carbonyl}amino)propyl]-1H-benzimidazol-5-yl}carbonyl)-3-piperidinyl]carbamate (1.83 g, 2.386 mmol, 51.2% yield) as an off-white foam.

LCMS (Method B): Rt 1.37 min, MH+ 767.

Intermediate 191: (R)-tert-Butyl (1-(1-(3-aminopropyl)-2-(1-ethyl-1H-indol-2-yl)-1H-benzo[d]imidazole-5-carbonyl)piperidin-3-yl)carbamate

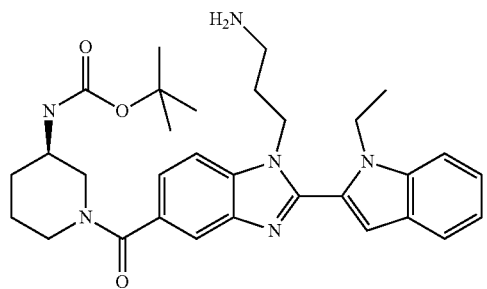 [SMILES: CCn1c(-c2nc3cc(C(=O)N4CCC[C@@H](NC(=O)OC(C)(C)C)C4)ccc3n2CCCN)cc2ccccc21]

1,1-Dimethylethyl [(3R)-1-({2-(1-ethyl-1H-indol-2-yl)-1-[3-({[(9H-fluoren-9-ylmethyl)oxy]carbonyl}amino)propyl]-1H-benzimidazol-5-yl}carbonyl)-3-piperidinyl]carbamate (112 mg, 0.146 mmol) and piperidine (0.289 mL, 2.92 mmol) were combined in dichloromethane (2 mL) and stirred at ambient temperature for 20 min. The reaction mixture was evaporated to dryness under vacuum. After ensuring all the piperidine had been evaporated, the sample was loaded in dichloromethane and purified by Biotage SP4 (SNAP 25 g silica) using a gradient of 0-5% 2M ammonia in methanol-dichloromethane over 10 column volumes followed by holding at 5% 2M ammonia in methanol-dichloromethane for 5 column volumes. The product remained on the column, so the column was washed using a gradient of 0-20% 2M ammonia in methanol-dichloromethane over 10 column volumes followed by holding at 20% 2M ammonia in methanol-dichloromethane for 5 column volumes. The appropriate fractions were combined and evaporated under vacuum to give the required product (R)-tert-butyl (1-(1-(3-aminopropyl)-2-(1-ethyl-1H-indol-2-yl)-1H-benzo[d]imidazole-5-carbonyl)piperidin-3-yl)carbamate (79 mg, 0.145 mmol, 99% yield) as a colourless glass.

LCMS (Method B): Rt 0.83 min, MH+ 545.

Intermediate 192: 1,1-Dimethylethyl ((3R)-1-{[2-(1-ethyl-1H-indol-2-yl)-1-methyl-1H-benzimidazol-5-yl]carbonyl}-3-piperidinyl)carbamate

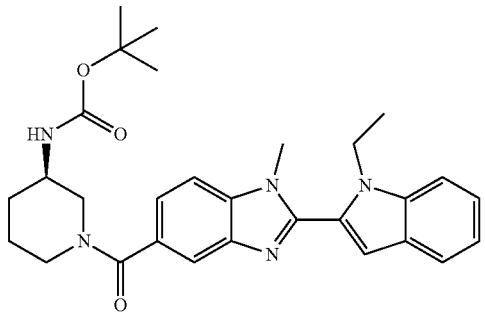 [SMILES: CCn1c(-c2nc3cc(C(=O)N4CCC[C@@H](NC(=O)OC(C)(C)C)C4)ccc3n2C)cc2ccccc21]

To a heterogeneous mixture of 1,1-dimethylethyl ((3R)-1-{[4-(methylamino)-3-nitrophenyl]carbonyl}-3-piperidinyl)carbamate (26.56 g, 70.2 mmol) and 1-ethyl-1H-indole-2-carbaldehyde (13.51 g, 70.2 mmol) in EtOH (487 mL) was added a solution of sodium hydrogen sulfate (14.38 g, 70.2 mmol) in water (244 mL) in a dropwise manner. The mixture was flushed with nitrogen then heated at 90° C. for 16 h. Further sodium hydrogen sulfate (8 g, 39.1 mmol) was added in one portion and the reaction mixture heated at 100° C. for a further 16 h. The mixture was allowed to cool then concentrated under reduced pressure and diluted with DCM (1 L) and partitioned with water (1 L) then filtered through a short pad of Celite. The organic layer was isolated then dried over sodium sulfate. The aqueous phase was further extracted with DCM (1 L x 2) and organic layers individually dried over sodium sulfate. The combined organic layers were concentrated under reduced pressure to around half the original volume by which time two liquid phases were still evident. The organic layer was isolated once more, then the aqueous layer reextracted with DCM (2×600 mL). The Celite pad was washed with MeOH until no more UV-active material eluted and the washings concentrated under reduced pressure. The resulting residue was redissolved in DCM (500 mL) then combined with the previously isolated DCM organic layers, dried over sodium sulfate then filtered and concentrated under reduced pressure to give the crude product (36 g) as a beige solid. The crude material was purified with column chromatography (eluted with cyclohexane and EtOAc from 0 to 100%) to give the title compound (14 g) as a pale yellow solid. The material was repurified with column chromatography (eluted with cyclohexane and EtOAc from 0 to 100%) to give the title compound as a pale yellow solid (11.7 g, 33%).

LCMS (Method B): Rt=1.15 min, MH+=502.3.

The following intermediates were prepared in a similar manner to Intermediate 192:

| Intermediate | Structure | Yield/% | LCMS |
|---|---|---|---|
| 193: 1,1-dimethylethyl ((3R)-1-{[2-(1-ethyl-1H-indol-2-yl)-1-methyl-7-(methyloxy)-1H-benzimidazol-5-yl]carbonyl}-3-piperidinyl)carbamate (prepared from (R)-tert-butyl (1-(3-methoxy-4-(methylamino)-5-nitrobenzoyl)piperidin-3-yl)carbamate and 1-ethyl-1H-indole-2-carbaldehyde). | 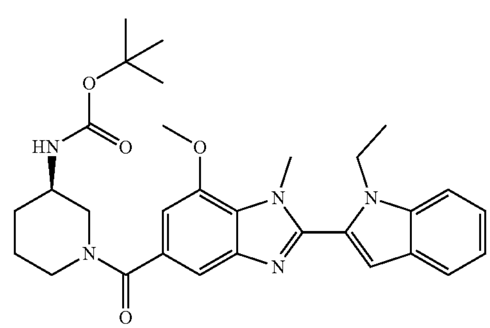 [SMILES: CCn1c(-c2nc3cc(C(=O)N4CCC[C@@H](NC(=O)OC(C)(C)C)C4)cc(OC)c3n2C)cc2ccccc21] | 100 | LCMS (Method B): Rt = 1.21 min, MH+ = 532.5 |

Intermediate 194: 1,1-Dimethylethyl {(3R)-1-[(2-{1-[(3-chlorophenyl)methyl]-1H-indol-2-yl}-1-methyl-1H-benzimidazol-5-yl)carbonyl]-3-piperidinyl}carbamate

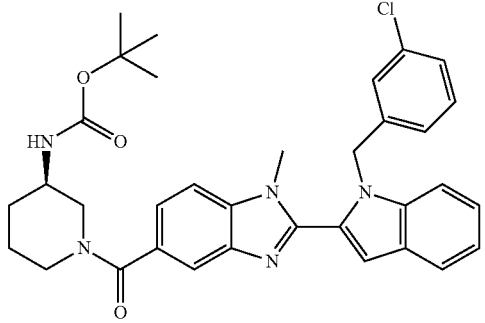 [SMILES: Cn1c(-c2cc3ccccc3n2Cc2cccc(Cl)c2)nc2cc(C(=O)N3CCC[C@@H](NC(=O)OC(C)(C)C)C3)ccc21]

Sodium hydrosulfite (162 mg, 0.793 mmol) dissolved in water (2 mL) was added to a solution of 1,1-dimethylethyl ((3R)-1-{[4-(methylamino)-3-nitrophenyl]carbonyl}-3-piperidinyl)carbamate (150 mg, 0.396 mmol) and 1-[(3-chlorophenyl)methyl]-1H-indole-2-carbaldehyde (107 mg, 0.396 mmol) in ethanol (4 mL) at rt under nitrogen in a 9 mL Reacti-vial. The reaction mixture was heated to 80° C. and stirred overnight (18 h). Methanol was added to the reaction mixture which was then dried with Na$_2$SO$_4$. The reaction mixture was then filtered via gravity through a hydrophobic frit and concentrated under vacuum. For purification, the reaction mixture was dissolved in 1:1 DMSO/Methanol and purified using MDAP (Method A). Product fractions were collected and concentrated under vacuum to produce a white solid—1,1-dimethylethyl {(3R)-1-[(2-{1-[(3-chlorophenyl)methyl]-1H-indol-2-yl}-1-methyl-1H-benzimidazol-5-yl)carbonyl]-3-piperidinyl}carbamate (97 mg, 41%).

LCMS (Method B): Rt=1.30 mins, MH$^+$=598.5

Intermediate 195: (R)-tert-Butyl (1-(2-(1-(3,4-dichlorobenzyl)-1H-indol-2-yl)-1-methyl-1H-benzo[d]imidazole-5-carbonyl)piperidin-3-yl)carbamate

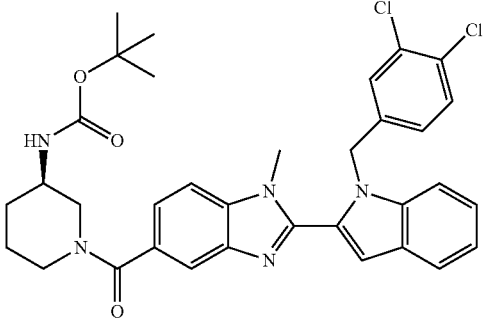 [SMILES: Cn1c(-c2cc3ccccc3n2Cc2ccc(Cl)c(Cl)c2)nc2cc(C(=O)N3CCC[C@@H](NC(=O)OC(C)(C)C)C3)ccc21]

Prepared in a similar manner to Intermediate 194, from 1,1-dimethylethyl ((3R)-1-{[4-(methylamino)-3-nitrophenyl]carbonyl}-3-piperidinyl)carbamate and 1-[(3,4-dichlorophenyl)methyl]-1H-indole-2-carbaldehyde LCMS (Method B): Rt=1.38 min, MH+=632.5.

Intermediate 196: 1,1-Dimethylethyl {(3R)-1-[(2-{1-[(4-chlorophenyl)methyl]-1H-indol-2-yl}-1-methyl-1H-benzimidazol-5-yl)carbonyl]-3-piperidinyl}carbamate

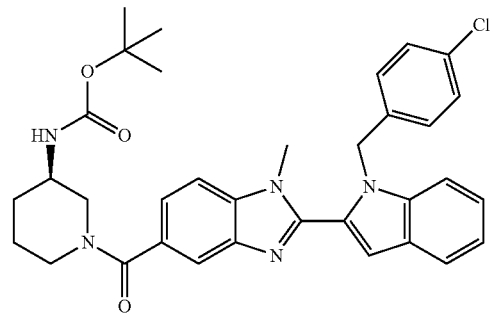 [SMILES: Cn1c(-c2cc3ccccc3n2Cc2ccc(Cl)cc2)nc2cc(C(=O)N3CCC[C@@H](NC(=O)OC(C)(C)C)C3)ccc21]

Sodium hydrosulfite (162 mg, 0.793 mmol) dissolved in water (1.35 mL) was added to a solution of 1,1-dimethylethyl ((3R)-1-{[4-(methylamino)-3-nitrophenyl]carbonyl}-3-piperidinyl)carbamate (100 mg, 0.264 mmol) and 1-[(4-chlorophenyl)methyl]-1H-indole-2-carbaldehyde (0.105 mL, 0.396 mmol) in ethanol (2.7 mL) at rt under nitrogen. The reaction mixture was heated to 80° C. and stirred overnight. The reaction was heated for a further 4 h and then allowed to cool to rt. The reaction mixture was diluted with MeOH (20 mL), Na$_2$SO$_4$ was added and the resultant suspension filtered and concentrated in vacuo to yield the crude product as a yellow oil. The crude product was purified on silica (25 g) using a gradient of 50% ethyl acetate/cyclohexane→100% ethyl acetate/cyclohexane. The appropriate fractions were combined and evaporated under vacuum to give the product which was still impure. The product was further purified in two batches by MDAP (Method B). The appropriate fractions were combined to afford the desired product as a white solid—1,1-dimethylethyl {(3R)-1-[(2-{1-[(4-chlorophenyl)methyl]-1H-indol-2-yl}-1-methyl-1H-benzimidazol-5-yl)carbonyl]-3-piperidinyl}carbamate (61 mg, 0.102 mmol, 38.6% yield).

LCMS (Method B): Rt=1.31 mins, MH$^+$=598.5

Other intermediates indicated in the following table were prepared in a manner similar to Intermediate 196.

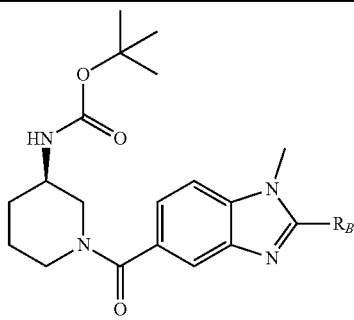

| Intermediate | $R_B$ | Yield/% | $^1$H NMR |
|---|---|---|---|
| 197: 1,1-Dimethylethyl {(3R)-1-[(1-methyl-2-{1-[(4-methylphenyl)methyl]-1H-indol-2-yl}-1H-benzimidazol-5-yl)carbonyl]-3-piperidinyl}carbamate (prepared from 1,1-dimethylethyl ((3R)-1-{[4-(methylamino)-3-nitrophenyl]carbonyl}-3-piperidinyl)carbamate and 1-[(4-methylphenyl)methyl]-1H-indole-2-carbaldehyde). | (structure) | 35 | $^1$H NMR (400 MHz) CDCl$_3$ δ 7.82 (1H, s), 7.65 (1H, d), 7.40-7.35 (2H, m), 7.32 (1H, d), 7.22 (1H, dt), 7.12 (1H, dt), 6.86-6.81 (3H, m), 6.67 (2H, d), 5.69 (2H, s), 4.80-4.40 (1H, m), 3.88-3.20 (8H, m), 2.13 (3H, s), 1.97-1.45 (4H, m), 1.34 (9H, br s) |

Intermediate 198: 1,1-Dimethylethyl [(3R)-1-({1-methyl-2-[1-(4-pyridinylmethyl)-1H-indol-2-yl]-1H-benzimidazol-5-yl}carbonyl)-3-piperidinyl]carbamate

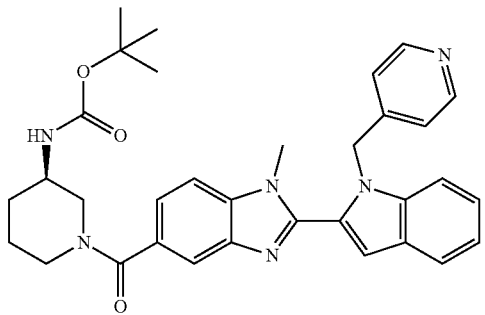 [SMILES: Cn1c(-c2cc3ccccc3n2Cc2ccncc2)nc2cc(C(=O)N3CCC[C@@H](NC(=O)OC(C)(C)C)C3)ccc21]

Sodium hydrosulfite (162 mg, 0.793 mmol) dissolved in water (2.0 mL) was added to a solution of 1,1-dimethylethyl ((3R)-1-{[4-(methylamino)-3-nitrophenyl]carbonyl}-3-piperidinyl)carbamate (150 mg, 0.396 mmol) and 1-(4-pyridinylmethyl)-1H-indole-2-carbaldehyde (103 mg, 0.436 mmol) in ethanol (4 mL) at rt under nitrogen. The reaction mixture was heated to 85° C. and stirred overnight. A further portion of sodium hydrosulfite (162 mg, 0.793 mmol) in water (2.0 mL) was added and the reaction was heated to 85° C. for a further ~3 h. The reaction was then heated at 95° C. for a further ~3 h. A further amount of sodium hydrosulfite (81 mg, 0.396 mmol) was added and the reaction heated at 95° C. overnight. The reaction mixture was diluted with MeOH (20 mL), Na$_2$SO$_4$ was added and the resultant suspension filtered and concentrated in vacuo to yield the crude product as a yellow oil. The crude product was purified by Biotage SP4 on silica (10 g) using a gradient of 0% (20% MeOH/DCM)/DCM →100% (20% MeOH/DCM)/DCM. The appropriate fractions were combined and evaporated under vacuum to give the product which was still impure. The product was further purified in two batches by MDAP (Method B). The appropriate fractions were combined to afford the desired product as a white solid—1,1-dimethylethyl [(3R)-1-({1-methyl-2-[1-(4-pyridinylmethyl)-1H-indol-2-yl]-1H-benzimidazol-5-yl}carbonyl)-3-piperidinyl]carbamate (107 mg, 0.189 mmol, 47.8% yield). LCMS (Method B): Rt=0.91 min, MH$^+$=565.5

Intermediate 199: tert-Butyl ((R)-1-(2-(1-((R)-3-hydroxy-2-methylpropyl)-1H-indol-2-yl)-7-methoxy-1-methyl-1H-benzo[d]imidazole-5-carbonyl)piperidin-3-yl)carbamate

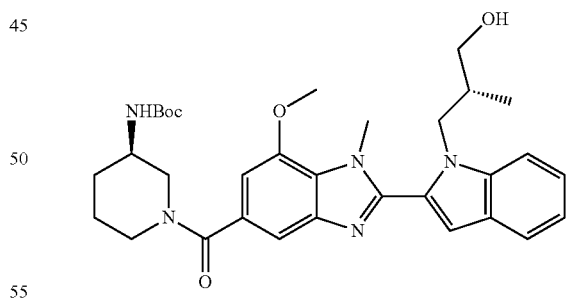

To a solution of (R)-1-(3-hydroxy-2-methylpropyl)-1H-indole-2-carbaldehyde (210 mg, 0.967 mmol) in ethanol (10 mL) was added (R)-tert-butyl (1-(3-methoxy-4-(methylamino)-5-nitrobenzoyl)piperidin-3-yl)carbamate (395 mg, 0.967 mmol) followed by a solution of sodium dithionite (269 mg, 1.547 mmol) in water (5.00 mL). This was heated at 95° C. for 18 h. The reaction mixture was partitioned between ethyl acetate and water. The aqueous was reextracted with ethyl acetate and the combined organics were passed through a hydrophobic frit. The organics were concentrated in vacuo to yield a crude product. This was dissolved in DCM and purified through silica (20 g) eluting with a gradient 0-100% ethyl acetate in DCM. Appropriate fractions were combined and concentrated in vacuo to yield the title compound as a cream gum that solidified on standing (310 mg).

LCMS (Method B): Rt 1.13 min, MH+=576.3.

Intermediate 200: (R)-tert-Butyl (1-(7-methoxy-1-methyl-2-(1-((tetrahydro-2H-pyran-4-yl)methyl)-1H-indol-2-yl)-1H-benzo[d]imidazole-5-carbonyl)piperidin-3-yl)carbamate

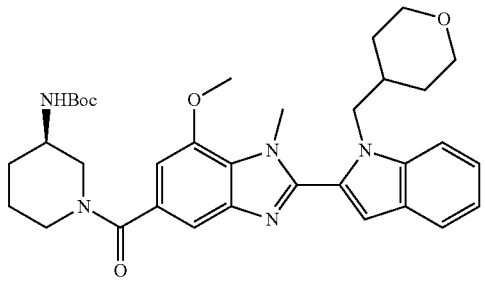 [SMILES: COc1cc(C(=O)N2CCC[C@@H](NC(=O)OC(C)(C)C)C2)cc2nc(-c3cc4ccccc4n3CC3CCOCC3)n(C)c12]

Prepared in a similar manner to Intermediate 199, from (R)-tert-butyl (1-(3-methoxy-4-(methylamino)-5-nitrobenzoyl)piperidin-3-yl)carbamate and 1-((tetrahydro-2H-pyran-4-yl)methyl)-1H-indole-2-carbaldehyde.

LCMS (Method B): Rt 1.16 min, MH+=602.3.

Intermediate 201: (R)-tert-Butyl (1-(7-methoxy-2-(1-(2-methoxyethyl)-1H-indol-2-yl)-1-methyl-1H-benzo[d]imidazole-5-carbonyl)piperidin-3-yl)carbamate

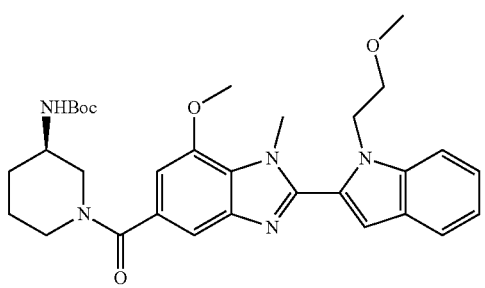 [SMILES: COCCn1c(-c2nc3cc(C(=O)N4CCC[C@@H](NC(=O)OC(C)(C)C)C4)cc(OC)c3n2C)cc2ccccc21]

Prepared in a similar manner to Intermediate 199, from (R)-tert-butyl (1-(3-methoxy-4-(methylamino)-5-nitrobenzoyl)piperidin-3-yl)carbamate and 1-(2-methoxyethyl)-1H-indole-2-carbaldehyde.

LCMS (Method B): Rt 1.15 min, MH+=562.3.

Intermediate 202: (R)-tert-Butyl (1-(2-(1-(2-hydroxyethyl)-1H-indol-2-yl)-7-methoxy-1-methyl-1H-benzo[d]imidazole-5-carbonyl)piperidin-3-yl)carbamate

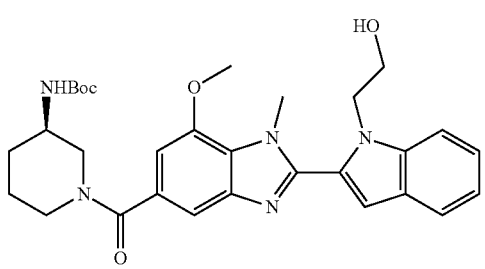 [SMILES: COc1cc(C(=O)N2CCC[C@@H](NC(=O)OC(C)(C)C)C2)cc2nc(-c3cc4ccccc4n3CCO)n(C)c12]

Prepared in a similar manner to Intermediate 199, from (R)-tert-butyl (1-(3-methoxy-4-(methylamino)-5-nitrobenzoyl)piperidin-3-yl)carbamate and 1-(2-hydroxyethyl)-1H-indole-2-carbaldehyde.

LCMS (Method B): Rt 1.02 min, MH+=548.3.

Intermediate 203: 1,1-Dimethylethyl [(3R)-1-({1-methyl-2-[1-(3-pyridinylmethyl)-1H-indol-2-yl]-1H-benzimidazol-5-yl}carbonyl)-3-piperidinyl]carbamate

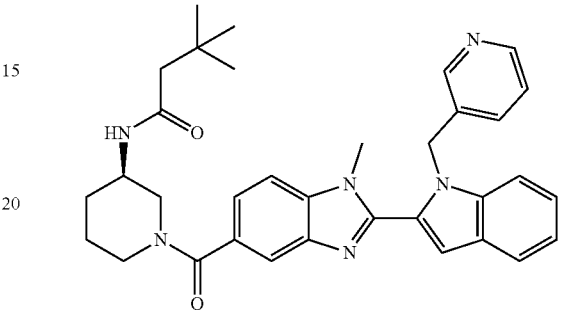

Sodium hydrosulfite (244.3 mg, 1.193 mmol) dissolved in water (1.5 mL) was added to a stirred solution of 1,1-dimethylethyl ((3R)-1-{[4-(methylamino)-3-nitrophenyl]carbonyl}-3-piperidinyl)carbamate (148.6 mg, 0.393 mmol) and 1-(3-pyridinylmethyl)-1H-indole-2-carbaldehyde (159.2 mg, 0.404 mmol) in ethanol (3.5 mL) at rt in a 5 mL microwave vial. The reaction mixture was then heated in a microwave for 2 h at 85° C. The reaction mixture was reheated in the microwave for 1 h at 90° C. Further sodium hydrosulfite (80 mg, 0.393 mmol) was added to the reaction mixture and heated in a microwave for 45 min at 100° C. Methanol was added to the reaction mixture which was then dried with $Na_2SO_4$. The reaction mixture was then filtered through a hydrophobic frit and concentrated under vacuum. The concentrated reaction mixture was purified on silica (25 g) using a gradient of 40-100% ethyl acetate/cyclohexane. Due to the polarity of the product the column was then eluted with a gradient of 0-100% (20% methanol in DCM)/DCM. The appropriate fractions from the second purification were collected and concentrated under vacuum to give a yellow/white solid—1,1-dimethylethyl [(3R)-1-({1-methyl-2-[1-(3-pyridinylmethyl)-1H-indol-2-yl]-1H-benzimidazol-5-yl}carbonyl)-3-piperidinyl]carbamate (133 mg, 60%).

LCMS (Method B): Rt=0.96 mins, MH+=565.3

Intermediate 204: 1,1-Dimethylethyl ((3R)-1-{[2-(2,3-dihydro[1,4]oxazino[2,3,4-hi]indol-5-yl)-1-methyl-1H-benzimidazol-5-yl]carbonyl}-3-piperidinyl)carbamate

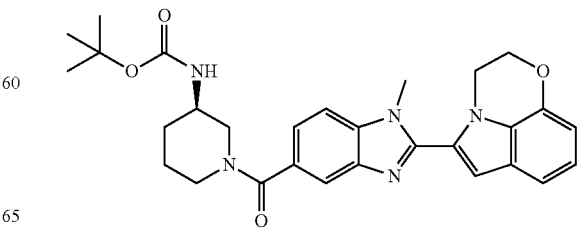

Sodium hydrogen sulfite (657 mg, 3.21 mmol) was dissolved in water (3 mL) then added to a solution of 1,1-dimethylethyl ((3R)-1-{[4-(methyl amino)-3-nitrophenyl]carbonyl}-3-piperidinyl)carbamate (404 mg, 1.07 mmol) and 2,3-dihydro[1,4]oxazino[2,3,4-hi]indole-5-carbaldehyde (200 mg, 1.07 mmol) in EtOH (12 mL) at rt. The reaction mixture was heated at 100° C. for 5 h using a microwave then allowed to cool to rt. The reaction mixture was then diluted with DCM (40 mL), then dried over magnesium sulfate and concentrated under reduced pressure to give 610 mg of the crude product as a yellow solid. The crude material was purified with column chromatography (eluted with cyclohexane and EtOAc from 40 to 100%) to give the title compound as a pale yellow solid (286 mg, 52%).

LCMS (Method B): Rt=1.10 min, MH+=516.5.

Other racemic intermediates indicated in following table were prepared in a manner similar to Intermediate 204.

| Intermediate | $R_C$ | Yield/% | LCMS |
|---|---|---|---|
| 205: 1,1-Dimethylethyl [1-({1-methyl-2-[1-(tetrahydro-2H-pyran-4-ylmethyl)-1H-indol-2-yl]-1H-benzimidazol-5-yl}carbonyl)-3-piperidinyl]carbamate (prepared from tert-butyl (1-(4-(methylamino)-3-nitrobenzoyl)piperidin-3-yl)carbamate and 1-(tetrahydro-2H-pyran-4-ylmethyl)-1H-indole-2-carbaldehyde). | (tetrahydropyranylmethyl-indol-2-yl) | 64 | LCMS (Method B): Rt = 1.15 min, MH+ = 572.5 |
| 206: 1,1-Dimethylethyl (1-{[2-(6-bromo-1-ethyl-1H-indol-2-yl)-1-methyl-1H-benzimidazol-5-yl]carbonyl}-3-piperidinyl)carbamate (prepared from tert-butyl (1-(4-(methylamino)-3-nitrobenzoyl)piperidin-3-yl)carbamate and 6-bromo-1-ethyl-1H-indole-2-carbaldehyde). | (6-bromo-1-ethyl-indol-2-yl) | 32 | LCMS (Method B): Rt = 1.36 min, MH+ = 582.4 |

Other intermediates in the following table were prepared in a manner similar to Intermediate 204:

| Intermediate | $R_D$ | $R_E$ | $R_F$ | LCMS |
|---|---|---|---|---|
| 207: 1,1-dimethylethyl [(3R)-1-({2-[1-ethyl-7-(methyloxy)-1H-indol-2-yl]-1-methyl-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3- | (1-ethyl-7-methoxy-indol-2-yl) | H | Me | LCMS (Method A) Rt = 1.24 min, MH+ = 532.3 |

-continued

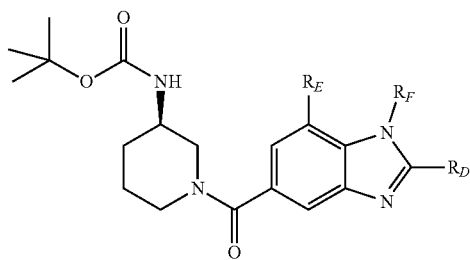

| Intermediate | $R_D$ | $R_E$ | $R_F$ | LCMS |
|---|---|---|---|---|
| piperidinyl)carbamate and 1-ethyl-7-(methyloxy)-1H-indole-2-carbaldehyde). | | | | |
| 208: 1,1-dimethylethyl ((3R)-1-{[2-(3,4-dihydro-2H-[1,4]oxazepino[2,3,4-hi]indol-6-yl)-1-methyl-1H-benzimidazol-5-yl]carbonyl}-3-piperidinyl)carbamate (prepared from (R)-tert-butyl (1-(4-(methylamino)-3-nitrobenzoyl)piperidin-3-yl)carbamate and 3,4-dihydro-2H-[1,4]oxazepino[2,3,4-hi]indole-6-carbaldehyde). | 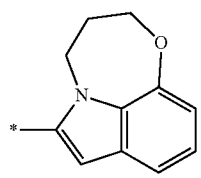 [SMILES: *c1cc2cccc3c2n1CCCO3] | H | Me | LCMS (Method A): Rt = 1.16 min, MH+ = 530.2 |
| 209: 1,1-dimethylethyl ((3R)-1-{[1-methyl-2-(3-methyl-2,3-dihydro[1,4]oxazino[2,3,4-hi]indol-5-yl)-1H-benzimidazol-5-yl]carbonyl}-3-piperidinyl)carbamate (prepared from (R)-tert-butyl (1-(4-(methylamino)-3-nitrobenzoyl)piperidin-3-yl)carbamate and 3-methyl-2,3-dihydro-[1,4]oxazino[2,3,4-hi]indole-5-carbaldehyde). | 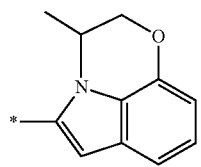 [SMILES: *c1cc2cccc3c2n1C(C)CO3] | H | Me | LCMS (Method B): Rt = 1.17 min, MH+ = 530.3 |
| 210: (R)-tert-Butyl (1-(1-ethyl-2-(1-ethyl-1H-indol-2-yl)-1H-benzo[d]imidazole-5-carbonyl)piperidin-3-yl)carbamate (prepared from (R)-tert-butyl (1-(4-(ethylamino)-3-nitrobenzoyl)piperidin-3-yl)carbamate and 1-ethyl-1H-indole-2-carbaldehyde). | 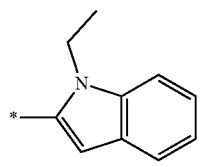 [SMILES: *c1cc2ccccc2n1CC] | H | Et | LCMS (Method B): Rt = 1.21 min, MH+ 516. |
| 211: 1,1-Dimethylethyl {(3R)-1-[(1-methyl-2-{1-[(1-methyl-1H-pyrazol-4-yl)methyl]-1H-indol-2-yl}-1H-benzimidazol-5-yl)carbonyl]-3-piperidinyl}carbamate (prepared from (R)-tert-butyl (1-(4-(methylamino)-3-nitrobenzoyl)piperidin-3-yl)carbamate and 1-[(1-methyl-1H-pyrazol-4-yl)methyl]-1H-indole-2-carbaldehyde). | 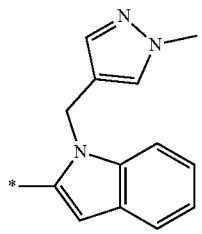 [SMILES: *c1cc2ccccc2n1Cc1cnn(C)c1] | H | Me | LCMS: (Method B) Rt = 1.03 min, MH+ = 568.3 |

-continued

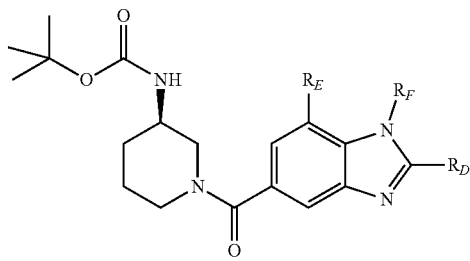

| Intermediate | $R_D$ | $R_E$ | $R_F$ | LCMS |
|---|---|---|---|---|
| 212: (R)-tert-Butyl (1-(2-(1-ethyl-5-fluoro-1H-indol-2-yl)-1-methyl-1H-benzo[d]imidazole-5-carbonyl)piperidin-3-yl)carbamate (prepared from (R)-tert-butyl (1-(4-(methylamino)-3-nitrobenzoyl)piperidin-3-yl)carbamate and 1-ethyl-5-fluoro-1H-indole-2-carbaldehyde). | 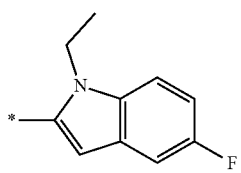 [SMILES: *c1cc2cc(F)ccc2n1CC] | H | Me | LCMS: (Method B) Rt = 1.17 min, MH+ = 520.3 |
| 213: 1,1-Dimethylethyl [(3R)-1-({2-[1-(cyclopropylmethyl)-5-(methyloxy)-1H-indol-2-yl]-1-methyl-1H-benzimidazol-5-yl}carbonyl)-3-piperidinyl]carbamate (prepared from (R)-tert-butyl (1-(4-(methylamino)-3-nitrobenzoyl)piperidin-3-yl)carbamate and 1-(cyclopropylmethyl)-5-methoxy-1H-indole-2-carbaldehyde). | 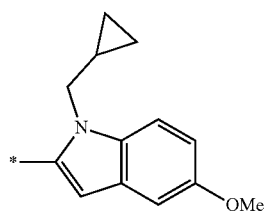 [SMILES: *c1cc2cc(OC)ccc2n1CC1CC1] | H | Me | LCMS (Method B) Rt = 1.16 min, MH+ = 558.3 |
| 214: 1,1-dimethylethyl [(3R)-1-({2-[1-(cyanomethyl)-1H-indol-2-yl]-1-methyl-1H-benzimidazol-5-yl}carbonyl)-3-piperidinyl]carbamate (prepared from (R)-tert-butyl (1-(4-(methylamino)-3-nitrobenzoyl)piperidin-3-yl)carbamate and 2-(2-formyl-1H-indol-1-yl)acetonitrile). | 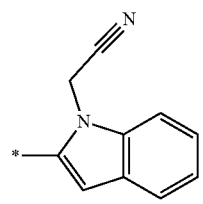 [SMILES: *c1cc2ccccc2n1CC#N] | H | Me | LCMS (Method B): Rt = 1.09 min, MH+ = 513.2 |
| 215: 1,1-Dimethylethyl [(3R)-1-({1-methyl-2-[1-(2,2,2-trifluoroethyl)-1H-indol-2-yl]-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidinyl)carbamate and 1-(2,2,2-trifluoroethyl)-1H-indole-2-carbaldehyde). | 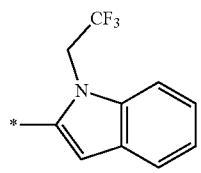 [SMILES: *c1cc2ccccc2n1CC(F)(F)F] | H | Me | LCMS (Method B): Rt = 1.20 min, MH+ = 556.2 |
| 216: 1,1-Dimethylethyl [(3R)-1-({1-methyl-2-[1-(1-methylethyl)-1H-indol-2-yl]-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidinyl)carbamate and 1-(1-methylethyl)-1H-indole-2-carbaldehyde). | 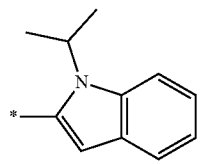 [SMILES: *c1cc2ccccc2n1C(C)C] | H | Me | LCMS (Method B): Rt = 1.18 min, MH+ = 516.4 |

-continued

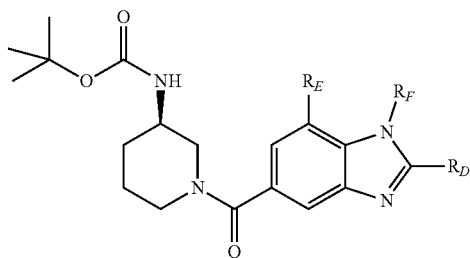

| Intermediate | $R_D$ | $R_E$ | $R_F$ | LCMS |
|---|---|---|---|---|
| 217: 1,1-Dimethylethyl ((3R)-1-{[2-(6-bromo-1-ethyl-1H-indol-2-yl)-1-methyl-1H-benzimidazol-5-yl]carbonyl}-3-piperidinyl)carbamate (prepared from 1,1-dimethylethyl ((3R)-1-{[4-(methylamino)-3-nitrophenyl]carbonyl}-3-piperidinyl)carbamate and 6-bromo-1-ethyl-1H-indole-2-carbaldehyde). | 1-ethyl-6-bromoindol-2-yl | H | Me | LCMS (Method B): Rt = 1.26 min, MH+ = 582.2 |
| 218: 1,1-Dimethylethyl [(3R)-1-({2-[1-(cyclopropylmethyl)-1H-indol-2-yl]-1-methyl-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidineyl)carbamate and 1-(cyclopropylmethyl)-1H-indole-2-carbaldehyde). | 1-(cyclopropylmethyl)indol-2-yl | H | Me | LCMS (Method B): Rt = 1.19 min, MH+ = 528.4 |
| 219: 1,1-Dimethylethyl ((3R)-1-{[2-(1H-indol-2-yl)-1-methyl-1H-benzimidazol-5-yl]carbonyl}-3-piperidinyl)carbamate (prepared from 1,1-dimethylethyl ((3R)-1-{[4-(methylamino)-3-nitrophenyl]carbonyl}-3-piperidinyl)carbamate and 1H-indole-2-carbaldehyde (commercially available from, for example, Sigma-Aldrich)). | 1H-indol-2-yl | H | Me | LCMS (Method B): Rt = 1.01 min, MH+ = 474.2 |
| 220: 1,1-Dimethylethyl [(3R)-1-({1-methyl-2-[1-(2-methylpropyl)-1H-indol-2-yl]-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidinyl)carbamate and 1-isobutyl-1H-indole-2-carbaldehyde). | 1-isobutylindol-2-yl | H | Me | LCMS (Method B): Rt = 1.27 min, MH+ = 530.3 |
| 221: 1,1-Dimethylethyl ((3R)-1-{[2-(5-chloro-1-ethyl-1H-indol-2-yl)-1-methyl-1H-benzimidazol-5-yl]carbonyl}-3-piperidinyl)carbamate (prepared from 1,1-dimethylethyl ((3R)-1-{[4-(methylamino)-3-nitrophenyl]carbonyl}-3-piperidinyl)carbamate and 5-chloro-1-ethyl-1H-indole-2-carbaldehyde). | 1-ethyl-5-chloroindol-2-yl | H | Me | LCMS (Method A): Rt = 1.30 min, MH+ = 536.2 |

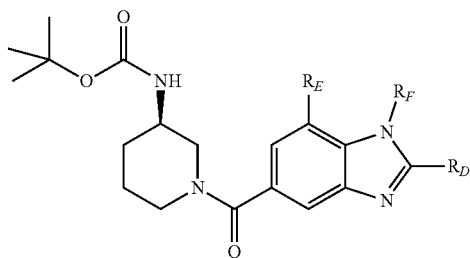

| Intermediate | $R_D$ | $R_E$ | $R_F$ | LCMS |
|---|---|---|---|---|
| 222: 1,1-Dimethylethyl {(3R)-1-[(1-methyl-2-{1-[2-(methyloxy)ethyl]-1H-indol-2-yl}-1H-benzimidazol-5-yl)carbonyl]-3-piperidinyl}carbamate (prepared from 1,1-dimethylethyl ((3R)-1-{[4-(methylamino)-3-nitrophenyl]carbonyl}-3-piperidinyl)carbamate and 1-[2-(methyloxy)ethyl]-1H-indole-2-carbaldehyde). | 2-(methoxyethyl)-indol-2-yl | H | Me | LCMS (Method B): Rt = 1.07 min, MH+ = 532.4 |
| 223: 1,1-Dimethylethyl [(3R)-1-({1-methyl-2-[1-(phenylmethyl)-1H-indol-2-yl]-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidinyl)carbamate and 1-(phenylmethyl)-1H-indole-2-carbaldehyde). | 1-benzyl-indol-2-yl | H | Me | LCMS (Method A): Rt = 1.30 min, MH+ = 564.4 |
| 224: 1,1-Dimethylethyl {(3R)-1-[(2-{1-[(4-iodophenyl)methyl]-1H-indol-2-yl}-1-methyl-1H-benzimidazol-5-yl)carbonyl]-3-piperidinyl}carbamate (prepared from 1,1-dimethylethyl ((3R)-1-{[4-(methylamino)-3-nitrophenyl]carbonyl}-3-piperidinyl)carbamate and 1-(4-iodobenzyl)-1H-indole-2-carbaldehyde). | 1-(4-iodobenzyl)-indol-2-yl | H | Me | LCMS (Method B): Rt = 1.35 min, MH+ = 690.4 |
| 225: 1,1-Dimethylethyl ((3R)-1-{[2-(1-ethyl-6-methyl-1H-indol-2-yl)-1-methyl-1H-benzimidazol-5-yl]carbonyl}-3-piperidinyl)carbamate (prepared from 1,1-dimethylethyl ((3R)-1-{[4-(methylamino)-3-nitrophenyl]carbonyl}-3-piperidinyl)carbamate and 1-ethyl-6-methyl-1H-indole)-2-carbaldehyde). | 1-ethyl-6-methyl-indol-2-yl | H | Me | LCMS (Method B): Rt = 1.21 min, MH+ = 516.3 |
| 226: 1,1-Dimethylethyl [(3R)-1-({1-methyl-2-[1-(2-pyridinylmethyl)-1H-indol-2-yl]-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidinyl)carbamate and 1-(2-pyridinylmethyl)-1H-indole-2-carbaldehyde). | 1-(2-pyridinylmethyl)-indol-2-yl | H | Me | LCMS (Method B): Rt = 1.01 min, MH+ = 565.6 |

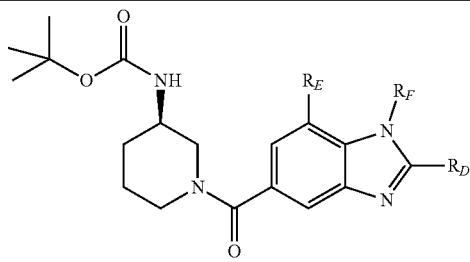

| Intermediate | $R_D$ | $R_E$ | $R_F$ | LCMS |
|---|---|---|---|---|
| 227: 1,1-Dimethylethyl [(3R)-1-({2-[1-(2-hydroxyethyl)-1H-indol-2-yl]-1-methyl-1H-benzimidazol-5-yl}carbonyl)-3-piperidinyl]carbamate (prepared from 1,1-dimethylethyl ((3R)-1-{[4-(methylamino)-3-nitrophenyl]carbonyl}-3-piperidinyl)carbamate and 1-(2-hydroxyethyl)-1H-indole-2-carbaldehyde). | 2-(1-(2-hydroxyethyl)-1H-indol-2-yl) | H | Me | LCMS (Method B): Rt = 0.98 min, MH+ = 518.5 |
| 228: (R)-tert-Butyl (1-(2-(1-ethyl-6,7-dimethoxy-1H-indol-2-yl)-1-methyl-1H-benzo[d]imidazole-5-carbonyl)piperidin-3-yl)carbamate (prepared from (R)-tert-butyl (1-(4-(methylamino)-3-nitrobenzoyl)piperidin-3-yl)carbamate and 1-ethyl-6,7-dimethoxy-1H-indole-2-carbaldehyde). | 2-(1-ethyl-6,7-dimethoxy-1H-indol-2-yl) | H | Me | LCMS (Method A): Rt = 1.21 min, MH+ = 562.33 |
| 229: 1,1-Dimethylethyl ((3R)-1-{[1-[2-({[(1,1-dimethylethyl)oxy]carbonyl}amino)ethyl]-2-(1-ethyl-1H-indol-2-yl)-1H-benzimidazol-5-yl]carbonyl}-3-piperidinyl)carbamate (prepared from 1,1-dimethylethyl {(3R)-1-[(4-{[2-({[(1,1-dimethylethyl)oxy]carbonyl}amino)ethyl]amino}-3-nitrophenyl)carbonyl]-3-piperidinyl}carbamate and 1-ethyl-1H-indole-2-carbaldehyde). | 2-(1-ethyl-1H-indol-2-yl) | H | 2-((tert-butoxycarbonyl)amino)ethyl | LCMS (Method B): Rt = 1.23 min, MH+ = 631.5. |
| 230: (R)-tert-Butyl (1-(2-(1-ethyl-1H-indol-2-yl)-1-methyl-7-(trifluoromethyl)-1H-benzo[d]imidazole-5-carbonyl)piperidin-3-yl)carbamate (prepared from (R)-tert-butyl (1-(4-(methylamino)-3-nitro-5-(trifluoromethyl)benzoyl)piperidin-3-yl)carbamate and 1-ethyl-1H-indole-2-carbaldehyde). | 2-(1-ethyl-1H-indol-2-yl) | CF$_3$ | Me | LCMS (Method B): Rt = 1.35 min, MH+ = 570.5. |
| 231: (R)-tert-butyl (1-(2-(1-(cyclopropylmethyl)-1H-indol-2-yl)-7-methoxy-1-methyl-1H-benzo[d]imidazole-5-carbonyl)piperidin-3-yl)carbamate (prepared from (R)-tert-butyl (1-(3-methoxy-4-(methylamino)-5-nitrobenzoyl)piperidin-3-yl)carbamate and 1-(cyclopropylmethyl)-1H-indole-2-carbaldehyde). | 2-(1-(cyclopropylmethyl)-1H-indol-2-yl) | OMe | Me | LCMS (Method B): Rt = 1.51 min, MH+ = 558.4 |

-continued

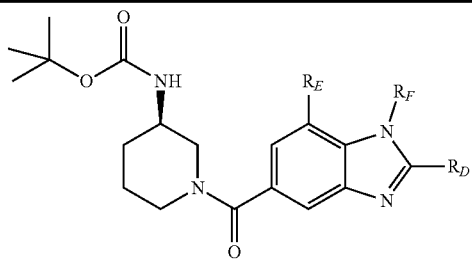

| Intermediate | $R_D$ | $R_E$ | $R_F$ | LCMS |
|---|---|---|---|---|
| 232: (R)-tert-butyl(1-(7-methoxy-1-methyl-2-(1-(2,2,2-trifluoroethyl)-1H-indol-2-yl)-1H-benzo[d]imidazole-5-carbonyl)piperidin-3-yl)carbamate (prepared from (R)-tert-butyl (1-(3-methoxy-4-(methylamino)-5-nitrobenzoyl)piperidin-3-yl)carbamate and 1-(2,2,2-trifluoroethyl)-1H-indole-2-carbaldehyde). | 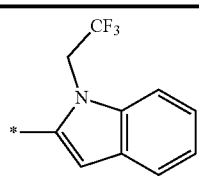 | OMe | Me | LCMS (Method B): Rt = 1.51 mins, MH+ = 586 |
| 233: (R)-tert-Butyl (1-(2-(1-(4-methoxybenzyl)-1H-indol-2-yl)-1-methyl-1H-benzo[d]imidazole-5-carbonyl)piperidin-3-yl)carbamate (prepared from 1,1-dimethylethyl ((3R)-1-{[4-(methylamino)-3-nitrophenyl]carbonyl}-3-piperidinyl)carbamate and 1-{[4-(methyloxy)phenyl]methyl}-1H-indole-2-carbaldehyde). | 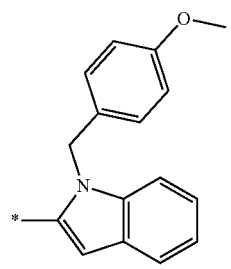 [SMILES: *c1cc2ccccc2n1Cc1ccc(OC)cc1] | H | Me | LCMS (Method B): Rt = 1.22 min, MH+ = 594.5. |
| 234: (R)-tert-Butyl (1-(7-methoxy-2-(1-(3-methoxypropyl)-1H-indol-2-yl)-1-methyl-1H-benzo[d]imidazole-5-carbonyl)piperidin-3-yl)carbamate (prepared from (R)-tert-butyl (1-(3-methoxy-4-(methylamino)-5-nitrobenzoyl)piperidin-3-yl)carbamate and 1-(3-methoxypropyl)-1H-indole-2-carbaldehyde). | 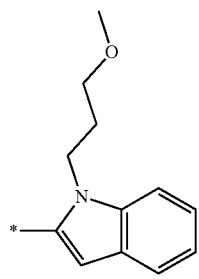 [SMILES: *c1cc2ccccc2n1CCCOC] | OMe | Me | LCMS (Method B): Rt = 1.18 min, MH+ = 576.3. |
| 235: tert-Butyl ((R)-1-(2-(1-((S)-3-hydroxy-2-methylpropyl)-1H-indol-2-yl)-7-methoxy-1-methyl-1H-benzo[d]imidazole-5-carbonyl)piperidin-3-yl)carbamate (prepared from (R)-tert-butyl (1-(3-methoxy-4-(methylamino)-5-nitrobenzoyl)piperidin-3-yl)carbamate and (S)-1-(3-hydroxy-2-methylpropyl)-1H-indole-2-carbaldehyde). | 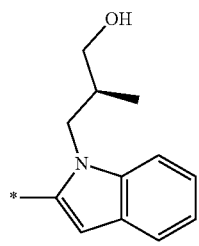 [SMILES: *c1cc2ccccc2n1C[C@H](C)CO] | OMe | Me | LCMS (Method B): Rt = 1.13 min, MH+ = 576.4. |
| 236: (R)-tert-Butyl (1-(2-(1-(cyanomethyl)-1H-indol-2-yl)-7-methoxy-1-methyl-1H-benzo[d]imidazole-5-carbonyl)piperidin-3-yl)carbamate (prepared from (R)-tert-butyl (1-(3-methoxy-4-(methylamino)-5-nitrobenzoyl)piperidin-3-yl)carbamate and 2-(2-formyl-1H-indol-1-yl)acetonitrile). | 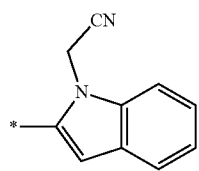 [SMILES: *c1cc2ccccc2n1CC#N] | OMe | Me | LCMS (Method B): Rt = 1.16 min, MH+ = 543.3. |

Intermediate 237: 1,1-Dimethylethyl (1-{[2-(1-ethyl-7-methyl-1H-indol-2-yl)-1-methyl-1H-benzimidazol-5-yl]carbonyl}-3-piperidinyl)carbamate

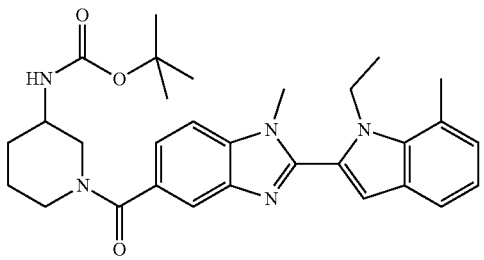 [SMILES: CCn1c(-c2nc3cc(C(=O)N4CCCC(NC(=O)OC(C)(C)C)C4)ccc3n2C)cc2cccc(C)c21]

Prepared in a similar manner to Intermediate 204 from 1,1-dimethylethyl (1-{[4-(methylamino)-3-nitrophenyl]carbonyl}-3-piperidinyl)carbamate and 1-ethyl-7-methyl-1H-indole-2-carbaldehyde VT $^1$H NMR (400 MHz): (DMSO-d6): δH 7.76 (1H, s), 7.65 (1H, d), 7.52 (1H, m), 7.39 (1H, dd), 7.05-7.01 (2H, m), 6.97 (1H, s), 6.28 (1H, bd), 4.66 (2H, q), 4.01 (1H, dd), 3.91 (3H, s), 3.82 (1H, m), 3.46 (1H, m), 3.12 (1H, m), 3.04 (1H, m), 2.78 (3H, s), 1.93 (1H, m), 1.77 (1H, m), 1.53 (2H, m), 1.37 (9H, s), 1.22 (3H, t).

Intermediate 238: 1,1-Dimethylethyl (1-{[2-(1-ethyl-5-methyl-1H-indol-2-yl)-1-methyl-1H-benzimidazol-5-yl]carbonyl}-3-piperidinyl)carbamate

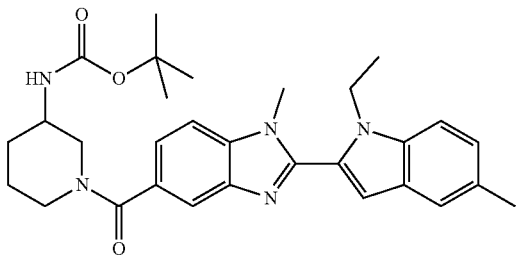 [SMILES: CCn1c(-c2nc3cc(C(=O)N4CCCC(NC(=O)OC(C)(C)C)C4)ccc3n2C)cc2cc(C)ccc21]

Prepared in a similar manner to Intermediate 204 from tert-butyl (1-(4-(methylamino)-3-nitrobenzoyl)piperidin-3-yl)carbamate and 1-ethyl-5-methyl-1H-indole-2-carbaldehyde.

LCMS (Method B): Rt=1.22 min, MH+ 516

Intermediate 239: 1,1-Dimethylethyl (1-{[2-(1-ethyl-4-methyl-1H-indol-2-yl)-1-methyl-1H-benzimidazol-5-yl]carbonyl}-3-piperidinyl)carbamate

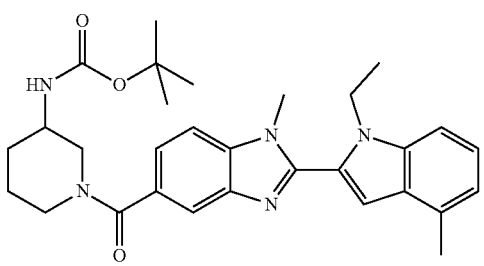 [SMILES: CCn1c(-c2nc3cc(C(=O)N4CCCC(NC(=O)OC(C)(C)C)C4)ccc3n2C)cc2c(C)cccc21]

Prepared in a similar manner to Intermediate 204 from 1,1-dimethylethyl (1-{[4-(methylamino)-3-nitrophenyl]carbonyl}-3-piperidinyl)carbamate and 1-ethyl-4-methyl-1H-indole-2-carbaldehyde LCMS (Method B): Rt=1.21 min, MH+ 516

Intermediate 240: tert-Butyl (1-(2-(1-ethyl-1H-indol-2-yl)-7-methoxy-1-methyl-1H-benzo[d]imidazole-5-carbonyl)pyrrolidin-3-yl)carbamate

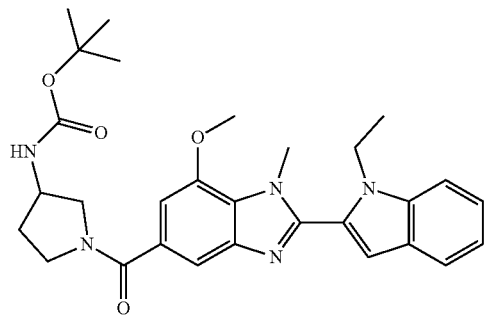 [SMILES: CCn1c(-c2nc3cc(C(=O)N4CCC(NC(=O)OC(C)(C)C)C4)cc(OC)c3n2C)cc2ccccc21]

Prepared in a similar manner to Intermediate 204 from tert-butyl (1-(3-methoxy-4-(methylamino)-5-nitrobenzoyl)pyrrolidin-3-yl)carbamate and 1-ethyl-1H-indole-2-carbaldehyde.

LCMS (Method B): Rt=1.17 min, MH+=518.3.

Intermediate 241: cis (+/−)-tert-Butyl (1-(2-(1-ethyl-1H-indol-2-yl)-1-methyl-1H-benzo[d]imidazole-5-carbonyl)-4-methoxypiperidin-3-yl)carbamate

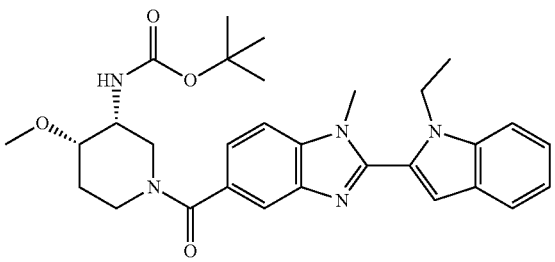 [SMILES: CCn1c(-c2nc3cc(C(=O)N4CC[C@H](OC)[C@H](NC(=O)OC(C)(C)C)C4)ccc3n2C)cc2ccccc21]

To a stirred solution of cis (+/−)-tert-butyl (1-(2-(1-ethyl-1H-indol-2-yl)-1-methyl-1H-benzo[d]imidazole-5-carbonyl)-4-hydroxypiperidin-3-yl)carbamate (53 mg, 0.102 mmol) in anhydrous DMF (0.4 mL) under nitrogen at rt was added 60% NaH in mineral oil (7.17 mg, 0.179 mmol). The mixture was allowed to stir for 10 min when iodomethane (7 μL, 0.112 mmol) was added. The mixture was continued to stir for 2 h. The reaction mixture was diluted with sat. NH$_4$Cl (aq) (1 mL) and EtOAc (1 mL). The organic layer was separated and washed with water (2×1 mL). The organic layer was dried through a hydrophobic frit and the solvent removed under vacuum. The residue was purified by MDAP (Method B). The appropriate fractions were combined and the solvent evaporated under a nitrogen stream to give the title compound as a colourless gum (27 mg, 0.051 mmol, 50%).

LCMS (Method B): Rt: 1.17 min, MH+ 532.

Intermediate 242: (R)-tert-Butyl (1-(2-(1-ethyl-1H-indol-2-yl)-7-hydroxy-1-methyl-1H-benzo[d]imidazole-5-carbonyl)piperidin-3-yl)carbamate

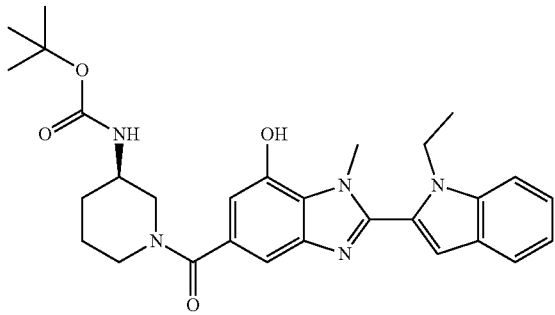 [SMILES: CCn1c(-c2nc3cc(C(=O)N4CCC[C@@H](NC(=O)OC(C)(C)C)C4)cc(O)c3n2C)cc2ccccc21]

To a round-bottomed flask equipped with a stirrer was added (R)-tert-butyl (1-(7-bromo-2-(1-ethyl-1H-indol-2-yl)-1-methyl-1H-benzo[d]imidazole-5-carbonyl)piperidin-3-yl)carbamate (500 mg, 0.861 mmol) followed by di-tert-butyl (2',4',6'-triisopropyl-[1,1'-biphenyl]-2-yl)phosphine (30 mg, 0.071 mmol) followed by tris(dibenzylideneacetone)dipalladium(0) (35 mg, 0.044 mmol) and KOH (29 mg, 2.58 mmol). The mixture was dissolved in 1,4-dioxane (5 mL) and then water was added (5 mL) and the mixture flushed with nitrogen then heated at 100° C. for 16 h. The mixture was concentrated under reduced pressure then partitioned with water (10 mL) and EtOAc (20 mL) then the organic layer isolated. The aqueous layer was re-extracted with EtOAc (2×20 mL) then combined organic layers passed through a hydrophobic frit then concentrated under reduced pressure to give the crude material as an orange gum. The material was purified by silica column chromatography, eluting with an acetone/cyclohexane solvent system (0 to 60%) to give the title compound as a white solid (250 mg, 56% yield).

LCMS (Method B): Rt=1.07 min, MH+=518.4

Intermediate 243: (R)-tert-Butyl (1-(7-cyano-2-(1-ethyl-1H-indol-2-yl)-1-methyl-1H-benzo[d]imidazole-5-carbonyl)piperidin-3-yl)carbamate

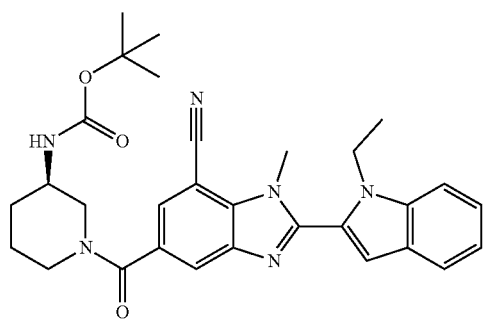 [SMILES: CCn1c(-c2nc3cc(C(=O)N4CCC[C@@H](NC(=O)OC(C)(C)C)C4)cc(C#N)c3n2C)cc2ccccc21]

(R)-tert-Butyl (1-(7-bromo-2-(1-ethyl-1H-indol-2-yl)-1-methyl-1H-benzo[d]imidazole-5-carbonyl)piperidin-3-yl)carbamate (50 mg, 0.086 mmol) was stirred in N,N-dimethylformamide (1 mL) with palladium tetrakis (4.98 mg, 4.31 µmol) and dicyanozinc (10.11 mg, 0.086 mmol) in a Biotage initiator microwave reactor at 150° C. for 4 hrs 15. The reaction mixture was partitioned between water and ethyl acetate. The aqueous layer was further extracted with ethyl acetate (×2). The organics were combined, washed with brine, passed through a hydrophobic cartridge and concentrated under vacuum to give a pale yellow oil. The oil was purified by Biotage SP4 chromatography on a 10 g silica SNAP cartridge, eluting with ethyl acetate in cyclohexane 0 to 50% over 10 column volumes then with 50% ethyl acetate in cyclohexane over 5 column volumes. The relevant fractions were combined and concentrated under vacuum to give the title product as a colourless oil (40 mg, 88%).

LCMS (Method B): Rt=1.24 mins, MH+=527.4

Intermediate 244: (R)-tert-Butyl (1-(2-(1-ethyl-1H-indol-2-yl)-1-methyl-7-(pyridin-3-yl)-1H-benzo[d]imidazole-5-carbonyl)piperidin-3-yl)carbamate

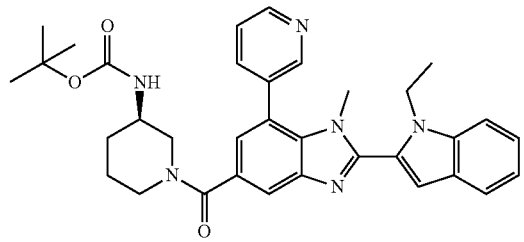 [SMILES: CCn1c(-c2nc3cc(C(=O)N4CCC[C@@H](NC(=O)OC(C)(C)C)C4)cc(-c4cccnc4)c3n2C)cc2ccccc21]

(R)-tert-Butyl (1-(7-bromo-2-(1-ethyl-1H-indol-2-yl)-1-methyl-1H-benzo[d]imidazole-5-carbonyl)piperidin-3-yl)carbamate (50 mg, 0.086 mmol) was stirred in 1,4-dioxane (0.9 mL) and water (0.3 mL) with pyridin-3-ylboronic acid (11.65 mg, 0.095 mmol), palladium tetrakis (9.95 mg, 8.61 µmol) and potassium carbonate (23.81 mg, 0.172 mmol) in a Biotage initiator microwave at 100° C. for 30 min. The reaction mixture was partitioned between water and ethyl acetate. The aqueous layer was further extracted with ethyl acetate (×2), passed through a hydrophobic cartridge and concentrated under reduced pressure. The residue was purified by Biotage SP4 chromatography on a 10 g silicagel SNAP cartridge, eluting with methanol in DCM 0 to 7% over 15 column volumes. The relevant fractions were combined and concentrated under vacuum to give the title product as a colourless oil (45 mg, 90%).

LCMS (Method B): Rt=1.09 mins, MH+=579.5

Intermediate 245: (R)-tert-Butyl (1-(7-carbamoyl-2-(1-ethyl-1H-indol-2-yl)-1-methyl-1H-benzo[d]imidazole-5-carbonyl)piperidin-3-yl)carbamate

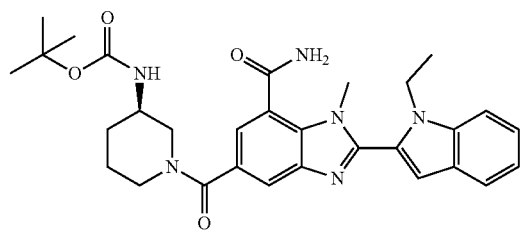 [SMILES: CCn1c(-c2nc3cc(C(=O)N4CCC[C@@H](NC(=O)OC(C)(C)C)C4)cc(C(N)=O)c3n2C)cc2ccccc21]

Hydrogen peroxide (0.067 mL, 0.760 mmol, 35% in water) was added dropwise to a stirred suspension of (R)-tert-butyl (1-(7-cyano-2-(1-ethyl-1H-indol-2-yl)-1-methyl-1H-benzo[d]imidazole-5-carbonyl)piperidin-3-yl)carbamate (40 mg, 0.076 mmol) and potassium carbonate (20.99 mg, 0.152 mmol) in dimethyl sulfoxide (3 mL) cooled down with an ice-water bath under nitrogen. The mixture was allowed to attain rt and was stirred at rt under nitrogen for 1 h. The reaction mixture was partitioned between water and ethyl acetate. The aqueous layer was further extracted with ethyl acetate (×2), passed through a hydrophobic cartridge and concentrated under reduced pressure to give the title product as a pale yellow oil (48 mg).

LCMS (Method B): Rt=1.05 mins, MH$^+$=545.4

Intermediate 246: (R)-tert-Butyl (1-(7-ethyl-2-(1-ethyl-1H-indol-2-yl)-1-methyl-1H-benzo[d]imidazole-5-carbonyl)piperidin-3-yl)carbamate

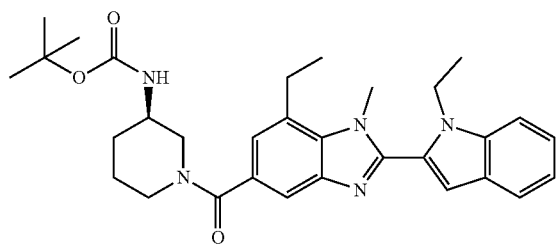 [SMILES: CCc1cc(C(=O)N2CCC[C@@H](NC(=O)OC(C)(C)C)C2)cc2nc(-c3cc4ccccc4n3CC)n(C)c12]

To a mixture of (R)-tert-butyl (1-(7-bromo-2-(1-ethyl-1H-indol-2-yl)-1-methyl-1H-benzo[d]imidazole-5-carbonyl)piperidin-3-yl)carbamate (150 mg, 0.258 mmol), Pd(dppf)Cl$_2$ (5.28 mg, 6.46 μmol) and cesium carbonate (253 mg, 0.775 mmol) under a nitrogen atmosphere was added dry tetrahydrofuran (THF) (4 mL). To the stirred suspension was added triethylborane (1M solution in THF) (0.8 mL, 0.800 mmol) in one portion, and the mixture was refluxed for 2 h. The reaction was cooled to rt and 50% aqueous acetic acid (4 mL) was added. The solution was refluxed for 1 h and left standing at rt overnight. The solution was extracted with diethyl ether (×2). The combined organics were washed with brine, dried using a hydrophobic frit and evaporated in vacuo to give an orange oil (149 mg). The residue was loaded in dichloromethane and purified on a Biotage SP4 silica (Si) SNAP 10 g column using a 0-5% dichloromethane-methanol gradient over 17 CV's. The fractions for the large UV peak were combined and evaporated to give a yellow oil (136 mg).

LCMS (Method B): Rt=1.21 mins, MH$^+$=530.3.

Intermediate 247: (2-(1-Ethyl-1H-indol-2-yl)-1-methyl-1H-benzo[d]imidazol-5-yl)(3-hydroxy-5-methylpiperidin-1-yl)methanone, Diastereomeric Mixture

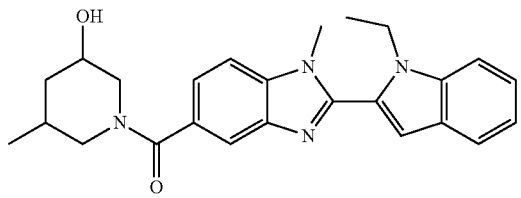 [SMILES: CCn1c(-c2nc3cc(C(=O)N4CC(C)CC(O)C4)ccc3n2C)cc2ccccc21]

To 2-(1-ethyl-1H-indol-2-yl)-1-methyl-1H-benzo[d]imidazole-5-carboxylic acid (200 mg, 0.626 mmol) in N,N-dimethylformamide (DMF) (4 mL) was added HATU (238 mg, 0.626 mmol) and Et$_3$N (0.175 mL, 1.253 mmol), followed by 5-methylpiperidin-3-ol (72.1 mg, 0.626 mmol) and the reaction mixture stirred overnight. The mixture was partitioned between DCM and saturated citric acid solution (×3). The combined organic layers were washed with citric acid (×2) and the solvent removed. The residue was dissolved in DCM and loaded onto silica eluting with 0-100% ethyl acetate in cyclohexane. The appropriate fractions were combined and the solvent removed to give a residue which was dried under high vacuum over the weekend to give a white foam (94 mg, 35%).

LCMS (method B): Rt=0.97 min, MH+=417.2,

Intermediate 248: 1-(2-(1-Ethyl-1H-indol-2-yl)-1-methyl-1H-benzo[d]imidazole-5-carbonyl)-5-methylpiperidin-3-yl methanesulfonate, Diastereomeric Mixture

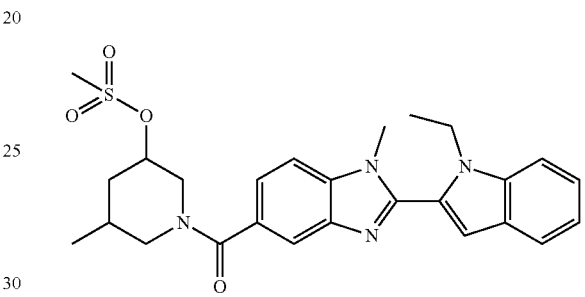

To (2-(1-ethyl-1H-indol-2-yl)-1-methyl-1H-benzo[d]imidazol-5-yl)(3-hydroxy-5-methylpiperidin-1-yl)methanone (92 mg, 0.221 mmol) in dichloromethane (DCM) (10 mL) was added mesyl chloride (0.021 mL, 0.265 mmol) and Et$_3$N (0.037 mL, 0.265 mmol) and the reaction left to stir overnight under nitrogen. Additional Et$_3$N (0.037 mL, 0.265 mmol) and mesyl chloride (0.021 mL, 0.265 mmol) were added and the reaction left for 3 h. The residue was partitioned between DCM and water (×3). The combined organic layers were washed with water and the solvent removed. The residue was dried under high vacuum for 1 h to afford the product (148 mg, 127%) as yellow oily solid which was carried forward crude.

LCMS (Method B): Rt=1.11 min, MH+=495.2,

Intermediate 249: (3-Azido-5-methylpiperidin-1-yl)(2-(1-ethyl-1H-indol-2-yl)-1-methyl-1H-benzo[d]imidazol-5-yl)methanone, Diastereomeric Mixture

To 1-(2-(1-ethyl-1H-indol-2-yl)-1-methyl-1H-benzo[d]imidazole-5-carbonyl)-5-methylpiperidin-3-yl methanesulfonate (109 mg, 0.221 mmol) in N-Methyl-2-pyrrolidone (NMP) (5 mL) was added sodium azide (28.7 mg, 0.442 mmol) and the reaction left to stir overnight at 90° C. under nitrogen. Additional NaN$_3$ (20 mg) was added and the reaction left overnight. The solution was partitioned between ethyl acetate and water (×3) and the combined organic layers washed with water and the solvent removed. The residue was dissolved in DCM and loaded onto silica eluting with 0-50% ethyl acetate in cyclohexane. The appropriate fractions were combined and the solvent was removed to give white needles which were dried under high vacuum for 2 h to give the desired product as a white solid (104 mg, 107%) which was carried forward crude.

LCMS (Method B): Rt=1.19 min, MH+=442.1.

Intermediate 250: (R)-tert-Butyl (1-(2-(1-ethyl-1H-indol-2-yl)-1-methyl-1H-benzo[d]imidazole-5-carbonothioyl)piperidin-3-yl)carbamate

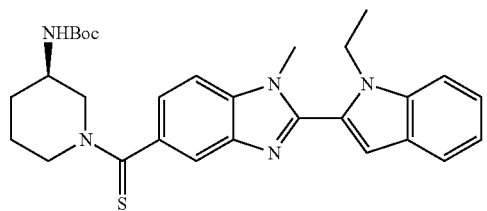 [SMILES: CCn1c(-c2nc3cc(C(=S)N4CCC[C@@H](NC(=O)OC(C)(C)C)C4)ccc3n2C)cc2ccccc21]

To a solution of 1,1-dimethylethyl ((3R)-1-{[2-(1-ethyl-1H-indol-2-yl)--methyl-H-benzimidazol-5-yl]carbonyl}-3-piperidinyl)carbamate (36 mg, 0.072 mmol) was successively added Lawesson's reagent (17.42 mg, 0.043 mmol). The reaction mixture was heated to reflux for 1 h. The reaction mixture was allowed to cool to rt, was concentrated in vacuo and was directly used in the subsequent reaction.

LCMS (Method B): Rt=1.24 min, MH+=518.3.

Intermediates 251 and 252: tert-Butyl ((3S,4R)-1-(2-(1-ethyl-1H-indol-2-yl)-1-methyl-1H-benzo[d]imidazole-5-carbonyl)-4-fluoropiperidin-3-yl)carbamate and tert-Butyl ((3R,4S)-1-(2-(1-ethyl-1H-indol-2-yl)-1-methyl-1H-benzo[d]imidazole-5-carbonyl)-4-fluoropiperidin-3-yl)carbamate Single Unknown Enantiomers

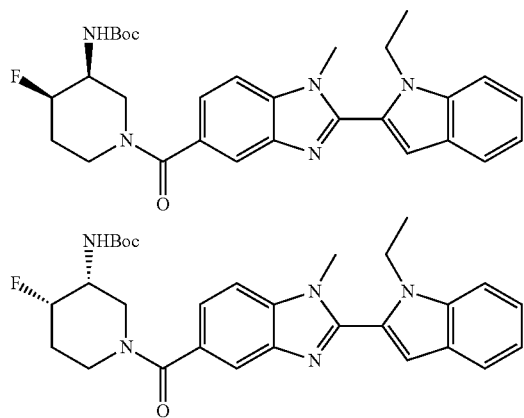

Di-tert-butyl dicarbonate (48.8 mg, 0.223 mmol) was added to a stirred solution of (cis-(+/−)-3-amino-4-fluoropiperidin-1-yl)(2-(1-ethyl-1H-indol-2-yl)-1-methyl-1H-benzo[d]imidazol-5-yl)methanone (85.2 mg, 0.203 mmol) in DCM (5 mL), followed by DIPEA (0.043 mL, 0.244 mmol). The resulting suspension was stirred at rt for 3 h then left standing for 16 h (overnight). The crude product was purified by silica gel chromatography on a Biotage SP4 using a 10 g Si SNAP cartridge and eluting with a 1-100% EtOAc in cyclohexane gradient over 10 CV. The appropriate fractions were combined and the volatiles were removed under reduced pressure to afford the crude racemic product (110 mg). The mixture was sent for chiral separation (Method N). Isomer 1 (45 mg) and isomer 2 (36 mg) were separately isolated Isomer 1: LCMS (Method B): Rt=1.16 min, MH+=520.3.
Isomer 2: LCMS (Method B): Rt=1.17 min, MH+=520.3.

Intermediate 253: (R)-tert-Butyl (1-(2-(1-(cyclopropylmethyl)-6-methoxy-1H-indol-2-yl)-1-methyl-1H-benzo[d]imidazole-5-carbonyl)piperidin-3-yl)carbamate

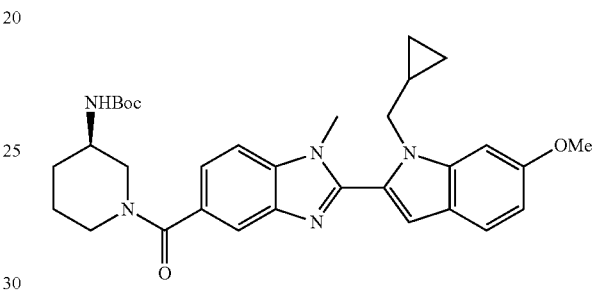

1-(Cyclopropylmethyl)-6-methoxy-1H-indole-2-carboxylic acid (169 mg, 0.517 mmol) was dissolved in DMF (2 mL) and to this solution, HATU (216 mg, 0.568 mmol) and DIPEA (0.271 mL, 1.550 mmol) were added. The reaction was allowed to stir for 30 min at rt, then (R)-tert-butyl (1-(3-amino-4-(methylamino)benzoyl)piperidin-3-yl)carbamate (180 mg, 0.517 mmol) was added. The reaction was left to stir at 45° C. for 5.5 h. The reaction mixture was cooled down and quenched with the addition of water (10 mL), then partitioned with EtOAc (10 mL). The mixture was extracted with EtOAc (3×10 mL) and the organics were combined and washed with NaHCO₃, then brine, dried and concentrated to give (324 mg) of dark blue crude product. The crude product was purified by silica gel chromatography on a Biotage SP4 using a 25 g Si SNAP cartridge and luting with 0-100% EtOAc in cyclohexane gradient over 15 CV. The appropriate fractions were combined and the volatiles were removed under reduced pressure to afford 207 mg of desired intermediate as a pale orange oil. This was dissolved in toluene (10 mL) and acetic acid (0.030 mL, 0.517 mmol) was added and the solution refluxed for 4 h, then left ageing for 16 h, then refluxed for a further 24 h. Another 30 □L of acetic acid was added and mixture refluxed for a further hour. The reaction mixture was allowed to cool down and the volatiles were removed under reduced pressure to afford 180 mg of crude product as a bright orange oil. The crude product was purified by silica gel chromatography on a Biotage SP4 using a 10 g Si SNAP cartridge and eluting with 0-100% EtOAc in cyclohexane gradient over 10 CV. The appropriate fractions were combined and the volatiles were removed under reduced pressure to afford (R)-tert-butyl (1-(2-(1-(cyclopropylmethyl)-6-methoxy-1H-indol-2-yl)-1-methyl-1H-benzo[d]imidazole-5-carbonyl)piperidin-3-yl)carbamate (147 mg, 0.264 mmol, 51.0% yield) as an orange oil.

LCMS (Method B): Rt=1.16 min, MH+=558.4.

Intermediate 254: 1-(Cyclopropylmethyl)-6-methoxy-1H-indole-2-carboxylic Acid

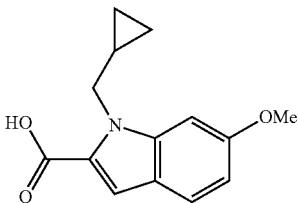 [SMILES: COc1ccc2cc(C(=O)O)n(CC3CC3)c2c1]

Methyl 6-methoxy-1H-indole-2-carboxylate (243 mg, 1.101 mmol) was dissolved in DMF (4 mL), to this solution, sodium hydride (44.0 mg, 1.101 mmol, 60% dispersion in mineral oil) was added. The reaction was stirred for 5 min and then (bromomethyl)cyclopropane (0.107 mL, 1.101 mmol) was added. After 40 min LCMS showed 53% starting material with 28% of the methyl ester of the desired product. The reaction was left to stir over the weekend.

LCMS showed an increase in the methyl ester of the desired product. Further (bromomethyl)cyclopropane (0.5 mL, 5.16 mmol) was added and the reaction was left stirring for a further 40 min. LCMS showed an increase in the methyl ester of the product (39%). The reaction was left stirring for a further 3 h. LCMS showed little change. A further aliquot of sodium hydride was added and the reaction was left to stir for 1 h. A further aliquot of bromomethylcyclopropane was added. Further sodium hydride (44.0 mg, 1.101 mmol) was added and the reaction was left stirring overnight. A further aliquot of bromomethylcyclopropane (0.5 mL, 5.16 mmol) was added to the reaction mixture. The solution was allowed to stir for a further 2.5 h. Further sodium hydride (44.0 mg, 1.101 mmol) was added to the solution and the reaction was allowed to stir at rt overnight. A further aliquot of bromomethylcyclopropane (0.5 mL, 5.16 mmol) was added to the reaction mixture and the solution was left to stir for 1 h. LCMS showed 13% starting material, 33% methyl ester of the desired product and 39% desired product. A further aliquot of bromomethylcyclopropane (0.5 mL, 5.16 mmol) was added to the reaction mixture and the solution was allowed to stir for 4 h. Sodium hydride (44 mg, 1.101 mmol) was added to the reaction and the solution was left to stir for 30 min. LCMS showed 64% conversion to the desired product. NaOH (1 mL, 2 mmol, 2M) was added cautiously to the reaction, and the solution was left to stir for 1.5 h. A further aliquot of NaOH (1 mL, 2 mmol) was added to the reaction and the solution was left to stir for a further 30 min. LCMS showed 78% conversion to the desired product. The aqueous layer was acidified with NH₄Cl (sat) and extracted with 3×EtOAc. The organic layers were combined, passed through a hydrophobic frit and the solvent removed under vacuum to give the crude product (366 mg) a brown solid. This was used crude in the subsequent reaction.

LCMS (Method B): Rt=1.01 min, MH+=246.0.

Intermediate 255: Methyl 6-methoxy-1H-indole-2-carboxylate

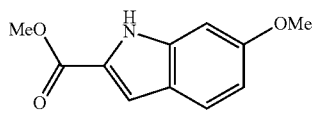

6-Methoxy-1H-indole-2-carboxylic acid acid (1 g, 5.23 mmol, commercially available from, for example, Amfinecom Inc.) was dissolved in methanol (16 mL), to this solution HCl (12.39 M, 1.689 mL, 20.92 mmol) was added. The reaction was stirred at 65° C. under nitrogen for 3 h. The reaction was left stirring at 65° C. under nitrogen overnight, LCMS showed 43% conversion to desired product. The reaction was left stirring at 65° C. under nitrogen for a further 4.5 h. The solution was then allowed to cool and taken to pH14 using NaOH (2 M). The desired product was filtered off to give the desired product (328 mg) a brown solid.

LCMS (Method B): Rt=0.92 min, MH+=442.1.

Intermediate 256: tert-Butyl 1-(2-(1-ethyl-1H-indol-2-yl)-1-methyl-1H-benzo[d]imidazole-5-carboxamido)-3-azabicyclo[4.1.0]heptane-3-carboxylate

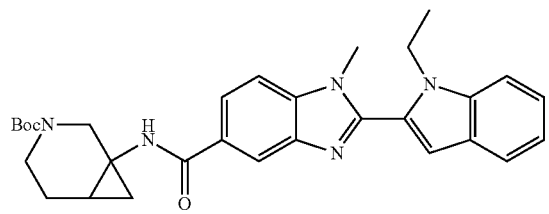 [SMILES: CCn1c(-c2nc3cc(C(=O)NC45CC4CCN(C(=O)OC(C)(C)C)C5)ccc3n2C)cc2ccccc21]

2-(1-Ethyl-1H-indol-2-yl)-1-methyl-1H-benzo[d]imidazole-5-carboxylic acid (149 mg, 0.466 mmol) and HATU (213 mg, 0.560 mmol) were added to a mixture of triethylamine (0.191 mL, 1.399 mmol) and tert-butyl 1-amino-3-azabicyclo[4.1.0]heptane-3-carboxylate (99 mg, 0.466 mmol) in DMF (5 mL). The reaction was then stirred at RT under nitrogen for 4 h. The reaction mixture was partitioned between DCM and water (×3), with the resultant organic layers combined and washed with water (×2). The solvent was then evaporated to leave a brown oil and LCMS showed that there were 2 major components left in the reaction mixture with retention times of 1.22 and 1.26. Separation was partially successful using a 25 g silica column with 0-50% ethyl acetate in cyclohexane. The appropriate fractions containing the product were recombined to give a more pure product. After drying, white solid tert-butyl 1-(2-(1-ethyl-1H-indol-2-yl)-1-methyl-1H-benzo[d]imidazole-5-carboxamido)-3-azabicyclo[4.1.0]heptane-3-carboxylate (144 mg, 0.255 mmol, 54.7%) was yielded which was used without further purification in subsequent chemistry.

LCMS (Method B): Rt=1.22 min, MH+=514.4.

Intermediate 257: tert-Butyl (1-(2-(1-benzyl-1H-indol-2-yl)-1-methyl-1H-benzo[d]imidazole-5-carbonyl)piperidin-3-yl)carbamate

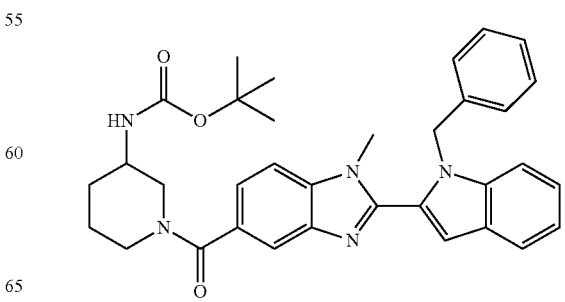

Prepared in a similar manner to Intermediate 145 from 1-methyl-2-[1-(phenylmethyl)-1H-indol-2-yl]-1H-benzimidazole-5-carboxylic acid and tert-butyl piperidin-3-ylcarbamate.

¹H NMR (400 MHz, DMSO-d₆, 393 K) δ ppm 7.76-7.69 (m, 2H) 7.59 (d, J=8.3 Hz, 1H) 7.52 (d, J=8.3 Hz, 1H) 7.36 (dd, J=8.3, 1.3 Hz, 1H) 7.26 (t, J=7.6 Hz, 1H) 7.19-7.08 (m, 5H) 7.00-6.93 (m, 2H) 6.17 (d, J=6.8 Hz, 1H) 5.84 (s, 2H) 3.99 (dd, J=12.7, 3.9 Hz, 1H) 3.87-3.74 (m, 4H) 3.52-3.39 (m, 1H) 3.12 (ddd, J=13.2, 9.9, 3.1 Hz, 1H) 3.04 (dd, J=12.7, 8.9 Hz, 1H) 1.97-1.89 (m, 1H) 1.79-1.71 (m, 1H) 1.59-1.46 (m, 2H) 1.35 (s, 9H).

Intermediate 258: (+/−)-(trans)-Benzyl 4-fluoro-3-hydroxypiperidine-1-carboxylate

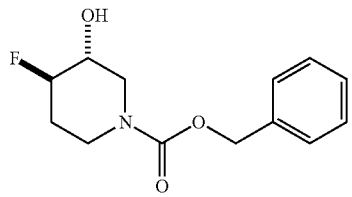 [SMILES: O=C(OCc1ccccc1)N1CC[C@@H](F)[C@H](O)C1]

Triethylamine hydrofluoride (2.502 mL, 15.35 mmol) was delivered from a clamped bottle into a PTFE tube where benzyl 7-oxa-3-azabicyclo[4.1.0]heptane-3-carboxylate (3.58 g, 15.35 mmol) was previously transferred. The resulting mixture was heated at 100° C. After 4 h, the mixture was allowed to cool down. The mixture (a clear pale yellow oil) was re-heated at 100° C. for a further 90 min then allowed to reach rt and left ageing over 14 h. The mixture (a clear pale yellow oil) was quenched by the careful dropwise addition to a stirred saturated aqueous solution of NaHCO₃ (25 mL) then extracted with DCM (50 mL×3). The organics were combined and washed with brine, dried on a hydrophobic frit and concentrated to give 4.35 g of a light orange oil (112%). The crude product was purified by silica gel chromatography (100 g Si SNAP cartridge) on a Biotage SP4, eluting with 0 to 50% EtOAc in cyclohexane gradient over 30 CV. The appropriate fractions were combined and the volatiles were removed under reduced pressure to afford the title compound (2.78 g, 10.98 mmol, 71.5% yield).

LCMS (Method B): Rt=0.85 min, MH+=254

Intermediate 259: (+/−)-(trans)-Benzyl 4-fluoro-3-((methyl sulfonyl)oxy)piperidine-1-carboxylate

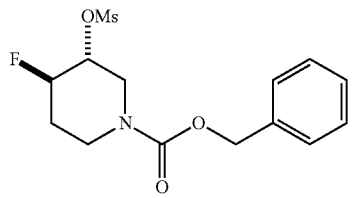

To a stirred solution of (+/−)-(trans)-benzyl 4-fluoro-3-hydroxypiperidine-1-carboxylate (2.78 g, 10.98 mmol) and triethylamine (3.82 mL, 27.4 mmol) in dry DCM (40 mL), cooled down using an ice bath, was added dropwise a solution of methanesulfonic anhydride (3.82 g, 21.95 mmol) in dry DCM (20 mL) under nitrogen (a small exotherm 3-4° C. noticed). At the end of the addition, the mixture was allowed to reach rt and stirred for 1 h. The reaction mixture was treated with a saturated solution of NaHCO₃ (aq) (50 mL) and brine (50 mL). The organic layer was dried through a hydrophobic frit and concentrated in vacuo to give the title compound as a dark orange oil. (4.51 g, 124%)

LCMS (Method B): Rt=0.97 min, MH+=332

Intermediate 260: (+/−)-(cis)-Benzyl 3-azido-4-fluoropiperidine-1-carboxylate

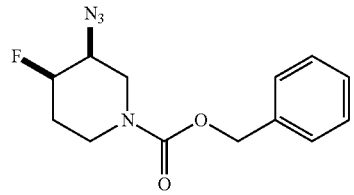 [SMILES: [N-]=[N+]=N[C@H]1CN(C(=O)OCc2ccccc2)CC[C@H]1F]

To a stirred solution of (+/−)-(cis)-benzyl 4-fluoro-3-((methyl sulfonyl)oxy)piperidine-1-carboxylate (2.9 g, 8.75 mmol) in dry DMF (11 mL), was added sodium azide (2.086 g, 32.1 mmol) under nitrogen. The resulting mixture was heated at 90° C. then left ageing over the weekend (57 hours). LCMS shows starting material. The resulting mixture was heated at 120° C. for 20 h. The mixture was allowed to cool down, quenched with the addition of water (30 mL) and extracted with EtOAc (3×60 mL). The organics were combined and washed with brine (3×60 mL), dried on Na₂SO₄ and the volatiles were removed under reduced pressure to afford 1.9 g of crude product. The crude product was purified by silica gel chromatography (100 g Si SNAP cartridge) on a Biotage SP4, eluting with 0-50% EtOAc in cyclohexane gradient over 20 CV. The appropriate fractions were combined and the volatiles were removed under reduced pressure to afford, after an overnight on the high vacuum line, the title compound (888 mg, 3.19 mmol, 36.5% yield) as a pale yellow oil.

LCMS (Method B): Rt=1.07 min, MH+=279

Intermediate 261: (+/−)-(cis)-Benzyl 3-amino-4-fluoropiperidine-1-carboxylate

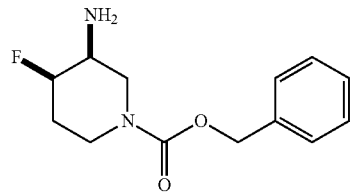 [SMILES: N[C@H]1CN(C(=O)OCc2ccccc2)CC[C@H]1F]

To a stirred solution of (+/−)-(cis)-benzyl 3-azido-4-fluoropiperidine-1-carboxylate (888 mg, 3.19 mmol) in tetrahydrofuran (THF) (25 mL) and water (0.625 mL), was added triphenylphosphine (1256 mg, 4.79 mmol) under nitrogen. The resulting mixture was heated at 35° C. for 2 h, then at 50° C. for a further 2 h, then left ageing at rt for 16 h. The mixture was loaded on a 10 g preequilibrated SCX cartridge, eluted with MeOH (3CV) followed by 2M NH₃ in MeOH (3CV). The basic fractions were combined and the volatiles were removed under reduced pressure to afford a crude mixture with the desired product and triphenylphosphine oxide. The mixture was diluted with a solution of 10% KH$_2$PO$_4$ and the pH measured, more solid KH$_2$PO$_4$ was added in order to reach pH=4 (up to the solubility limit). As the solution pH stayed at 5, the solution was neutralised again with solid NaHCO$_3$, (effervescence!) and 10% citric acid in water was used to attempt to acidify to pH=4. No success and the pH stayed at pH=5. The resulting solution was extracted with EtOAc, analyticals shows no separation between desired product and triphenylphosphine oxide. At the second extraction, methanol instead of EtOAc was used by mistake. The aqueous+methanol solution was reduced in vacuo, and combined with the organics layer, then reduced in vacuo. The resulting mixture was acidified using 1.0M HCl to pH=2 and extracted with EtOAc (×3), then neutralised with powdered NaHCO$_3$, (care effervescence!). The neutralised aqueous was extracted with EtOAc (×3), the organics combined, washed with brine, dried on Na$_2$SO$_4$ and the volatiles were removed under reduced pressure to afford the title compound (523 mg, 2.074 mmol, 65.0% yield) as an off white solid.

LCMS (Method B): Rt=0.53 min, MH+=253.1

Intermediate 262: (+/−)-(cis)-Benzyl 3-((tert-butoxycarbonyl)amino)-4-fluoropiperidine-1-carboxylate

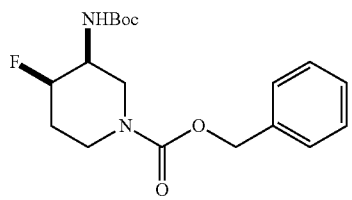 [SMILES: CC(C)(C)OC(=O)N[C@H]1CN(C(=O)OCc2ccccc2)CC[C@H]1F]

To a stirred solution of (+/−)-(cis)-benzyl 3-amino-4-fluoropiperidine-1-carboxylate (523 mg, 2.074 mmol) in chloroform (6 mL) and triethylamine (0.347 mL, 2.489 mmol), was added di-tert-butyl dicarbonate (498 mg, 2.282 mmol). The resulting mixture was stirred for 3 hours. The mixture was then diluted with the addition of DCM and extracted with NaHCO$_3$ (3×60 mL), dried on a hydrophobic frit and the volatiles were removed under reduced pressure to afford 0.87 g of crude product. The crude product was purified by silica gel chromatography (25 g SNAP Si cartridge) using a Biotage SP4 and eluting with 0-50% EtOAc in cyclohexane gradient over 10 CV. The appropriate fractions were combined and the volatiles were removed under reduced pressure to afford, after 2 h on the high vacuum line, the title compound (700 mg, 1.986 mmol, 96%) as a colourless oil.

LCMS (Method B): Rt=1.14 min, MH+=353

Intermediate 263: (+/−)-tert-Butyl ((cis)-4-fluoropiperidin-3-yl)carbamate

(+/−)-(cis)-Benzyl 3-((tert-butoxycarbonyl)amino)-4-fluoropiperidine-1-carboxylate (700 mg, 1.986 mmol) in methanol (40 mL) was hydrogenated using a flow apparatus (H-cube, settings, flow 1 mL/min, full hydrogen, 1 atm. pressure, ambient temperature). TLC and NMR of the sample after 10 min showed full conversion. The volatiles were removed under reduced pressure to afford the title compound (457 mg, 2.094 mmol, 105% yield) as a white powder.

$^1$H NMR (400 MHz, 393 K, DMSO-d$_6$) ☐ ppm 5.90 (br. s., 1H) 4.76 (ddt, J=50.1, 6.0, 2.9, 2.9 Hz, 1H) 3.54-3.68 (m, 1H) 2.58-2.79 (m, 4H) 1.60-1.89 (m, 2H) 1.42 (s, 9H)

Example 1a: (3R)-1-{[2-(1-Ethyl-1H-indol-2-yl)-1-methyl-1H-benzimidazol-5-yl]carbonyl})-3-piperidinamine

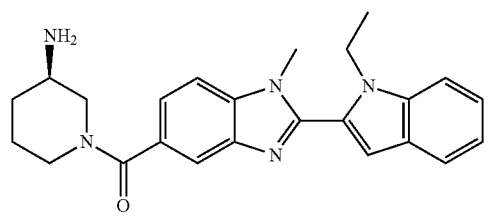 [SMILES: CCn1c(-c2nc3cc(C(=O)N4CCC[C@@H](N)C4)ccc3n2C)cc2ccccc21]

To a solution of (R)-tert-butyl (1-(2-(1-ethyl-1H-indol-2-yl)-1-methyl-1H-benzo[d]imidazole-5-carbonyl)piperidin-3-yl)carbamate (874 mg, 1.742 mmol) in dichloromethane (DCM) (7 mL) was added TFA (1.879 mL, 24.39 mmol) and the reaction stirred at rt for 2 h. The reaction mixture was concentrated in vacuo to afford a yellow oil.

This was dissolved in methanol and loaded onto an SCX cartridge (10 g). It was eluted with methanol (3 column volumes) and the product eluted as free base with 2M ammonia in methanol. The filtrate from the ammonia fractions was concentrated in vacuo to yield a yellow solid—(R)-(3-aminopiperidin-1-yl)(2-(1-ethyl-1H-indol-2-yl)-1-methyl-1H-benzo[d]imidazol-5-yl)methanone (652 mg, 1.624 mmol, 93% yield) LCMS (Formic): Rt=0.79 mins, MH+=402.2

$^1$H NMR (400 MHz, DMSO-d$_6$) ☐ ppm: 7.78-7.69 (m, 3H), 7.63 (d, 1H), 7.36 (d, 1H), 7.31 (dd, 1H), 7.15 (dd, 1H), 7.09 (m, 1H), 4.61 (q, 2H), 4.35-4.01 (m, 1H), 3.98 (s, 3H), 3.75-3.35 (m, 1H), 3.02-2.87 (m, 1H), 2.79-2.58 (m, 2H), 1.93-1.83 (m, 1H), 1.79-1.54 (m, 2H), 1.53-1.42 (m, 1H), 1.28 (t, 3H).

Example 1b: (3R)-1-{[2-(1-Ethyl-1H-indol-2-yl)-1-methyl-1H-benzimidazol-5-yl]carbonyl})-3-piperidinamine, Hydrochloride Salt

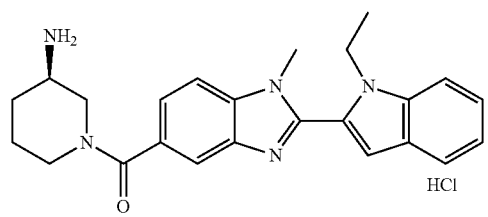 [SMILES: CCn1c(-c2nc3cc(C(=O)N4CCC[C@@H](N)C4)ccc3n2C)cc2ccccc21 ; Cl]

To a solution of (R)-(3-aminopiperidin-1-yl)(2-(1-ethyl-1H-indol-2-yl)-1-methyl-1H-benzo[d]imidazol-5-yl)methanone (214 mg, 0.533 mmol) in dichloromethane (DCM) (5 mL) in a 20 mL vial was added HCl (1.0M in Et$_2$O) (0.533 mL, 0.533 mmol) and the reaction stirred at rt for 15 min. An initial precipitate appeared on addition of the HCl, but this disappeared upon agitation. The solvent was removed under a positive pressure of nitrogen and the sample dried in vacuo to afford the product as a pale yellow solid—(R)-(3-aminopiperidin-1-yl)(2-(1-ethyl-1H-indol-2-yl)-1-methyl-1H-benzo[d]imidazol-5-yl)methanone, Hydrochloride (231 mg, 0.527 mmol, 99% yield) LCMS (Formic): Rt=0.78 mins, MH$^+$=402.2

$^1$H NMR (400 MHz, DMSO-d$_6$) □ ppm: 8.28 (br. s, 3H), 7.88 (s, 1H), 7.84 (d, 1H), 7.73 (d, 1H), 7.66 (d, 1H), 7.49 (d, 1H), 7.34 (dd, 1H), 7.20 (s, 1H), 7.20-7.15 (m, 1H), 4.58 (q, 2H), 4.32-4.05 (m, 1H), 4.02 (s, 3H), 3.75-3.35 (m, 1H), 3.35-3.03 (m, 3H), 2.12-2.01 (m, 1H), 1.84-1.73 (m, 1H), 1.73-1.61 (m, 1H), 1.61-1.47 (m, 1H), 1.27 (t, 3H).

Other Examples indicated in following table were prepared similarly to Example 1a. In some cases further purification by Mass Directed Autoprep was required using standard procedures.

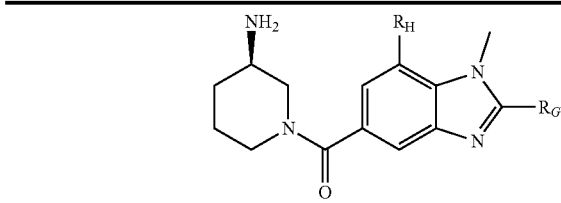

| Example | R$_G$ | R$_H$ | LCMS |
|---|---|---|---|
| 2: (3R)-1-({2-[1-ethyl-7-(methyloxy)-1H-indol-2-yl]-1-methyl-1H-benzimidazol-5-yl}carbonyl)-3-piperidinamine (prepared from (R)-tert-butyl (1-(2-(1-ethyl-7-methoxy-1H-indol-2-yl)-1-methyl-1H-benzo[d]imidazole-5-carbonyl)piperidin-3-yl)carbamate). | | H | LCMS (Method A) Rt = 1.00 min, MH+ = 432.2 |
| 3: (3R)-1-{[2-(3,4-dihydro-2H-[1,4]oxazepino[2,3,4-hi]indol-6-yl)-1-methyl-1H-benzimidazol-5-yl]carbonyl}-3-piperidinamine (prepared from (R)-tert-butyl (1-(2-(3,4-dihydro-2H-[1,4]oxazepino[2,3,4-hi]indol-6-yl)-1-methyl-1H-benzo[d]imidazole-5-carbonyl)piperidin-3-yl)carbamate). | | H | LCMS (Method A): Rt = 0.91 min, MH+ = 430.2 |
| 4: (3R)-1-{[2-(2,3-dihydro[1,4]oxazino[2,3,4-hi]indol-5-yl)-1-methyl-1H-benzimidazol-5-yl]carbonyl}-3-piperidinamine (prepared from 1,1-dimethylethyl ((3R)-1-{[2-(2,3-dihydro[1,4]oxazino[2,3,4-hi]indol-5-yl)-1-methyl-1H-benzimidazol-5-yl]carbonyl}-3-piperidinyl)carbamate). | | H | LCMS (Method B): MH+ = 416.3, Rt = 0.74 min |
| 5: (3R)-1-{[1-methyl-2-(3-methyl-2,3-dihydro[1,4]oxazino[2,3,4-hi]indol-5-yl)-1H-benzimidazol-5-yl]carbonyl}-3-piperidinamine (prepared from tert-butyl ((3R)-1-(1-methyl-2-(3-methyl-2,3-dihydro-[1,4]oxazino[2,3,4-hi]indol-5-yl)-1H-benzo[d]imidazole-5-carbonyl)piperidin-3-yl(carbamate). | | H | LCMS (Method B): Rt = 0.77 min, MH+ = 430.1 |

-continued

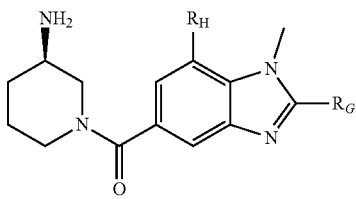

| Example | $R_G$ | $R_H$ | LCMS |
|---|---|---|---|
| 6a: (3R)-1-{[2-(1-ethyl-1H-indol-2-yl)-1-methyl-7-(methyloxy)-1H-benzimidazol-5-yl]carbonyl}-3-piperidinamine (prepared from (R)-tert-butyl (1-(2-(1-ethyl-1H-indol-2-yl)-7-methoxy-1-methyl-1H-benzo[d]imidazole-5-carbonyl)piperidin-3-yl)carbamate). | 1-ethyl-1H-indol-2-yl | OMe | LCMS (Method A): Rt = 1.07 min, MH+ = 432.1 |
| 7: (3R)-1-({2-[1-(Cyclopropylmethyl)-5-(methyloxy)-1H-indol-2-yl]-1-methyl-1H-benzimidazol-5-yl}carbonyl)-3-piperidinamine (prepared from (R)-tert-butyl (1-(2-(1-(cyclopropylmethyl)-5-methoxy-1H-indol-2-yl)-1-methyl-1H-benzo[d]imidazole-5-carbonyl)piperidin-3-yl)carbamate). | 1-(cyclopropylmethyl)-5-methoxy-1H-indol-2-yl | H | LCMS (Method B): Rt = 0.83 min, MH+ = 458.3 |
| 8: (3R)-1-({2-[1-Ethyl-6-(methyloxy)-1H-indol-2-yl]-1-methyl-1H-benzimidazol-5-yl}carbonyl)-3-piperidinamine (prepared from (R)-tert-butyl (1-(2-(1-ethyl-6-methoxy-1H-indol-2-yl)-1-methyl-1H-benzo[d]imidazole-5-carbonyl)piperidin-3-yl)carbamate). | 1-ethyl-6-methoxy-1H-indol-2-yl | H | LCMS (Method A): Rt = 0.95 min, MH+ = 432.2 |
| 9: [2-(5-{[(3R)-3-Amino-1-piperidinyl]carbonyl}-1-methyl-1H-benzimidazol-2-yl)-1H-indol-1-yl]acetonitrile (prepared from (R)-tert-butyl (1-(2-(1-(cyanomethyl)-1H-indol-2-yl)-1-methyl-1H-benzo[d]imidazole-5-carbonyl)piperidin-3-yl)carbamate). | 1-(cyanomethyl)-1H-indol-2-yl | H | LCMS (Method A): Rt = 0.90 min, MH+ = 413.2 |
| 10: (3R)-1-{[2-(1-Ethyl-6-fluoro-1H-indol-2-yl)-1-methyl-1H-benzimidazol-5-yl]carbonyl}-3-piperidinamine (prepared from (R)-tert-butyl1-(2-(1-ethyl-6-fluoro-1H-indol-2-yl)-1-methyl-1H-benzo[d]imidazole-5-carbonyl)piperidin-3-yl)carbamate). | 1-ethyl-6-fluoro-1H-indol-2-yl | H | LCMS (Method A): Rt = 0.99 min, MH+ = 420.2 |

-continued

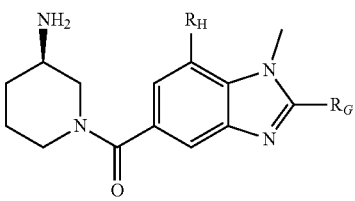

| Example | $R_G$ | $R_H$ | LCMS |
|---|---|---|---|
| 11a: (3R)-1-({1-Methyl-2-[1-(2,2,2-trifluoroethyl)-1H-indol-2-yl]-1H-benzimidazol-5-yl}carbonyl)-3-piperidinamine (prepared from 1,1-dimethylethyl [(3R)-1-({1-methyl-2-[1-(2,2,2-trifluoroethyl)-1H-indol-2-yl]-1H-benzimidazol-5-yl}carbonyl)-3-piperidinyl]carbamate). | *-CH2-N(indole)-CF3 | H | LCMS (Method B): Rt = 0.85 min, MH+ = 456.4 |
| 12: (3R)-1-({1-Methyl-2-[1-(1-methylethyl)-1H-indol-2-yl]-1H-benzimidazol-5-yl}carbonyl)-3-piperidinamine (prepared from 1,1-dimethylethyl [(3R)-1-({1-methyl-2-[1-(1-methylethyl)-1H-indol-2-yl]-1H-benzimidazol-5-yl}carbonyl)-3-piperidinyl]carbamate). | *-(N-isopropyl indole) | H | LCMS (Method B): Rt = 0.82 min, MH+ = 416.4 |
| 13: 2-(5-{[(3R)-3-Amino-1-piperidinyl]carbonyl}-1-methyl-1H-benzimidazol-2-yl)-1-ethyl-1H-indole-6-carbonitrile (prepared from (R)-tert-butyl (1-(2-(6-cyano-1-ethyl-1H-indol-2-yl)-1-methyl-1H-benzo[d]imidazole-5-carbonyl)piperidin-3-yl)carbamate). | *-(1-ethyl-6-cyano indol-2-yl) | H | LCMS (Method A): Rt = 0.91 min, MH+ = 427.2 |
| 14: (3R)-1-[(2-{1-[(3-Chlorophenyl)methyl]-1H-indol-2-yl}-1-methyl-1H-benzimidazol-5-yl)carbonyl]-3-piperidinamine (prepared from 1,1-dimethylethyl {(3R)-1-[(2-{1-[(3-chlorophenyl)methyl]-1H-indol-2-yl}-1-methyl-1H-benzimidazol-5-yl)carbonyl]-3-piperidinyl}carbamate). | *-(1-(3-chlorobenzyl)indol-2-yl) | H | LCMS (Method B): Rt = 0.94 min, MH+ = 498.4 |
| 15: (3R)-1-({1-Methyl-2-[1-(3-pyridinylmethyl)-1H-indol-2-yl]-1H-benzimidazol-5-yl}carbonyl)-3-piperidinamine (prepared from 1,1-dimethylethyl [(3R)-1-({1-methyl-2-[1-(3-pyridinylmethyl)-1H-indol-2-yl]-1H-benzimidazol-5-yl}carbonyl)-3-piperidinyl]carbamate). | *-(1-(3-pyridinylmethyl)indol-2-yl) | H | LCMS (Method A): Rt = 0.90 min, MH+ = 465.2 |

-continued

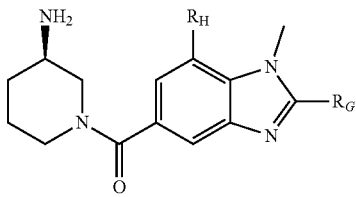

| Example | R_G | R_H | LCMS |
|---|---|---|---|
| 16: (3R)-1-({2-[1-(Cyclopropylmethyl)-1H-indol-2-yl]-1-methyl-1H-benzimidazol-5-yl}carbonyl)-3-piperidinamine (prepared from 1,1-dimethylethyl [(3R)-1-({2-[1-(cyclopropylmethyl)-1H-indol-2-yl]-1-methyl-1H-benzimidazol-5-yl}carbonyl)-3-piperidinyl]carbamate). | 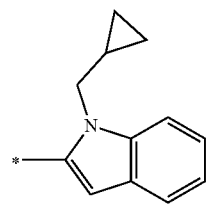 | H | LCMS (Method B): Rt = 0.83 min, MH+ = 428.2 |
| 17: (3R)-1-[(1-Methyl-2-{1-[(4-methylphenyl)methyl]-1H-indol-2-yl}-1H-benzimidazol-5-yl)carbonyl]-3-piperidinamine (prepared from 1,1-dimethylethyl {(3R)-1-[(1-methyl-2-{1-[(4-methylphenyl)methyl]-1H-indol-2-yl}-1H-benzimidazol-5-yl)carbonyl]-3-piperidinyl}carbamate). | 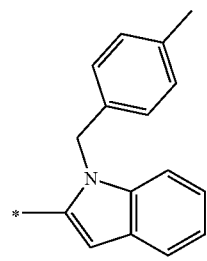 | H | LCMS (Method B): Rt = 0.94 min, MH+ = 478.4 |
| 18: (3R)-1-{[2-(1H-Indol-2-yl)-1-methyl-1H-benzimidazol-5-yl]carbonyl}-3-piperidinamine (prepared from (R)-tert-butyl (1-(2-(1H-indol-2-yl)-1-methyl-1H-benzo[d]imidazole-5-carbonyl)piperidin-3-yl)carbamate). | 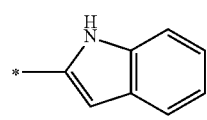 | H | LCMS (Method A): Rt = 0.89 min, MH+ = 374.2 |
| 19: (3R)-1-({1-Methyl-2-[1-(2-methylpropyl)-1H-indol-2-yl]-1H-benzimidazol-5-yl}carbonyl)-3-piperidinamine (prepared from (R)-tert-butyl (1-(2-(1-isobutyl-1H-indol-2-yl)-1-methyl-1H-benzo[d]imidazole-5-carbonyl)piperidin-3-yl)carbamate). | 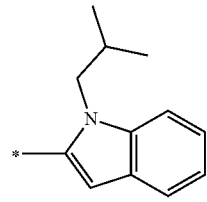 | H | LCMS (Method A): Rt = 1.08 min, MH+ = 430.4 |
| 20a: (3R)-1-[(1-methyl-2-{1-[(1-methyl-1H-pyrazol-4-yl)methyl]-1H-indol-2-yl}-1H-benzimidazol-5-yl)carbonyl]-3-piperidinamine (prepared from (R)-tert-butyl (1-(1-methyl-2-(1-((1-methyl-1H-pyrazol-4-yl)methyl)-1H-indol-2-yl)-1H-benzo[d]imidazole-5-carbonyl)piperidin-3-yl)carbamate). | 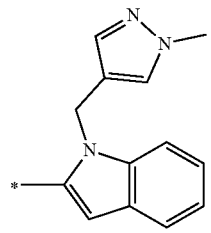 | H | LCMS (Method A): Rt = 0.86 min, MH+ = 468.2 |

-continued

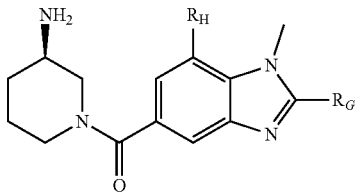

| Example | $R_G$ | $R_H$ | LCMS |
|---|---|---|---|
| 21: (3R)-1-{[2-(5-Chloro-1-ethyl-1H-indol-2-yl)-1-methyl-1H-benzimidazol-5-yl]carbonyl}-3-piperidinamine (prepared from (R)-tert-butyl (1-(2-(5-chloro-1-ethyl-1H-indol-2-yl)-1-methyl-1H-benzo[d]imidazole-5-carbonyl)piperidin-3-yl)carbamate). | 5-chloro-1-ethylindol-2-yl | H | LCMS (Method A): Rt = 1.07 min, MH+ = 436.2 |
| 22: (3R)-1-[(1-methyl-2-{1-[2-(methyloxy)ethyl]-1H-indol-2-yl}-1H-benzimidazol-5-yl)carbonyl]-3-piperidinamine (prepared from 1,1-dimethylethyl {(3R)-1-[(1-methyl-2-{1-[2-(methyloxy)ethyl]-1H-indol-2-yl}-1H-benzimidazol-5-yl)carbonyl]-3-piperidinyl}carbamate). | 1-(2-methoxyethyl)indol-2-yl | H | LCMS (Method A): Rt = 0.94 min, MH+ = 432.1 |
| 23: (3R)-1-{[2-(6-Bromo-1-ethyl-1H-indol-2-yl)-1-methyl-1H-benzimidazol-5-yl]carbonyl}-3-piperidinamine (prepared from (R)-tert-butyl (1-(2-(6-bromo-1-ethyl-1H-indol-2-yl)-1-methyl-1H-benzo[d]imidazole-5-carbonyl)piperidin-3-yl)carbamate). | 6-bromo-1-ethylindol-2-yl | H | LCMS (Method A): Rt = 1.10 min, MH+ = 482.2 |
| 24: (3R)-1-({1-Methyl-2-[1-(phenylmethyl)-1H-indol-2-yl]-1H-benzimidazol-5-yl}carbonyl)-3-piperidinamine (prepared from 1,1-dimethylethyl [(3R)-1-({1-methyl-2-[1-(phenylmethyl)-1H-indol-2-yl]-1H-benzimidazol-5-yl}carbonyl)-3-piperidinyl]carbamate). | 1-benzylindol-2-yl | H | LCMS (Method B): Rt = 0.92 min, MH+ = 464.3 |
| 25: (3R)-1-[(2-{1-[(4-Iodophenyl)methyl]-1H-indol-2-yl}-1-methyl-1H-benzimidazol-5-yl)carbonyl]-3-piperidinamine (prepared from (R)-tert-butyl (1-(2-(1-(4-iodobenzyl)-1H-indol-2-yl)-1-methyl-1H-benzo[d]imidazole-5-carbonyl)piperidin-3-yl)carbamate). | 1-(4-iodobenzyl)indol-2-yl | H | LCMS (Method B): Rt = 1.00 min, MH+ = 590.3 |

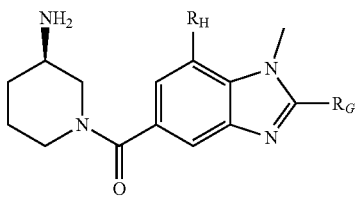

| Example | $R_G$ | $R_H$ | LCMS |
|---|---|---|---|
| 26: (3R)-1-{[2-(1-Ethyl-6-methyl-1H-indol-2-yl)-1-methyl-1H-benzimidazol-5-yl]carbonyl}-3-piperidinamine (prepared from (R)-tert-butyl (1-(2-(1-ethyl-6-methyl-1H-indol-2-yl)-1-methyl-1H-benzo[d]imidazole-5-carbonyl)piperidin-3-yl)carbamate). | 1-ethyl-6-methyl-1H-indol-2-yl | H | LCMS (Method B): Rt = 0.84 min, MH+ = 416.1 |
| 27: (3R)-1-({1-Methyl-2-[1-(2-pyridinylmethyl)-1H-indol-2-yl]-1H-benzimidazol-5-yl}carbonyl)-3-piperidinamine (prepared from 1,1-dimethylethyl [(3R)-1-({1-methyl-2-[1-(2-pyridinylmethyl)-1H-indol-2-yl]-1H-benzimidazol-5-yl}carbonyl)-3-piperidinyl]carbamate). | 1-(2-pyridinylmethyl)-1H-indol-2-yl | H | LCMS (Method B): Rt = 0.72 min, MH+ = 465.2 |
| 28: (3R)-1-({1-Methyl-2-[1-(4-pyridinylmethyl)-1H-indol-2-yl]-1H-benzimidazol-5-yl}carbonyl)-3-piperidinamine (prepared from 1,1-dimethylethyl [(3R)-1-({1-methyl-2-[1-(4-pyridinylmethyl)-1H-indol-2-yl]-1H-benzimidazol-5-yl}carbonyl)-3-piperidinyl]carbamate). | 1-(4-pyridinylmethyl)-1H-indol-2-yl | H | LCMS (Method B): Rt = 0.61 min, MH+ = 465.2 |
| 29: 2-[2-(5-{[(3R)-3-Amino-1-piperidinyl]carbonyl}-1-methyl-1H-benzimidazol-2-yl)-1H-indol-1-yl]ethanol (prepared from 1,1-dimethylethyl [(3R)-1-({2-[1-(2-hydroxyethyl)-1H-indol-2-yl]-1-methyl-1H-benzimidazol-5-yl}carbonyl)-3-piperidinyl]carbamate). | 1-(2-hydroxyethyl)-1H-indol-2-yl | H | LCMS (Method B): Rt = 0.67 min, MH+ = 418.2 |
| 30: (3R)-1-[(2-{1-[(4-Chlorophenyl)methyl]-1H-indol-2-yl}-1-methyl-1H-benzimidazol-5-yl)carbonyl]-3-piperidinamine (prepared from 1,1-dimethylethyl {(3R)-1-[(2-{1-[(4-chlorophenyl)methyl]-1H-indol-2-yl}-1-methyl-1H-benzimidazol-5-yl)carbonyl]-3-piperidinyl}carbamate). | 1-[(4-chlorophenyl)methyl]-1H-indol-2-yl | H | LCMS (Method B): Rt = 0.96 min, MH+ = 498.4 |

-continued

| Example | $R_G$ | $R_H$ | LCMS |
|---|---|---|---|
| 31: (R)-(3-aminopiperidin-1-yl)(2-(1-ethyl-6,7-dimethoxy-1H-indol-2-yl)-1-methyl-1H-benzo[d]imidazol-5-yl)methanone (prepared from (R)-tert-butyl (1-(2-(1-ethyl-6,7-dimethoxy-1H-indol-2-yl)-1-methyl-1H-benzo[d]imidazole-5-carbonyl)piperidin-3-yl)carbamate). | 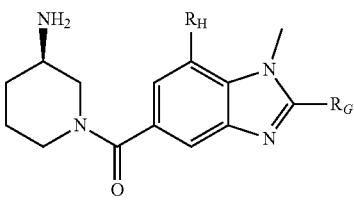 | H | LCMS (Method A): Rt = 0.97 min, MH+ = 462.29 |
| 32: (R)-(3-Aminopiperidin-1-yl)(2-(6-ethoxy-1-ethyl-1H-indol-2-yl)-1-methyl-1H-benzo[d]imidazol-5-yl)methanone (prepared from (R)-tert-butyl (1-(2-(6-ethoxy-1-ethyl-1H-indol-2-yl)-1-methyl-1H-benzo[d]imidazole-5-carbonyl)piperidin-3-yl)carbamate). | 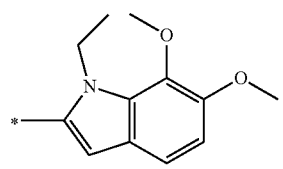 | H | LCMS (Method B): Rt = 0.83 min, MH+ = 446.25 |
| 33a: ((R)-3-Aminopiperidin-1-yl)(2-(1-((R)-3-hydroxy-2-methylpropyl)-1H-indol-2-yl)-7-methoxy-1-methyl-1H-benzo[d]imidazol-5-yl)methanone (prepared from tert-butyl ((R)-1-(2-(1-((R)-3-hydroxy-2-methylpropyl)-1H-indol-2-yl)-7-methoxy-1-methyl-1H-benzo[d]imidazole-5-carbonyl)piperidin-3-yl)carbamate). | 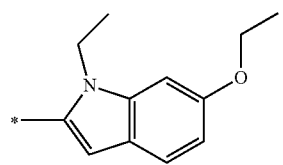 | OMe | LCMS (Method B) Rt 0.79 min, MH+ = 476.3. |
| 34: (R)-(3-Aminopiperidin-1-yl)(2-(1-ethyl-1H-indol-2-yl)-1-methyl-7-(trifluoromethoxy)-1H-benzo[d]imidazol-5-yl)methanone (prepared from (R)-tert-butyl (1-(2-(1-ethyl-1H-indol-2-yl)-1-methyl-7-(trifluoromethoxy)-1H-benzo[d]imidazole-5-carbonyl)piperidin-3-yl)carbamate). | 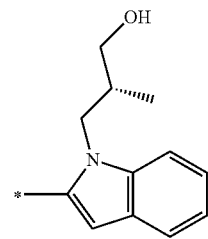 | $OCF_3$ | LCMS (Method A): Rt = 1.17 min, MH$^+$ = 486.3 |
| 35: (R)-5-(3-Aminopiperidine-1-carbonyl)-2-(1-ethyl-1H-indol-2-yl)-1-methyl-1H-benzo[d]imidazole-7-carbonitrile, hydrochloride salt (prepared from (R)-tert-butyl (1-(7-cyano-2-(1-ethyl-1H-indol-2-yl)-1-methyl-1H-benzo[d]imidazole-5-carbonyl)piperidin-3-yl)carbamate). | 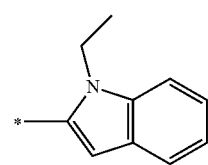 | CN | LCMS (Method B): Rt = 0.84 mins, MH$^+$ = 427.2 |

-continued

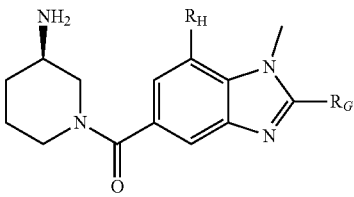

| Example | $R_G$ | $R_H$ | LCMS |
|---|---|---|---|
| 36: (R)-(3-Aminopiperidin-1-yl)(7-bromo-2-(1-ethyl-1H-indol-2-yl)-1-methyl-1H-benzo[d]imidazol-5-yl)methanone (prepared from (R)-tert-butyl (1-(7-bromo-2-(1-ethyl-1H-indol-2-yl)-1-methyl-1H-benzo[d]imidazole-5-carbonyl)piperidin-3-yl)carbamate). | 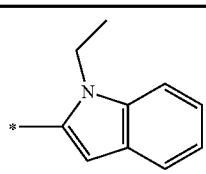 | Br | LCMS (Method B): Rt = 0.88 mins, MH$^+$ = 480.2 |
| 37: (R)-(3-Aminopiperidin-1-yl)(1-methyl-2-(1-methyl-1H-indol-2-yl)-1H-benzo[d]imidazol-5-yl)methanone (prepared from 1,1-dimethylethyl ((3R)-1-{[1-methyl-2-(1-methyl-1H-indol-2-yl)-1H-benzimidazol-5-yl]carbonyl}-3-piperidinyl)carbamate). | 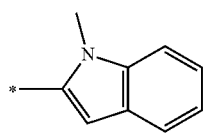 | H | LCMS (Method B): Rt = 0.69 min, MH+ = 388.2 |
| 38: (R)-(3-Aminopiperidin-1-yl)(2-(1-(3,4-dichlorobenzyl)-1H-indol-2-yl)-1-methyl-1H-benzo[d]imidazol-5-yl)methanone (prepared from 1,1-dimethylethyl {(3R)-1-[(2-{1-[(3,4-dichlorophenyl)methyl]-1H-indol-2-yl}-1-methyl-1H-benzimidazol-5-yl)carbonyl]-3-piperidinyl}carbamate). | 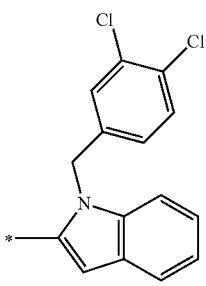 | H | LCMS (Method B): Rt = 1.00 min, MH+ = 532.2. |
| 39: (R)-(3-Aminopiperidin-1-yl)(2-(1-(4-methoxybenzyl)-1H-indol-2-yl)-1-methyl-1H-benzo[d]imidazol-5-yl)methanone (prepared from 1,1-dimethylethyl ((3R)-1-{[1-methyl-2-(1-{[4-(methyloxy)phenyl]methyl}-1H-indol-2-yl)-1H-benzimidazol-5-yl]carbonyl}-3-piperidinyl)carbamate). | 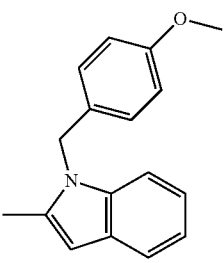 | H | .LCMS (Method B): Rt = 0.89 min, MH+ = 494.4 |

The examples indicated in following table were prepared similarly to example 1a. In some cases further purification by Mass Directed Autoprep was performed.

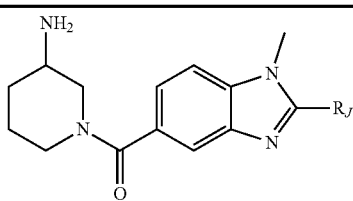

| Example | $R_J$ | Yield/% | |
|---|---|---|---|
| 40: 1-({1-Methyl-2-[1-(tetrahydro-2H-pyran-4-ylmethyl)-1H-indol-2-yl]-1H-benzimidazol-5-yl}carbonyl)-3-piperidinamine (prepared from tert-butyl (1-(1-methyl-2-(1-((tetrahydro-2H-pyran-4-yl)methyl)-1H-indol-2-yl)-1H-benzo[d]imidazole-5-carbonyl)piperidin-3-yl)carbamate). | 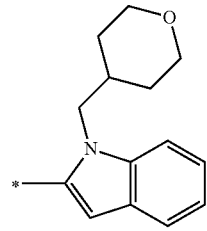 | 89 | LCMS (Method B) Rt = 0.81 min, MH+ = 472.4 |
| 41: 1-([2-(6-Bromo-1-ethyl-1H-indol-2-yl)-1-methyl-1H-benzimidazol-5-yl]carbonyl}-3-piperidinamine (prepared from tert-butyl (1-(2-(6-bromo-1-ethyl-1H-indol-2-yl)-1-methyl-1H-benzo[d]imidazole-5-carbonyl)piperidin-3-yl)carbamate). | 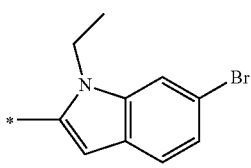 | 95 | LCMS (Method A) Rt = 1.11 min, MH+ = 480.1 |

Example 42: (R)-(3-Aminopiperidin-1-yl)(2-(1-ethyl-1H-indol-2-yl)-1,6-dimethyl-1H-benzo[d]imidazol-5-yl)methanone

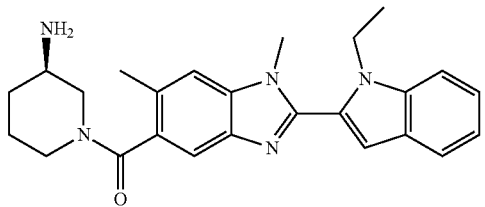 [SMILES: CCn1c(-c2nc3cc(C(=O)N4CCC[C@@H](N)C4)c(C)cc3n2C)cc2ccccc21]

Prepared in a similar manner to Example 1a from (R)-tert-butyl (1-(2-(1-ethyl-1H-indol-2-yl)-1,6-dimethyl-1H-benzo[d]imidazole-5-carbonyl)piperidin-3-yl)carbamate.
LCMS (Method B): Rt 0.83 min, MH+=416.

Example 11b: (3R)-1-({1-Methyl-2-[1-(2,2,2-trifluoroethyl)-1H-indol-2-yl]-1H-benzimidazol-5-yl})carbonyl)-3-piperidinamine, Hydrochloride Salt

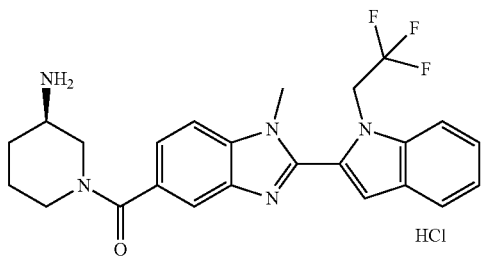 [SMILES: Cn1c(-c2cc3ccccc3n2CC(F)(F)F)nc2cc(C(=O)N3CCC[C@@H](N)C3)ccc21 ; Cl]

Prepared in a similar manner to Example 1b from (R)-(3-aminopiperidin-1-yl)(1-methyl-2-(1-(2,2,2-trifluoroethyl)-1H-indol-2-yl)-1H-benzo[d]imidazol-5-yl)methanone.

LCMS (Method A): Rt=1.01 mins, MH+=456.2

Example 33b: ((R)-3-Aminopiperidin-1-yl)(2-(1-((R)-3-hydroxy-2-methylpropyl)-1H-indol-2-yl)-7-methoxy-1-methyl-1H-benzo[d]imidazol-5-yl)methanone, Hydrochloride Salt

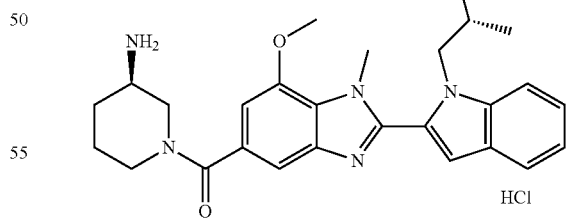

Prepared in a similar manner to Example 1b, from ((R)-3-aminopiperidin-1-yl)(2-(1-((R)-3-hydroxy-2-methylpropyl)-1H-indol-2-yl)-7-methoxy-1-methyl-1H-benzo[d]imidazol-5-yl)methanone.

LCMS (Method C): Rt 0.76 min, MH+=476.3.

Example 43: (R)-(3-Aminopiperidin-1-yl)(2-(1-(cyclopropylmethyl)-1H-indol-2-yl)-7-methoxy-1-methyl-1H-benzo[d]imidazol-5-yl)methanone, Hydrochloride Salt

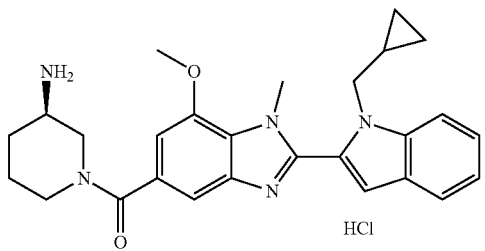 [SMILES: COc1cc(C(=O)N2CCC[C@@H](N)C2)cc2nc(-c3cc4ccccc4n3CC3CC3)n(C)c12 ; Cl]

Prepared in a similar manner to Example 1b, from (R)-tert-butyl (1-(2-(1-(cyclopropylmethyl)-1H-indol-2-yl)-7-methoxy-1-methyl-1H-benzo[d]imidazole-5-carbonyl)piperidin-3-yl)carbamate LCMS (Method B): Rt=0.89 min, MH+=458.3

Example 44: (R)-(3-Aminopiperidin-1-yl)(7-methoxy-1-methyl-2-(1-(2,2,2-trifluoroethyl)-1H-indol-2-yl)-1H-benzo[d]imidazol-5-yl)methanone, Hydrochloride Salt

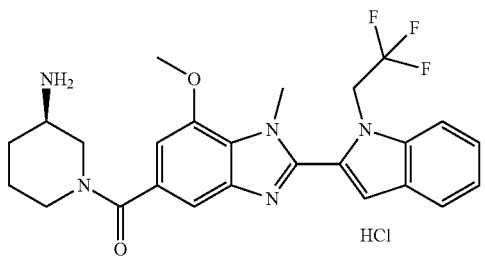 [SMILES: COc1cc(C(=O)N2CCC[C@@H](N)C2)cc2nc(-c3cc4ccccc4n3CC(F)(F)F)n(C)c12 ; Cl]

Prepared in a similar manner to Example 1b, from (R)-tert-butyl (1-(7-methoxy-1-methyl-2-(1-(2,2,2-trifluoroethyl)-1H-indol-2-yl)-1H-benzo[d]imidazole-5-carbonyl)piperidin-3-yl)carbamate.

LCMS (Method B): Rt=0.89 min, MH+=458.3

Example 45: (3S)-1-({1-Methyl-2-[1-(phenylmethyl)-1H-indol-2-yl]-1H-benzimidazol-5-yl}carbonyl)-3-piperidinamine

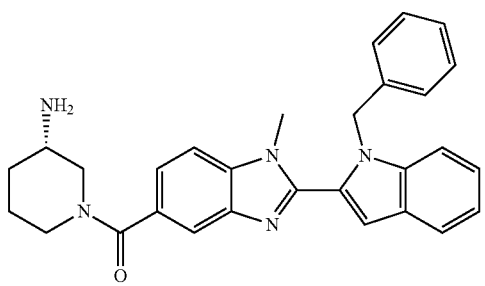 [SMILES: Cn1c(-c2cc3ccccc3n2Cc2ccccc2)nc2cc(C(=O)N3CCC[C@H](N)C3)ccc21]

Prepared in a similar manner to Example 1a from 1,1-dimethylethyl [(3S)-1-({1-methyl-2-[1-(phenylmethyl)-1H-indol-2-yl]-1H-benzimidazol-5-yl}carbonyl)-3-piperidinyl]carbamate.

LCMS (Method B): Rt=0.88 min, MH+=464.4.

Example 46: (S)-(3-Aminopiperidin-1-yl)(1-methyl-2-(1-methyl-1H-indol-2-yl)-1H-benzo[d]imidazol-5-yl)methanone

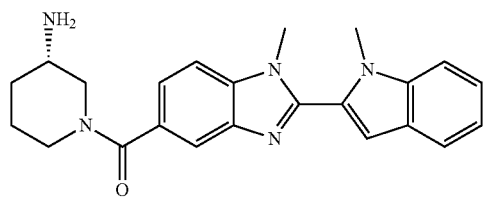 [SMILES: Cn1c(-c2nc3cc(C(=O)N4CCC[C@H](N)C4)ccc3n2C)cc2ccccc21]

Prepared in a similar manner to Example 1a from 1,1-dimethylethyl ((3S)-1-{[1-methyl-2-(1-methyl-1H-indol-2-yl)-1H-benzimidazol-5-yl]carbonyl}-3-piperidinyl)carbamate LCMS (Method B): Rt=0.69 min, MH+=388.2

Example 47: (1R,5S)-3-{[2-(1-Ethyl-1H-indol-2-yl)-1-methyl-1H-benzimidazol-5-yl]carbonyl}-3-azabicyclo[3.1.0]hexan-1-amine

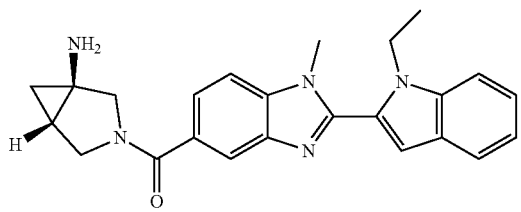 [SMILES: CCn1c(-c2nc3cc(C(=O)N4C[C@@H]5C[C@]5(N)C4)ccc3n2C)cc2ccccc21]

Prepared in a similar manner to Example 1a from tert-butyl ((1R,5S)-3-(2-(1-ethyl-1H-indol-2-yl)-1-methyl-1H-benzo[d]imidazole-5-carbonyl)-3-azabicyclo[3.1.0]hexan-1-yl)carbamate.

LCMS (Method B): Rt=0.77 min, MH+=400.1

Example 48: (R)-(1-(2-Aminoethyl)-2-(1-ethyl-1H-indol-2-yl)-1H-benzo[d]imidazol-5-yl)(3-aminopiperidin-1-yl)methanone

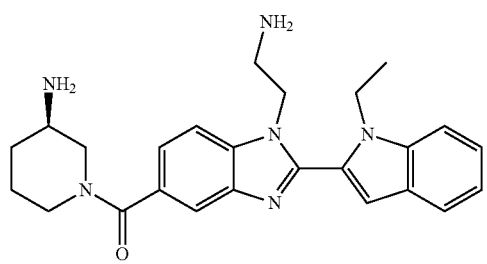 [SMILES: CCn1c(-c2nc3cc(C(=O)N4CCC[C@@H](N)C4)ccc3n2CCN)cc2ccccc21]

Prepared in a similar manner to Example 1a, from 1,1-dimethylethyl ((3R)-1-{[1-[2-({[(1,1-dimethylethyl)oxy]

carbonyl}amino)ethyl]-2-(1-ethyl-1H-indol-2-yl)-1H-benzimidazol-5-yl]carbonyl}-3-piperidinyl)carbamate
LCMS (Method A): Rt=0.80 min, MH⁺=431.24

Example 49: (R)-(3-Aminopiperidin-1-yl)(2-(1-ethyl-1H-indol-2-yl)-1-methyl-7-(trifluoromethyl)-1H-benzo[d]imidazol-5-yl)methanone

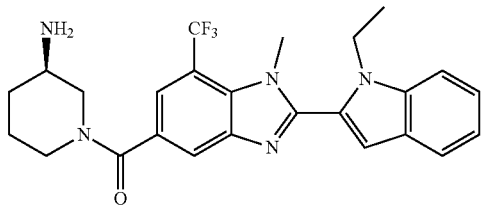 [SMILES: CCn1c(-c2nc3cc(C(=O)N4CCC[C@@H](N)C4)cc(C(F)(F)F)c3n2C)cc2ccccc21]

Prepared in a similar manner to Example 1a, from (R)-tert-butyl (1-(2-(1-ethyl-1H-indol-2-yl)-1-methyl-7-(trifluoromethyl)-1H-benzo[d]imidazole-5-carbonyl)piperidin-3-yl)carbamate
LCMS (Method B): Rt=0.92 min, MH⁺=470.3

Example 50: (+/−)-cis-(3-Amino-4-ethoxypiperidin-1-yl)(2-(1-ethyl-1H-indol-2-yl)-1-methyl-1H-benzo[d]imidazol-5-yl)methanone

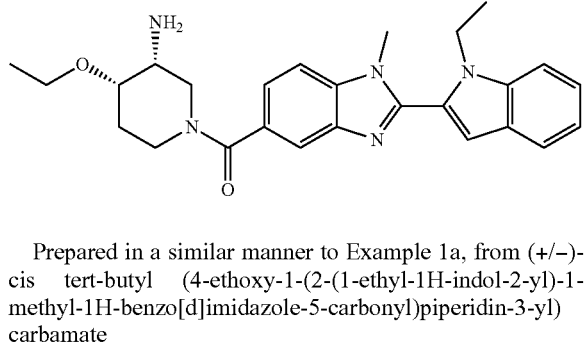

Prepared in a similar manner to Example 1a, from (+/−)-cis tert-butyl (4-ethoxy-1-(2-(1-ethyl-1H-indol-2-yl)-1-methyl-1H-benzo[d]imidazole-5-carbonyl)piperidin-3-yl)carbamate
LCMS (Method B): Rt=0.86 min, MH⁺=446.3.

Example 51: (+/−)-((trans)-3-Amino-4-methoxypiperidin-1-yl)(2-(1-ethyl-1H-indol-2-yl)-1-methyl-1H-benzo[d]imidazol-5-yl)methanone

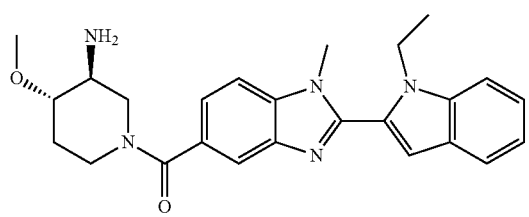 [SMILES: CCn1c(-c2nc3cc(C(=O)N4CC[C@H](OC)[C@@H](N)C4)ccc3n2C)cc2ccccc21]

Prepared in a similar manner to Example 1a, from (+/−)-tert-butyl ((cis)-1-(2-(1-ethyl-1H-indol-2-yl)-1-methyl-1H-benzo[d]imidazole-5-carbonyl)-4-methoxypiperidin-3-yl)carbamate
LCMS (Method A): Rt=0.97 min, MH⁺=432.22

Example 52: cis-(3-Amino-2-methylpiperidin-1-yl)(2-(1-ethyl-1H-indol-2-yl)-1-methyl-1H-benzo[d]imidazol-5-yl)methanone hydrochloride salt, single unknown enantiomer with Known Relative Stereochemistry

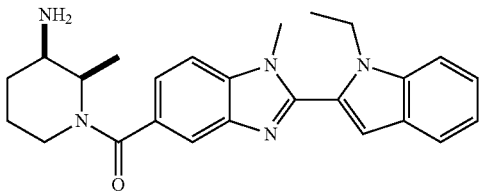 [SMILES: CCn1c(-c2nc3cc(C(=O)N4CCC[C@@H](N)[C@H]4C)ccc3n2C)cc2ccccc21]

Prepared in a similar manner to example 1a, from tert-butyl-cis-(1-(2-(1-ethyl-1H-indol-2-yl)-1-methyl-1H-benzo[d]imidazole-5-carbonyl)-2-methylpiperidin-3-yl)carbamate.
LCMS (Method B): Rt=0.80 min, MH+=416.2.

Example 53: cis-(5-Amino-2-methylpiperidin-1-yl)(2-(1-ethyl-1H-indol-2-yl)-1-methyl-1H-benzo[d]imidazol-5-yl)methanone Hydrochloride Salt,
Single Unknown Enantiomer with Known Relative Stereochemistry

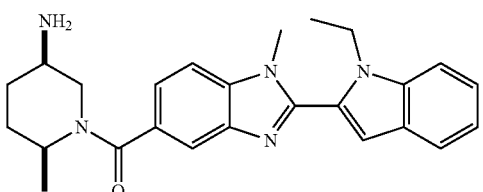

Prepared in a similar manner to Example 1a, from tert-butyl-((cis)-1-(2-(1-ethyl-1H-indol-2-yl)-1-methyl-1H-benzo[d]imidazole-5-carbonyl)-6-methylpiperidin-3-yl)carbamate
LCMS (Method B): Rt=0.81 min, MH+=416.1.

Example 54: cis-(5-Amino-2-methylpiperidin-1-yl)(2-(1-ethyl-1H-indol-2-yl)-1-methyl-1H-benzo[d]imidazol-5-yl)methanone Hydrochloride Salt,
Single Unknown Enantiomer with Known Relative Stereochemistry

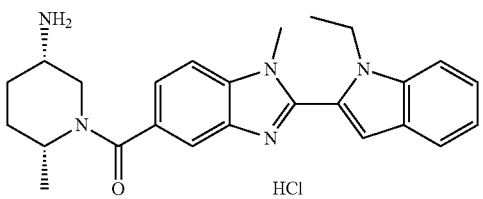 [SMILES: CCn1c(-c2nc3cc(C(=O)N4C[C@@H](N)CC[C@H]4C)ccc3n2C)cc2ccccc21 ; Cl]

Prepared in a similar manner to example 1a, from tert-butyl-((cis)-1-(2-(1-ethyl-1H-indol-2-yl)-1-methyl-1H-benzo[d]imidazole-5-carbonyl)-6-methylpiperidin-3-yl)carbamate.
LCMS (Method B): Rt=0.81 min, MH+=416.1.

Example 55: N-(Azepan-3-yl)-2-(1-(cyclopropylmethyl)-1H-indol-2-yl)-1-methyl-1H-benzo[d]imidazole-5-carboxamide Hydrochloride Salt

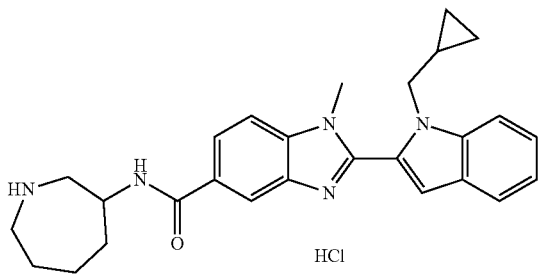 [SMILES: Cn1c(-c2cc3ccccc3n2CC2CC2)nc2cc(C(=O)NC3CCCCNC3)ccc21 ; Cl]

Was prepared in a similar manner to example 1a, from tert-butyl 3-(2-(1-(cyclopropylmethyl)-1H-indol-2-yl)-1-methyl-1H-benzo[d]imidazole-5-carboxamido)azepane-1-carboxylate LCMS (Method B): Rt=0.84 min, MH+=442.3.

Example 56: (3-Aminopyrrolidin-1-yl)(2-(1-ethyl-1H-indol-2-yl)-7-methoxy-1-methyl-1H-benzo[d]imidazol-5-yl)methanone Hydrochloride Salt

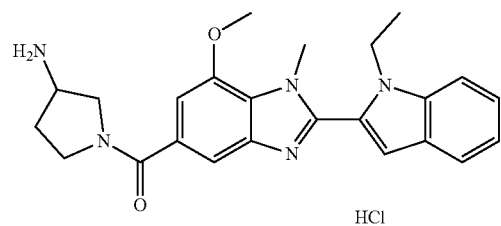 [SMILES: CCn1c(-c2nc3cc(C(=O)N4CCC(N)C4)cc(OC)c3n2C)cc2ccccc21 ; Cl]

Prepared in a similar manner to Example 1a, from tert-butyl (1-(2-(1-ethyl-1H-indol-2-yl)-7-methoxy-1-methyl-1H-benzo[d]imidazole-5-carbonyl)pyrrolidin-3-yl)carbamate.

LCMS (Method B): Rt=0.81 min, MH+=418.3.

Example 57: (3-Aminopyrollidin-1-yl)(2-(1-benzyl-1H-indol-2-yl)-1-methyl-1H-benzo[d]imidazol-5-yl)methanone

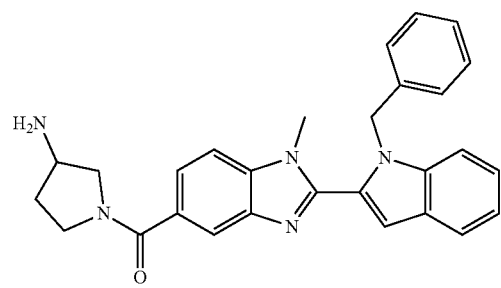 [SMILES: Cn1c(-c2cc3ccccc3n2Cc2ccccc2)nc2cc(C(=O)N3CCC(N)C3)ccc21]

Prepared in a similar manner to Example 1a, from 1,1-dimethylethyl [1-({1-methyl-2-[1-(phenylmethyl)-1H-indol-2-yl]-1H-benzimidazol-5-yl}carbonyl)-3-pyrrolidinyl]carbamate LCMS (Method B): Rt=0.86 min, MH+=450.4

Example 58a: ((3S,4R)-3-Amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone

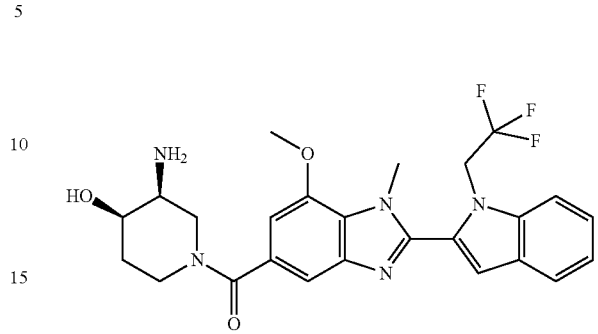

Prepared in a similar manner to Example 1a, from tert-butyl (4-hydroxy-1-(7-methoxy-1-methyl-2-(1-(2,2,2-trifluoroethyl)-1H-indol-2-yl)-1H-benzo[d]imidazole-5-carbonyl)piperidin-3-yl)carbamate.

LCMS (Method B): Rt=0.88 mins, MH+=502.3

Example 58b: ((3S,4R)-3-Amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone, Hydrochloride Salt

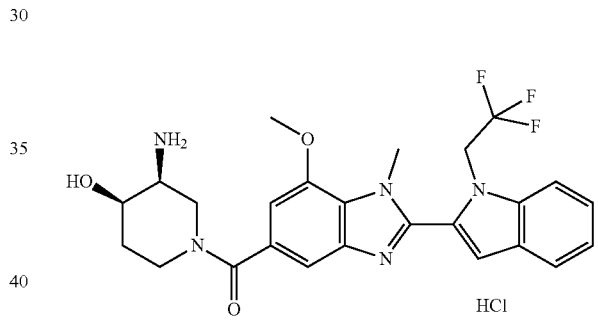

Prepared in a similar manner to Example 1b, from ((3S,4R)-3-amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone.

LCMS (Method B): Rt=0.86 mins, MH+=502.1.

Example 59: ((3R,4S)-3-Amino-4-hydroxypiperidin-1-yl)(7-methoxy-1-methyl-2-(1-(2,2,2-trifluoroethyl)-1H-indol-2-yl)-1H-benzo[d]imidazol-5-yl)methanone

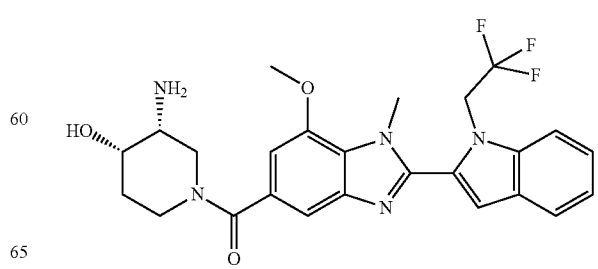

Prepared in a similar manner to example 1a, from tert-butyl ((3R,4S)-4-hydroxy-1-(7-methoxy-1-methyl-2-(1-(2,2,2-trifluoroethyl)-1H-indol-2-yl)-1H-benzo[d]imidazole-5-carbonyl)piperidin-3-yl)carbamate.

LCMS (Method B): Rt=0.82 mins, MH$^+$=502.3.

Example 20b: (3R)-1-[(1-Methyl-2-{1-[(1-methyl-1H-pyrazol-4-yl)methyl]-1H-indol-2-yl}-1H-benzimidazol-5-yl)carbonyl]-3-piperidinamine Hydrochloride Salt

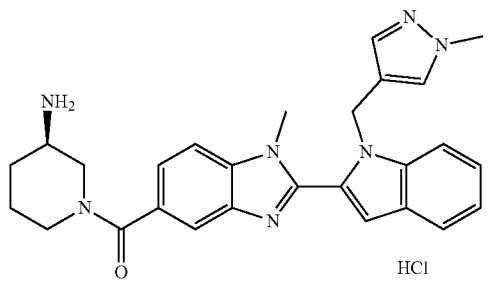 [SMILES: Cn1cc(Cn2c(-c3nc4cc(C(=O)N5CCC[C@@H](N)C5)ccc4n3C)cc3ccccc32)cn1 ; Cl]

TFA (0.6 ml, 7.79 mmol) was added to a solution of (R)-tert-butyl (1-(1-methyl-2-(1-((1-methyl-1H-pyrazol-4-yl)methyl)-1H-indol-2-yl)-1H-benzo[d]imidazole-5-carbonyl)piperidin-3-yl)carbamate (144 mg, 0.254 mmol) in dichloromethane (DCM) (6 mL) and left stirring for 40 min at rt. The reaction mixture was concentrated under vacuum and then dissolved in MeOH and loaded onto a 5 g SCX cartridge. The cartridge was eluted with MeOH (3 column volumes) and the product eluted as a free base using 2M ammonia in MeOH (4 column volumes). Product fractions were collected and concentrated under vacuum to give a yellow solid. The product was dissolved in a minimum volume of DCM and hydrochloric acid (1M in Diethyl Ether) (0.178 mL, 0.178 mmol) was added to form the corresponding HCl salt. The solvent was removed under nitrogen then dried under vacuum to afford (3R)-1-[(1-methyl-2-{1-[(1-methyl-1H-pyrazol-4-yl)methyl]-1H-indol-2-yl}-1H-benzimidazol-5-yl)carbonyl]-3-piperidinamine hydrochloride salt (64 mg, 50%).

LCMS (Method A): Rt=0.86 mins, MH$^+$=468.2

Example 6b: (3R)-1-{[2-(1-ethyl-1H-indol-2-yl)-1-methyl-7-(methyloxy)-1H-benzimidazol-5-yl]carbonyl}-3-piperidinamine Hydrochloride

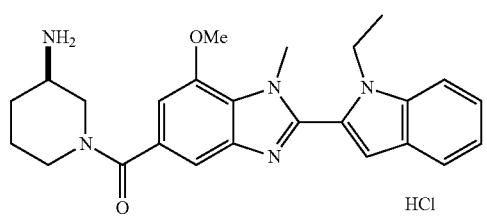 [SMILES: CCn1c(-c2nc3cc(C(=O)N4CCC[C@@H](N)C4)cc(OC)c3n2C)cc2ccccc21 ; Cl]

Prepared similarly to Example 20b from (R)-tert-butyl (1-(2-(1-ethyl-1H-indol-2-yl)-7-methoxy-1-methyl-1H-benzo[d]imidazole-5-carbonyl)piperidin-3-yl)carbamate LCMS (Method B): Rt 0.80 min, MH+=432.3

Example 60: (R)-(3-Aminopiperidin-1-yl)(2-(1-ethyl-5-fluoro-1H-indol-2-yl)-1-methyl-1H-benzo[d]imidazol-5-yl)methanone, Hydrochloride Salt

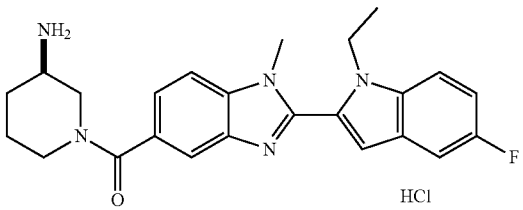 [SMILES: CCn1c(-c2nc3cc(C(=O)N4CCC[C@@H](N)C4)ccc3n2C)cc2cc(F)ccc21 ; Cl]

Prepared similarly to Example 20b from (R)-tert-butyl (1-(2-(1-ethyl-5-fluoro-1H-indol-2-yl)-1-methyl-1H-benzo[d]imidazole-5-carbonyl)piperidin-3-yl)carbamate LCMS (Method B): Rt 0.79 min, MH+=420.1

Example 61: (R)-(3-Aminopiperidin-1-yl)(2-(1-ethyl-1H-indol-2-yl)-1-methyl-7-(pyridin-3-yl)-1H-benzo[d]imidazol-5-yl)methanone, Hydrochloride Salt

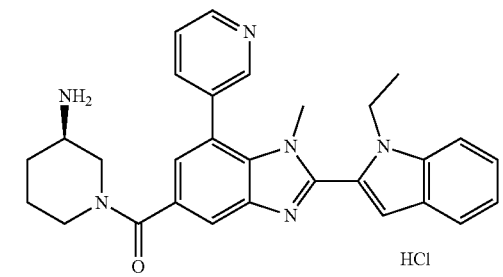 [SMILES: CCn1c(-c2nc3cc(C(=O)N4CCC[C@@H](N)C4)cc(-c4cccnc4)c3n2C)cc2ccccc21 ; Cl]

Prepared in a similar manner to Example 20b, from (R)-tert-butyl (1-(2-(1-ethyl-1H-indol-2-yl)-1-methyl-7-(pyridin-3-yl)-1H-benzo[d]imidazole-5-carbonyl)piperidin-3-yl)carbamate.

LCMS (Method B): Rt=0.84 mins, MH$^+$=479.3

Example 62: (R)-5-(3-Aminopiperidine-1-carbonyl)-2-(1-ethyl-1H-indol-2-yl)-1-methyl-1H-benzo[d]imidazole-7-carboxamide, Hydrochloride Salt

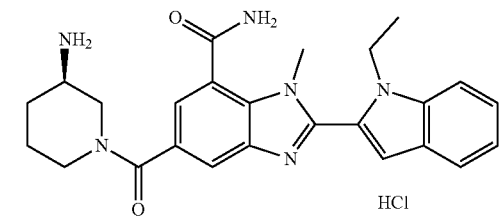 [SMILES: CCn1c(-c2nc3cc(C(=O)N4CCC[C@@H](N)C4)cc(C(N)=O)c3n2C)cc2ccccc21 ; Cl]

Prepared in a similar manner to Example 20b, from (R)-tert-butyl (1-(7-carbamoyl-2-(1-ethyl-1H-indol-2-yl)-1-methyl-1H-benzo[d]imidazole-5-carbonyl)piperidin-3-yl)carbamate.

LCMS (Method B): Rt=0.72 mins, MH$^+$=445.2

Example 63: (R)-(3-Aminopiperidin-1-yl)(7-(dimethylamino)-2-(1-ethyl-1H-indol-2-yl)-1-methyl-1H-benzo[d]imidazol-5-yl)methanone, Hydrochloride Salt

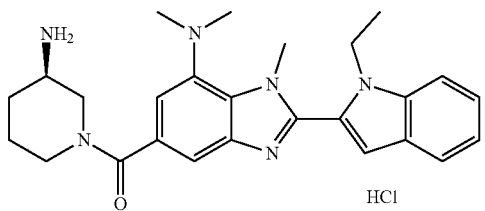 [SMILES: CCn1c(-c2nc3cc(C(=O)N4CCC[C@@H](N)C4)cc(N(C)C)c3n2C)cc2ccccc21 ; Cl]

Prepared in a similar manner to Example 20b, from (R)-tert-butyl (1-(7-(dimethylamino)-2-(1-ethyl-1H-indol-2-yl)-1-methyl-1H-benzo[d]imidazole-5-carbonyl)piperidin-3-yl)carbamate LCMS (Method A): Rt=1.09 min, MH+=445.4.

Example 64: 2-(1-Ethyl-1H-indol-2-yl)-1-methyl-N-(1,4-oxazepan-6-yl)-1H-benzo[d]imidazole-5-carboxamide Hydrochloride Salt

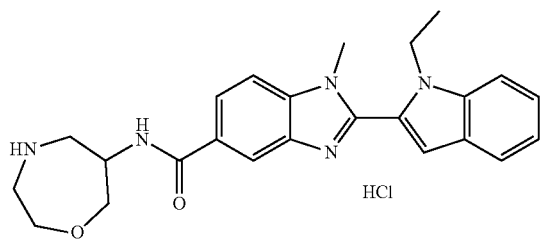 [SMILES: CCn1c(-c2nc3cc(C(=O)NC4CNCCOC4)ccc3n2C)cc2ccccc21 ; Cl]

Prepared in a similar manner to Example 20b, from tert-butyl 6-(2-(1-ethyl-1H-indol-2-yl)-1-methyl-1H-benzo[d]imidazole-5-carboxamido)-1,4-oxazepane-4-carboxylate.

LCMS (Method B): Rt=0.79 min, MH+=418.3.

Example 65: ((3S,4R)-3-Amino-4-hydroxypiperidin-1-yl)(2-(1-(cyclopropylmethyl)-1H-indol-2-yl)-1-methyl-1H-benzo[d]imidazol-5-yl)methanone Hydrochloride Salt

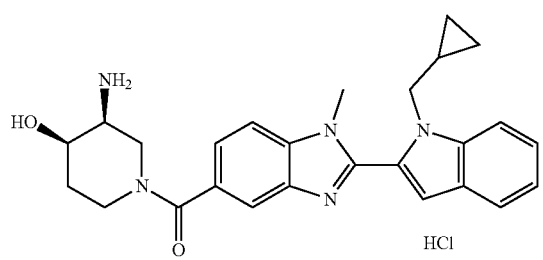 [SMILES: Cn1c(-c2cc3ccccc3n2CC2CC2)nc2cc(C(=O)N3CC[C@@H](O)[C@@H](N)C3)ccc21 ; Cl]

Prepared in a similar manner to Example 20b, from tert-butyl ((3S,4R)-1-(2-(1-(cyclopropylmethyl)-1H-indol-2-yl)-1-methyl-1H-benzo[d]imidazole-5-carbonyl)-4-hydroxypiperidin-3-yl)carbamate.

LCMS (Method B): Rt=0.83 mins, MH+=444.3

Example 66: ((3S,4R)-3-Amino-4-hydroxypiperidin-1-yl)(2-(1-(cyclopropylmethyl)-1H-indol-2-yl)-7-methoxy-1-methyl-1H-benzo[d]imidazol-5-yl)methanone, Hydrochloride Salt

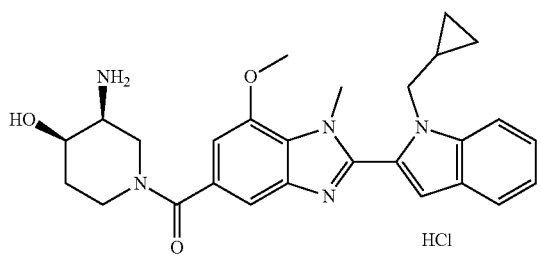 [SMILES: COc1cc(C(=O)N2CC[C@@H](O)[C@@H](N)C2)cc2nc(-c3cc4ccccc4n3CC3CC3)n(C)c12 ; Cl]

Prepared in a similar manner to example 20b, from tert-butyl ((3S,4R)-1-(2-(1-(cyclopropylmethyl)-1H-indol-2-yl)-7-methoxy-1-methyl-1H-benzo[d]imidazole-5-carbonyl)-4-hydroxypiperidin-3-yl)carbamate.

LCMS (Method B): Rt=0.85 min, MH+=474.2

Example 67: ((3S,4R)-3-Amino-4-hydroxypiperidin-1-yl)(2-(1-ethyl-1H-indol-2-yl)-7-methoxy-1-methyl-1H-benzo[d]imidazol-5-yl)methanone, Hydrochloride Salt

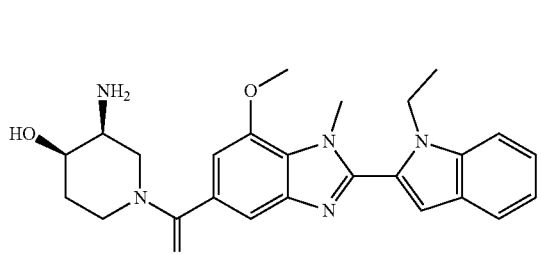

Prepared in a similar manner to Example 20b, from tert-butyl ((3S,4R)-1-(2-(1-ethyl-1H-indol-2-yl)-7-methoxy-1-methyl-1H-benzo[d]imidazole-5-carbonyl)-4-hydroxypiperidin-3-yl)carbamate.

LCMS (Method B): Rt=0.82 min, MH+=448.3

Example 68: (R)-(3-Aminopiperidin-1-yl)(2-(1-ethyl-1H-indol-2-yl)-1-methyl-7-(methylamino)-1H-benzo[d]imidazol-5-yl)methanone, Hydrochloride Salt

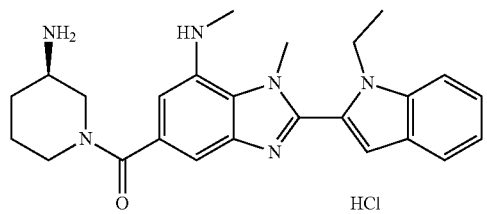 [SMILES: CCn1c(-c2nc3cc(C(=O)N4CCC[C@@H](N)C4)cc(NC)c3n2C)cc2ccccc21 ; Cl]

Prepared in a similar manner to Example 20b, from (R)-tert-butyl (5-(3-((tert-butoxycarbonyl)amino)piperidine-1-carbonyl)-2-(1-ethyl-1H-indol-2-yl)-1-methyl-1H-benzo[d]imidazol-7-yl)(methyl)carbamate.

LCMS (Method B): Rt=0.71 min, MH+=431.2

Example 69: (R)-(3-Aminopiperidin-1-yl)(7-methoxy-2-(1-(3-methoxypropyl)-1H-indol-2-yl)-1-methyl-1H-benzo[d]imidazol-5-yl)methanone, Hydrochloride Salt

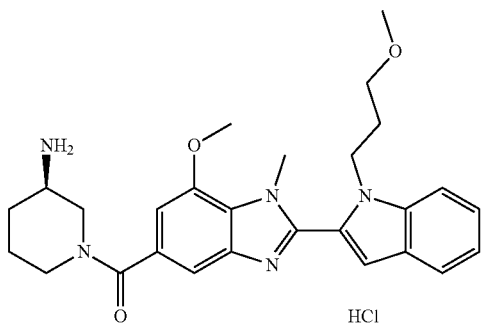 [SMILES: COCCCn1c(-c2nc3cc(C(=O)N4CCC[C@@H](N)C4)cc(OC)c3n2C)cc2ccccc21 ; Cl]

Prepared in a similar manner to Example 20b, from (R)-tert-butyl (1-(7-methoxy-2-(1-(3-methoxypropyl)-1H-indol-2-yl)-1-methyl-1H-benzo[d]imidazole-5-carbonyl)piperidin-3-yl)carbamate.
LCMS (Method A): Rt=1.03 min, MH+=476.3.

Example 70: (R)-(3-Aminopiperidin-1-yl)(7-methoxy-1-methyl-2-(1-((tetrahydro-2H-pyran-4-yl)methyl)-1H-indol-2-yl)-1H-benzo[d]imidazol-5-yl)methanone, Hydrochloride Salt

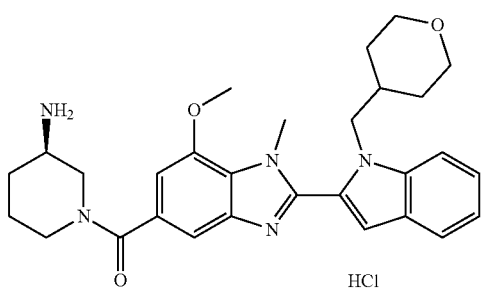 [SMILES: COc1cc(C(=O)N2CCC[C@@H](N)C2)cc2nc(-c3cc4ccccc4n3CC3CCOCC3)n(C)c12 ; Cl]

Prepared in a similar manner to Example 20b, from (R)-tert-butyl (1-(7-methoxy-1-methyl-2-(1-((tetrahydro-2H-pyran-4-yl)methyl)-1H-indol-2-yl)-1H-benzo[d]imidazole-5-carbonyl)piperidin-3-yl)carbamate.
LCMS (Method B): Rt=0.88 min, MH+=502.4.

Example 71: (R)-(3-Aminopiperidin-1-yl)(7-methoxy-2-(1-(2-methoxyethyl)-1H-indol-2-yl)-1-methyl-1H-benzo[d]imidazol-5-yl)methanone, Hydrochloride Salt

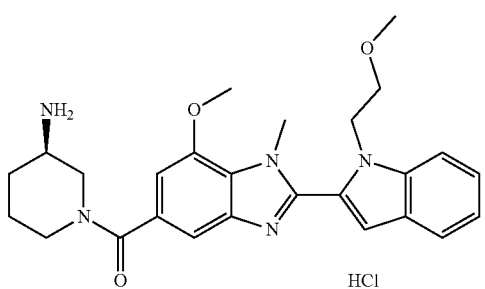 [SMILES: COCCn1c(-c2nc3cc(C(=O)N4CCC[C@@H](N)C4)cc(OC)c3n2C)cc2ccccc21 ; Cl]

Prepared in a similar manner to Example 20b, from (R)-tert-butyl (1-(7-methoxy-2-(1-(2-methoxyethyl)-1H-indol-2-yl)-1-methyl-1H-benzo[d]imidazole-5-carbonyl)piperidin-3-yl)carbamate.
LCMS (Method C): Rt=0.73 min, MH+=462.3.

Example 72: (R)-(3-Aminopiperidin-1-yl)(2-(1-(2-hydroxyethyl)-1H-indol-2-yl)-7-methoxy-1-methyl-1H-benzo[d]imidazol-5-yl)methanone, Hydrochloride Salt

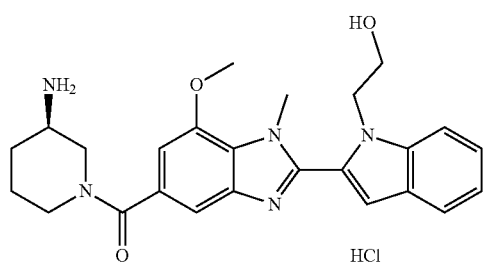 [SMILES: COc1cc(C(=O)N2CCC[C@@H](N)C2)cc2nc(-c3cc4ccccc4n3CCO)n(C)c12 ; Cl]

Prepared in a similar manner to Example 20b, from (R)-tert-butyl (1-(2-(1-(2-hydroxyethyl)-1H-indol-2-yl)-7-methoxy-1-methyl-1H-benzo[d]imidazole-5-carbonyl)piperidin-3-yl)carbamate.
LCMS (Method B): Rt=0.76 min, MH+=448.4.

Example 73: ((R)-3-Aminopiperidin-1-yl)(2-(1-((S)-3-hydroxy-2-methylpropyl)-1H-indol-2-yl)-7-methoxy-1-methyl-1H-benzo[d]imidazol-5-yl)methanone, Hydrochloride Salt

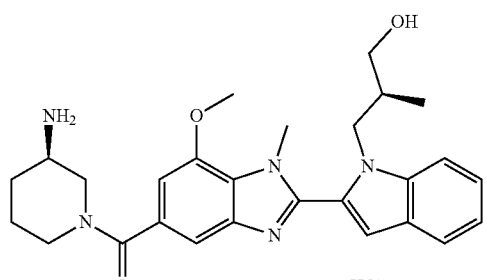

Prepared in a similar manner to Example 20b, from tert-butyl ((R)-1-(2-(1-((S)-3-hydroxy-2-methylpropyl)-1H-indol-2-yl)-7-methoxy-1-methyl-1H-benzo[d]imidazole-5-carbonyl)piperidin-3-yl)carbamate.
LCMS (Method B): Rt=0.84 min, MH+=476.3.

Example 74: (R)-2-(2-(5-(3-Aminopiperidine-1-carbonyl)-7-methoxy-1-methyl-1H-benzo[d]imidazol-2-yl)-1H-indol-1-yl)acetonitrile, Hydrochloride Salt

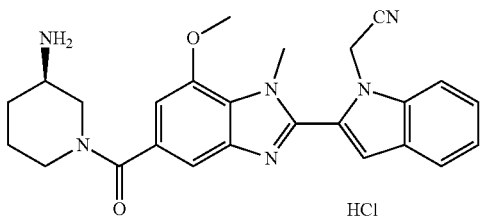 [SMILES: COc1cc(C(=O)N2CCC[C@@H](N)C2)cc2nc(-c3cc4ccccc4n3CC#N)n(C)c12 ; Cl]

Prepared in a similar manner to Example 20b, from (R)-tert-butyl (1-(2-(1-(cyanomethyl)-1H-indol-2-yl)-7-methoxy-1-methyl-1H-benzo[d]imidazole-5-carbonyl)piperidin-3-yl)carbamate.

LCMS (Method B): Rt=0.81 min, MH+=443.2.

Example 75: (R)-(3-Aminopiperidin-1-yl)(7-ethyl-2-(1-ethyl-1H-indol-2-yl)-1-methyl-1H-benzo[d]imidazol-5-yl)methanone, Hydrochloride Salt

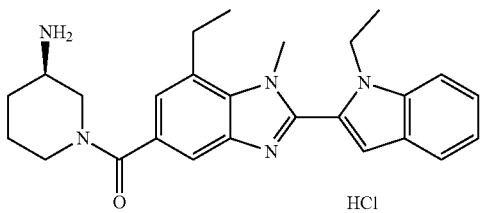 [SMILES: CCc1cc(C(=O)N2CCC[C@@H](N)C2)cc2nc(-c3cc4ccccc4n3CC)n(C)c12 ; Cl]

Prepared in a similar manner to Example 20b, from (R)-tert-butyl (1-(7-ethyl-2-(1-ethyl-1H-indol-2-yl)-1-methyl-1H-benzo[d]imidazole-5-carbonyl)piperidin-3-yl)carbamate.

LCMS (Method B): Rt=0.85 min, MH+=430.3.

Example 76: N-(Azepan-3-yl)-2-(1-ethyl-1H-indol-2-yl)-1-methyl-1H-benzo[d]imidazole-5-carboxamide

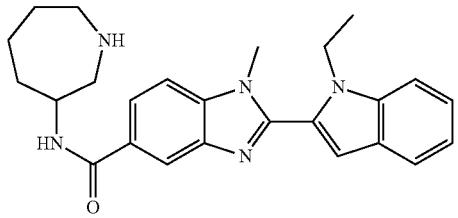 [SMILES: CCn1c(-c2nc3cc(C(=O)NC4CCCCNC4)ccc3n2C)cc2ccccc21]

Trifluoroacetic acid (0.223 mL, 3.00 mmol) was added to a stirred solution of tert-butyl 3-(2-(1-ethyl-1H-indol-2-yl)-1-methyl-1H-benzo[d]imidazole-5-carboxamido)azepane-1-carboxylate (103 mg, 0.20 mmol) in DCM (1 mL). After 17 h of stirring at rt the reaction mixture was concentrated under a stream of nitrogen in the Radleys blowdown apparatus to give a yellow oil. The residue was loaded in MeOH onto a 5 g SCX column which was preconditioned with MeOH. The column was washed with MeOH (4 CVs) and the product was eluted using methanolic ammonia (2 M) (4 CVs). The appropriate fractions were combined and the solvent was removed under reduced pressure to give the crude product. The residue was dissolved in MeOH/DMSO (1:1) (1 mL) and purified by MDAP (Method A). The appropriate fractions were combined and the solvent was removed under reduced pressure to give the required product N-(azepan-3-yl)-2-(1-ethyl-1H-indol-2-yl)-1-methyl-1H-benzo[d]imidazole-5-carboxamide (59 mg, 0.14 mmol, 71.1% yield) as a white solid.

LCMS (Method B): Rt=0.84 mins, MH+=416.2

Example 77: (S)—N-(Azepan-3-yl)-2-(1-ethyl-1H-indol-2-yl)-1-methyl-1H-benzo[d]imidazole-5-carboxamide

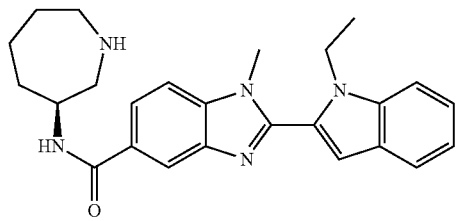 [SMILES: CCn1c(-c2nc3cc(C(=O)N[C@H]4CCCCNC4)ccc3n2C)cc2ccccc21]

Prepared from N-(azepan-3-yl)-2-(1-ethyl-1H-indol-2-yl)-1-methyl-1H-benzo[d]imidazole-5-carboxamide by chiral purification chromatography (Method I). The appropriate fractions from the first eluting isomer were combined and concentrated under reduced pressure to give (S)—N-(azepan-3-yl)-2-(1-ethyl-1H-indol-2-yl)-1-methyl-1H-benzo[d]imidazole-5-carboxamide (9 mg, 0.022 mmol) as a clear oil.

LCMS (Method B): Rt=0.84 min, MH+=416.2

Example 78: (R)—N-(1-(2-(1-Benzyl-1H-indol-2-yl)-1-methyl-1H-benzo[d]imidazole-5-carbonyl)piperidin-3-yl)-2-chloroacetimidamide

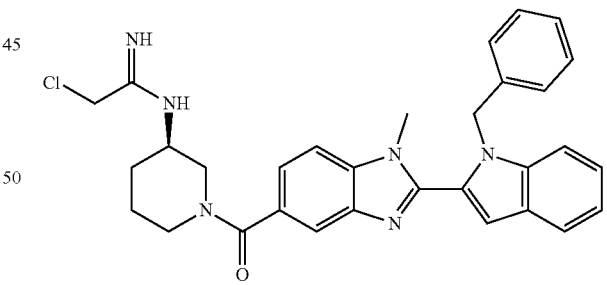

To a flask containing (3R)-1-({1-methyl-2-[1-(phenylmethyl)-1H-indol-2-yl]-1H-benzimidazol-5-yl}carbonyl)-3-piperidinamine (21 mg, 0.045 mmol) and N,N-dimethylformamide (DMF) (1 mL) was added ethyl 2-chloroethanimidoate (10.74 mg, 0.068 mmol, preparation reported in Bioorg. Med. Chem. 2011, 19, 156). Triethylamine (0.019 mL, 0.136 mmol) was then added and the reaction allowed to stir at rt for 40 h in total. The solvent was blown off under a positive pressure of nitrogen to afford the crude product as a black solid. The crude product was purified by MDAP (Method A) which afforded the product in two fractions, the second of which contained pure product. This fraction was concentrated in vacuo to afford a colourless gum—(R)—N-(1-(2-(1-benzyl-1H-indol-2-yl)-1-methyl-1H-benzo[d]imidazole-5-carbonyl)piperidin-3-yl)-2-chloroacetimidamide (3.1 mg, 5.75 μmol, 12.69% yield).

LCMS (Method A): Rt=1.17 mins, MH$^+$=539.2

Example 79: (R)-(3-Aminopiperidin-1-yl)(2-(7-ethyl-1H-indol-2-yl)-1-methyl-1H-benzo[d]imidazol-5-yl)methanone

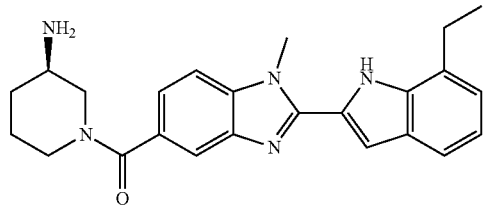 [SMILES: CCc1cccc2cc(-c3nc4cc(C(=O)N5CCC[C@@H](N)C5)ccc4n3C)[nH]c12]

7-Ethyl-1H-indole-2-carboxylic acid (41 mg, 0.217 mmol, commercially available from, for example, ACB Blocks) and HATU (90 mg, 0.237 mmol) were mixed in DMF (1.0 mL) to give a yellow solution. The solution was left at ambient temperature for ~5 min and then added to a solution of (R)-tert-butyl (1-(3-amino-4-(methylamino)benzoyl)piperidin-3-yl)carbamate (75 mg, 0.215 mmol) and DIPEA (112 μL, 0.237 mmol) in DMF (1.0 mL). The resulting yellow solution was left at ambient temperature (air atm.) for ~4 h. The reaction was diluted with water and extracted with DCM (×3). The combined organic extracts were dried (hydrophobic frit) and reduced to dryness under a stream of nitrogen to give a brown oil. The oil was treated with p-toluenesulphonic acid (45 mg, 0.237 mmol) in toluene (5.0 mL) and heated at reflux for ~6 h. The reaction was left at ambient temperature overnight, diluted with methanol and filtered through an aminopropyl SPE (5 g). The SPE was washed with methanol and the combined filtrate and washings reduced to dryness under a stream of nitrogen. The residue was dissolved in DMSO/methanol (1:1, 1 mL) and purified by MDAP (Method A). The appropriate fractions were reduced to dryness under a stream of nitrogen. The residue was dissolved in DCM and washed with water. The organic phase was dried (hydrophobic frit) and reduced to dryness under a stream of nitrogen to give (R)-(3-aminopiperidin-1-yl)(2-(7-ethyl-1H-indol-2-yl)-1-methyl-1H-benzo[d]imidazol-5-yl)methanone (24 mg) as a glass.

LCMS (Method B): Rt 0.80 min, MH$^+$ 402

Example 80: (R)-(3-Aminopiperidin-1-yl)(2-(1-ethyl-5,6-dimethoxy-1H-indol-2-yl)-1-methyl-1H-benzo[d]imidazol-5-yl)methanone

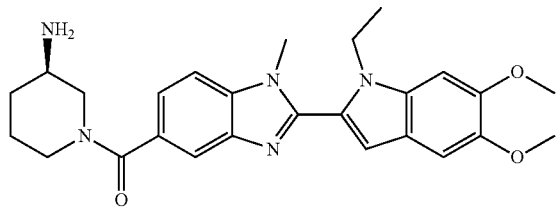 [SMILES: CCn1c(-c2nc3cc(C(=O)N4CCC[C@@H](N)C4)ccc3n2C)cc2cc(OC)c(OC)cc21]

Prepared in a similar manner to Example 79, from 1-ethyl-5,6-dimethoxy-1H-indole-2-carboxylic acid, lithium salt and (R)-tert-butyl (1-(3-amino-4-(methylamino)benzoyl)piperidin-3-yl)carbamate.

LCMS (Method B): Rt=0.68 mins, MH$^+$=462.2

Example 81: (R)-(3-Aminopiperidin-1-yl)(2-(3-ethyl-1H-indol-2-yl)-1-methyl-1H-benzo[d]imidazol-5-yl)methanone

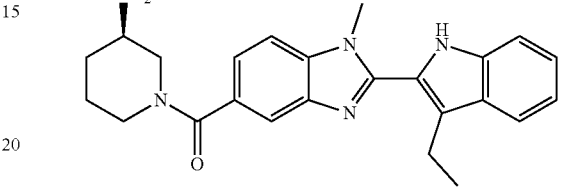

3-Ethyl-1H-indole-2-carboxylic acid (41 mg, 0.217 mmol, commercially available from, for example, ABCR Product List) and HATU (90 mg, 0.237 mmol) were mixed in DMF (1 mL) to give a brown solution. The mixture was stirred at ambient temperature for ~5 min and then treated with a solution of (R)-tert-butyl (1-(3-amino-4-(methylamino)benzoyl)piperidin-3-yl)carbamate (75 mg, 0.215 mmol) and DIPEA (112 μL, 0.646 mmol) in DMF (1 mL). The resulting brown solution was stirred at ambient temperature (air atm.) for ~1 h and then left at ambient temperature over a weekend. The reaction was diluted with water and extracted with DCM (×3). The combined organic extracts were dried (hydrophobic frit) and reduced to dryness under a stream of nitrogen to give a brown oil.

A portion of this oil (60 mg) was treated with p-toluenesulphonic acid.monohydrate (30 mg, 0.158 mmol) in toluene (5 mL) and the mixture heated at reflux for ~4 h and then left at ambient temperature overnight. The reaction was diluted with methanol to give a solution and filtered through an aminopropyl SPE (5 g). The SPE was washed with methanol and the combined filtrate and washings reduced to dryness under a stream of nitrogen to give a pale brown glass (26 mg).

The remainder of the oil was treated with p-toluenesulphonic acid.monohydrate (30 mg, 0.158 mmol) in toluene (5 mL) and the mixture heated at reflux for ~4 h and allowed to cool to ambient temperature overnight. The reaction was diluted with methanol to give a solution and filtered through an aminopropyl SPE (5 g). The SPE was washed with methanol, the filtrate and washings combined with the glass previously produced and the resulting solution reduced to dryness under a stream of nitrogen. The residue was dissolved in DMSO/methanol (1:1, 1 mL) and purified by MDAP (Method A). The appropriate fractions were reduced to dryness under a stream of nitrogen. The residue was dissolved in DCM and washed with water. The organic phase was dried (hydrophobic frit) and reduced to dryness under a stream of nitrogen to give to give (R)-(3-aminopiperidin-1-yl)(2-(3-ethyl-1H-indol-2-yl)-1-methyl-1H-benzo[d]imidazol-5-yl)methanone (10 mg).

LCMS (Method B): Rt=0.74 min, MH$^+$=402

Example 82: 1-{[2-(1-Ethyl-7-methyl-1H-indol-2-yl)-1-methyl-1H-benzimidazol-5-yl]carbonyl}-3-piperidinamine

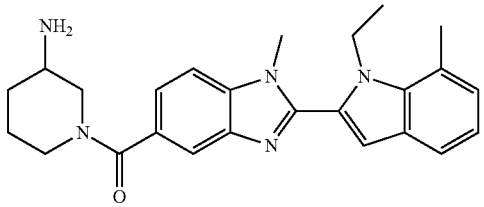 [SMILES: CCn1c(-c2nc3cc(C(=O)N4CCCC(N)C4)ccc3n2C)cc2cccc(C)c21]

1,1-Dimethylethyl (1-{[2-(1-ethyl-7-methyl-1H-indol-2-yl)-1-methyl-1H-benzimidazol-5-yl]carbonyl}-3-piperidinyl)carbamate (105 mg, 0.204 mmol) was treated with hydrogen chloride in 1,4-dioxane (4 M, 2 mL, 8.0 mmol) and the mixture stirred at ambient temperature for ~2 h. The volatiles were evaporated under a stream of nitrogen and the residual pink solid dissolved in methanol. The solution was filtered through an aminopropyl SPE (2 g). The SPE was washed with methanol and the combined filtrate and washings reduced to dryness under a stream of nitrogen to give 1-{[2-(1-ethyl-7-methyl-1H-indol-2-yl)-1-methyl-1H-benzimidazol-5-yl]carbonyl}-3-piperidinamine as a pale brown gum.

LCMS (Method B): Rt 0.82 min, MH$^+$ 416

Example 83: N-(2-Aminoethyl)-1-methyl-2-[1-(phenylmethyl)-1H-indol-2-yl]-1H-benzimidazole-5-carboxamide

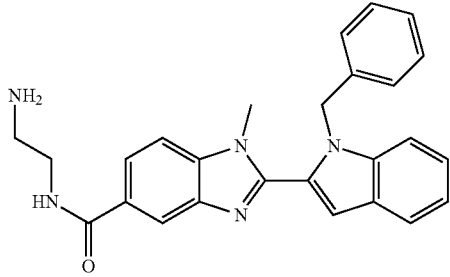 [SMILES: Cn1c(-c2cc3ccccc3n2Cc2ccccc2)nc2cc(C(=O)NCCN)ccc21]

Prepared in a similar manner to Example 82 from 1,1-Dimethylethyl {2-[({1-methyl-2-[1-(phenylmethyl)-1H-indol-2-yl]-1H-benzimidazol-5-yl}carbonyl)amino]ethyl}carbamate LCMS (Method B): Rt=0.97 min, MH$^+$=424

Example 84: 1-{[2-(1-Ethyl-5-methyl-1H-indol-2-yl)-1-methyl-1H-benzimidazol-5-yl]carbonyl}-3-piperidinamine

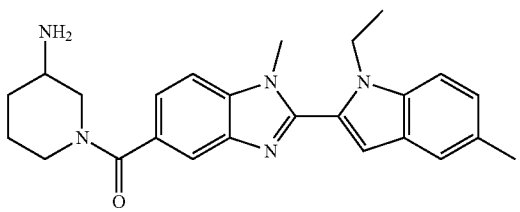 [SMILES: CCn1c(-c2nc3cc(C(=O)N4CCCC(N)C4)ccc3n2C)cc2cc(C)ccc21]

Prepared in a similar manner to Example 82 from 1,1-dimethylethyl (1-{[2-(1-ethyl-5-methyl-1H-indol-2-yl)-1-methyl-1H-benzimidazol-5-yl]carbonyl}-3-piperidinyl)carbamate LCMS (Method B): Rt=0.87 min, MH$^+$=416

Example 85: 1-{[2-(1-Ethyl-4-methyl-1H-indol-2-yl)-1-methyl-1H-benzimidazol-5-yl]carbonyl}-3-piperidinamine

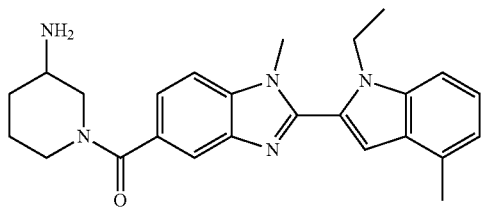 [SMILES: CCn1c(-c2nc3cc(C(=O)N4CCCC(N)C4)ccc3n2C)cc2c(C)cccc21]

Prepared in a similar manner to Example 82 from 1,1-dimethylethyl (1-{[2-(1-ethyl-4-methyl-1H-indol-2-yl)-1-methyl-1H-benzimidazol-5-yl]carbonyl}-3-piperidinyl)carbamate LCMS (Method B): Rt=0.85 min, MH$^+$=416

Example 86: (R)-2-(5-(3-Aminopiperidine-1-carbonyl)-1-methyl-1H-benzo[d]imidazol-2-yl)-1-ethyl-1H-indole-5-carbonitrile

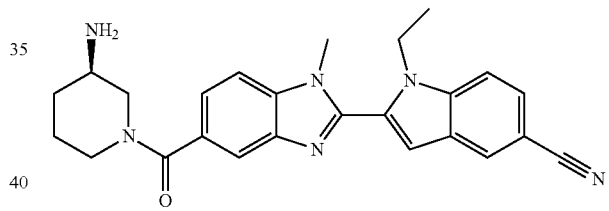

To a solution of 5-cyano-1-ethyl-1H-indole-2-carboxylic acid (61.5 mg, 0.287 mmol), HATU (120 mg, 0.316 mmol) in N,N-dimethylformamide (DMF) (5 mL), was added DIPEA (0.150 mL, 0.861 mmol) followed by (R)-tert-butyl (1-(3-amino-4-(methylamino)benzoyl)piperidin-3-yl)carbamate (100 mg, 0.287 mmol) and the resulting solution was stirred at rt under nitrogen for 2 h. Further 5-cyano-1-ethyl-1H-indole-2-carboxylic acid (13.2 mg) was added and the mixture was left ageing for 16 h (overnight). The reaction mixture was diluted with water and extracted with DCM×3. The combined organics were washed with brine (×3), dried on Na$_2$SO$_4$, and the volatiles were removed under reduced pressure to afford 150 mg of a dark yellow oil. The oil was treated with p-toluenesulfonic acid monohydrate (60 mg, 0.315 mmol) in toluene (10 mL) and the resulting solution was refluxed for 6 h, then allowed to reach rt and left ageing overnight. The mixture was loaded onto a 20 g preequilibrated NH$_2$ cartridge and eluted with MeOH (3CV). The methanolic fractions were combined and volatiles were removed under reduce pressure to afford 66 mg of crude. The crude was purified by silica gel chromatography, on a 10 g Si SNAP cartridge using a 20% 2M NH$_3$ in MeOH in DCM gradient over 20 CV. The relevant fractions were combined and the volatiles were removed under reduced pressure to afford 35 mg of impure material. This material was purified by MDAP (Method A). The relevant fractions were combined and the volatiles were removed under reduced pressure to afford (R)-2-(5-(3-aminopiperidine-1-carbonyl)-1-methyl-1H-benzo[d]imidazol-2-yl)-1-ethyl-1H-indole-5-carbonitrile (4.1 mg, 9.61 µmol, 3.35% yield).

LCMS: (Method B) Rt 0.73 min, MH+=427.1.

Example 87: 2-(1-Ethyl-1H-indol-2-yl)-1-methyl-N-(piperidin-3-yl)-1H-benzo[d]imidazole-5-carboxamide

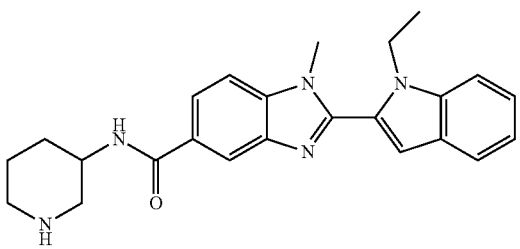 [SMILES: CCn1c(-c2nc3cc(C(=O)NC4CCCNC4)ccc3n2C)cc2ccccc21]

A mixture of HATU (385 mg) and 2-(1-ethyl-1H-indol-2-yl)-1-methyl-1H-benzo[d]imidazole-5-carboxylic acid (294 mg) was suspended in anhydrous DMF (4.5 mL) and treated with DIPEA (0.324 mL). The mixture was sonicated and a solution formed which was allowed to stand in a stoppered vessel for 15 min at rt. The reaction mixture was dispensed evenly (0.8 mL) into six vessels. One vessel contained tert-butyl 3-aminopiperidine-1-carboxylate (62 mg, 0.310 mmol, commercially available from, for example, ABCR) and the reaction was left to stand in a stoppered vessel for 15 h. The reaction mixture was evaporated in a vacuum centrifuge. The gum was dissolved in EtOAc (1.0 mL) and washed sequentially with a 0.5 M aqueous solution of HCl (1 mL), a saturated aqueous solution of NaHCO$_3$ (1 mL) and water (1 mL). The organic layer was dried through a hydrophobic frit and the solvent evaporated under a stream of nitrogen. The gum was purified by MDAP (Method B). The appropriate fractions were combined and the solvent evaporated in vacuo. The gum was dissolved in anhydrous 1,4-dioxane (0.3 mL) and treated with HCl (4 M solution in 1,4-dioxane, 0.7 mL). The reaction mixture was left to stand in a stoppered vessel for 1 h and evaporated under a stream of nitrogen. The solid was dissolved in MeOH (0.5 mL) and applied to MeOH preconditioned 1 g SCX-2 cartridge. The cartridge was washed with MeOH (5 mL) followed by a 2 M solution of ammonia in MeOH (5 mL) and the basic fraction evaporated under a stream of nitrogen to give the title compound (44 mg, 0.110 mmol, 68%).

LCMS (Method B): Rt: 0.80 min, MH+ 402.

Example 88: (S)-(3-(Aminomethyl)pyrrolidin-1-yl)(2-(1-ethyl-1H-indol-2-yl)-1-methyl-1H-benzo[d]imidazol-5-yl)methanone

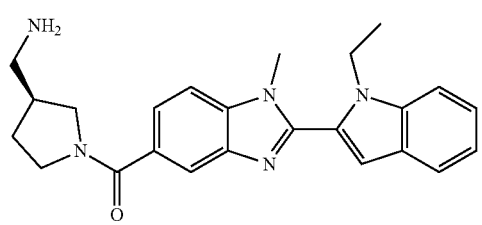 [SMILES: CCn1c(-c2nc3cc(C(=O)N4CC[C@@H](CN)C4)ccc3n2C)cc2ccccc21]

Prepared in a similar manner to Example 87, from 2-(1-ethyl-1H-indol-2-yl)-1-methyl-1H-benzo[d]imidazole-5-carboxylic acid and (R)-tert-butyl (pyrrolidin-3-ylmethyl)carbamate (commercially available from, for example, Astatech).

LCMS (Method B): Rt: 0.76 min, MH+ 402.

Example 89: (2-(1-Ethyl-1H-indol-2-yl)-1-methyl-1H-benzo[d]imidazol-5-yl)(3-(methylamino)piperidin-1-yl)methanone

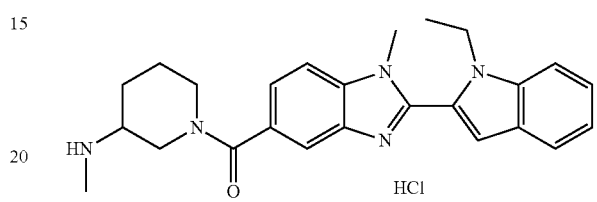

2-(1-Ethyl-1H-indol-2-yl)-1-methyl-1H-benzimidazole-5-carboxylic acid (210 mg, 0.658 mmol), HATU (275 mg, 0.723 mmol) and DIPEA (0.345 mL, 1.973 mmol) were added to a round bottomed flask. DMF (3.5 mL) was then added and the reaction mixture was left to stir at rt under nitrogen for 20 min. The reaction solution was distributed evenly between three vessels. One vessel contained 1,1-dimethylethyl methyl(3-piperidinyl)carbamate (51.7 mg, 0.241 mmol, commercially available from, for example, Activate Scientific) and was allowed to react at rt for 2 h. The sample was diluted with H$_2$O (1 mL) and extracted with EtOAc (3×1 mL), the organics were combined and the solvent evaporated under a stream of nitrogen in a blowdown. The sample was dissolved in 1:1 MeOH:DMSO (1 mL) and purified by MDAP (Method B). The solvent was evaporated in vacuo. 4 M HCl in 1,4-dioxane (0.5 mL) was added and allowed to react for 30 min at rt. The solvent was removed under nitrogen in a blowdown to give the title compound (6 mg, 6%) as a hydrochloride salt.

LCMS (Method B): Rt: 0.81 min, MH+ 416.

Example 90: N-(2-Aminoethyl)-2-(1-ethyl-1H-indol-2-yl)-1-methyl-1H-benzo[d]imidazole-5-carboxamide

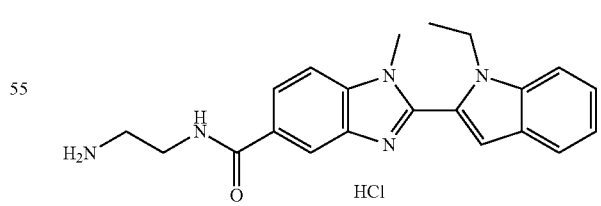

Prepared in a similar manner to Example 89 from 2-(1-ethyl-1H-indol-2-yl)-1-methyl-1H-benzimidazole-5-carboxylic acid and 1,1-dimethylethyl (2-aminoethyl)carbamate (commercially available from, for example, Fluorochem).

LCMS (Method B): Rt: 0.78 min, MH+ 362.

Example 91: (3,4-cis)-1-{[2-(1-Ethyl-1H-indol-2-yl)-1-methyl-1H-benzimidazol-5-yl]carbonyl}-3,4-piperidinediamine (Single Enantiomer, with Cis-Relative Stereochemistry and Unknown Absolute Stereochemistry)

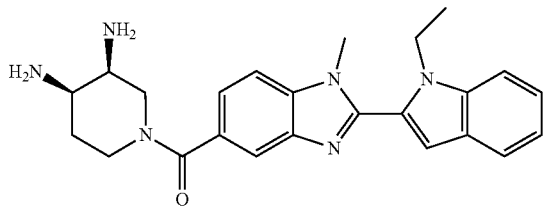 [SMILES: CCn1c(-c2nc3cc(C(=O)N4CC[C@@H](N)[C@@H](N)C4)ccc3n2C)cc2ccccc21]

To a solution of N,N'-((3,4-cis)-1-(2-(1-ethyl-1H-indol-2-yl)-1-methyl-1H-benzo[d]imidazole-5-carbonyl)piperidine-3,4-diyl)bis(2,2,2-trifluoroacetamide) (31 mg, 0.051 mmol) in methanol (1.2 mL)/water (0.4 mL) was added potassium carbonate (34.8 mg, 0.252 mmol) and the reaction stirred under nitrogen at 60° C. overnight. The reaction mixture was added directly to a 5 g SCX cartridge. The column was eluted with MeOH (3 column volumes) and the product eluted as a free base with 2M ammonia in methanol (3 column volumes). The product fractions were concentrated under vacuum and then dissolved in a minimum volume of MeOH and transferred to a vial. The solvent was removed under nitrogen and dried under vacuum overnight to afford (3,4-cis)-1-{[2-(1-ethyl-H-indol-2-yl)-1-methyl-1H-benzimidazol-5-yl]carbonyl}-3,4-piperidinediamine (20 mg, 93%).

LCMS (High pH): Rt=0.87 mins, MH$^+$=417.2.

Example 92: (+/−)-((cis)-4-Amino-2-methylpyrrolidin-1-yl)(2-(1-ethyl-1H-indol-2-yl)-1-methyl-1H-benzo[d]imidazol-5-yl)methanone, Hydrochloride Salt

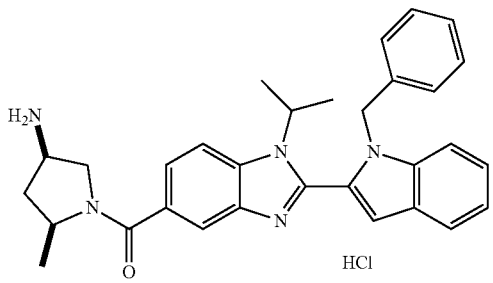 [SMILES: CC(C)n1c(-c2cc3ccccc3n2Cc2ccccc2)nc2cc(C(=O)N3C[C@H](N)C[C@@H]3C)ccc21 ; Cl]

To a solution of N-((cis)-1-(2-(1-ethyl-1H-indol-2-yl)-1-methyl-1H-benzo[d]imidazole-5-carbonyl)-5-methylpyrrolidin-3-yl)-2,2,2-trifluoroacetamide (33 mg, 0.066 mmol) in methanol (5 mL) and water (2.5 mL), was added K$_2$CO$_3$ (44.4 mg, 0.33 mmol) and the reaction heated at 60° C. for 3 h. The solvent was then concentrated in vacuo and the resultant residue partitioned between DCM and water (×3). The organic layer was dried (Na$_2$SO$_4$) and concentrated in vacuo to afford the crude product. This was purified by MDAP (Method A). The appropriate fractions were concentrated in vacuo to afford the desired free base. This was dissolved in DCM (1 mL) and HCl (18 µL, 0.036 mmol, 2M in Et$_2$O) was added. The suspension was sonicated for 5 min and allowed to stand for 15 min before the solvent was removed under a stream of N$_2$ to afford the title compound (17.1 mg).

LCMS (Method B): Rt=0.74 min, MH+=402.2.

Example 93: (R)-(3-Aminopiperidin-1-yl)(2-(1-ethyl-1H-indol-2-yl)-1,7-dimethyl-1H-benzo[d]imidazol-5-yl)methanone

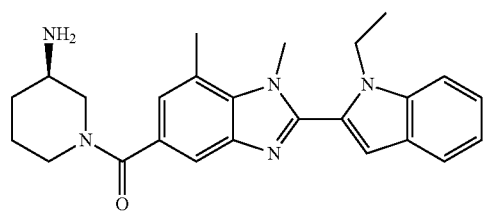 [SMILES: CCn1c(-c2nc3cc(C(=O)N4CCC[C@@H](N)C4)cc(C)c3n2C)cc2ccccc21]

To a mixture of 2-(1-ethyl-1H-indol-2-yl)-1,7-dimethyl-1H-benzo[d]imidazole-5-carboxylic acid (6 mg, 0.018 mmol), (R)-tert-butyl piperidin-3-ylcarbamate (33.9 mg, 0.169 mmol) and HATU (25.3 mg, 0.067 mmol) in N,N-dimethylformamide (1 mL) was added DIPEA (39.2 µL, 0.225 mmol) and the reaction mixture stirred at rt for 2.5 h. The reaction mixture was blown down under a stream of nitrogen and the residue loaded in dichloromethane and purified by SPE (aminopropyl, 2 g), eluted using 10% methanol in dichloromethane. The appropriate fractions were combined and dried under a stream of nitrogen to give a brown gum. The gum was dissolved in DMSO (0.5 ml) and purified by MDAP (method B). The solvent was dried under a stream of nitrogen to give a colourless gum. Dichloromethane (0.8 mL) was added, followed by trifluoroacetic acid (200 µL, 2.60 mmol), and the reaction mixture stirred at rt for 3 h. The reaction mixture was blown down under a stream of nitrogen and the residue loaded in dichloromethane and purified by SPE (aminopropyl, 2 g), eluted using 10% methanol in dichloromethane. The appropriate fractions were combined and dried under a stream of nitrogen to give the required product (R)-(3-aminopiperidin-1-yl)(2-(1-ethyl-1H-indol-2-yl)-1,7-dimethyl-1H-benzo[d]imidazol-5-yl)methanone (4.3 mg, 10.35 µmol, 57.5% yield) as a colourless gum.

LCMS (Method B): Rt 0.79 min, MH+ 416.

Example 94: (R)-(3-Aminopiperidin-1-yl)(1-(3-aminopropyl)-2-(1-ethyl-1H-indol-2-yl)-1H-benzo[d]imidazol-5-yl)methanone, Bis-Hydrochloride Salt

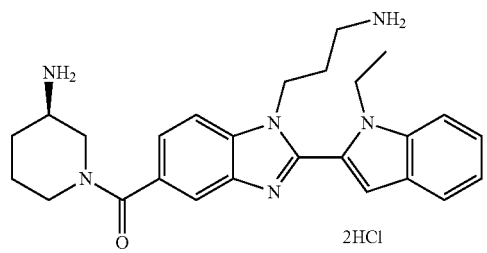 [SMILES: CCn1c(-c2nc3cc(C(=O)N4CCC[C@@H](N)C4)ccc3n2CCCN)cc2ccccc21]

4M Hydrochloric acid in 1,4-dioxane (918 µL, 3.67 mmol) was added to (R)-tert-butyl (1-(1-(3-aminopropyl)-2-(1-ethyl-1H-indol-2-yl)-1H-benzo[d]imidazole-5-carbonyl)piperidin-3-yl)carbamate (25 mg, 0.046 mmol) and the mixture stirred at rt for approximately 6 h before being evaporated to dryness under a stream of nitrogen to leave the required product (R)-(3-aminopiperidin-1-yl)(1-(3-aminopropyl)-2-(1-ethyl-1H-indol-2-yl)-1H-benzo[d]imidazol-5-yl)methanone, bis-hydrochloride salt (15 mg, 0.029 mmol, 63.2% yield).

LCMS (Method A): Rt=0.80 min, MH$^+$=445.

Example 95: (R)-(3-Aminopiperidin-1-yl)(1-ethyl-2-(1-ethyl-1H-indol-2-yl)-1H-benzo[d]imidazol-5-yl)methanone, Hydrochloride Salt

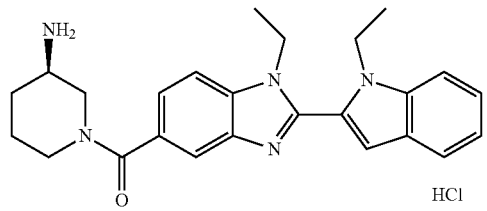 [SMILES: CCn1c(-c2nc3cc(C(=O)N4CCC[C@@H](N)C4)ccc3n2CC)cc2ccccc21 ; Cl]

4M Hydrochloric acid in 1,4-dioxane (1 mL, 4.00 mmol) was added to (R)-tert-butyl (1-(1-ethyl-2-(1-ethyl-1H-indol-2-yl)-1H-benzo[d]imidazole-5-carbonyl)piperidin-3-yl)carbamate (140 mg, 0.272 mmol) in 1,4-dioxane (3 mL) for 2 h. The reaction mixture was evaporated to dryness under a stream of nitrogen, triturated with ether (2 mL), filtered and dried in a vacuum oven to leave (R)-(3-aminopiperidin-1-yl)(1-ethyl-2-(1-ethyl-1H-indol-2-yl)-1H-benzo[d]imidazol-5-yl)methanone, hydrochloride salt (98 mg, 0.217 mmol, 80% yield).

LCMS (Method B): Rt=0.84 min, MH+ 416.

Example 96: (R)-(3-Aminopiperidin-1-yl)(2-(1-ethyl-1H-indol-2-yl)-3-methyl-3H-imidazo[4,5-b]pyridin-6-yl)methanone, Hydrochloride Salt

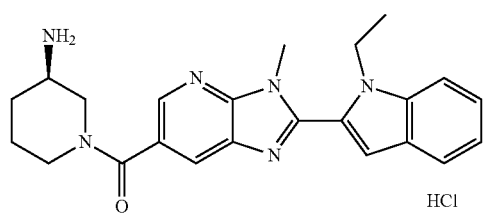 [SMILES: CCn1c(-c2nc3cc(C(=O)N4CCC[C@@H](N)C4)cnc3n2C)cc2ccccc21 ; Cl]

Prepared in a similar manner to Example 95, from (R)-tert-butyl (1-(1-ethyl-2-(1-ethyl-1H-indol-2-yl)-1H-benzo[d]imidazole-5-carbonyl)piperidin-3-yl)carbamate.

LCMS (Method B): Rt=0.79 min, MH+ 403.3.

Example 97: trans (+/−)-3-Amino-4-fluoropiperidin-1-yl)(2-(1-ethyl-1H-indol-2-yl)-1-methyl-1H-benzo[d]imidazol-5-yl)methanone

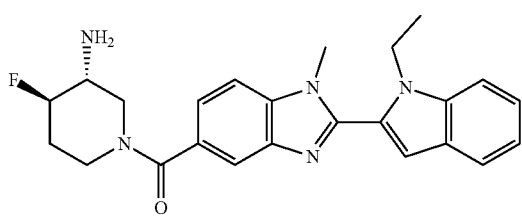 [SMILES: CCn1c(-c2nc3cc(C(=O)N4CC[C@@H](F)[C@H](N)C4)ccc3n2C)cc2ccccc21]

A solution of trans (+/−) tert-butyl (1-(2-(1-ethyl-1H-indol-2-yl)-1-methyl-1H-benzo[d]imidazole-5-carbonyl)-4-fluoropiperidin-3-yl)carbamate (45 mg, 0.087 mmol) in anhydrous 1,4-dioxane (0.4 mL) was treated with HCl (4 M in 1,4-dioxane) (0.4 mL, 1.600 mmol) and left to stir in a stoppered vessel at rt for 1 h. The reaction mixture was evaporated under vacuum and the solid dissolved in MeOH (1 mL). The solution was applied to a MeOH preconditioned 1 g SCX-2 cartridge which was washed with MeOH (6 mL) followed by 2 M solution of ammonia in MeOH (6 mL). The basic wash was evaporated under a stream of nitrogen and the gum dissolved in ether. The solvent was removed under a stream of nitrogen and the solid dried in a vacuum oven overnight to give the title compound as a white powder (33 mg, 0.079 mmol, 91%).

LCMS (Method B): Rt: 0.82 min, MH$^+$ 420

Example 98: cis-((+/−)-3-Amino-4-hydroxypiperidin-1-yl)(2-(1-ethyl-1H-indol-2-yl)-1-methyl-1H-benzo[d]imidazol-5-yl)methanone

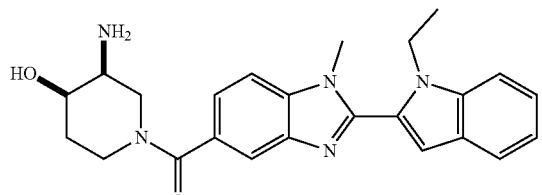

Prepared in a similar manner to Example 97, from cis-(+/−)-tert-butyl (1-(2-(1-ethyl-1H-indol-2-yl)-1-methyl-1H-benzo[d]imidazole-5-carbonyl)-4-hydroxypiperidin-3-yl)carbamate LCMS (Method B): Rt=0.79 mins, MH$^+$=418.2

Example 99: trans-((+/−)-3-Amino-4-hydroxypiperidin-1-yl)(2-(1-ethyl-1H-indol-2-yl)-1-methyl-1H-benzo[d]imidazol-5-yl)methanone

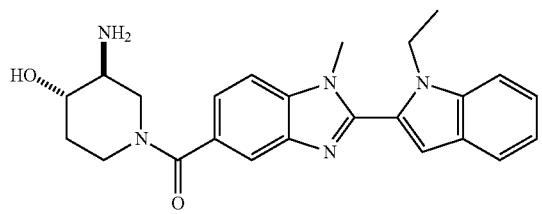 [SMILES: CCn1c(-c2nc3cc(C(=O)N4CC[C@H](O)[C@@H](N)C4)ccc3n2C)cc2ccccc21]

Prepared in a similar manner to Example 97, from trans (+/−)-tert-butyl (1-(2-(1-ethyl-1H-indol-2-yl)-1-methyl-1H-benzo[d]imidazole-5-carbonyl)-4-hydroxypiperidin-3-yl)carbamate LCMS (Method B): Rt=0.74 mins, MH$^+$=418.2

Example 100: cis (+/−)-3-Amino-4-methoxypiperidin-1-yl)(2-(1-ethyl-1H-indol-2-yl)-1-methyl-1H-benzo[d]imidazol-5-yl)methanone

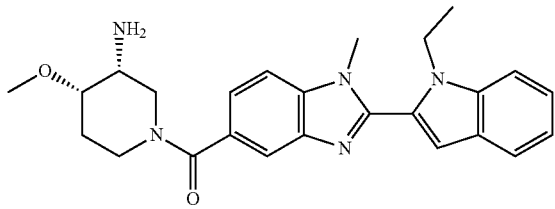 [SMILES: CCn1c(-c2nc3cc(C(=O)N4CC[C@H](OC)[C@H](N)C4)ccc3n2C)cc2ccccc21]

Prepared in a similar manner to Example 97, from cis (+/−)-tert-butyl (1-(2-(1-ethyl-1H-indol-2-yl)-1-methyl-1H-benzo[d]imidazole-5-carbonyl)-4-methoxypiperidin-3-yl)carbamate.

LCMS (Method B): Rt: 0.84 min, MH+ 432.

Example 101: (3R)-1-{[2-(7-Bromo-1-ethyl-1H-indol-2-yl)-1-methyl-1H-benzimidazol-5-yl]carbonyl}-3-piperidinamine

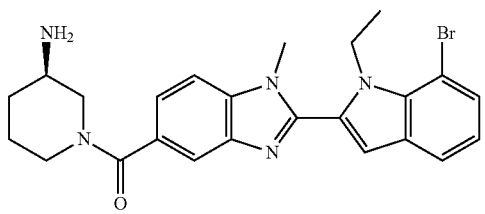 [SMILES: CCn1c(-c2nc3cc(C(=O)N4CCC[C@@H](N)C4)ccc3n2C)cc2cccc(Br)c21]

A solution of 7-bromo-1-ethyl-1H-indole-2-carboxylic acid (300 mg, 1.12 mmol) and HATU (468 mg, 1.23 mmol) in DMF (2 mL) was stirred for around 5 min at rt. To this was added a solution of 1,1-dimethylethyl ((3R)-1-{[3-amino-4-(methylamino)phenyl]carbonyl}-3-piperidinyl)carbamate (390 mg, 1.12 mmol) and DIPEA (0.586 ml, 3.36 mmol) in DMF (5 mL) and the mixture stirred under nitrogen at rt for 16 h. The mixture was partitioned using EtOAc (50 mL) and water (40 mL), the organic layer was isolated, then the aqueous layer reextracted with EtOAc (2×50 mL). The combined organic layers were passed through a hydrophobic frit then concentrated under reduced pressure and azeotroped with toluene give the crude amide intermediate. The crude material was dissolved in toluene (12.5 mL) and acetic acid (0.070 mL, 1.23 mmol) added. The reaction mixture was refluxed for 5 h then allowed to stir for a further 48 h and then concentrated under reduced pressure. The crude material was loaded in MeOH onto an SCX-II SPE column which was eluted with MeOH then 2M ammonia in MeOH. The desired product eluted in the ammonia fractions which were combined then concentrated under reduced pressure to give 610 mg of the crude product as a brown gum. The crude material was purified with column chromatography (eluted with 0 to 15% 2N ammonia in MeOH/100 to 85% EtOAc) to give the title compound as a pale yellow solid (300 mg, 56%).

LCMS (Method B): MH+=480.1/482.1, Rt=0.88 min

¹H NMR (400 MHz, DMSO-d₆) □ ppm: 7.85-7.76 (m, 3H), 7.59 (d, 1H), 7.44 (d, 1H), 7.19 (s, 1H), 7.13 (dd, 1H), 4.90 (q, 2H), 4.41-4.04 (m, 1H), 3.98 (s, 3H), 3.87-3.41 (m, 1H), 3.08-2.93 (m, 1H), 2.83-2.64 (m, 2H), 1.99-1.86 (m, 1H), 1.79-1.59 (m, 2H), 1.58-1.48 (m, 1H), 1.34 (t, 3H)

Example 102: 2-(5-{[(3R)-3-Amino-1-piperidinyl]carbonyl}-1-methyl-1H-benzimidazol-2-yl)-1-ethyl-1H-indol-7-ol

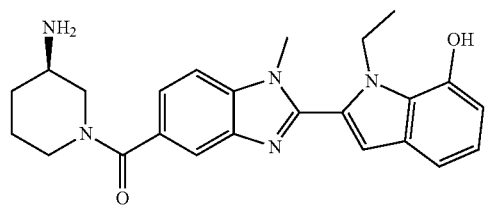 [SMILES: CCn1c(-c2nc3cc(C(=O)N4CCC[C@@H](N)C4)ccc3n2C)cc2cccc(O)c21]

To a solution of (3R)-1-({2-[1-ethyl-7-(methyloxy)-1H-indol-2-yl]-1-methyl-1H-benzimidazol-5-yl}carbonyl)-3-piperidinamine (61 mg, 0.14 mmol) in DCM (1.5 mL) under nitrogen and cooled to around 0° C. was added dropwise a solution of boron tribromide (1M in DCM, 0.14 mL, 0.14 mmol). The reaction mixture was stirred in an ice-water bath for 15 min, then allowed to warm to rt for 1.5 h. MeOH (5 mL) was added, then the mixture concentrated under reduced pressure. The mixture was loaded in MeOH onto an SCX SPE column then washed with MeOH and product eluted with 10% ammonia in MeOH then purified by mass directed autoprep to give the title compound as a brown solid (21 mg, 36%).

LCMS: (Method A) Rt=0.83 mins, MH+=418.3

¹H NMR (400 MHz, DMSO-d₆) □ ppm: 9.86 (br. s., 1H), 7.78-7.69 (m, 2H), 7.37 (d, 1H), 7.11 (d, 1H), 6.94 (s, 1H), 6.90 (dd, 1H), 6.66 (d, 1H), 4.75 (q, 2H), 4.41-4.08 (m, 1H), 3.93 (s, 3H), 3.80-3.48 (m, 1H), 3.08-2.87 (m, 2H), 2.84-2.65 (m, 2H), 1.95-1.82 (m, 1H), 1.78-1.59 (m, 1H), 1.54-1.37 (m, 1H), 1.24 (t, 3H)

Example 103: 2-(5-{[(3R)-3-Amino-1-piperidinyl]carbonyl}-1-methyl-1H-benzimidazol-2-yl)-1-(cyclopropylmethyl)-1H-indol-5-ol

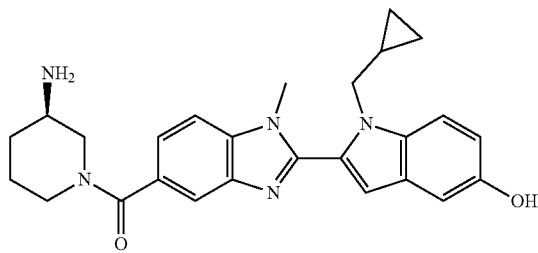 [SMILES: Cn1c(-c2cc3cc(O)ccc3n2CC2CC2)nc2cc(C(=O)N3CCC[C@@H](N)C3)ccc21]

(R)-(3-Aminopiperidin-1-yl)(2-(1-(cyclopropylmethyl)-5-methoxy-1H-indol-2-yl)-1-methyl-1H-benzo[d]imidazol-5-yl)methanone (56 mg, 0.122 mmol) was dissolved in dichloromethane (DCM) (1 mL) and cooled to ~78° C. Boron tribromide (0.122 mL, 0.122 mmol) was added dropwise and the reaction stirred for 1 h. The reaction was warmed to 0° C. and stirred for a further 1 h. A further aliquot of boron tribromide (0.244 mL, 0.244 mmol) was added and the reaction warmed to rt and stirred for a further 1 h. A further aliquot of boron tribromide (0.244 mL, 0.244 mmol) was added and the reaction stirred for a further 1 h.

The reaction was quenched with MeOH (5 mL) and the reaction mixture concentrated in vacuo. A further amount of MeOH (5 mL) was added and the solvent again removed in vacuo. The crude product was dissolved in MeOH and added directly to a 2 g SCX cartridge. It was eluted with methanol (3 column volumes) and product eluted as free base with 2M ammonia in methanol. The filtrate from the ammonia fractions was concentrated in vacuo to yield the crude product as a green oil. The crude product was further purified by MDAP (Method A). The appropriate fractions from the MDAP were combined and concentrated in vacuo to afford the product as a beige solid—(R)-(3-aminopiperidin-1-yl) (2-(1-(cyclopropylmethyl)-5-hydroxy-1H-indol-2-yl)-1-methyl-1H-benzo[d]imidazol-5-yl)methanone (32 mg, 0.072 mmol, 58.9% yield).

LCMS (Method B): Rt=0.64 min, MH+=444.2

Example 104: 2-(5-{[(3R)-3-Amino-1-piperidinyl]carbonyl}-1-methyl-1H-benzimidazol-2-yl)-1-ethyl-1H-indol-6-ol

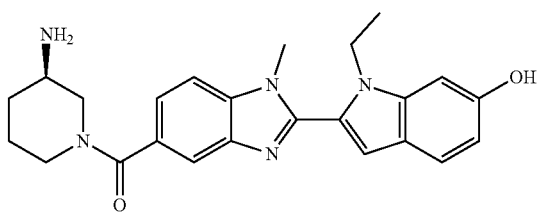 [SMILES: CCn1c(-c2nc3cc(C(=O)N4CCC[C@@H](N)C4)ccc3n2C)cc2ccc(O)cc21]

Prepared in a similar manner to Example 103 from (R)-(3-aminopiperidin-1-yl)(2-(1-ethyl-6-methoxy-1H-indol-2-yl)-1-methyl-1H-benzo[d]imidazol-5-yl)methanone in 86% yield.

LCMS (Method A): Rt=0.78 min, MH+=418.2

Example 105: (3R)-1-{[2-(1-Ethyl-7-fluoro-1H-indol-2-yl)-1-methyl-1H-benzimidazol-5-yl]carbonyl}-3-piperidinamine

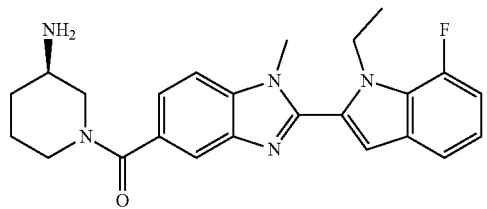 [SMILES: CCn1c(-c2nc3cc(C(=O)N4CCC[C@@H](N)C4)ccc3n2C)cc2cccc(F)c21]

To a solution of 1-ethyl-7-fluoro-1H-indole-2-carboxylic acid (89 mg, 0.43 mmol) and HATU (180 mg, 0.47 mmol) in DMF (2 mL) that had been stirred at rt for around 5 min was added a solution of 1,1-dimethylethyl ((3R)-1-{[3-amino-4-(methylamino)phenyl]carbonyl}-3-piperidinyl)carbamate (150 mg, 0.43 mmol) and DIPEA (0.225 ml, 1.29 mmol) in DMF (2 mL). The reaction mixture was stirred at rt under nitrogen for 2 h then further 1-ethyl-7-fluoro-1H-indole-2-carboxylic acid (89 mg, 0.43 mmol) and HATU (180 mg, 0.47 mmol) was added and the reaction mixture allowed to stir for a further 17 h and then concentrated under reduced pressure. The crude material was loaded onto an SCX SPE column, eluting with MeOH then 2N ammonia in MeOH. The desired amide intermediate eluted in the ammonia fractions which were combined then concentrated under reduced pressure, then azeotroped with cyclohexane to give the crude amide intermediate as a cream solid.

To the crude intermediate was added a solution of 4-methylbenzenesulfonic acid monohydrate in acetic acid (0.056 mL, 0.32 mmol) and toluene (10.0 mL) and the mixture refluxed for 5 h and allowed to cool to rt overnight.

The mixture was concentrated under reduced pressure and DCM (3 mL) and TFA (3 mL) added. The reaction mixture was stirred under nitrogen at rt for 40 min and concentrated under reduced pressure. The mixture was loaded in MeOH onto a SCX SPE column which was eluted with MeOH then 2M ammonia in MeOH. The desired product eluted in the ammonia-based fractions which were combined then concentrated under reduced pressure to give the crude product as a brown oil that solidified on standing. The material was purified by MDAP (Method A) to give the title compound as an off-white solid (63 mg). An impurity remained so material was purified once more by MDAP (Method C). Material was loaded in MeOH onto a SCX SPE column which was eluted with MeOH then 2M ammonia in MeOH. Desired product eluted in the ammonia fractions which were combined then concentrated under reduced pressure to give the title compound as a colourless oil (37 mg, 18%)

LCMS (Method C): MH+=420.1, Rt=0.77 min $^1$H NMR (400 MHz, DMSO-$d_6$) □ ppm: 7.82-7.68 (m, 2H), 7.57-7.48 (m, 1H), 7.38 (d, 1H), 7.20-7.06 (m, 3H), 4.63 (q, 2H), 4.43-4.09 (m, 1H), 3.97 (s, 3H), 3.76-3.21 (m, 2H), 3.07-2.55 (m, 2H), 2.32-2.09 (m, 1H), 1.95-1.81 (m, 1H), 1.80-1.56 (m, 1H), 1.55-1.38 (m, 1H), 1.34 (t, 3H)

Example 106: (R)-(3-Aminopiperidin-1-yl)(2-(1-ethyl-4-fluoro-1H-indol-2-yl)-1-methyl-1H-benzo[d]imidazol-5-yl)methanone

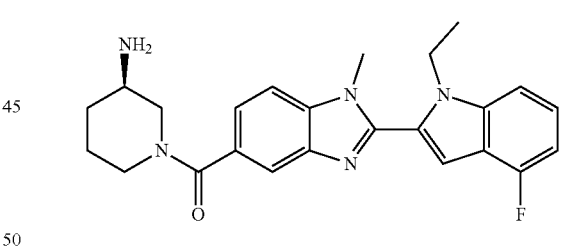

HATU (50.5 mg, 0.133 mmol) and DIPEA (0.063 mL, 0.362 mmol) were added to a solution of 1-ethyl-4-fluoro-1H-indole-2-carboxylic acid (25 mg, 0.121 mmol, commercially available from, for example, Apollo Scientific) in N,N-dimethylformamide (2 mL). The mixture was left to stir for a few minutes then (R)-tert-butyl (1-(3-amino-4-(methylamino)benzoyl)piperidin-3-yl)carbamate (42.0 mg, 0.121 mmol) was added. The reaction was left at rt overnight, then was concentrated under reduced pressure. The residue was dissolved in DMF (2 mL) and 4-toluene sulphonic acid monohydrate (27.3 mg, 0.144 mmol) was added. The reaction was heated to 110° C. for 3 h after which it was concentrated under reduced pressure. The residue was purified by MDAP (Method B) to provide a colourless oil (14 mg, 28%).

LCMS (Method B): Rt=0.80 mins, MH+=420.2

Example 107: 2-(5-{[(3R)-3-Amino-1-piperidinyl]carbonyl}-1-methyl-1H-benzimidazol-2-yl)-1-ethyl-1H-indole-7-carbonitrile

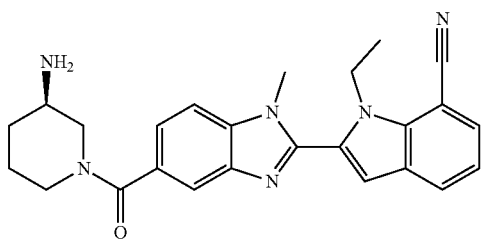 [SMILES: CCn1c(-c2nc3cc(C(=O)N4CCC[C@@H](N)C4)ccc3n2C)cc2cccc(C#N)c21]

To a stirred solution of (3R)-1-{[2-(7-bromo-1-ethyl-1H-indol-2-yl)-1-methyl-1H-benzimidazol-5-yl]carbonyl}-3-piperidinamine (50 mg, 0.104 mmol) in DMF (1 mL) in a dried 2 mL microwave vial under nitrogen was added zinc cyanide (100 mg, 0.85 mmol) then the mixture was allowed to stir for 20 min. Palladium tetrakistriphenylphosphine (15 mg, 0.013 mmol) was added to the reaction mixture and the vial heated at 110° C. for 2 h using a microwave. Further palladium tetrakis (15 mg, 0.013 mmol) was added then the reaction mixture heated at 110° C. for a further 2 h. The crude mixture was loaded in MeOH onto an SCX-II SPE column, washed with MeOH then eluted with 2N ammonia in MeOH. Desired product eluted in the ammonia/MeOH fractions which were combined then concentrated under reduced pressure to give the crude product which was purified by MDAP (Method A). Fractions containing desired product were combined then concentrated under reduced pressure to give the title compound as a pale yellow solid (15.4 mg, 35%).

LCMS (Method B): MH+=427.2, Rt=0.79 min $^1$H NMR (400 MHz, DMSO-$d_6$) ☐ ppm 8.10 (d, 1H), 7.82 (d, 1H), 7.79-7.68 (m, 2H), 7.39 (d, 1H), 7.36-7.27 (m, 2H), 4.81 (q, 2H), 4.43-4.01 (m, 1H), 3.96 (s, 3H), 3.75-3.45 (m, 1H), 3.03-2.86 (m, 1H), 2.81-2.58 (m, 2H), 1.93-1.81 (m, 1H), 1.78-1.57 (m, 2H), 1.42 (t, 3H), 1.37-1.12 (m, 1H)

Example 108: (5-Amino-5,6-dihydropyridin-1(2H)-yl)(2-(1-ethyl-1H-indol-2-yl)-1-methyl-1H-benzo[d]imidazol-5-yl)methanone

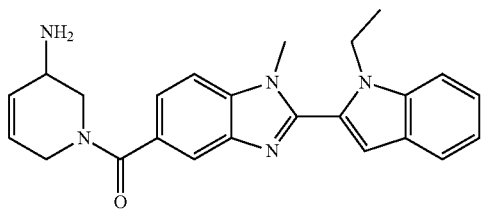 [SMILES: CCn1c(-c2nc3cc(C(=O)N4CC=CC(N)C4)ccc3n2C)cc2ccccc21]

To a stirred solution of (5-azido-5,6-dihydropyridin-1(2H)-yl)(2-(1-ethyl-1H-indol-2-yl)-1-methyl-1H-benzo[d]imidazol-5-yl)methanone (71.4 mg, 0.168 mmol) in THF (8 mL) was added triphenylphosphine (66 mg, 0.252 mmol), followed by water (0.2 mL). After 66 h the mixture was heated to reflux for 2 min then allowed to cool to rt. After a further 21 h the mixture was concentrated in vacuo. Water was added to the residue and potassium dihydrogenorthophosphate added to take the solution to pH 4. The mixture was extracted with EtOAc (×3). The aqueous was then basified with NaHCO$_3$ and extracted with DCM. The DCM extracts were then dried (Na$_2$SO$_4$), filtered, and concentrated in vacuo to give a residue. This residue was taken up in DCM and loaded onto a silica cartridge (25 g) and eluted with (NH$_3$ $_{[2}$M] in MeOH) in DCM, 0-10%, to give the title compound as a colourless gum (52 mg).

LCMS (Method B): Rt=0.78 min, MH+=400.1

Example 109: (R)-(3-Aminopiperidin-1-yl)(2-(1-ethyl-1H-indol-2-yl)-7-(3-hydroxypropoxy)-1-methyl-1H-benzo[d]imidazol-5-yl)methanone

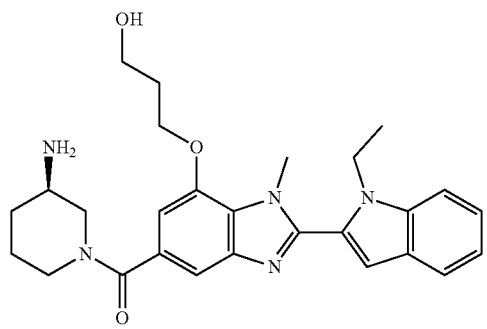 [SMILES: CCn1c(-c2nc3cc(C(=O)N4CCC[C@@H](N)C4)cc(OCCCO)c3n2C)cc2ccccc21]

To a solution of (R)-tert-butyl (1-(2-(1-ethyl-1H-indol-2-yl)-7-hydroxy-1-methyl-1H-benzo[d]imidazole-5-carbonyl)piperidin-3-yl)carbamate (50 mg, 0.097 mmol) in THF (2 mL) was added 3-((tert-butyldimethylsilyl)oxy)propan-1-ol (0.041 mL, 0.194 mmol) and triphenylphosphine (51 mg, 0.194 mmol). The mixture was flushed with nitrogen then cooled to around 0° C. using an ice/water bath and then a solution of di-tert-butyl diazene-1,2-dicarboxylate (45 mg, 0.195 mmol) in THF (2 mL) was added dropwise. The mixture was allowed to stir at rt for 20 h then further THF (4 mL) was added. Further 3-((tert-butyldimethylsilyl)oxy)propan-1-ol (0.041 mL, 0.194 mmol) was added, followed by triphenylphosphine (51 mg, 0.194 mmol) and di-tert-butyl azodicarboxylate (45 mg, 0.195 mmol) and the mixture allowed to stir 4.5 h. The mixture was concentrated under reduced pressure to give the crude product as a yellow oil. The material was dissolved in DCM (3 mL) then TFA (3 mL) was added dropwise. The mixture was stirred for 30 min then concentrated under reduced pressure and the resulting residue dissolved in DMSO (3 mL) then purified in three portions by MDAP (Method A) to give a mixture of the title compound and triphenylphosphine. The mixture was loaded onto an SCX SPE column which was eluted with methanol followed by ammonia in methanol (2M). Fractions containing desired product were combined then concentrated under reduced pressure and the resulting material redissolved in DMSO (1 mL) then further purified by MDAP (Method A) to give the title compound as a white solid (7 mg, 15%).

LCMS (Method B): Rt=0.95 min, MH+=476.3

Example 110: (R)-(3-Aminopiperidin-1-yl)(7-ethoxy-2-(1-ethyl-1H-indol-2-yl)-1-methyl-1H-benzo[d]imidazol-5-yl)methanone

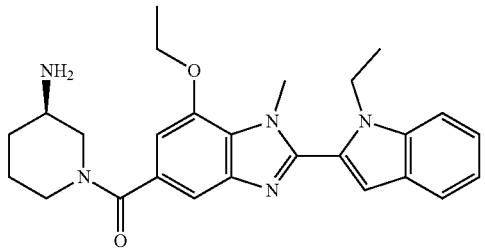 [SMILES: CCOc1cc(C(=O)N2CCC[C@@H](N)C2)cc2nc(-c3cc4ccccc4n3CC)n(C)c12]

To a solution of (R)-tert-butyl (1-(2-(1-ethyl-1H-indol-2-yl)-7-hydroxy-1-methyl-1H-benzo[d]imidazole-5-carbonyl)piperidin-3-yl)carbamate (50 mg, 0.097 mmol) in THF (2 mL) was added anhydrous EtOH (11 μL, 0.195 mmol) followed by triphenylphosphine (51 mg, 0.194 mmol). The mixture was flushed with nitrogen then cooled to around 0° C. using an ice/water bath and then a solution of di-tert-butyl diazene-1,2-dicarboxylate (45 mg, 0.195 mmol) in THF (2 mL) was added to the mixture in a dropwise fashion. The reaction mixture was allowed to stir for 16 h at rt then further di-tert-butyl diazene-1,2-dicarboxylate (45 mg, 0.195 mmol), triphenylphosphine (51 mg, 0.194 mmol) and EtOH (11 μL, 0.195 mmol) were added and the mixture allowed to stir under nitrogen for a further 16 h. The reaction mixture was concentrated under reduced pressure and the resulting material dissolved in DCM (2 mL) and TFA (2 mL) added. The reaction mixture was allowed to stir under nitrogen for 2 h, then concentrated under reduced pressure. The material was dissolved in a 1:1 mixture of DMSO and MeOH then purified in two portions by MDAP (Method A) to give the title compound (45 mg, 89%).

LCMS (Method B): Rt=0.90 min, MH$^+$=446.2

Example 111: (R)-(3-Aminopiperidin-1-yl)(2-(1-ethyl-1H-indol-2-yl)-7-(2-methoxyethoxy)-1-methyl-1H-benzo[d]imidazol-5-yl)methanone

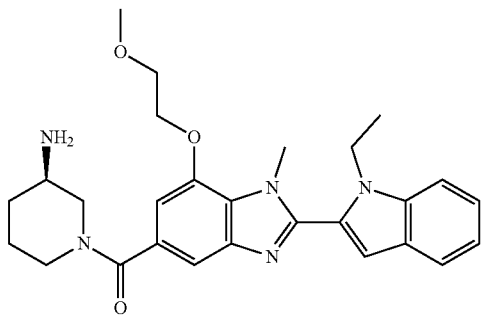 [SMILES: CCn1c(-c2nc3cc(C(=O)N4CCC[C@@H](N)C4)cc(OCCOC)c3n2C)cc2ccccc21]

Prepared in a similar manner to Example 110, from (R)-tert-butyl (1-(2-(1-ethyl-1H-indol-2-yl)-7-hydroxy-1-methyl-1H-benzo[d]imidazole-5-carbonyl)piperidin-3-yl)carbamate and 2-methoxyethanol.

LCMS (Method B): Rt=0.84 min, MH$^+$=476.3

Example 112: (R)-(3-Aminopiperidin-1-yl)(2-(1-ethyl-1H-indol-2-yl)-7-(2-hydroxyethoxy)-1-methyl-1H-benzo[d]imidazol-5-yl)methanone

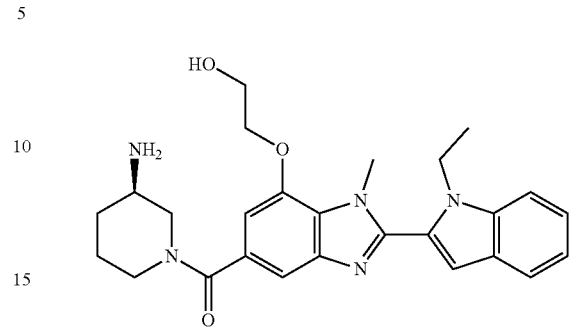

To a solution of (R)-tert-butyl (1-(2-(1-ethyl-1H-indol-2-yl)-7-hydroxy-1-methyl-1H-benzo[d]imidazole-5-carbonyl)piperidin-3-yl)carbamate (50 mg, 0.097 mmol) in DMF (5 mL) was added (2-bromoethoxy)(tert-butyl)dimethylsilane (21 μL, 0.098 mmol) and cesium carbonate (63 mg, 0.193 mmol). The mixture was flushed with nitrogen and then stirred for 17 h at rt. The reaction mixture was concentrated under reduced pressure then partitioned between water (15 mL) and EtOAc (15 mL), and the layers separated. The aqueous layer was re-extracted with EtOAc (2×15 mL) then the combined organic layers backwashed with water (20 mL) before being passed through a hydrophobic frit and concentrated under reduced pressure. The resulting material was dissolved in DCM (2 mL) then TFA (2 mL) added dropwise and the reaction stirred at rt for 18 h. The reaction mixture was concentrated under reduced pressure, then loaded in MeOH onto an SCX SPE column, eluting the crude product using a solution of ammonia in MeOH (2M). Fractions containing product were combined then concentrated under reduced pressure, then the material was dissolved in DMSO (1 mL) and purified by MDAP (Method A) to give the title compound as a white solid (12 mg, 27% yield).

LCMS (Method B): Rt=0.91 min, MH$^+$=462.4

Example 113: (R)-2-((5-(3-Aminopiperidine-1-carbonyl)-2-(1-ethyl-1H-indol-2-yl)-1-methyl-1H-benzo[d]imidazol-7-yl)oxy)acetonitrile

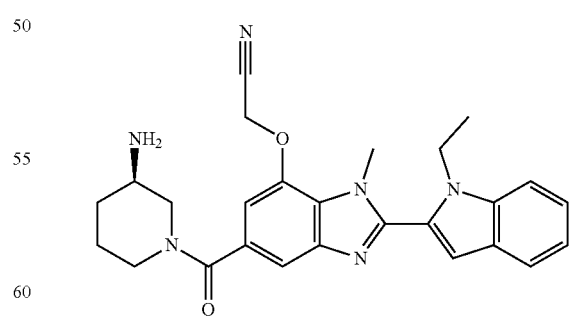

Prepared in a similar manner to Example 112, from (R)-tert-butyl (1-(2-(1-ethyl-1H-indol-2-yl)-7-hydroxy-1-methyl-1H-benzo[d]imidazole-5-carbonyl)piperidin-3-yl)carbamate and 2-bromoacetonitrile.

LCMS (Method A): Rt=1.02 min, MH$^+$=457.3

Example 114: (R)-2-((5-(3-Aminopiperidine-1-carbonyl)-2-(1-ethyl-1H-indol-2-yl)-1-methyl-1H-benzo[d]imidazol-7-yl)oxy)acetamide

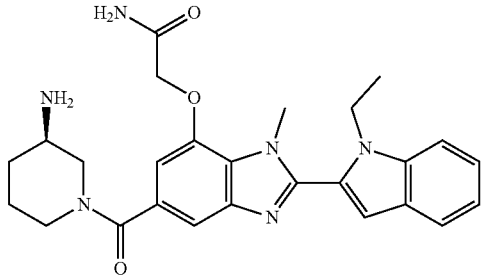 [SMILES: CCn1c(-c2nc3cc(C(=O)N4CCC[C@@H](N)C4)cc(OCC(N)=O)c3n2C)cc2ccccc21]

Prepared in a similar manner to Example 112, from (R)-tert-butyl (1-(2-(1-ethyl-1H-indol-2-yl)-7-hydroxy-1-methyl-1H-benzo[d]imidazole-5-carbonyl)piperidin-3-yl)carbamate and 2-bromoacetamide.

LCMS (Method A): Rt=0.88 min, MH$^+$=475.3

Example 115: (R)-(3-Aminopiperidin-1-yl)(2-(1-ethyl-1H-indol-2-yl)-7-hydroxy-1-methyl-1H-benzo[d]imidazol-5-yl)methanone

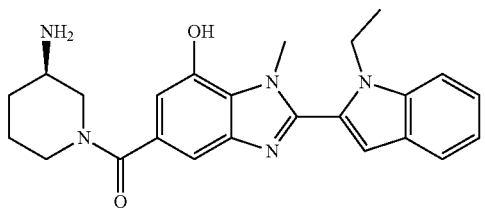 [SMILES: CCn1c(-c2nc3cc(C(=O)N4CCC[C@@H](N)C4)cc(O)c3n2C)cc2ccccc21]

A 3 necked flask was dried (132° C.) for 4 h. The flask was cooled under nitrogen, evacuated and back filled 4 times, then was charged with (R)-(3-aminopiperidin-1-yl)(2-(1-ethyl-1H-indol-2-yl)-7-methoxy-1-methyl-1H-benzo[d]imidazol-5-yl)methanone (59 mg, 0.137 mmol) dissolved in dichloromethane (2 mL). This solution was cooled to 0° C. then boron tribromide (0.137 mL, 0.137 mmol) was added dropwise. The reaction mixture was left in the ice bath for 20 min then was allowed to warm to rt. LCMS analysis showed partial conversion therefore the solution was cooled to 0° C. and boron tribromide (0.137 mL, 0.137 mmol) was added. The resultant solution was allowed to warm to rt. Extra boron tribromide (0.137 mL, 0.137 mmol) was successively added another 5 times under the same process until an increase in by-product was observed. The reaction was quenched by slow addition of methanol (5 mL). A further 5 mL of methanol was added and the solvent was removed under vacuum. The crude mixture was purified by MDAP (Method A) to afford a colourless oil that was dried in a vacuum oven overnight to afford the title product as a colourless oil (22 mg, 39%).

LCMS (Method B): Rt=0.74 min, MH$^+$=418.1

Example 116: (+/−)-(3-Amino-4-methylpiperidin-1-yl)(2-(1-ethyl-1H-indol-2-yl)-1-methyl-1H-benzo[d]imidazol-5-yl)methanone, Trans-Isomer

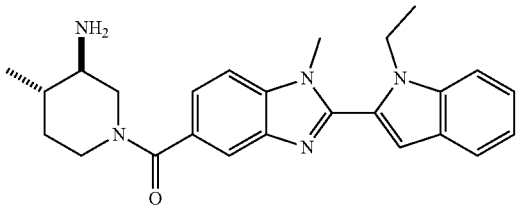 [SMILES: CCn1c(-c2nc3cc(C(=O)N4CC[C@H](C)[C@@H](N)C4)ccc3n2C)cc2ccccc21]

N-(1-(2-(1-Ethyl-1H-indol-2-yl)-1-methyl-1H-benzo[d]imidazole-5-carbonyl)-4-methylpiperidin-3-yl)-2,2,2-trifluoroacetamide, trans-isomer (140 mg, 0.274 mmol) was stirred in methanol (4 mL) and water (1 mL) with potassium carbonate (76 mg, 0.547 mmol) at 50° C. for 20 h. The reaction mixture was partitioned between brine and DCM. The aqueous layer was further extracted with DCM. The organics were combined, passed through a hydrophobic cartridge and concentrated under vacuum. The residue was purified by Biotage SP4 chromatography on a 10 g silica SNAP cartridge, eluting with 2M NH$_3$/MeOH in DCM 0 to 10% over 12 column volumes to afford the desired product as a colourless oil (74 mg, 65%).

LCMS (Method B): Rt 0.82 min, m/z 416.1 (MH$^+$)

Example 117 and 118: trans-3-Amino-4-methylpiperidin-1-yl)(2-(1-ethyl-1H-indol-2-yl)-1-methyl-1H-benzo[d]imidazol-5-yl)methanone, Hydrochloride Salt, Single Unknown Enantiomers

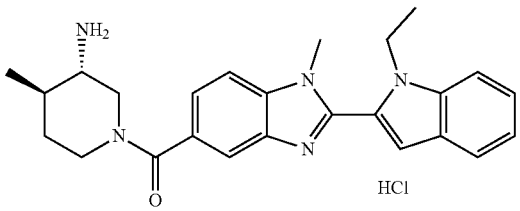 [SMILES: CCn1c(-c2nc3cc(C(=O)N4CC[C@@H](C)[C@H](N)C4)ccc3n2C)cc2ccccc21 ; Cl]

Both enantiomers of trans-3-amino-4-methylpiperidin-1-yl)(2-(1-ethyl-1H-indol-2-yl)-1-methyl-1H-benzo[d]imidazol-5-yl)methanone were chirally separated from 80 mg mixture (Method J) to give the two enantiomers:

Enantiomer A: 20 mg from chiral separation (25%), then HCl salt made (15 mg, 69%).

LCMS (method B): Rt=0.81 mins, MH$^+$=416.3

Enantiomer B: 10 mg from chiral separation (13%), then HCl salt made (10.3 mg, 95%).

LCMS (method B): Rt=0.82 mins, MH$^+$=416.4

Example 119: (+/−)-(3-Amino-4-methylpiperidin-1-yl)(2-(1-ethyl-1H-indol-2-yl)-1-methyl-1H-benzo[d]imidazol-5-yl)methanone, Cis-Isomer

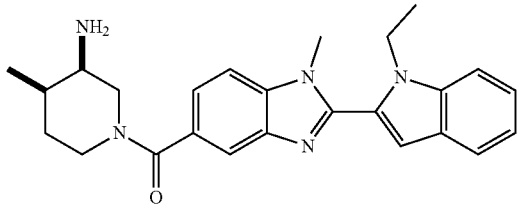 [SMILES: CCn1c(-c2nc3cc(C(=O)N4CC[C@@H](C)[C@@H](N)C4)ccc3n2C)cc2ccccc21]

Prepared in a manner similar to Example 116 from N-(1-(2-(1-ethyl-1H-indol-2-yl)-1-methyl-1H-benzo[d]imidazole-5-carbonyl)-4-methylpiperidin-3-yl)-2,2,2-trifluoroacetamide, cis-isomer.

LCMS (Method B): Rt=0.81 mins, MH$^+$=416.2

Example 120: cis-3-Amino-4-methylpiperidin-1-yl)(2-(1-ethyl-1H-indol-2-yl)-1-methyl-1H-benzo[d]imidazol-5-yl)methanone, Hydrochloride Salt, Single Unknown Enantiomer

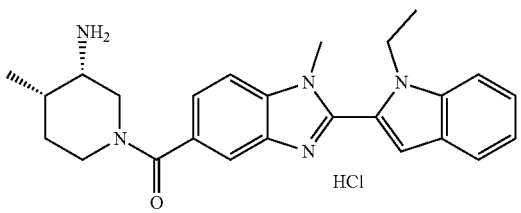 [SMILES: CCn1c(-c2nc3cc(C(=O)N4CC[C@H](C)[C@H](N)C4)ccc3n2C)cc2ccccc21 ; Cl]

Both enantiomers of cis-3-amino-4-methylpiperidin-1-yl)(2-(1-ethyl-1H-indol-2-yl)-1-methyl-1H-benzo[d]imidazol-5-yl)methanone were chirally separated (Method K) to give the second eluted isomer as a colourless oil (77 mg, 28%). The oil was taken up in tetrahydrofuran (1 ml) to which solution hydrogen chloride 1M in diethyl ether (0.185 mL, 0.185 mmol) was added. The suspension was stirred at rt for 5 min then was concentrated to give a white solid (73 mg, 87%).

LCMS (Method B): Rt=0.80 mins, MH$^+$=416.3

Example 121: (+/−)-cis-5-Amino-1-(2-(1-ethyl-1H-indol-2-yl)-1-methyl-1H-benzo[d]imidazole-5-carbonyl)piperidine-3-carboxamide

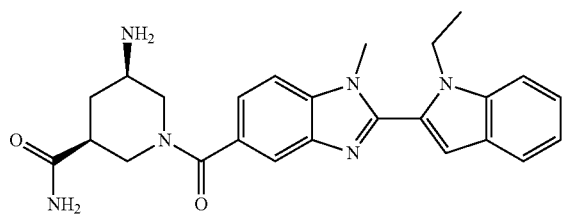 [SMILES: CCn1c(-c2nc3cc(C(=O)N4C[C@H](N)C[C@H](C(N)=O)C4)ccc3n2C)cc2ccccc21]

Prepared in a manner similar to Example 116 from cis-1-(2-(1-ethyl-1H-indol-2-yl)-1-methyl-1H-benzo[d]imidazole-5-carbonyl)-5-(2,2,2-trifluoroacetamido)piperidine-3-carboxamide.

LCMS (method B): Rt=0.71 mins, MH$^+$=445.1

Example 122: (3-Amino-5-methylpiperidin-1-yl)(2-(1-ethyl-1H-indol-2-yl)-1-methyl-1H-benzo[d]imidazol-5-yl)methanone Hydrochloride Salt, Diastereomeric Mixture

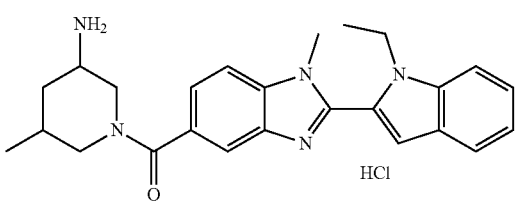 [SMILES: CCn1c(-c2nc3cc(C(=O)N4CC(C)CC(N)C4)ccc3n2C)cc2ccccc21 ; Cl]

To N-(1-(2-(1-ethyl-1H-indol-2-yl)-1-methyl-1H-benzo[d]imidazole-5-carbonyl)-5-methylpiperidin-3-yl)-2,2,2-trifluoroacetamide (42 mg, 0.082 mmol) in methanol (5 mL) and water (2.5 mL) was added K$_2$CO$_3$ (56.7 mg, 0.411 mmol) and the reaction heated to 60° C. for 2 h. The solution was concentrated in vacuo and partitioned between DCM and water (×2), and the aqueous layer extracted with ethyl acetate. The organic layers were combined, the solvent removed and the crude organic re-dissolved in DCM and purified on silica eluting with 0-10% 2M methanolic ammonia in DCM. The appropriate fractions were combined and the solvent removed. The residue was dried under high vacuum overnight to give a clear oil, which was dissolved in DCM (1 mL) and 1.0M ethereal HCl (12 □L) added. The solvent was removed to give the title compound (5 mg, 14%).

LCMS (Method B): Rt=0.82 min, MH+=416.2,

Example 123 and Example 124: cis-(3-Amino-5-methylpiperidin-1-yl)(2-(1-ethyl-1H-indol-2-yl)-1-methyl-1H-benzo[d]imidazol-5-yl)methanone Hydrochloride Salt, Single Unknown Enantiomers

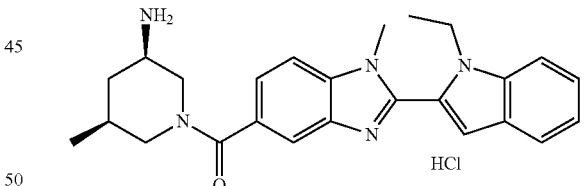

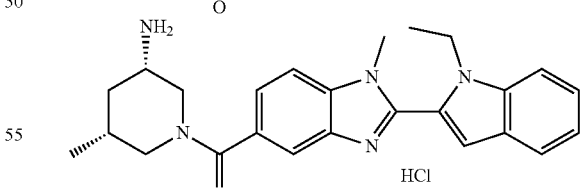

To N-(1-(2-(1-ethyl-1H-indol-2-yl)-1-methyl-1H-benzo[d]imidazole-5-carbonyl)-5-methylpiperidin-3-yl)-2,2,2-trifluoroacetamide (310 mg, 0.606 mmol) in methanol (10 mL) and water (5 mL) was added K$_2$CO$_3$ (419 mg, 3.03 mmol) and the reaction heated to 60° C. for 4 h. The mixture was concentrated in vacuo and partitioned between DCM and brine (×2). The organic layers were combined and the solvent removed to give a white foaming solid. This was separated by chiral preparative HPLC (Method L). The residues were dissolved in DCM (1 mL) and 1.0M ethereal HCl added (0.099 mL & 0.084 mL) and the solvents removed to give the title compounds as off white solids (45 mg, 16% and 30 mg, 11%).

Example 123

LCMS (Method B): MH+=416.3, Rt=0.81 min.

Example 124

LCMS (method B): MH+=416.3, Rt=0.80 min.

Example 125 and Example 126: trans-(3-Amino-5-methylpiperidin-1-yl)(2-(1-ethyl-1H-indol-2-yl)-1-methyl-1H-benzo[d]imidazol-5-yl)methanone hydrochloride salt, Single Enantiomers with Unknown Relative Stereochemistry

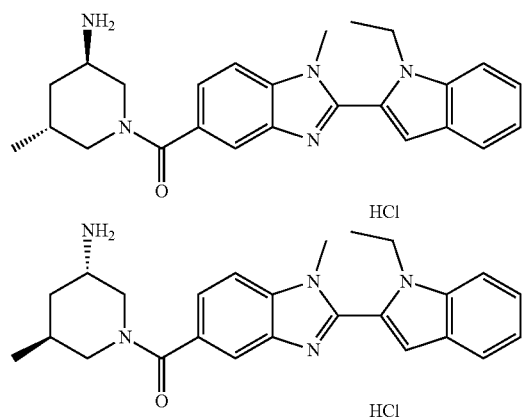

To (3-azido-5-methylpiperidin-1-yl)(2-(1-ethyl-1H-indol-2-yl)-1-methyl-1H-benzo[d]imidazol-5-yl)methanone (104 mg, 0.236 mmol) in ethanol (10 mL) was added Pd(OH)$_2$ (16.54 mg, 0.024 mmol) and the reaction left to stir overnight at rt under a hydrogen atmosphere. The suspension was filtered through celite and washed with ethanol and the solvent then removed. The residue was dissolved in DCM and loaded onto silica eluting with 0-10% 2M methanolic ammonia in DCM. The appropriate fractions were combined and the solvent removed to give a clear oil. The enantiomers were then separated by chiral preparative HPLC (Method M) and dissolved in DCM (1 mL) and ethereal HCl (1.0 M, 36 uL or 31 uL) added. The solvents were removed to give beige solids (9 mg, 8% and 10 mg, 9%).

Example 125

LCMS (Method B): Rt=0.82 min, MH+=416.2.

Example 126

LCMS (Method B): Rt=0.81 min, MH+=416.2.

Example 127: (3-Amino-5-fluoropiperidin-1-yl)(2-(1-ethyl-1H-indol-2-yl)-1-methyl-1H-benzo[d]imidazol-5-yl)methanone, Diastereomeric Mixture

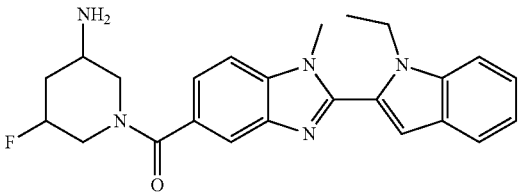 [SMILES: CCn1c(-c2nc3cc(C(=O)N4CC(N)CC(F)C4)ccc3n2C)cc2ccccc21]

To N-(1-(2-(1-ethyl-1H-indol-2-yl)-1-methyl-1H-benzo[d]imidazole-5-carbonyl)-5-fluoropiperidin-3-yl)-2,2,2-trifluoroacetamide (11 mg, 0.021 mmol) in methanol (10 mL) and water (5 mL) was added K$_2$CO$_3$ (14.75 mg, 0.107 mmol) and the reaction heated to 60° C. for 4 h. The solution was concentrated in vacuo and partitioned between DCM and water (×2). The combined organic layers were evaporated and the residue dissolved in methanol and purified by MDAP (Method A). The appropriate fractions were combined and the solvent removed to give a white film (5.1 mg, 57%).

LCMS (Method B): Rt=0.78 min, MH+=420.1.

Example 128: (+/−)-((cis)-3,5-Diaminopiperidin-1-yl)(2-(1-ethyl-1H-indol-2-yl)-1-methyl-1H-benzo[d]imidazol-5-yl)methanone, Hydrochloride Salt

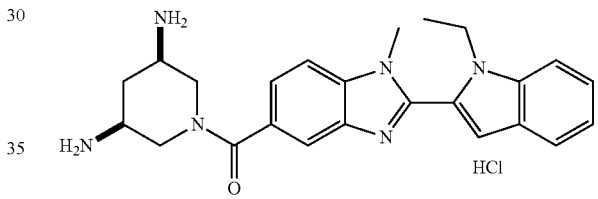

To cis-N,N'-(-1-(2-(1-ethyl-1H-indol-2-yl)-1-methyl-1H-benzo[d]imidazole-5-carbonyl)piperidine-3,5-diyl)bis(2,2,2-trifluoroacetamide) (413 mg, 0.679 mmol) in methanol (10 mL) and water (5 mL) was added K$_2$CO$_3$ (469 mg, 3.39 mmol) and the reaction stirred at 60° C. for 3 h. The solution was concentrated in vacuo and suspended in DCM and partitioned between DCM and water (×3) and the combined organic layers washed with water (×2) and evaporated. The residue was dried under high vacuum overnight and dissolved in DCM (1 mL) and 1.0M ethereal HCl then added (0.353 mL, 1 eq). The solvent was removed to give a pale yellow solid (148 mg, 48%).

LCMS (Method B): Rt=0.70 min, MH+=417.2.

Example 129: (+/−)-((trans)-3-Amino-5-methoxypiperidin-1-yl)(2-(1-ethyl-1H-indol-2-yl)-1-methyl-1H-benzo[d]imidazol-5-yl)methanone, Hydrochloride Salt

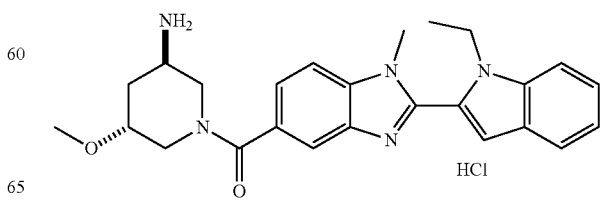

Prepared in a similar manner to Example 128, from N-((trans)-1-(2-(1-ethyl-1H-indol-2-yl)-1-methyl-1H-benzo[d]imidazole-5-carbonyl)-5-methoxypiperidin-3-yl)-2,2,2-trifluoroacetamide.
LCMS (Method B): Rt=0.79 min, MH+=432.3.

Example 130: (3-Amino-5-hydroxypiperidin-1-yl)(2-(1-ethyl-1H-indol-2-yl)-1-methyl-1H-benzo[d]imidazol-5-yl)methanone, Hydrochloride Salt, Diastereomeric Mixture

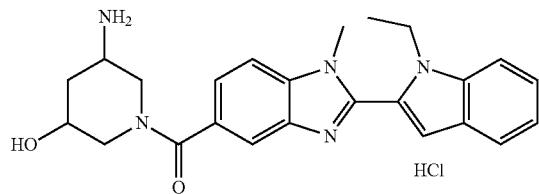 [SMILES: CCn1c(-c2nc3cc(C(=O)N4CC(N)CC(O)C4)ccc3n2C)cc2ccccc21 ; Cl]

Prepared in a similar manner to Example 128, from N-(1-(2-(1-ethyl-1H-indol-2-yl)-1-methyl-1H-benzo[d]imidazole-5-carbonyl)-5-hydroxypiperidin-3-yl)-2,2,2-trifluoroacetamide.
LCMS (Method B): Rt=0.73 min, MH+=418.3.

Example 131: (+/−)-cis-3-Amino-1-(2-(1-ethyl-1H-indol-2-yl)-1-methyl-1H-benzo[d]imidazole-5-carbonyl)piperidine-4-carboxamide, Hydrochloride Salt

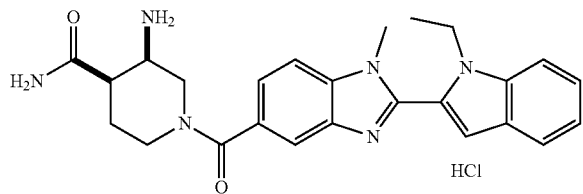 [SMILES: CCn1c(-c2nc3cc(C(=O)N4CC[C@@H](C(N)=O)[C@@H](N)C4)ccc3n2C)cc2ccccc21 ; Cl]

Prepared in a similar manner to Example 128, from cis-1-(2-(1-ethyl-1H-indol-2-yl)-1-methyl-1H-benzo[d]imidazole-5-carbonyl)-3-(2,2,2-trifluoroacetamido)piperidine-4-carboxamide
LCMS (Method B): Rt=0.77 min, MH+=445.3.

Example 132: (3-Aminopiperidin-1-yl)(1-methyl-2-(1-methyl-1H-indol-2-yl)-1H-benzo[d]imidazol-5-yl)methanone

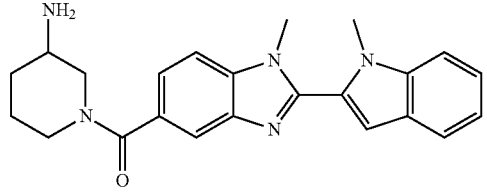 [SMILES: Cn1c(-c2nc3cc(C(=O)N4CCCC(N)C4)ccc3n2C)cc2ccccc21]

To a solution of 4-fluoro-3-nitrobenzoic acid (18.51 mg, 100 µmol, commercially available from, for example, Sigma-Aldrich) in EtOH (1 mL) was added methylamine hydrochloride (6.75 mg, 100 µmol) and DIPEA (52.4 µL, 300 µmol). The reaction mixture was stirred at 80° C. for 6 h and then concentrated. It was redissolved in DMF (1 mL), treated with tert-butyl piperidin-3-ylcarbamate (20.03 mg, 100 µmol) and HATU (38.0 mg, 100 µmol). The reaction mixture was stirred at rt overnight. Standard work-up gave the amide which was dissolved in EtOH (1 ml), treated with 1-methyl-1H-indole-2-carbaldehyde (15.92 mg, 100 µmol, commercially available from, for example, Sigma-Aldrich) and sodium hydrosulfite (0.3 □mol, 65 mg) in water (0.5 mL). The reaction mixture was stirred at 85° C. overnight, cooled to rt, concentrated and partitioned between EtOAc/NaHCO₃. The organics were dried, concentrated, treated with 50% TFA in DCM for 3 h, concentrated and purified by HPLC to afford the title compound.
LCMS (Method B): Rt=0.64 mins, MH+=388.1.

Example 133: (R)-(3-Aminopiperidin-1-yl)(2-(1-benzyl-1H-indol-2-yl)-1-(2-methoxyethyl)-1H-benzo[d]imidazol-5-yl)methanone

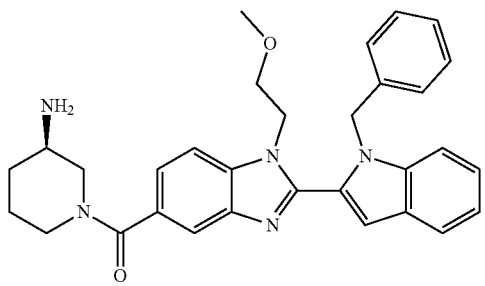 [SMILES: COCCn1c(-c2cc3ccccc3n2Cc2ccccc2)nc2cc(C(=O)N3CCC[C@@H](N)C3)ccc21]

To a solution of 4-fluoro-3-nitrobenzoic acid (18.51 mg, 100 µmol) in DMF (1 mL) was added HATU (38.0 mg, 100 µmol) and DIPEA (52.4 µL, 300 µmol) followed by 1,1-dimethylethyl (3R)-3-piperidinylcarbamate (20.03 mg, 100 µmol, commercially available from, for example, Apollo Scientific). The reaction mixture was stirred at rt for 5 h, standard work-up afforded the (R)-tert-butyl (1-(4-fluoro-3-nitrobenzoyl)piperidin-3-yl)carbamate. To the above prepared amide in EtOH (1 mL) was added 2-methoxyethanamine (7.51 mg, 100 mol) and DIPEA (52.4 µL, 300 µmol). The reaction mixture was stirred at 60° C. overnight, concentrated. re-dissolved in EtOH (1 ml) and treated with 1-benzyl-1H-indole-2-carbaldehyde (23.53 mg, 100 µmol) and sodium hydrosulfite (0.3 umol, 65 mg) in water (0.5 mL). The reaction mixture was stirred at 85° C. overnight, cooled to rt, concentrated and partitioned between EtOAc/NaHCO₃. The organics were dried, concentrated, treated with 50% TFA in DCM for 3 h, concentrated and purified by HPLC to afford the desired product.
LCMS (Method B): Rt=0.83 mins, MH+=508.3.

Example 134: (R)-(3-Aminopiperidin-1-yl)(2-(1-benzyl-1H-indol-2-yl)-1-isopropyl-1H-benzo[d]imidazol-5-yl)methanone

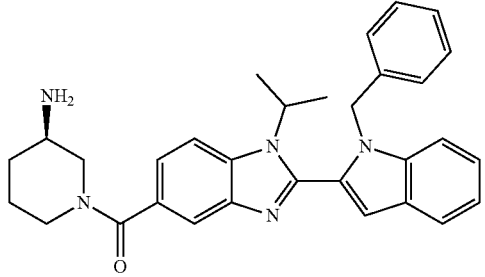 [SMILES: CC(C)n1c(-c2cc3ccccc3n2Cc2ccccc2)nc2cc(C(=O)N3CCC[C@@H](N)C3)ccc21]

To a solution of 4-fluoro-3-nitrobenzoic acid (18.51 mg, 100 µmol) in DMF (1 mL) was added HATU (45.6 mg, 120 µmol) and DIPEA (52.4 µL, 300 µmol). The reaction mixture was stirred at rt for 5 min and (R)-tert-butyl piperidin-3-ylcarbamate (20.03 mg, 100 µmol) was added and the reaction mixture was further stirred at rt for 3 h. Standard work-up gave the amide (⅓ di-addition observed). The crude amide was dissolved in EtOH (1 mL) and the propan-2-amine (29.6 mg, 500 µmol) was added and the reaction mixture was stirred at 80° C. overnight, concentrated, re-dissolved in EtOH (1 ml) and treated with 1-benzyl-1H-indole-2-carbaldehyde (23.53 mg, 100 µmol) and sodium hydrosulfite (0.3 umol, 65 mg) in water (0.5 mL). The reaction mixture was stirred at 85° C. overnight, cooled to rt, concentrated and partitioned between EtOAc/NaHCO₃. The organics were dried, concentrated and treated with 50% TFA in DCM for 3 h, concentrated and purified by HPLC to afford the desired product.

LCMS (Method B): Rt=0.87 mins, MH+=492.3.

Example 135: (R)-(3-Aminopiperidin-1-yl)(2-(1-ethyl-1H-indol-2-yl)-1-methyl-1H-benzo[d]imidazol-5-yl)methanethione Hydrochloride Salt

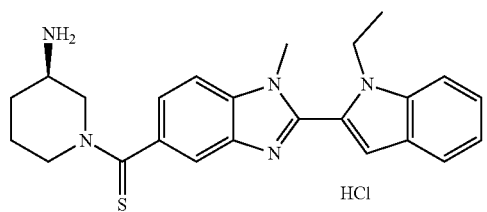 [SMILES: CCn1c(-c2nc3cc(C(=S)N4CCC[C@@H](N)C4)ccc3n2C)cc2ccccc21 ; Cl]

A solution of 4N HCl in dioxane was added to 1,1-dimethylethyl ((3R)-1-{[2-(1-ethyl-1H-indol-2-yl)-1-methyl-1H-benzimidazol-5-yl]carbonothioyl}-3-piperidinyl)carbamate (81 mg, 0.156 mmol) and the resulting mixture was stirred at rt for 1 h. The reaction mixture was concentrated in vacuo, and Et₂O was added to the residue. The resulting precipitate was filtered, washed with Et₂O and dried in vacuo to give the title compound (74 mg) as a yellow solid LCMS (Method A): Rt=1.03 min, MH+=418.2.

Example 136: (cis-(+/−)-3-Amino-4-fluoropiperidin-1-yl)(2-(1-ethyl-1H-indol-2-yl)-1-methyl-1H-benzo[d]imidazol-5-yl)methanone

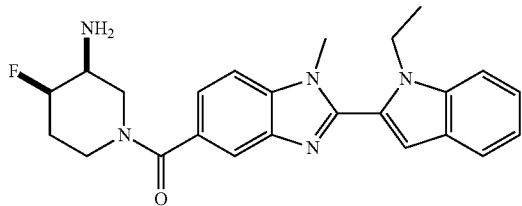 [SMILES: CCn1c(-c2nc3cc(C(=O)N4CC[C@@H](F)[C@@H](N)C4)ccc3n2C)cc2ccccc21]

HATU (157 mg, 0.413 mmol) was added to a stirred solution of 2-(1-ethyl-1H-indol-2-yl)-1-methyl-1H-benzo[d]imidazole-5-carboxylic acid (110 mg, 0.344 mmol) in DMF (2 mL) followed by DIPEA (0.072 mL, 0.413 mmol). After 30 min of stirring at rt, tert-butyl (cis-(+/−)-4-fluoropiperidin-3-yl)carbamate (150 mg, 0.344 mmol) was added to the reaction mixture and this was stirred for 2 h at rt and was allowed to stand without stirring for 64 h. The solvent was removed under reduced pressure and water (10 mL) was added to the residue. A cream white precipitate was filtered off and rinsed with water (2×5 mL). The precipitate was dried in a vacuum oven for 2 h, affording 220 mg (123%) of a cream solid (the Boc-protected product). A small amount of cream solid was purified by MDAP (method A). The appropriate fractions were transferred to a vial and the volatiles were removed under reduced pressure to afford the desired intermediate amide, still Boc-protected (3.2 mg) and this was sent for chiral separation. The bulk remaining Boc-protected product was then taken up in DCM (5 mL) and treated with TFA (1.5 mL, 19.47 mmol). After 30 min of stirring at rt the solvent was removed under reduced pressure and the dark purple residue was loaded in MeOH on a 2 g SCX column (previously conditioned with MeOH). The column was washed with MeOH (3 CV) and the product eluted with methanolic ammonia (2N) (3 CV). The ammonia fractions were combined and evaporated under reduced pressure. The residue (189 mg) was loaded in DCM on a 10 g SNAP silica column and purified by SP4 flash chromatography, eluting with a 0-10% methanolic ammonia (2N) in DCM over (10 CV). The appropriate fractions were combined and evaporated in vacuo to give the title compound (98 mg, 0.234 mmol, 67.8% yield) as a solid.

LCMS (Method B): Rt=0.78 min, MH+=420.2.

Example 137: (+/−)-(2-(Aminomethyl)piperidin-1-yl)(2-(1-ethyl-1H-indol-2-yl)-1-methyl-1H-benzo[d]imidazol-5-yl)methanone

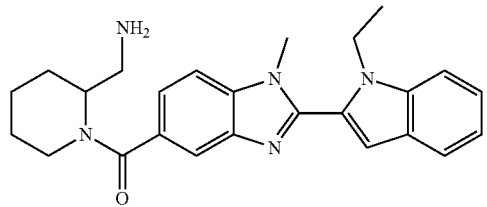 [SMILES: CCn1c(-c2nc3cc(C(=O)N4CCCCC4CN)ccc3n2C)cc2ccccc21]

HATU (157 mg, 0.413 mmol) was added to a stirred solution of 2-(1-ethyl-1H-indol-2-yl)-1-methyl-1H-benzo[d]imidazole-5-carboxylic acid (110 mg, 0.344 mmol) in DMF (2 mL) followed by DIPEA (0.072 mL, 0.413 mmol). After 30 min of stirring at rt, (+/−)-tert-butyl (piperidin-2-ylmethyl)carbamate (81 mg, 0.379 mmol) was added to the reaction mixture and this was stirred for 2 h at rt. The solvent was removed under reduced pressure and water (10 mL) was added to the residue. A cream white precipitate was filtered off and rinsed with water (2×5 mL). The precipitate was dried in a vacuum oven for 2 h, affording 220 mg (113%) of a cream solid (the Boc-protected product). The Boc-protected product was then taken up in DCM (5 mL) and treated with TFA (1.5 mL, 19.47 mmol). After 30 min of stirring at rt the solvent was removed under reduced pressure and the dark purple residue was loaded in MeOH on a 2 g SCX column (previously conditioned with MeOH). The column was washed with MeOH (3CV) and eluted with methanolic ammonia (2N) (3 CV). The ammonia fractions were combined and evaporated under reduced pressure. The residue (189 mg) was loaded in DCM on a 10 g SNAP silica column and purified by SP4 flash chromatography, eluting with a 0-10% methanolic ammonia (2N) in DCM over (10 CV). The appropriate fractions were combined and evaporated in vacuo to give (+/−)-(2-(aminomethyl)piperidin-1-yl)(2-(1-ethyl-1H-indol-2-yl)-1-methyl-1H-benzo[d]imidazol-5-yl)methanone (11.4 mg, 0.027 mmol, 7.97% yield) as a white solid.

LCMS (Method B): Rt=0.80 min, MH+=416.2.

Example 138a: ((3S,4R)-3-Amino-4-fluoropiperidin-1-yl)(2-(1-ethyl-1H-indol-2-yl)-1-methyl-1H-benzo[d]imidazol-5-yl)methanone Single Unknown Enantiomer Example 138b: ((3S,4R)-3-Amino-4-fluoropiperidin-1-yl)(2-(1-ethyl-1H-indol-2-yl)-1-methyl-1H-benzo[d]imidazol-5-yl)methanone, Hydrochloride, Single Unknown Enantiomer

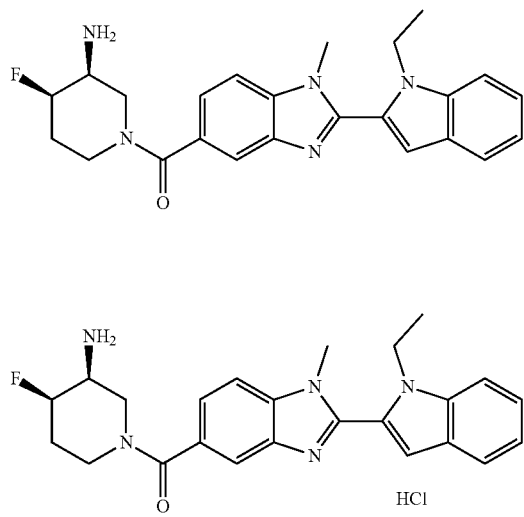

TFA (6.67 µL, 0.087 mmol) was added to a stirred solution of tert-butyl ((3S,4R)-1-(2-(1-ethyl-1H-indol-2-yl)-1-methyl-1H-benzo[d]imidazole-5-carbonyl)-4-fluoropiperidin-3-yl)carbamate (45 mg, 0.087 mmol) in DCM (5 mL). The resulting solution was stirred at rt for 3 h. The mixture was loaded on a 2 g preequilibrated SCX cartridge and eluted with MeOH (3 CV) followed by 2M NH₃ in MeOH (3 CV). The basic fractions were combined and the volatiles were removed under reduced pressure to afford ((3S,4R)-3-amino-4-fluoropiperidin-1-yl)(2-(1-ethyl-1H-indol-2-yl)-1-methyl-1H-benzo[d]imidazol-5-yl)methanone (26.3 mg, 0.063 mmol, 72.4% yield).

LCMS (Method B): Rt=0.78 min, MH+=420.2.

3 mg of the free base was removed for assay, 1.1 eq of 1.0M HCl in ether was added to the remaining material, dissolved in the minimum amount of DCM. The mixture was triturated with ether and dried under a stream of N₂ to afford ((3S,4R)-3-amino-4-fluoropiperidin-1-yl)(2-(1-ethyl-1H-indol-2-yl)-1-methyl-1H-benzo[d]imidazol-5-yl)methanone, hydrochloride (23.6 mg, 0.052 mmol, 59.8% yield) as a yellow/white solid/powder.

LCMS (Method B) Rt=0.79, MH+=420.2

Example 139a: ((3R,4S)-3-Amino-4-fluoropiperidin-1-yl)(2-(1-ethyl-1H-indol-2-yl)-1-methyl-1H-benzo[d]imidazol-5-yl)methanone Single Unknown Enantiomer Example 139b: ((3R,4S)-3-Amino-4-fluoropiperidin-1-yl)(2-(1-ethyl-1H-indol-2-yl)-1-methyl-1H-benzo[d]imidazol-5-yl)methanone, Hydrochloride, Single Unknown Enantiomer

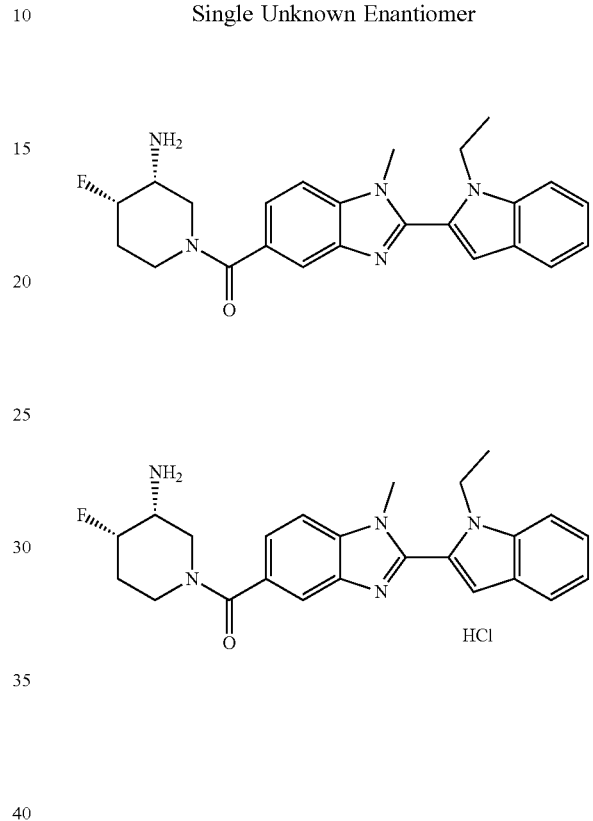

TFA (5.34 µL, 0.069 mmol) was added to a stirred solution of tert-butyl ((3R,4S)-1-(2-(1-ethyl-1H-indol-2-yl)-1-methyl-1H-benzo[d]imidazole-5-carbonyl)-4-fluoropiperidin-3-yl)carbamate (36 mg, 0.069 mmol) in DCM (5 mL). The resulting solution was stirred at rt for 3 h. The mixture was loaded on a 2 g preequilibrated SCX cartridge and eluted with MeOH (3 CV) followed by 2M NH₃ in MeOH (3 CV). The basic fractions were combined and the volatiles were removed under reduced pressure to afford ((3R,4S)-3-amino-4-fluoropiperidin-1-yl)(2-(1-ethyl-1H-indol-2-yl)-1-methyl-1H-benzo[d]imidazol-5-yl)methanone (24 mg, 0.057 mmol, 83% yield).

LCMS (Method B): Rt=0.79 min, MH+=420.1.

2.5 mg was removed for assay, 1.1 eq of 1.0M HCl in ether was added to the remaining material, dissolved in the minimum amount of DCM. The mixture was triturated with ether and dried under a stream of N₂ to afford ((3R,4S)-3-amino-4-fluoropiperidin-1-yl)(2-(1-ethyl-1H-indol-2-yl)-1-methyl-1H-benzo[d]imidazol-5-yl)methanone, hydrochloride (18.8 mg, 0.041 mmol, 59.5% yield) as a yellow/white solid/powder.

LCMS (Method B) Rt=0.79, MH+=420.2

Example 140a: (R)-(3-Aminopiperidin-1-yl)(2-(1-(cyclopropylmethyl)-6-methoxy-1H-indol-2-yl)-1-methyl-1H-benzo[d]imidazol-5-yl)methanone Example 140b: (R)-(3-Aminopiperidin-1-yl)(2-(1-(cyclopropylmethyl)-6-methoxy-1H-indol-2-yl)-1-methyl-1H-benzo[d]imidazol-5-yl)methanone, Hydrochloride

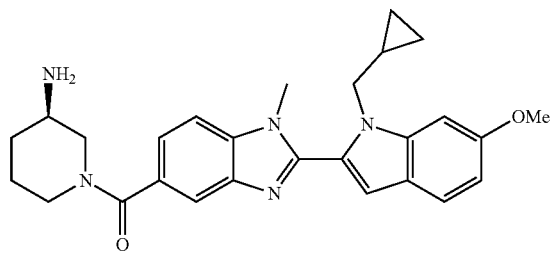

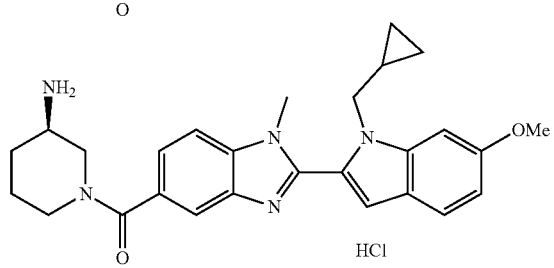

To a solution of (R)-tert-butyl (1-(2-(1-(cyclopropylmethyl)-6-methoxy-1H-indol-2-yl)-1-methyl-1H-benzo[d]imidazole-5-carbonyl)piperidin-3-yl)carbamate (147 mg, 0.264 mmol) in DCM (5 mL), was added TFA (1 mL, 12.98 mmol). The reaction was allowed to stir for 90 min at rt. The volatiles were removed under reduced pressure to afford a dark orange oil. The crude mixture was loaded onto a 5 g preequilibrated SCX cartridge and eluted with MeOH (3 CV) followed by 2M NH$_3$ in MeOH (3 CV). The basic fractions were combined and the volatiles were removed under reduced pressure to afford (R)-(3-aminopiperidin-1-yl)(2-(1-(cyclopropylmethyl)-6-methoxy-1H-indol-2-yl)-1-methyl-1H-benzo[d]imidazol-5-yl)methanone (113 mg, 0.247 mmol, 94% yield) as an orange oil.

LCMS (Method A): Rt=1.00 min, MH+=458.3.

5.0 mg was removed for assay, 1.1 eq of 1.0M HCl in ether was added to the remaining material, dissolved in the minimum amount of DCM. The mixture was triturated with ether and dried under a stream of N$_2$ to afford (R)-(3-aminopiperidin-1-yl)(2-(1-(cyclopropylmethyl)-6-methoxy-1H-indol-2-yl)-1-methyl-1H-benzo[d]imidazol-5-yl)methanone, hydrochloride (110 mg, 0.223 mmol, 84% yield) as a brown solid.

LCMS (Method A) Rt=1.00, MH+=458.3

Example 141: N-(3-Azabicyclo[4.1.0]heptan-1-yl)-2-(1-ethyl-1H-indol-2-yl)-1-methyl-1H-benzo[d]imidazole-5-carboxamide

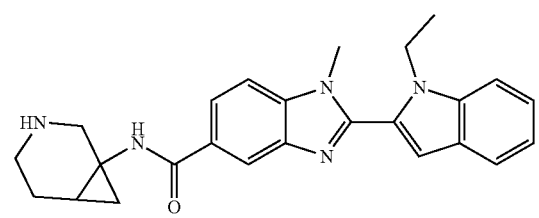 [SMILES: CCn1c(-c2nc3cc(C(=O)NC45CNCCC4C5)ccc3n2C)cc2ccccc21]

2,2,2-Trifluoroacetic acid (1 mL, 12.98 mmol) was added to a suspension of tert-butyl 1-(2-(1-ethyl-1H-indol-2-yl)-1-methyl-1H-benzo[d]imidazole-5-carboxamido)-3-azabicyclo[4.1.0]heptane-3-carboxylate (128 mg, 0.249 mmol) in DCM (5 mL) and stirred overnight. The reaction mixture was then evaporated and redissolved in methanol before being loaded onto a 10 g SCX-2 cartridge and washed with methanol to remove the TFA. The product was eluted with 2 M methanolic ammonia which was then evaporated. The product was dissolved in 1:1 DMSO and methanol and purified by MDAP (Method B). The appropriate fractions were combined and loaded onto a 10 g SCX-2 cartridge. Methanol was used to elute the formic acid and the product was eluted with 2 M methanolic ammonia. The solvent was then evaporated. After being left under high vacuum for 4 h, yellow sticky solid N-(3-azabicyclo[4.1.0]heptan-1-yl)-2-(1-ethyl-1H-indol-2-yl)-1-methyl-1H-benzo[d]imidazole-5-carboxamide (64 mg, 0.155 mmol, 62.1% yield) was yielded.

LCMS (Method B): Rt=0.83 min, MH+=414.2.

Example 142: (3-Aminopiperidin-1-yl)(2-(1-benzyl-1H-indol-2-yl)-1-methyl-1H-benzo[d]imidazol-5-yl)methanone

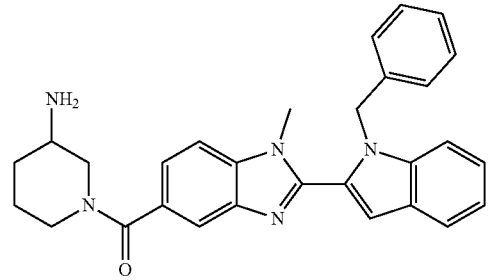 [SMILES: Cn1c(-c2cc3ccccc3n2Cc2ccccc2)nc2cc(C(=O)N3CCCC(N)C3)ccc21]

Prepared in a similar manner to Example 82 from tert-butyl (1-(2-(1-benzyl-1H-indol-2-yl)-1-methyl-1H-benzo[d]imidazole-5-carbonyl)piperidin-3-yl)carbamate.

LCMS (Method B): Rt 0.91 min, MH+ 464.3

Biological Data

PAD4 Enzyme Expression

Recombinant human PAD4 (residues 1-663) was expressed in E. coli as an N-terminal GST-tagged fusion protein. During purification of the protein, the GST tag was removed by cleavage with PreScission Protease (GE Healthcare). Activity of the final PAD4 enzyme and batch consistency was determined by employing the enzyme in the FLINT NH$_3$ release assay in the presence of N-a-benzoyl-L-arginine ethyl ester (BAEE) substrate and measuring the levels of NH$_3$ release at a known substrate/enzyme concentration.

PAD4 Enzyme Assay: Conditions A

8 µl of PAD4 enzyme diluted to an assay concentration of 75 nm in assay buffer (a): (100 mM HEPES, 50 mM NaCl, 2 mM DTT and 0.6 mg/ml BSA pH 8), or in assay buffer (b): (100 mM HEPES, 50 mM NaCl, 2 mM DTT, 7.5% glycerol and 1.5 mM CHAPS pH 8), and added to wells containing 0.1 µl of various concentrations of compound or DMSO vehicle (0.8% final) in a Greiner high volume 384 well black plate. Following 30 mins pre-incubation at rt, the reaction was initiated by the addition of 4 µl of substrate buffer containing 3 mM N-a-benzoyl-L-arginine ethyl ester (BAEE), 100 mM HEPES, 50 mM NaCl, 600 uM CaCl$_2$ (2H₂O) and 2 mM DTT, pH 8.0. The reaction was stopped after 100 mins with the addition of 38 μl stop/detection buffer containing 50 mM EDTA, 2.6 mM phthalaldehyde and 2.6 mM DTT. Assay incubated at rt for 90 mins before measuring fluorescent signal ($\lambda_{ex}$ 413/$\lambda_{em}$ 476) on an Envision plate reader (Perkin Elmer Life Sciences, Waltham, Mass., USA)

PAD4 Enzyme Assay: Conditions B

8 μl of PAD4 enzyme diluted to an assay concentration of 30 nM in assay buffer (100 mM HEPES, 50 mM NaCl, 2 mM DTT and 0.6 mg/ml BSA pH 8), and added to wells containing 0.1 μl of various concentrations of compound or DMSO vehicle (0.8% final) in a Greiner high volume 384 well black plate. Following 30 mins pre-incubation at rt, the reaction was initiated by the addition of 4 μl of substrate buffer containing 3 mM N-a-benzoyl-L-arginine ethyl ester (BAEE), 100 mM HEPES, 50 mM NaCl, 600 uM CaCl₂ (2H₂O) and 2 mM DTT, pH 8.0. The reaction was stopped after 60 mins with the addition of 38 μl stop/detection buffer containing 50 mM EDTA, 2.6 mM phthalaldehyde and 2.6 mM DTT. Assay incubated at rt for 90 mins before measuring fluorescent signal ($\lambda_{ex}$ 405/$\lambda_{em}$ 460) on an Envision plate reader (Perkin Elmer Life Sciences, Waltham, Mass., USA)

PAD2 Enzyme Expression

Recombinant human PAD2 (residues 1-665) was expressed in baculovirus-infected Sf9 insect cells as an N-terminal 6His-FLAG-tagged fusion protein. Activity of the final product was determined using a FLINT NH₃ release assay.

PAD2 Enzyme Assay

8 μl of PAD2 enzyme diluted to an assay concentration of 30 nM in assay buffer (100 mM HEPES, 50 mM NaCl, 2 mM DTT, 7.5% glycerol and 1.5 mM CHAPS pH 8), and added to wells containing 0.1 μl of various concentrations of compound or DMSO vehicle (0.8% final) in a Greiner high volume 384 well black plate. Following 30 mins pre-incubation at rt, the reaction was initiated by the addition of 4 μl of substrate buffer containing 180 uM N-a-benzoyl-L-arginine ethyl ester (BAEE), 100 mM HEPES, 50 mM NaCl, 240 uM CaCl₂ (2H₂O) and 2 mM DTT, pH 8.0. The reaction was stopped after 90 mins with the addition of 38p stop/detection buffer containing 50 mM EDTA, 2.6 mM phthalaldehyde and 2.6 mM DTT. Assay incubated at rt for 90 mins before measuring fluorescent signal ($\lambda_{ex}$ 405/$\lambda_{em}$ 460) on an Envision plate reader (Perkin Elmer Life Sciences, Waltham, Mass., USA).

The compounds of Examples 1a-142 were tested essentially as described above. Those of skill in the art will recognise that in vitro binding assays and cell-based assays for functional activity are subject to experimental variability. Accordingly, it is to be understood that the pIC₅₀ values given below are exemplary only.

Results

Examples 1a-142 were tested in the PAD4 enzyme assay above or similar assays and had mean pIC₅₀ values in the range of 5.1 to 7.4.

Examples 6, 11a, 15, 16, 20b, 24, 43, 44, 58a and 65 were tested in the PAD4 enzyme assay above or similar assays and had mean pIC₅₀ values in the range 6.4 to 7.4. Examples 15 and 20b were tested in the PAD4 enzyme assay above or similar assays and had mean pIC₅₀ values of 6.4. Examples 11a, 24 and 65 were tested in the PAD4 enzyme assay above or similar assays and had mean pIC₅₀ values of 6.8. Example 16 was tested in the PAD4 enzyme assay above or similar assays and had a mean pIC₅₀ value of 6.9. Example 6 was tested in the PAD4 enzyme assay above or similar assays and had a mean pIC₅₀ value of 7.0. Example 58a was tested in the PAD4 enzyme assay above or similar assays and had a mean pIC₅₀ value of 7.1. Example 44 was tested in the PAD4 enzyme assay above or similar assays and had a mean pIC₅₀ value of 7.3. Example 43 was tested in the PAD4 enzyme assay above or similar assays and had a mean pIC₅₀ value of 7.4.

To assess selectivity for PAD4 over PAD2, the following examples—Examples 1a, 2, 12, 16, 18, 19, 20a, 20b, 22, 29, 32, 34, 37, 43-45, 48, 51, 54, 58a, 58b, 59, 63, 65-68, 70, 74, 75, 95, 96, 111, 113, 114, 124 and 135—were tested in the PAD2 enzyme assay above or similar assays and had mean pIC₅₀ values in the range of <4.1 to 5.0. The mean pIC₅₀ values for Examples 22, 29, 37, 51, 54, 63, 65, 67, 68, 70, 95, 96, 114 and 124 were all <4.1.

We claim:

1. A compound of formula (I):

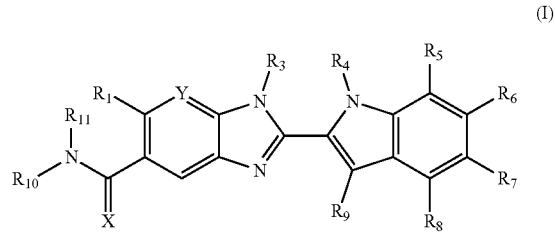

and salts thereof;
wherein:
X is O or S;
Y is N or CR₂;
R₁ is H or —C₁₋₆alkyl;
R₂ is —H, —OH, —C₁₋₆ alkyl, —CN, -halo, —C(=O)NH₂, —C₁₋₆haloalkyl, —O—C₁₋₆alkyl-O—C₁₋₆alkyl, —O—C₁₋₆alkyl-OH, —O—C₁₋₆alkyl-C(=O)NH₂, —O—C₁₋₆alkyl-CN, —O—C₁₋₆haloalkyl, —NH—C₁₋₆alkyl, —N(C₁₋₆alkyl)₂ or heteroaryl;
R₃ is —C₁₋₆alkyl, —C₁₋₆alkyl-NH₂, or —C₁₋₆alkyl-O—C₁₋₆alkyl;
R₄ is H, —C₁₋₆alkyl, —C₁₋₆haloalkyl, —C₁₋₆alkyl-heteroaryl (wherein the heteroaryl group is optionally substituted by one, two or three C₁₋₆alkyl groups), —C₁₋₆alkyl-phenyl (wherein the phenyl group is optionally substituted by one, two or three substituents selected from the list consisting of halo, C₁₋₆alkyl and —O—C₁₋₆alkyl), —C₁₋₆alkyl-heterocyclyl, —C₁₋₆alkyl-C₃₋₆cycloalkyl, —C₁₋₆alkyl-OH, —C₁₋₆alkyl-CN or —C₁₋₆alkyl-O—C₁₋₆ alkyl;
R₅ is —H, —C₁₋₆alkyl, —OH, -halo, or —CN;
or R₄ together with R₅ are —(R₄)—CH₂CH₂O—(R₅)—, —(R₄)—CH₂CH₂CH₂O—(R₅)— or —(R₄)—CH(Me)CH₂O—(R₅)—, wherein —(R₄)— and —(R₅)— denote the positions of attachment of the alkenyloxy chain to the respective ring atoms;
R₆ is —H, -halo, —CN, —C₁₋₆alkyl, —O—C₁₋₆alkyl, or —OH;
R₇ is —H, -halo, —CN, —C₁₋₆alkyl, —O—C₁₋₆alkyl, or —OH;
R₈ is —H, —F or —C₁₋₆alkyl;
R₉ is —H or —C₁₋₆alkyl;
NR₁₀R₁₁ taken together form a 5-7 membered mono- or bi-cyclic saturated or unsaturated heterocycle containing one nitrogen atom, wherein the heterocycle is substituted by one, two or three substituents independently selected from the list consisting of —NH₂, —C$_{1-6}$alkyl-NH$_2$, —NH—C$_{1-6}$alkyl, —NHC(=NH)CH$_2$Cl, —C$_{1-6}$alkyl, -halo, —O—C$_{1-6}$alkyl, —OH and —C(O)NH$_2$, and wherein said compound is other than:

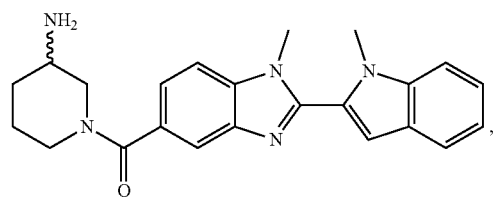
1,

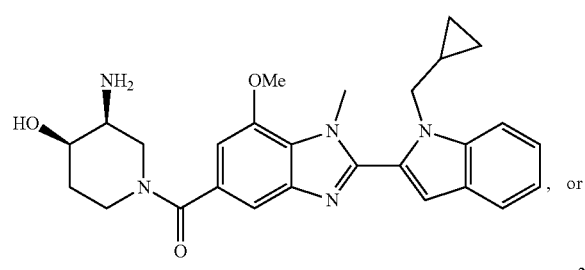
2, or

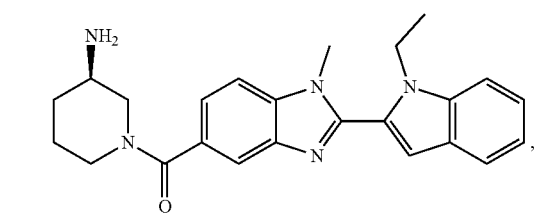
3, or salts thereof.

2. A compound or salt thereof according to claim 1 wherein X is O.

3. A compound or salt thereof according to claim 1, wherein Y is CR$_2$.

4. A compound or salt thereof according to claim 1, wherein R$_2$ is —H, —O—Me, —O—CF$_3$, —CN, —Br, —CF$_3$, -3-pyridinyl, —C(=O)NH$_2$, —NMe$_2$, —NHMe, ethyl, methyl, —O—CH$_2$CH$_2$CH$_2$—OH, —O-Et, —O—CH$_2$CH$_2$—O—CH$_3$, —O—CH$_2$CH$_2$—OH, —OCH$_2$CN, —O—CH$_2$C(O)NH$_2$, or —OH.

5. A compound or salt thereof according to claim 1, wherein R$_3$ is -methyl, —CH$_2$CH$_2$NH$_2$, —CH$_2$CH$_2$CH$_2$NH$_2$, -ethyl, —CH$_2$CH$_2$OCH$_3$, or -isopropyl.

6. A compound or salt thereof according to claim 1, wherein R$_4$ is H, —C$_{1-6}$alkyl, —C$_{1-6}$ haloalkyl, —C$_{1-6}$ alkyl-heteroaryl (optionally substituted by one methyl), —C$_{1-6}$ alkyl-phenyl (optionally substituted by one or two substituents selected from the list consisting of Cl, I, Me and OMe), —C$_{1-6}$ alkyl-heterocyclyl, —C$_{1-6}$ alkyl-C$_{3-6}$ cycloalkyl, —C$_{1-6}$ alkyl-CN or —C$_{1-6}$—O—C$_{1-6}$ alkyl.

7. A compound or salt thereof according to claim 1, wherein —NR$_{10}$R$_{11}$ is selected from the list consisting of piperidinyl (optionally substituted by one or two substituents selected from the list consisting of —NH$_2$, —NH—C$_{1-6}$alkyl, —C$_{1-6}$ alkyl-NH$_2$, —O—C$_{1-6}$alkyl, —OH, —C$_{1-6}$ alkyl, halo, —C(=O)NH$_2$, and —NHC(=NH)CH$_2$Cl), dihydropiperidinyl (optionally substituted by —NH$_2$), azabicyclo[3.1.0]hexanyl (optionally substituted by —NH$_2$) and pyrrolidinyl (optionally substituted by one or two substituents selected from the list consisting of —NH$_2$, —C$_{1-6}$ alkyl and —C$_{1-6}$ alkyl-NH$_2$).

8. A compound selected from the list consisting of:

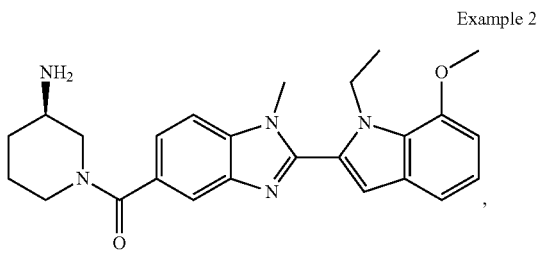
Example 2,

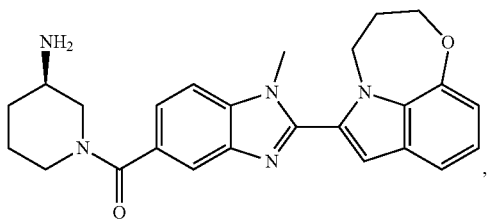
Example 3,

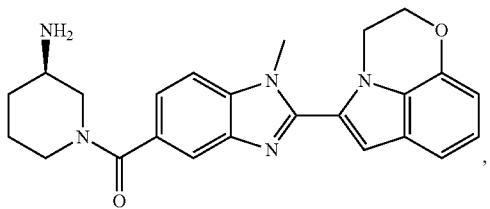
Example 4,

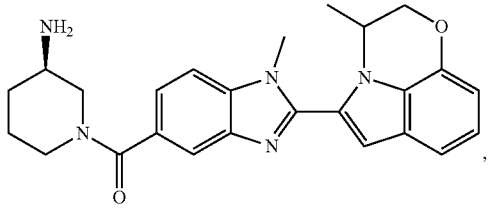
Example 5,

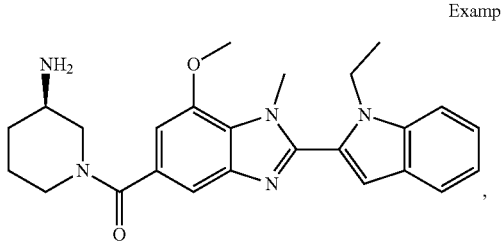
Example 6a,

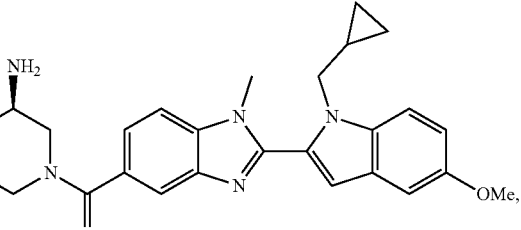
Example 7

Example 8
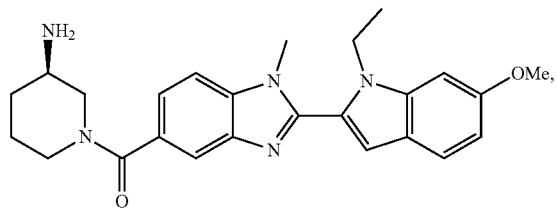
Example 9
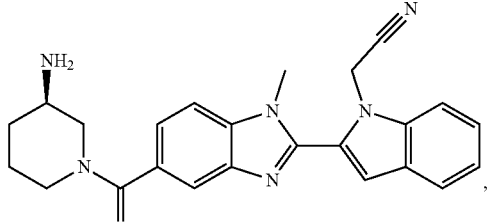
Example 10
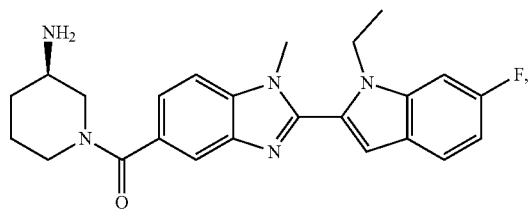
Example 11a
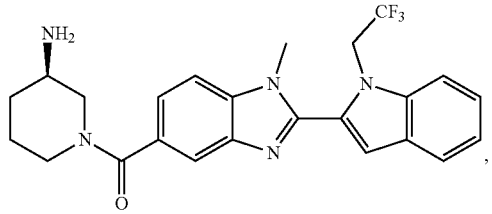
Example 12
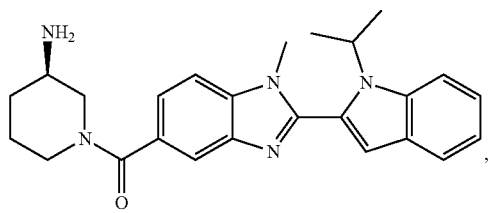
Example 13
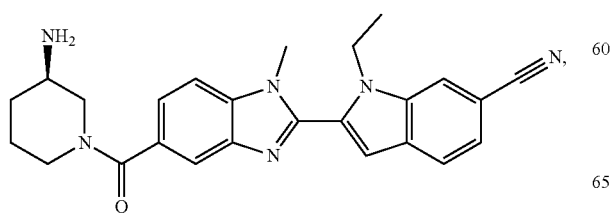
Example 14
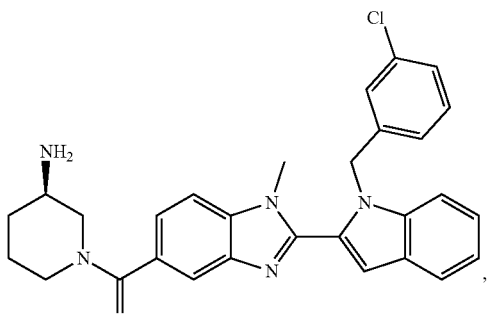
Example 15
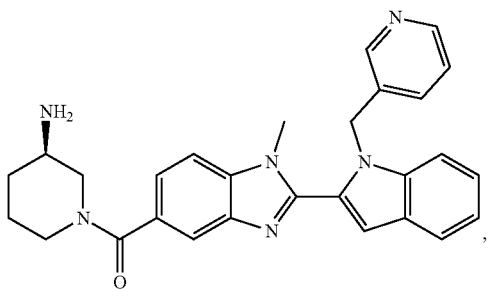
Example 16
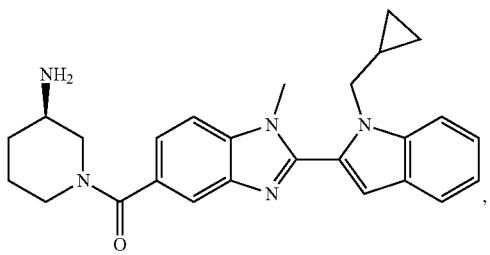
Example 17
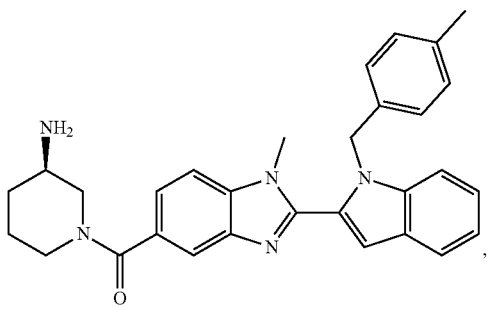
Example 18
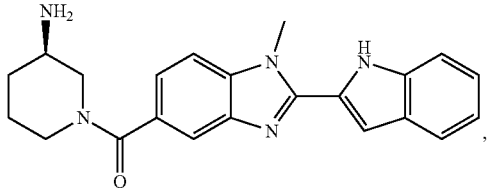

Example 19
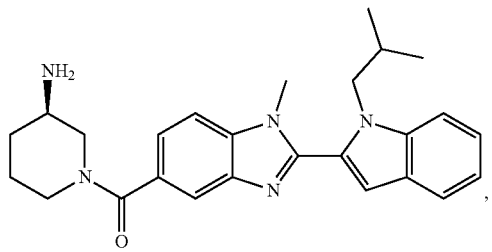
Example 20a
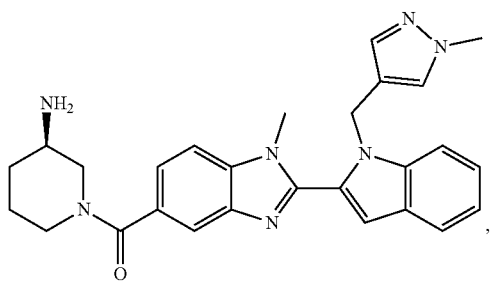
Example 21
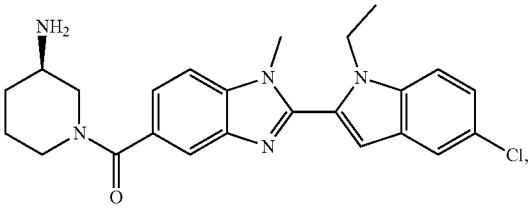
Example 22
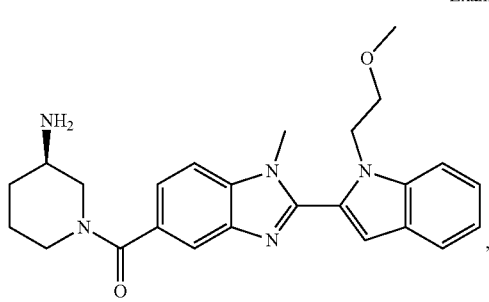
Example 23
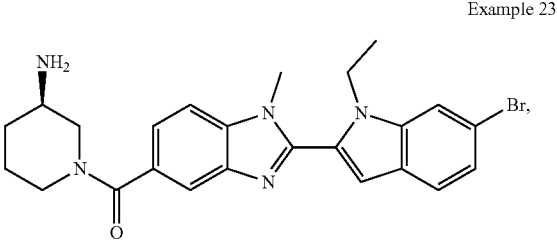
Example 24
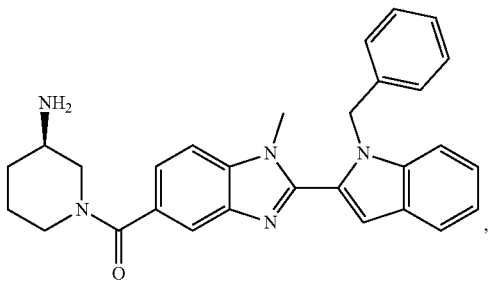
Example 25
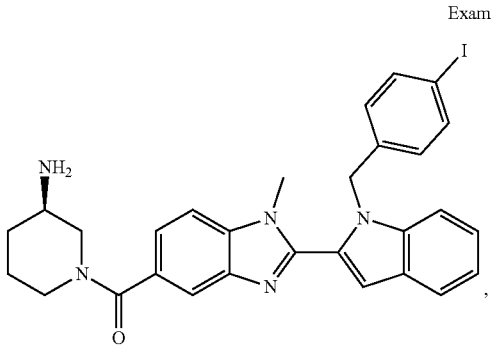
Example 26
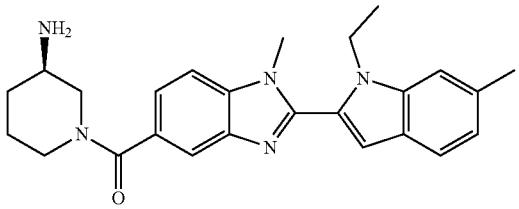
Example 27
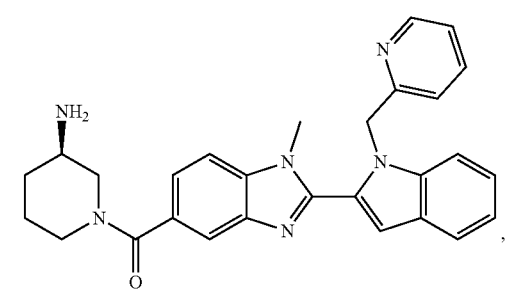
Example 28
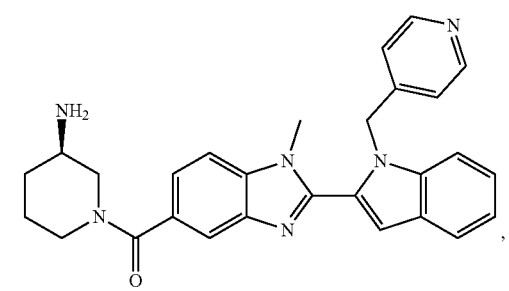

Example 29
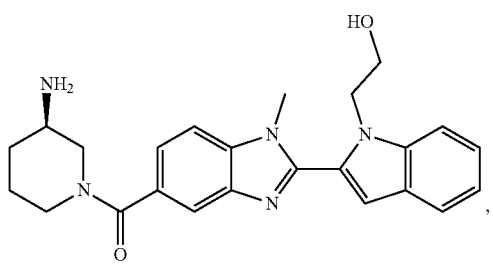
Example 30
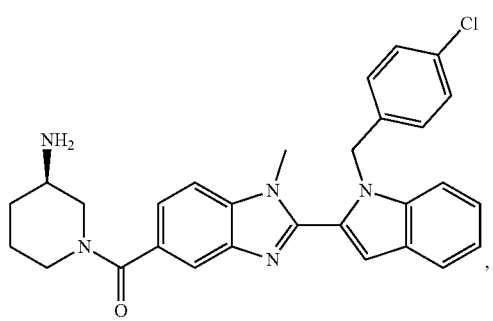
Example 31
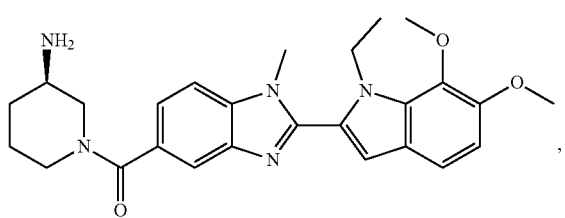
Example 32
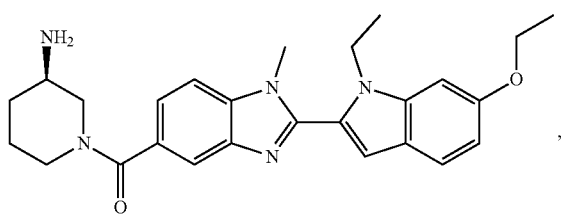
Example 33a
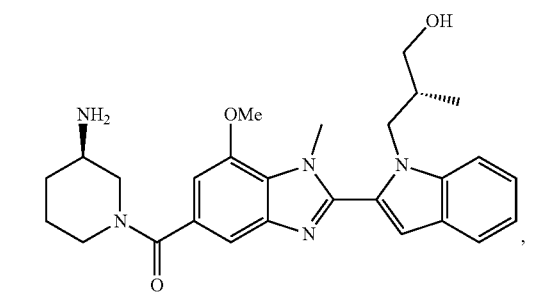
Example 34
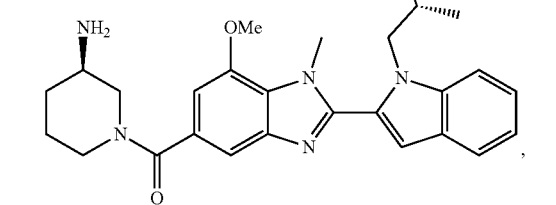
Example 35
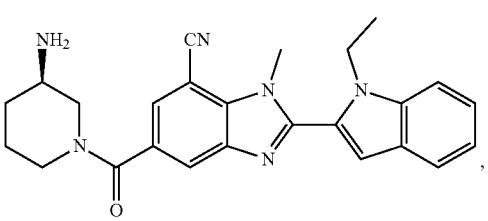
Example 36
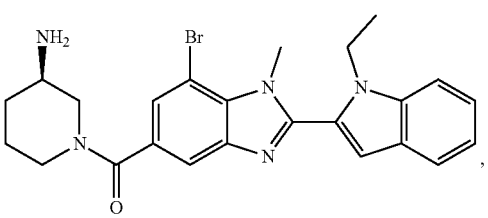
Example 37
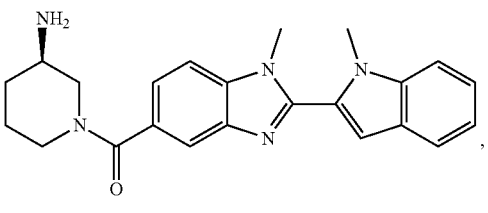
Example 38
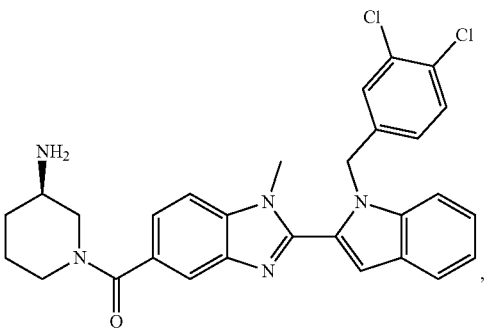
Example 39
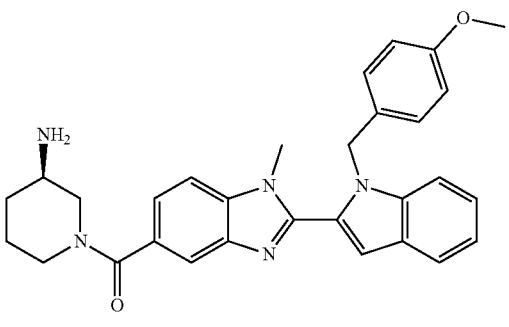

Example 40

Example 41

Example 42

Example 11b

Example 33b

Example 43

Example 44

Example 45

Example 46

Example 47

Example 48

Example 49

Example 50
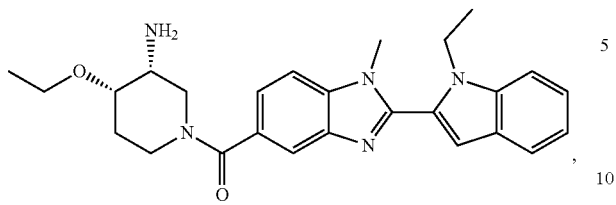
Example 51
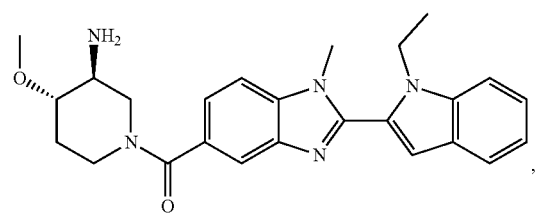
Example 52
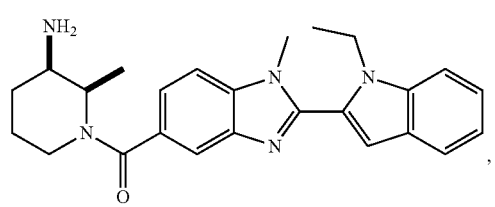
Example 53
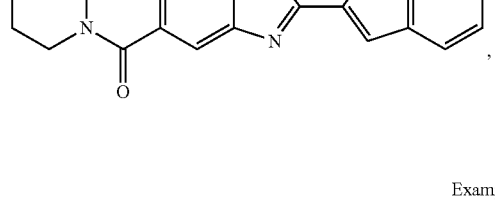
Example 54
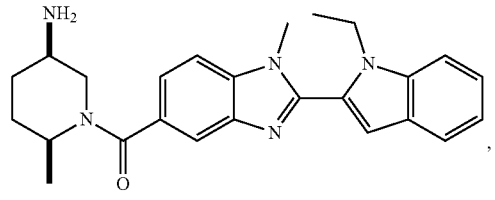
Example 56
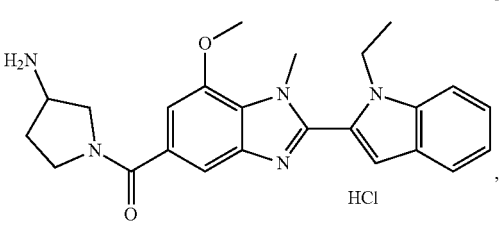
Example 57
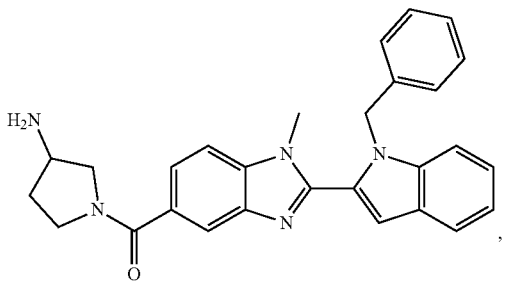
Example 58a
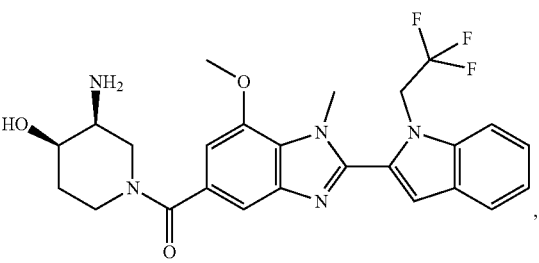
Example 58b
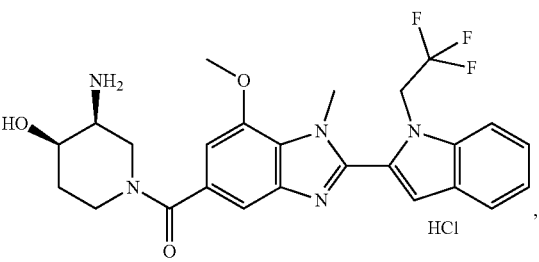
Example 59
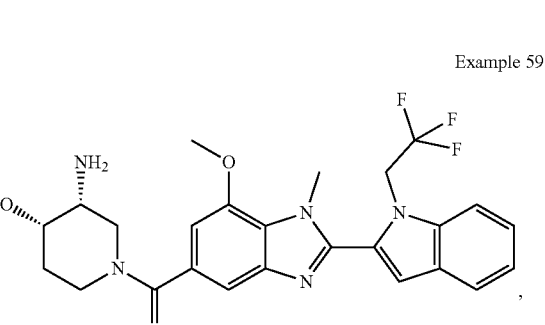
Example 20b
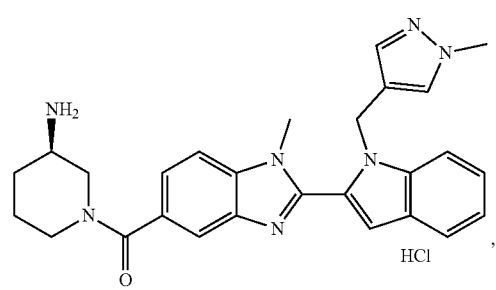

Example 6b
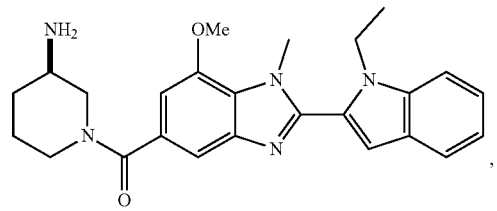
Example 60
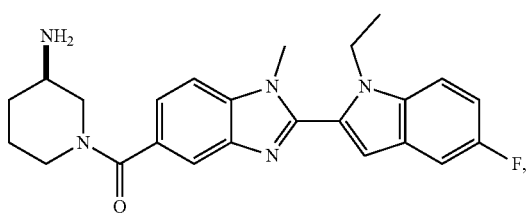
Example 61
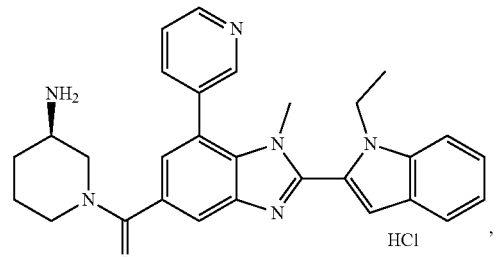
Example 62
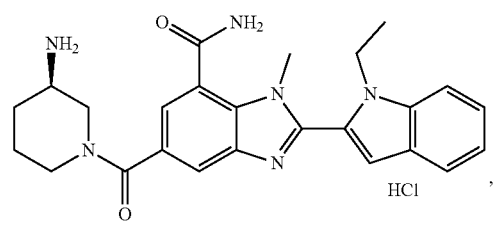
Example 63
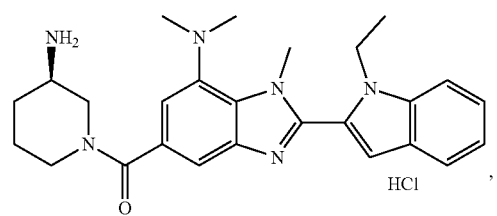
Example 65
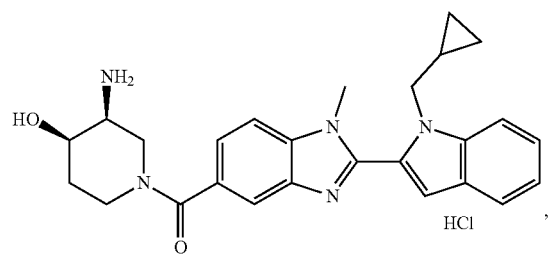
Example 67
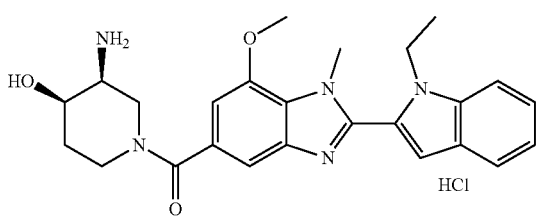
Example 68
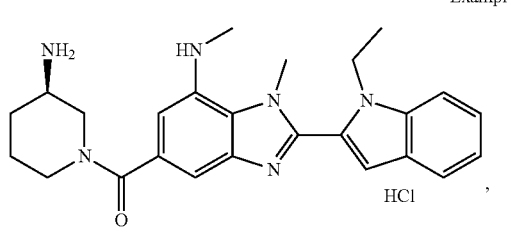
Example 69
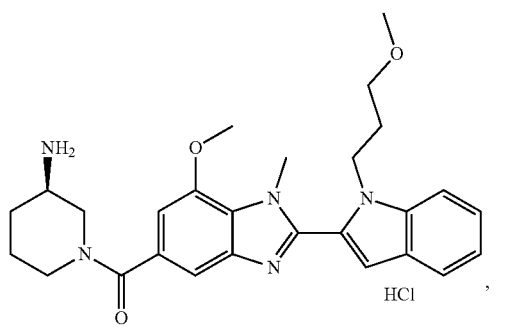
Example 70
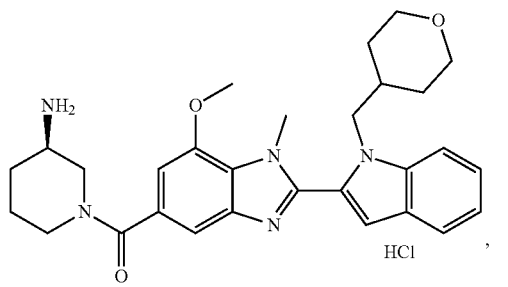
Example 71
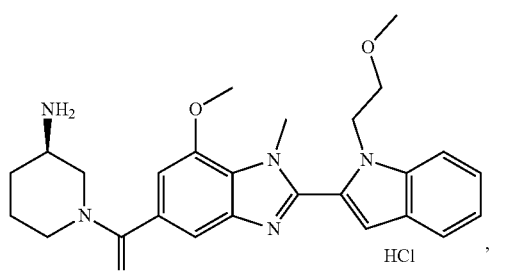

Example 72
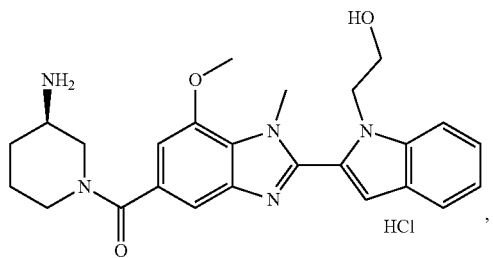
Example 73
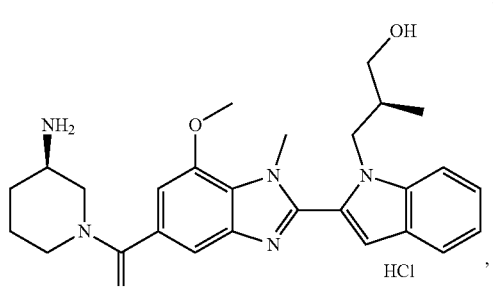
Example 74
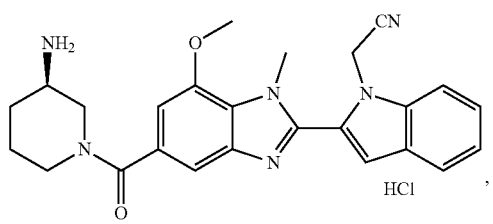
Example 75
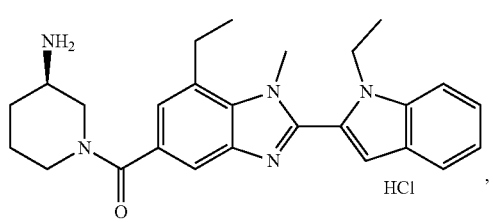
Example 78
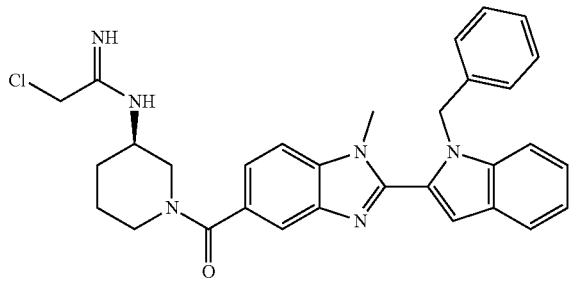
Example 79
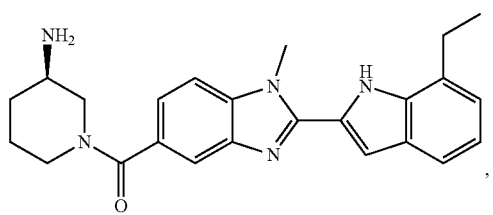
Example 80
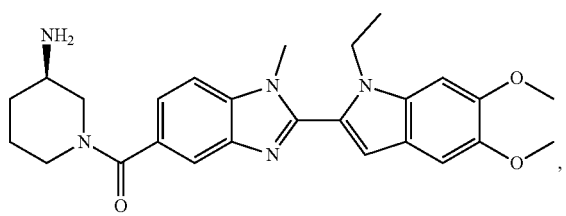
Example 81
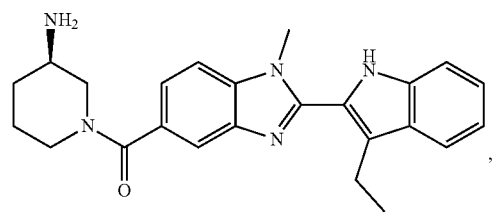
Example 82
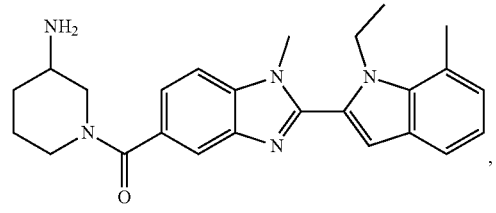
Example 84
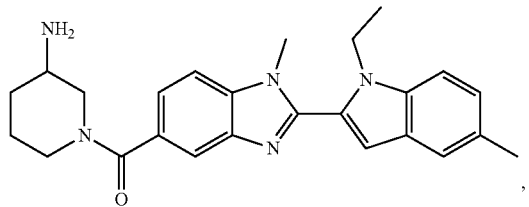
Example 85
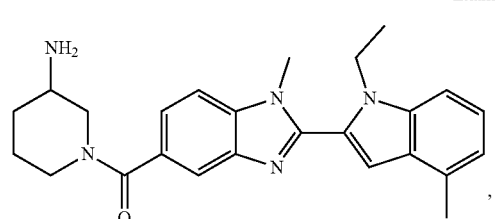
Example 86
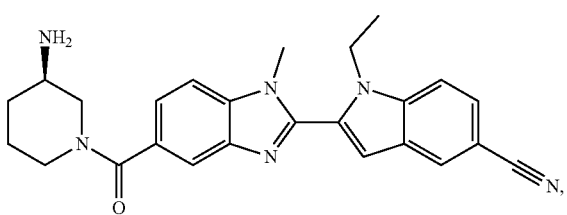

Example 88, Example 89, Example 91, Example 92, Example 93, Example 94, Example 95, Example 96, Example 97, Example 98, Example 99, Example 100

Example 101

Example 102

Example 103

Example 104

Example 105

Example 106

Example 107

Example 108

Example 109

Example 110

Example 111

-continued
Example 112
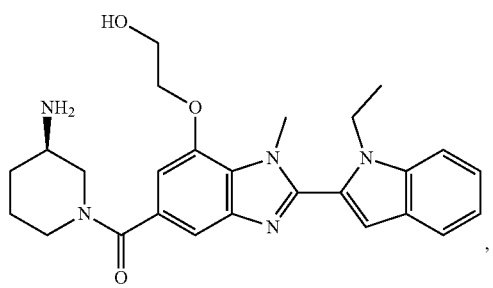
Example 113
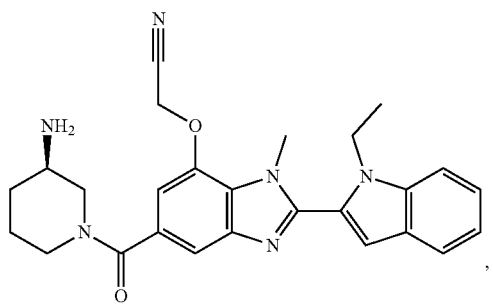
Example 114
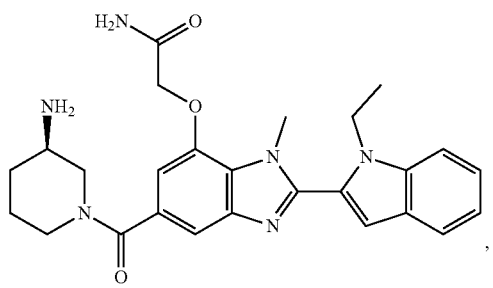
Example 115
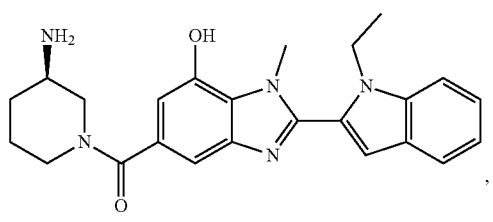
Example 116
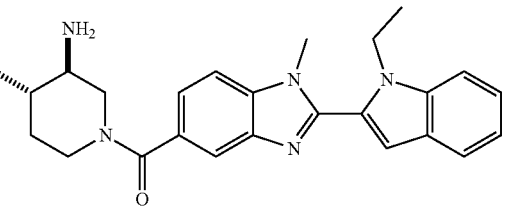
Example 117/118
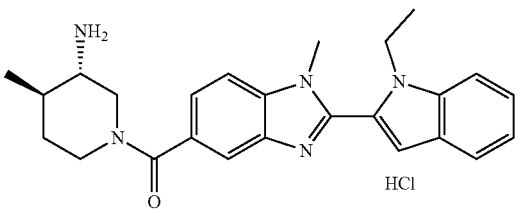
-continued
Example 119
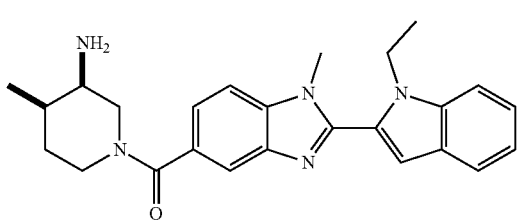
Example 120
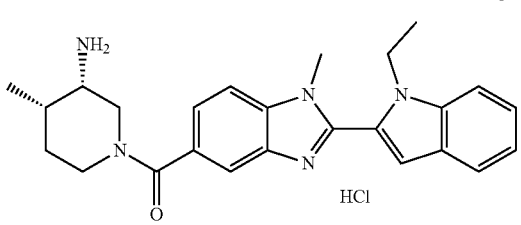
Example 121
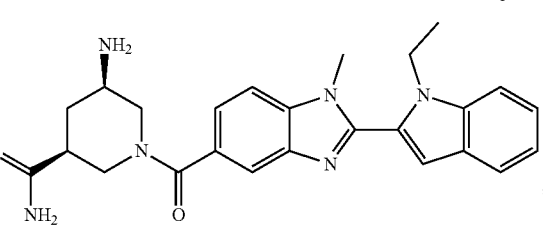
Example 122
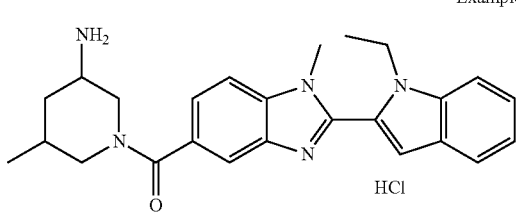
Example 123
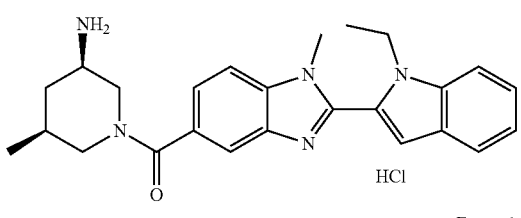
Example 124
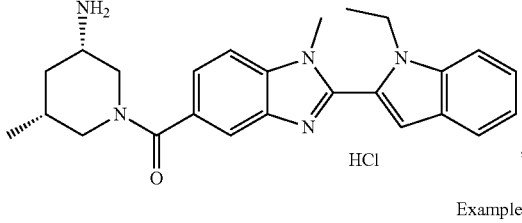
Example 125
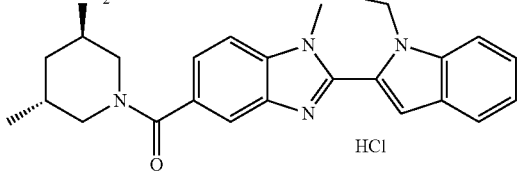

Example 126
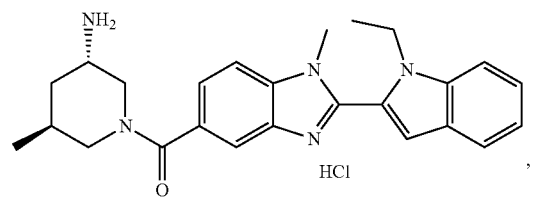
HCl
Example 127
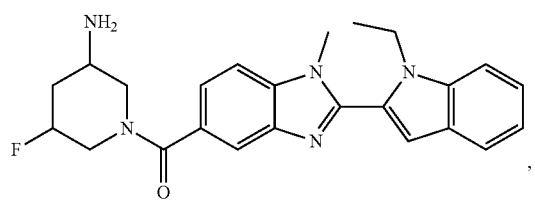
Example 128
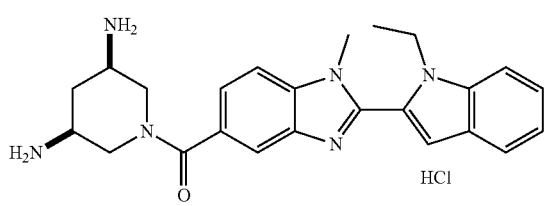
HCl
Example 129
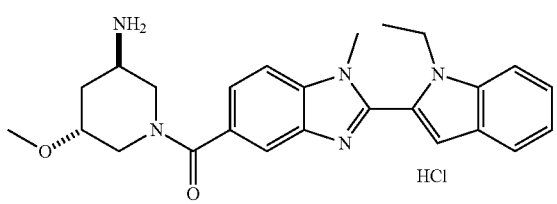
HCl
Example 130
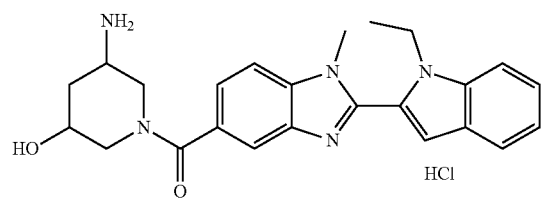
HCl
Example 131
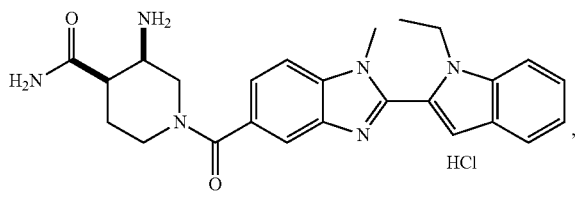
HCl
Example 133
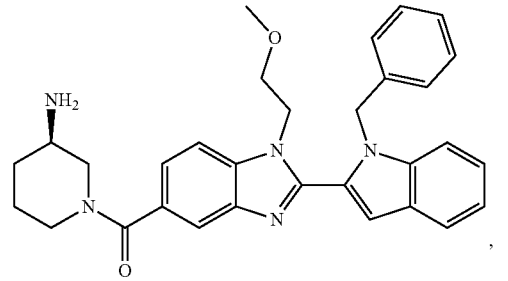
Example 134
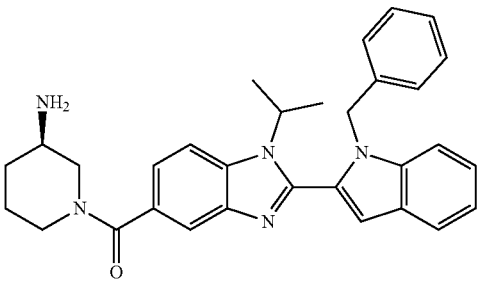
Example 135
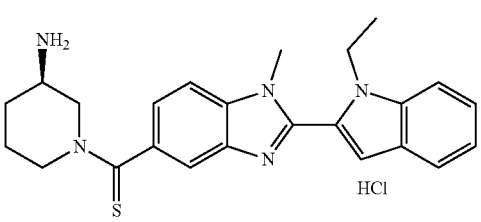
HCl
Example 136
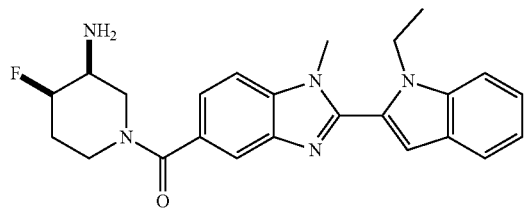
Example 137
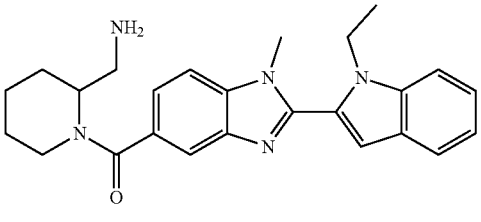
Example 138a/138b
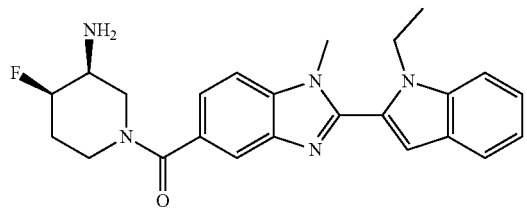
Example 139a/139b
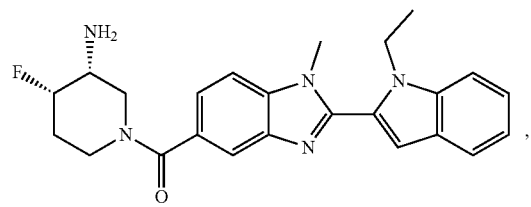

-continued

Example 140a/140b

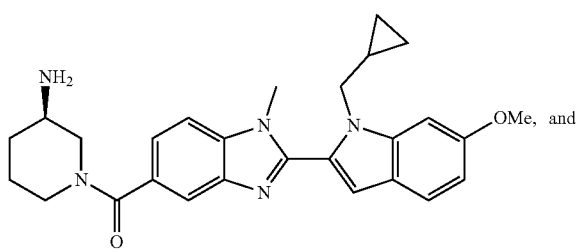

Example 142

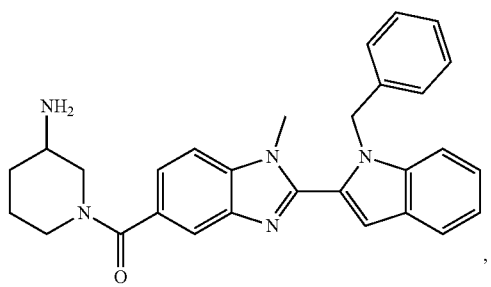

or a pharmaceutically acceptable salt thereof.

9. A compound selected from the list consisting of:
(3R)-1-[2-(1-benzyl-1H-indol-2-yl)-1-methyl-1H-1,3-benzodiazole-5-carbonyl]piperidin-3-amine;
(3R)-1-{1-methyl-2-[1-(pyridin-3-ylmethyl)-1H-indol-2-yl]-1H-1,3-benzodiazole-5-carbonyl}piperidin-3-amine;
(3R)-1-{1-methyl-2-[1-(2,2,2-trifluoroethyl)-1H-indol-2-yl]-1H-1,3-benzodiazole-5-carbonyl}piperidin-3-amine;
(3R)-1-{2-[1-(cyclopropylmethyl)-1H-indol-2-yl]-1-methyl-1H-1,3-benzodiazole-5-carbonyl}piperidin-3-amine;
(3R)-1-(1-methyl-2-{1-[(1-methyl-1H-pyrazol-4-yl)methyl]-1H-indol-2-yl}-1H-1,3-benzodiazole-5-carbonyl)piperidin-3-amine;
(3R)-1-[2-(1-ethyl-1H-indol-2-yl)-7-methoxy-1-methyl-1H-1,3-benzodiazole-5-carbonyl]piperidin-3-amine;
(3R)-1-{2-[1-(cyclopropylmethyl)-1H-indol-2-yl]-7-methoxy-1-methyl-1H-1,3-benzodiazole-5-carbonyl}piperidin-3-amine;
(3R)-1-{7-methoxy-1-methyl-2-[1-(2,2,2-trifluoroethyl)-1H-indol-2-yl]-1H-1,3-benzodiazole-5-carbonyl}piperidin-3-amine;
(3S,4R)-3-amino-1-{7-methoxy-1-methyl-2-[1-(2,2,2-trifluoroethyl)-1H-indol-2-yl]-1H-1,3-benzodiazole-5-carbonyl}piperidin-4-ol; and
(3S,4R)-3-amino-1-{2-[1-(cyclopropylmethyl)-1H-indol-2-yl]-1-methyl-1H-1,3-benzodiazole-5-carbonyl}piperidin-4-ol;
and salts thereof.

10. A compound of formula (I) according to claim 1 as a pharmaceutically acceptable salt.

11. A method of treating a disorder mediated by PAD4 activity, comprising administering a safe and effective amount of a compound of formula (I) as defined in claim 1, or a pharmaceutically acceptable salt thereof, to a patient in need thereof.

12. A method of treating rheumatoid arthritis, vasculitis, systemic lupus erythematosus, ulcerative colitis, cancer, cystic fibrosis, asthma, cutaneous lupus erythematosis, or psoriasis, which method comprises administering to a patient in need thereof, a therapeutically effective amount of a compound of formula (I) as defined in claim 1, or a pharmaceutically acceptable salt thereof.

13. A compound of formula (I) as defined in claim 1, or a pharmaceutically acceptable salt thereof, for use in therapy.

14. A compound of formula (I), as defined in claim 1, or a pharmaceutically acceptable salt thereof, for use in the treatment of a disorder mediated by PAD4 activity.

15. A compound of formula (I) as defined in claim 1, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis.

16. A pharmaceutical composition comprising a compound of formula (I) as defined in claim 1, or a pharmaceutically acceptable salt thereof, and one or more pharmaceutically acceptable excipients.

* * * * *